US006933273B2

(12) United States Patent
Tryggvason et al.

(10) Patent No.: US 6,933,273 B2
(45) Date of Patent: Aug. 23, 2005

(54) ISOLATED LAMININ 10

(76) Inventors: Karl Tryggvason, Division of Matrix Biology, Department of Medical Biochemistry and Biophysics, Karolinska Institutet, S-171 77 Stockholm (SE); Masayuki Doi, Division of Matrix Biology, Department of Medical Biochemistry and Biophysics, Karolinska Institutet Scheelesvag2, B1, plan4, S-171 77 Stockholm (SE); Jill Thyboll, Karolinska Institutet, Department of Medical Biochemistry and Biophysics, Divsion of Matrix Biology Matrix Biology, MBB, SE-17177 Stockholm (SE)

( * ) Notice: Subject to any disclaimer, the term of this patent is extended or adjusted under 35 U.S.C. 154(b) by 387 days.

(21) Appl. No.: 10/037,182

(22) Filed: Dec. 21, 2001

(65) Prior Publication Data

US 2003/0044899 A1 Mar. 6, 2003

Related U.S. Application Data

(60) Provisional application No. 60/257,449, filed on Dec. 21, 2000, provisional application No. 60/279,282, filed on Mar. 28, 2001, and provisional application No. 60/350,558, filed on Nov. 13, 2001.

(51) Int. Cl.[7] .............................................. C07K 14/00
(52) U.S. Cl. ......................................... 514/2; 530/350
(58) Field of Search .............................. 530/350; 514/2

(56) References Cited

FOREIGN PATENT DOCUMENTS

| WO | WO 00/66730 | 11/2000 |
| WO | WO 00/66731 | 11/2000 |
| WO | WO 00/66732 | 11/2000 |

OTHER PUBLICATIONS

Sasaki et al. 1987. P.N.A.S. 84: 935–939.*
Pikkarainen et al. 1987.J. Biol. Chem 262:10454–10462.*
Sasaki et al. 1987. J. Biol. Chem 262: 17111–17117.*
Pikkarainen et al. 1988.J. Biol. Chem 263:6751–6758.*
Altschul, et al., (1990), *J. Mol. Biol.,* 215:403–410.
Altschul, et al., (1997), *Nucleic Acids. Res.,* 25:3389–3402.
Aumailley and Kreig, (1996), *J. Invest. Dermatology,* 106:209–214.
Aumailley, et al., (1996), In The Laminins, Timpl and Ekblom, eds., Harwood Academic Publishers, Amsterdam, 127–158.
Aumailley, M., and Smyth, N., (1998), *J. Anat.,* 193(Pt 1): 1–21.
Champliaud, MF, et al., (2000), *Experiment Cell Research,* 259(2): 326–35.
Church, HJ, et al., (1998), *Biochemical Journal,* 332(2): 491–8.
Clark, E. A. et al., (1995), *Science,* 268(5208): 233–9.

Cleland, et al., (1993), *Crit. Rev. Therapeutic Drug Carrier Systems,* 10:307–377.
Colognato, J., (1999), *J. Cell Biol.,* 145:619–631.
Davis, G. E., et al., (1995), *Exp. Cell Res.,* 216(1): 113–23.
De Arcangelis, A., et al., (2001), *International Journal of Cancer,* 94(1): 44–53.
Dejana, E., et al., (1993), *Kidney Int.,* 43(1): 61–5.
Dixit, P., et al., (2001), *J. Biomed. Mater. Res.,* 56(4): 545–55.
Durkin, ME, (1997), *FEBS Letters,* 411(2–3): 296–300.
Durkin, ME, "Homo sapiens laminin, alpha 5 (LAMA5), MRNA, "Accession No. NM005560, May 30, 2001.
Eble, JA, (1998), *Biochemistry,* 37(31): 10945–55.
Ekblom, M., Flak, M., (1998), *Annals of the New York Academy of Sciences,* 857:194–211.
El Nemer, W., et al., (2001), *Journal of Biological Chemistry,* 276(26): 23757–62.
Engel, J., (1994), Methods *Enzymol.,* 245:469–88.
Faury, Ristori, G., et al., (1995), *Journal of Vascular Research,* 32(2): 112–9.
Ferletta, M. et al., (1999), *J. Cell Sci.,* 112(Pt. 1): 1–10.
Frojdman, K., et al., (1999), *Differentiation,* 64(3): 151–9.
Fujiwara, H., et al., (2001), *J. Biol. Chem.,* 276(20): 17550–8.
Geberhiwot, T., et al., (2001), *Journal of Cell Science,* 114(Pt. 2): 423–33.
Goodwin, AE, et al., (1995), *Journal of Immunological Methods,* 187(2): 213–9.
Gu, J., (2001), *Journal of Biological Chemistry,* 276(29): 27090–7.
Gu, Y., et al., (1999), *Blood,* 93(8):2533–42.
Haegerstrand, A., et al., (1992), *J. Vasc. Surg.,* 16(2): 280–5.
Hellivwell, TR, et al., (1998), *Neuromuscular Disorders,* 8(3–4): 152–61.
Hunter, D.D., et al., (1989), *Cell,* 59(5): 905–13.
Iivanainen, A., et al., (1997), *J. Biol. Chem.,* 272(44): 27862–8.
Jansson, K., et al., (1998), *Eur. J. Vasc. Endovasc. Surg.,* 16(4): 334–41.
John, St., PL, et al., (2001), *Kidney International,* 60(3): 1037–46.
Kamiguchi, et al., (1998), *Ann. Rev. Neurosci.,* 21:97–125.
Kanda, S., et al., (1999), *Exp. Cell Res.,* 248(1): 203–13.
Karlin and Altschul, (1990), *Proc. Natl. Acad. Sci. USA,* 87:2264–2268.

(Continued)

*Primary Examiner*—Karen Cochrane Carlson
(74) *Attorney, Agent, or Firm*—McDonnell Boehnen Hulbert & Berghoff LLP

(57) ABSTRACT

The present invention provides isolated laminin 10, methods for making recombinant laminin 10, host cells that express recombinant laminin 10, and methods for using the recombinant laminin 10 to accelerate the healing of injuries to vascular tissue, and to promote cell attachment and migration. The present invention also provides nucleic acid sequences encoding full length human laminin α5 chain, expression vectors and host cells thereof, and isolated full length human laminin α5 polypeptide chain.

15 Claims, 7 Drawing Sheets

OTHER PUBLICATIONS

Karlin and Altschul, (1993), *Proc. Natl. Acad. Sci USA*, 90:5873–5877.
Kikkawa, Y., et al., (1998), *J. Biol. Chem.*, 273(25): 15854–9.
Kikkawa, Y., et al., (2000, *J. Cell Sci.*, 113(Pt. 5): 869–76.
Kohler and Milstein, (1975), *Nature*, 256:495–497.
Kortesmaa, J. et al., (2000), *J. Biol. Chem.*, 275(20): 14853–9.
Kozak, M., (1991), *J. Cell Biol.*, 115(4): 997–903.
Lallier, T., et al., (1991), *Development*, 113(4): 1069–84.
Lange, TS, et al., (1994), *Experimental Cell Research*, 214(1): 381–8.
Ling, A. Dai, et al., (1999), *Hypertension*, 34(5): 1141–6.
Lin, L., et al., (2000), *Experimental Eye Research*, 70(4): 537–46.
Ljubimov AV, et al., (1998), *Journal of Histochemistry & Cytochemistry*, 46(9): 1033–41.
Madri, J.A., et al., (1988), *Am. J. Pathol.*, 132(1):18–27.
Madri, J.A., et al., (1991), *J. Cell Biochem.*, 45(2):123–30.
Malinda and Kleinman, (1996), Cell Biol., *Int. J. Biochem*, 28:957–959.
Miner, J.H., et al., (1995),*J. Biol. Chem.*, 270(48): 28523–6.
Miner, J.H., et al., (1997), *J. Cell Biol.*, 137(3): 685–701.
Miner, J.H. et al., "Mus Musculus laminin alpha 5 chain (Lama5) MRNA, partial cds.," Accession No. U37501, Nov. 10, 1997.
Miner, J.H., et al., (1998), *J. Cell Biol.*, 143(6): 1713–23.
Miner, J.H., et al., (2000), *Dev. Biol.*, 217(2): 278–89.
Nielsen, P.K., et al., (2000), *Journal of Biological Chemistry*, 275(19): 14517–23.
Nielsen, P.K., et al., (2001), *J. Biol. Chem.*, 276(14): 10906–12.
Parsons, SF, et al., (2001), *Blood*, 97(1): 312–20.
Patton, B. L., et al., (1997), *J. Cell Biol.*, 139(6): 1507–21.
Pedraza, C. Gerberhiwot, (2000), *Journal of Immunology*, 165(10): 5831–8.
Pevec, W. C., et al., (1992), *J. Vasc. Surg.*, 16(1): 60–5.
Pierschbacher, M.D., et al., (1984), *Nature*, 309(5963): 30–3.
Pikkarainen, T., et al., (1992), *Eur. J. Biochem.*, 209(2):571–82.
Pinckard, et al., (1967), *Clin. Exp. Immunol.*, 2:331–340.
Pouliot, N., et al., (2000), *Experimental Cell Research*, 261(2): 360–71.
Pouliot, N., et al., (2001), *Exp. Cell Res.*, 266(1), 1–10.
Robbins, et al., (1987), *Diabetes*, 36:838–845.
Sanes, JR., et al., (1998), *Journal of Physiology*, 92(3–4): 167–72.
Seebacher, T., et al., (1997), *Experimental Cell Research*, 237(1): 70–6.
Shah, BH, et al., (1992), *Brain Research*, 589(2): 268–74.
Shattil, S.J., et al., (1997), *J. Clin. Invest.*, 100(11 Suppl), S91–5.
Siler, U., Seiffert M., (2000), *Blood*, 96(13): 4194–203.
Sixt, M., (2001), *Journal of Cell Biology*, 153(5): 933–46.
Sixt, M., et al., (2001), *J. Biol. Chem.*, 276(22), 18878–87.
Skelton, HG, (1998), *American Journal of Dermatopathology*, 20(6): 547–50.
Sorokin, L. M., et al., (1997), *Dev. Biol.*, 189(2): 285–300.
Sorokin, L. M., et al., (1997), *Dev. Dyn.*, 210(4):446–62.
Sorokin, L., et al., (1994), *Eur. J. Biochem.*, 223(2):603–10.
Spessotto, P. Yin, et al., (2001), *Cancer Research*, 61(1): 339–47.
Tani, T., et al., (1999), *Exp. Cell Res.*, 248(1): 115–21.
Timpl, R., and Brown, J.C., (1994), *Matrix Biol.*, 14(4): 275–281.
Tokida, Y., et al., (1990), *J. Biol. Chem.*, 265(30): 18123–9.
Vanderboom, RJ, et al., (1989), *Journal of Reproduction & Fertility*, 87(1): 81–7.
Varani, J., et al., (1995), *Journal of Biomedical Materials Research*, 29(8): 993–7.
Virtanen, I., et al., (1997), *Am. J. Pathol.*, 150(4):1421–31.
Wang, YG, Samarel, et al., (2000), *Journal of Physiology*, 526(Pt. 1): 57–68.
Watelet, J., et al., (1997), *Ann. Vasc. Surg.*, 11(5): 510–9.
Wayner, E.A., et al., (1993),*J. Cell Biol.*, 121(5): 1141–52.
Wewer and Engvall, (1996), *Neuromusc. Disord.*, 6:409–418.
Woerly, S., et al., (1996), *Neuroscience Letters*, 205(3) 197–201.
Yurchenco, et al., (1997), *Proc. Natl. Acad. Sci.*, 94:10189–10194.

* cited by examiner

ISOLATED LAMININ 10

CROSS REFERENCE

This application claims priority to U.S. provisional applications Ser. No. 60/257,449, filed Dec. 21, 2000, Ser. No. 60/279,282, filed Mar. 28, 2001, and Ser. No. 60/350,558, filed Nov. 13, 2001.

FIELD OF THE INVENTION

This application relates to cell biology, molecular biology, proteins, nucleic acids, and laminins.

BACKGROUND OF THE INVENTION

Basal laminae (basement membranes) are sheet-like, cell-associated extracellular matrices that play a central role in cell growth, tissue development, and tissue maintenance. They are present in virtually all tissues, and appear in the earliest stages of embryonic development.

Basal laminae are central to a variety of architectural and cell-interactive functions (See for example, Malinda and Kleinman, Int. J. Biochem. Cell Biol. 28:957–959 (1996); Aumailley and Krieg, J. Invest. Dermatology 106:209–214 (1996)). For example:

1. They serve as architectural supports for tissues, providing adhesive substrata for cells.
2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.
3. Basal laminae create highly interactive surfaces that can promote cell migration and cell elongation during embryogenesis and wound repair. Following an injury, they provide a surface upon which cells regenerate to restore normal tissue function.
4. Basal laminae present information encoded in their structure to contacting cells that is important for differentiation and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. To date, six type IV collagen chains and at least twelve laminin subunits have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors, and by forming laminin networks, and they are important signaling molecules that can strongly influence cellular function. Laminins are important in both maintaining cell/tissue phenotype as well as promoting cell growth and differentiation in tissue repair and development.

Laminins are large, multi-domain proteins, with a common structural organization. The laminin molecule integrates various matrix and cell interactive functions into one molecule.

A laminin molecule is comprised of an $\alpha$-, $\beta$-, and $\gamma$-chain subunit joined together through a coiled-coil domain. Within this structure are identifiable domains that possess binding activity towards other laminin and basal lamina molecules, and membrane-bound receptors. Domains VI, IVb, and IVa form globular structures, and domains V, IIIb, and IIIa (which contain cysteine-rich EGF-like elements) form rod-like structures (Kamiguchi et al., Ann. Rev. Neurosci. 21:97–125 (1998)). Domains I and II of the three chains participate in the formation of a triple-stranded coiled-coil structure (the long arm).

Table 1 shows the individual chains that each laminin type is composed of:

TABLE 1

| Known laminin family members | |
|---|---|
| Protein | Chains |
| Laminin-1 | $\alpha1\beta1\gamma1$ |
| Laminin-2 | $\alpha2\beta1\gamma1$ |
| Laminin-3 | $\alpha1\beta2\gamma1$ |
| Laminin-4 | $\alpha2\beta2\gamma1$ |
| Laminin-5 | $\alpha3\beta3\gamma2$ |
| Laminin-6 | $\alpha3\beta1\gamma1$ |
| Laminin-7 | $\alpha3\beta2\gamma1$ |
| Laminin-8 | $\alpha4\beta1\gamma1$ |
| Laminin-9 | $\alpha4\beta2\gamma1$ |
| Laminin-10 | $\alpha5\beta1\gamma1$ |
| Laminin-11 | $\alpha5\beta2\gamma1$ |
| Laminin-12 | $\alpha2\beta1\gamma3$ |

Four structurally-defined family groups of laminins have been identified. The first group of five identified laminin molecules, including laminin 10 all share the $\beta1$ and $\gamma1$ chains, and vary by their $\alpha$-chain composition ($\alpha1$ to $\alpha5$ chain). The second group of five identified laminin molecules all share the $\beta2$ and $\gamma1$ chain, and again vary by their $\alpha$-chain composition. The third group of identified laminin molecules has one identified member, laminin 5, with a chain composition of $\alpha3\beta3\gamma2$. The fourth group of identified laminin molecules has one identified member, laminin 12, with the newly identified $\gamma3$ chain ($\alpha2\beta1\gamma3$).

Some progress has been made in elucidating the relationship between domain structure and function (See, for example, Wewer and Engvall, Neuromusc. Disord. 20 6:409–418 (1996)). The overall sequence similarity among the homologous domains in different chains varies, but it is highest in domain VI (thought to play a key role in laminin polymerization), followed by domains V (possibly involved in protein-protein interactions) and III (entactin/nidogen binding; possible cell adhesion sites), and is lowest in domains I, II (both thought to be involved in intermolecular assembly, and containing possible cell adhesion sites), and G. Not all domains are present in all 3 types of chains. The globular G domain (thought to be involved in cell receptor binding) is present only in the $\alpha$ chains. Other domains may not be present in all chains within a certain chain type. For example, domain VI is absent from $\alpha3$, $\alpha4$, and $\gamma2$ chains (Wewer and Engvall, 1996).

As a result of their large size (>600 kD) and unique structure, the laminin molecules can be resolved in the electron microscope (Wewer and Engvall, 1996). Typically, laminins appear as cross-shaped molecules in an EM. The three short arms of the cross represent the amino terminal portions of each of the three separate laminin chains (one short arm per chain). The long arm of the cross is composed of the C-terminal parts of the three chains, which together form a coiled coil structure (Wewer and Engvall, 1996). The long arm ends with the globular G domain.

The coiled-coil domain of the long arm is crucial for assembly of the three chains of laminin (Yurchenco et al., Proc. Natl. Acad. Sci. 94:10189–10194 (1997)). Disulfide bonds bridge and stabilize all three chains in the most proximal region of the long arm and join the β and γ chains in the most distal region of the long arm.

A model of laminin receptor-facilitated self-assembly, based on studies conducted with cultured skeletal myotubes and Schwann cells, predicts that laminins bind to their receptors, which freely diffuse in a fluidic membrane, when ligand-free. Receptor engagement forces the laminins into a high local two-dimensional concentration, facilitating their mass-action driven assembly into ordered surface polymers. In this process, the engaged receptors are also reorganized, accompanied by cytoskeletal rearrangements (Colognato, J. Cell Biol. 145:619–631 (1999)). This reorganization activates the receptors, causing signal transduction with the alteration of cell expression, shape and/or behavior. The evidence is that laminins must possess both cell-interacting and architecture-forming sites, which are located in different protein domains and on different subunits.

One class of laminin receptors are the integrins, which are cell surface receptors that mediate many cell-matrix and cell-cell interactions. Integrins are heterodimers, consisting of an α and a β subunit. 16 α- and 8 β-subunits are known, and at least 22 combinations of α and β subunits have been identified to date. Some integrins have only one or a few known ligands, whereas others appear to be very promiscuous. Binding to integrins is generally of low affinity, and is dependent on divalent cations. Integrins, activated through binding to their ligands, transduce signals via kinase activation cascades, such as focal adhesion and mitogen-activated kinases. Several different integrins bind different laminin isoforms more or less specifically (Aumailley et al., In The Laminins, Timpl and Ekblom, eds., Harwood Academic Publishers, Amsterdam. pp. 127–158 (1996)).

Laminin isoforms are expressed in tissue-specific and developmentally regulated patterns and they play significant roles in adhesion, migration, proliferation and differentiation of many cell types (Timpl, R., and Brown, J. C. (1994) *Matrix Biol.* 14(4), 275–81.; Ekblom, P., Timpl, R. (ed) (1996) *The laminins* Vol. 2. Cell Adhesion & Communication. Edited by Goridis, C., Harwood Academic Publishers GmbH, Amsterdam; Sorokin, L. M., et al. (1997) *Dev. Biol.* 189(2), 285–300.; Aumailley, M., and Smyth, N. (1998) *J. Anat.* 193(Pt 1), 1–21).

The laminin α5 chain, a component of laminin-10 (α5β1γ1) and laminin-11 (α5β2γ1), is expressed widely in adult tissues including placenta, heart, lung, skeletal muscle, kidney, and pancreas (Sorokin, L. M., et al. (1997) *Dev. Biol.* 189(2), 285–300; Patton, B. L., et al. (1997) *J. Cell Biol.* 139(6), 1507–21; Miner, J. H., et al. (1997) *J. Cell Biol.* 137(3), 685–701; Miner, J. H., et al. (1995) J. Biol. Chem. 270(48), 28523–6; Sorokin, L. M., et al. (1997) *Dev. Dyn.* 210(4), 446–62). Embryos lacking laminin α5 exhibit several developmental abnormalities, such as exencephaly and syndactyly, as well as dysmorphogenesis of the placental labyrinth and die late in embryogenesis (Miner, J. H., et al. (2000) *Dev. Biol.* 217(2), 278–89; Miner, J. H., et al. (1998) *J. Cell Biol.* 143(6), 1713–23). Laminin α5 chain-containing isoforms may therefore be important in placental endothelial cell migration and blood vessel branching, and in formation of proper basal laminae.

Integrin-mediated recognition of ECM molecules results in intracellular signaling that affects a range of cell behaviors (Clark, E. A. et al., Science 268(5208), 233–9 (1995)). In endothelial cells, these signals affect focal adhesions and cytoskeletal organization. Therefore, integrin-mediated endothelial cell recognition of laminin and other BM molecules may determine cell-to-matrix adhesiveness and mediate signals that are essential for the maintenance and normal functioning of blood vessels (Davis, G. E. et al., Exp. Cell Res. 216(1), 113–23 (1995); Dejana, E. et al., Kidney Int. 43(1), 61–5 (1993); and Shattil, S. J. et al., J. Clin. Invest. 100(11 Suppl), S91–5 (1997)). Laminin-8 and laminin-10 are secreted by endothelial cells, and are major components of the subendothelial basement membrane (Sorokin, L. M. et al., Dev. Biol. 189(2), 285–300 (1997); Iivanainen, A. et al., J. Biol. Chem. 272(44), 27862–8 (1997); Patton, B. L. et al., J. Cell Biol. 139(6), 1507–21 (1997), Miner, J. H. et al., J. Cell Biol. 137(3), 685–701 (1997); Sorokin, L. et al., Eur. J. Biochem. 223(2), 603–10 (1994); and Tokida, Y. et al., J. Biol. Chem. 265(30), 18123–9 (1990)).

There have been no reports of isolated laminin 10 that is free of other laminin chains. Studies on the function of laminin-10 have frequently used commercial preparations, which are normally prepared using proteolytic digestion and subsequent immunoaffinity chromatography resulting in a truncated mixture of α5-chain containing laminin isoforms (Sixt, M. et al., J. Biol. Chem. 276(22), 18878–87 (2001)). Attempts to purify laminin 10 from cell sources by affinity chromatography using laminin chain antibodies have been unsuccessful in eliminating, for example, laminin β2 chain, which is a component of laminin 11. (See, for example, Sixt, M. et al., J. Biol. Chem. 276(22), 18878–87 (2001)) Thus, such preparations represent a mixture of laminin 10 and laminin 11.

Despite the broad tissue distribution of the laminin α5 chain and laminin 10, the full length human laminin α5 chain sequence is not known, nor is there a means to isolate laminin 10 away from other laminins, nor has a means for recombinant expression of laminin 10 previously been developed. Isolated laminin 10 would have numerous research and therapeutic purposes including, but are not limited to, treating injuries to vascular tissue, promoting cell attachment and migration, ex vivo cell therapy, improving the biocompatibility of medical devices, and preparing improved cell culture devices and media.

Thus, there is a need in the art for isolated laminin-10 for research and therapeutic purposes, and methods for making isolated laminin 10.

SUMMARY OF THE INVENTION

In one aspect, the present invention provides an isolated nucleic acid encoding a full-length human laminin α5 chain consisting of the nucleic acid sequence of SEQ ID NO:1, or the complement thereof, as well as vectors comprising the sequence, and host cells transfected with such vectors. In another aspect, the present invention provides isolated laminin α5 chain protein consisting of the amino acid sequence of SEQ ID NO:2.

In another aspect, the present invention provides isolated laminin 10, and methods for producing isolated laminin 10. In a further aspect, the present invention provides recombinant host cells that express laminin 10 chains and secrete recombinant laminin 10.

In a further aspect, the present invention provides pharmaceutical compositions, comprising isolated laminin 10 together with a pharmaceutically acceptable carrier. Such pharmaceutical compositions can optionally be provided with other extracellular matrix components.

In another aspect, the present invention provides methods and kits for accelerating the healing of injuries to vascular tissue, and for improving the biocompatibility of grafts used for treating such injuries. In specific examples, laminin 10 or pharmaceutical compositions thereof are used to:

a. promote re-endothelialization at the site of vascular injuries;
b. improve the "take" of grafts;
c. improve the biocompatibility of medical devices; and/or
d. promote cell attachment and subsequent cell stasis, proliferation, differentiation, and/or migration.

by providing an amount effective of isolated laminin 10 for the various methods. In preferred embodiments of all of these methods, recombinant laminin 10 is used. The kits comprise an amount of isolated laminin 10, or pharmaceutical compositions thereof, effective for the desired effect, and instructions for the use thereof.

In a further aspect, the present invention provides improved medical devices and grafts, wherein the improvement comprises providing medical devices and grafts with an amount effective of isolated laminin 10, or a pharmaceutical composition of the invention.

In a further aspect, the invention provides improved cell culture devices, and methods for preparing improved cell culture devices, for the growth and maintenance of cells in culture, by providing an amount effective to a cell culture device of isolated laminin 10 for cell attachment and subsequent cell stasis, proliferation, differentiation, and/or migration.

BRIEF DESCRIPTION OF THE FIGURES

FIGS. 1A and 1B. cDNA-derived amino acid sequence of the human laminin 5 chain and alignment with the mouse chain. Upper sequence, human α5 chain; Lower sequence, mouse sequence. Domain boundaries are depicted, and adhesive tripeptide sequences RGD and LRE are boxed. The potential cleavage site of the signal peptide is indicated by a solid triangle (Predicted by PSORT II). The five possible polymorphisms are shown as bold italic characters above the human sequence. The sequence submitted to GenBank by the Human Genome Project (accession NM_005560 (May 30, 2001)) differed from the present sequence at a few sites, indicated above the sequence in the figure. At these sites, the present sequence did not differ from the incomplete genomic sequences reported by Celera.

TABLE 2

Figure 2A:
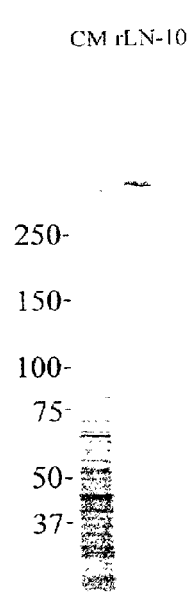
FIGS. 2A, 2B, and 2C. Characterization of r-laminin-10 using SDS-PAGE. (A) Silver stain: Conditioned medium of triple-transfected HEK293 cells (CM) and recombinant purified laminin-10 (r-laminin-10), were analyzed by SDS-PAGE on 4–15% gradient gels under reducing conditions; (B) Immunoblot of CM and r-laminin-10 under reducing conditions: Separated proteins on 5% gels were transferred onto PVDF membranes followed by staining with mAbs against laminin α5 (15H5), β1 (DG10), γ1 (clone 22) and FLAG-M2.; (C) Silver stain and immunoblot of rLN-10 under non-reducing conditions: Separated proteins on 5% gels were visualized by silver staining or transferred onto PVDF membranes followed by staining with mAbs against laminin α5 (15H5), β1 (DG10), γ1 (2E8). The positions of molecular size markers are shown.

Primers used in laminin 5 expression construct preparation.
Upper row, forward primer; Lower row, reverse primer.

| plasmid | primer | primer sequence | |
|---|---|---|---|
| KBX3 | KZK1 | 5'-gccaccatggcgaagcggctctg-3' | (SEQ ID NO.:21) |
| | Ba3r | 5'-aagggcaggatccactgggg-3' | (SEQ ID NO.:22) |
| BBL3 | Bam4 | 5'-ctactgcgaagctggctctt-3' | (SEQ ID NO.:23) |
| | Bcl1r | 5'-ccaggtggtcctgggtatc-3' | (SEQ ID NO.:24) |
| BNK2' | Bcl2 | 5'-gcgacaactgcctcctctac-3' | (SEQ ID NO.:25) |
| | Not4r | 5'-agtgggttcccaaagaatcc-3' | (SEQ ID NO.:26) |
| BNL12 | Bpu1F | 5'-cctctgtgacgagctcacg-3' | (SEQ ID NO.:27) |
| | Not4r | 5'-agtgggttcccaaagaatcc-3' | (SEQ ID NO.:27) |
| D29D301 | D29 | 5'-gatgtgtcccttgtcagtgccat-3' | (SEQ ID NO.:28) |
| | D301 | 5'-tgtcgtgttcagccgcttgaggt-3' | (SEQ ID NO.:29) |

TABLE 2-continued

Primers used in laminin 5 expression construct preparation.
Upper row, forward primer; Lower row, reverse primer.

| plasmid | primer | primer sequence | |
|---|---|---|---|
| NSK5 | Not3 | 5'-ctctcagtgccttccaacaac-3' | (SEQ ID NO.:30) |
| | Sal4r | 5'-ctgactgtcgaagctgatgc-3' | (SEQ ID NO.:31) |
| SFK2 | Sal5 | 5'-ggaggtggtcagcctctaca-3' | (SEQ ID NO.:32) |
| | FLAG1 | 5'-ttacttgtcatcgtcgtccttgtagtcggcggctgggcag-3' | (SEQ ID NO.:33) |
| SFL13 | Sal5 | 5'-ggaggtggtcagcctctaca-3' | (SEQ ID NO.:34) |
| | m19R | 5'-aatggtgccagactcagg-3' | (SEQ ID NO.:35) |

DETAILED DESCRIPTION OF THE PREFERRED EMBODIMENTS

All references, patents and patent applications are hereby incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

In one aspect, the present invention provides an isolated nucleic acid encoding a full length laminin α5 chain polypeptide consisting of the amino acid sequence of SEQ ID NO:2. In a preferred embodiment, the isolated nucleic acid consists of the sequence of SEQ ID NO: 1, the complement thereof, or the RNA expression product thereof.

In an additional aspect, the present invention provides an isolated nucleic acid comprising a nucleic acid sequence encoding the 2,743 N-terminal amino acids (SEQ ID NO:36) of the human laminin α5 chain, which has not previously been reported. In a preferred embodiment, the isolated nucleic acid consists of the sequence of SEQ ID NO:35, the complements thereof, or the RNA expression product thereof.

An used herein, an "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). An "isolated" laminin α5 chain nucleic acid sequence according to the present invention may, however, be linked to other nucleotide sequences that do not normally flank the recited sequence, such as a heterologous promoter sequence, or other vector sequences. It is not necessary for the isolated nucleic acid sequence to be free of other cellular material to be considered "isolated", as a nucleic acid sequence according to the invention may be part of an expression vector that is used to transfect host cells (see below).

In another aspect, the present invention provides recombinant expression vectors comprising a full length laminin α5 chain nucleic acid sequence, or a nucleic acid sequence expressing the 2,743 N-terminal amino acids (SEQ ID NO:36) of the human laminin α5 chain. In one embodiment, the expression vectors comprise a nucleic acid encoding a polypeptide selected from the group consisting of SEQ ID NO:2 and SEQ ID NO:36, operatively linked to a heterologous (i.e.: is not the naturally occurring α5 laminin chain promoter) promoter. In a preferred embodiment, the isolated nucleic acid consists of a sequence selected from the group consisting of SEQ ID NO:1 and SEQ ID NO:35. A promoter and a laminin α5 chain nucleic acid sequence are "operatively linked" when the promoter is capable of driving expression of the laminin α5 chain DNA into RNA.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In the present invention, the expression of the laminin polypeptide sequence is directed by the promoter sequences of the invention, by operatively linking the promoter sequences of the invention to the gene to be expressed. In general, expression vectors of utility in recombinant DNA techniques are often in the form of plasmids. In the present specification, "plasmid" and "vector" may be used interchangeably, as the plasmid is the most commonly used form of vector. However, the invention is intended to include other forms of expression vectors, such as viral vectors (e.g., replication defective retroviruses, adenoviruses and adeno-associated viruses), which serve equivalent flnctions.

The vector may also contain additional sequences, such as a polylinker for subcloning of additional nucleic acid sequences, or a polyadenylation signal to effect proper polyadenylation of the transcript. The nature of the polyadenylation signal is not believed to be crucial to the successful practice of the invention, and any such sequence may be employed, including but not limited to the SV40 and bovine growth hormone poly-A sites. Also contemplated as an element of the vector is a termination sequence, which can serve to enhance message levels and to minimize read through from the construct into other sequences. Additionally, expression vectors typically have selectable markers, often in the form of antibiotic resistance genes, that permit selection of cells that carry these vectors.

In a further embodiment, the present invention provides host cells transfected with the laminin α5 chain-expressing recombinant expression vectors disclosed herein. As used herein, the term "host cell" is intended to refer to a cell into which a nucleic acid of the invention, such as a recombinant expression vector of the invention, has been introduced. Such cells may be prokaryotic, which can be used, for example, to rapidly produce a large amount of the expression vectors of the invention, or may be eukaryotic, for functional studies.

The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The host cells can be transiently or stably transfected with one or more of the expression vectors of the invention. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique, $2^{nd}$ Ed.* (R. I. Freshney. 1987. Liss, Inc. New York, N.Y.).

In another aspect, the present invention provides an isolated full length human laminin α5 chain polypeptide consisting of amino acid sequence of SEQ ID NO:2. In a further embodiment, of this aspect, the invention provides an isolated polypeptide consisting of the 2,743 N-terminal amino acids (SEQ ID NO:36) of the human laminin α5 chain.

As used herein, an "isolated polypeptide" refers to a polypeptide that is substantially free of other proteins, including other laminin chains, and gel agents, such as polyacrylamide and agarose. In a preferred embodiment, the isolated laminin polypeptide is free of detectable contaminating laminin chains. Thus, the protein can either be isolated from natural sources, or recombinant protein can be isolated from the transfected host cells disclosed above.

In a further aspect, the invention provides methods for detecting the presence of the laminin α5 chain in a protein sample, comprising providing a protein sample to be screened, contacting the protein sample to be screened with an antibody against the 2,743 N-terminal amino acids (SEQ ID NO:36) of the human laminin α5 chain, or fragments thereof, and detecting the formation of antibody-antigen complexes.

The antibody can be either polyclonal or monoclonal, although monoclonal antibodies are preferred. As used herein, the term "protein sample" refers to any sample that may contain the laminin α5 chain, including but not limited to tissues and portions thereof, tissue sections, intact cells, cell extracts, purified or partially purified protein samples, bodily fluids, nucleic acid expression libraries. Accordingly, this aspect of the present invention is useful for a variety of purposes including, but not limited to, immunolocalization, immunofluorescence analysis, Western blot analysis, ELISAs, and nucleic acid expression library screening. In one embodiment, the techniques may determine only the presence or absence of the human laminin α5 chain. Alternatively, the techniques may be quantitative, and provide information about the relative amount of laminin α5 chain in the sample. For quantitative purposes, ELISAs are preferred.

Detection of immunocomplex formation between the human laminin α5 chain and antibodies or fragments thereof directed against an amino acid sequence of SEQ ID NO:36, or fragments thereof, can be accomplished by standard detection techniques. For example, detection of immunocomplexes can be accomplished by using labeled antibodies or secondary antibodies.

Antibodies can be made by well-known methods, such as described in Harlow and Lane, Antibodies; A Laboratory Manual, Cold Spring Harbor Laboratory, Cold Spring Harbor, N.Y., (1988). For example, all or a portion of the amino acid sequence of SEQ ID NO:36, together with an appropriate adjuvant, can be injected into an animal in an amount and at intervals sufficient to elicit an immune response. Animals are bled at regular intervals, preferably weekly, to determine antibody titer. Polyclonal antibodies against laminin α5 chain can then be purified directly by passing serum collected from the animal through a column to which non-antigen-related proteins prepared from the same expression system without laminin α5 chain bound.

Monoclonal antibodies can be produced by obtaining spleen cells from the animal. (See Kohler and Milstein, Nature 256, 495–497 (1975)). In one example, monoclonal antibodies (mAb) of interest are prepared by immunizing inbred mice with peptide fragments of the amino acid sequence of SEQ ID NO:36. The mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route. Lymphocytes, from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

In yet another aspect, the invention provides methods for detecting the presence in a sample of nucleic acid sequences encoding the human laminin α5 chain, comprising providing a nucleic acid sample to be screened, contacting the sample with a nucleic acid probe consisting of the nucleic acid sequence of SEQ ID NO:35 or fragments thereof, and detecting complex formation.

As used herein, the term "sample" refers to any sample that may contain nucleic acid sequences encoding the human laminin α5 chain, including but not limited to tissues and portions thereof, tissue sections, intact cells, cell extracts, purified or partially purified nucleic acid samples, DNA libraries, and bodily fluids. Accordingly, this aspect of the present invention may be used to test for the presence of laminin α5 chain mRNA or DNA in these various samples by standard techniques including, but not limited to, in situ hybridization, Northern blotting, Southern blotting, DNA library screening, polymerase chain reaction (PCR) or reverse transcription-PCR (RT-PCR). In one embodiment, the techniques may determine only the presence or absence of the nucleic acid of interest. Alternatively, the techniques may be quantitative, and provide information about the relative amount of the nucleic acid of interest in the sample. For quantitative purposes, quantitative PCR and RT-PCR are preferred. Thus, in one example, RNA is isolated from a sample, and contacted with an oligonucleotide derived from the nucleic acid sequence of SEQ ID NO:35, or its complement, together with reverse transcriptase under suitable buffer and temperature conditions to produce cDNAs from the laminin α5 chain RNA. The cDNA is then subjected to PCR using primer pairs derived from the nucleic acid sequence of interest. For detecting laminin α5 chain nucleic acid sequences, standard labeling techniques can be used to label the probe, the nucleic acid of interest, or the complex between the probe and the nucleic acid of interest, including, but not limited to radio-, enzyme-, chemiluminescent-, or avidin or biotin-labeling techniques, all of which are well known in the art. (See, for example, *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.); *PCR Protocols: A Guide to Methods and Applications* (Innis, et al. 1990. Academic Press, San Diego, Calif.)).

In another aspect, the present invention provides isolated laminin 10. As used herein "laminin 10" encompasses both r-laminin 10 and heterotrimeric laminin 10 from naturally occurring sources. In a preferred embodiment, the laminin 10 comprises recombinant laminin 10 (or "r-laminin 10").

As used herein, the term "r-laminin 10" refers to recombinant heterotrimeric laminin 10, expressed by a host cell that has been transfected with one or more expression vectors comprising at least one nucleic acid sequence encoding a laminin 10 chain selected from the α5, β1 and γ1 chains, or processed/secreted forms thereof. Such r-laminin 10 can thus comprise α5, β1, and γ1 sequences from a single organism, or from different organisms. Various laminin 10 chain DNA sequences are known in the art, and the use of each to prepare the r-laminin 10 of the invention is contemplated. (See, for example, Pouliot, N. et al., Experimental Cell Research 261(2):360–71, (2000); Kikkawa, Y. et al., Journal of Cell Science 113 (Pt 5):869–76, (2000); Church, H J. et al., Biochemical Journal 332 (Pt 2):491–8, (1998); Sorokin, L M. et al., Developmental Biology 189(2):285–300, (1997); Miner, J H. et al., Journal of Biological Chemistry 270(48):28523–6, (1995); Sorokin, L. et al., European Journal of Biochemistry 223(2):603–10, (1994); all references incorporated by reference herein in their entirety). In a preferred embodiment, the r-laminin 10 comprises recombinant human α5, β1, and γ1 polypeptide chains.

As used herein, "isolated" means that the laminin 10 is substantially free of other proteins, including the laminin β2 chain polypeptide chain, and gel agents, such as polyacrylamide and agarose. In a preferred embodiment, the isolated laminin 10 is free of detectable laminin β2 polypeptide chains.

The invention encompasses those laminin molecules wherein one or two chains that make up the recombinant heterotrimeric laminin 10 are encoded by endogenous laminin 10 chains. In a preferred embodiment, each of the α5, β1, and γ1 polypeptide chains are expressed recombinantly.

Laminin 10 is a secreted protein, which is capable of being directed to the endoplasmic reticulum (ER), secretory vesicles, and the extracellular space as a result of a signal sequence. If the secreted protein is released into the extracellular space, the secreted protein can undergo extracellular processing to produce a "mature" protein. Such processing event can be variable, and thus may yield different versions of the final "mature protein". The isolated laminin 10 of the present invention includes heterotrimers comprising both the full length and any such processed laminin 10 polypeptide chains.

As used herein, a laminin 10 polypeptide chain refers to a polypeptide chain according to one or more of the following:

(a) comprises a polypeptide structure selected from the group consisting of:

| | |
|---|---|
| 1. | R1-R2-R3 |
| 2. | R1-R2-R3(e) |
| 3. | R3 |
| 4. | R3(e) |
| 5. | R1-R3 |
| 6. | R1-R3(e) |
| 7. | R2-R3 |
| 8. | R2-R3(e) | wherein R1 is an amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted laminin chain selected from group consisting of the α5, β1, and γ1 chains; and R3(e) is a secreted laminin chain selected from the α5, β1, and γ1 chains that further comprises an epitope tag (such as those described below), which can be placed at any position within the laminin chain amino acid sequence; and/or (b) is encoded by a polynucleotide that hybridizes under high or low stringency conditions to the coding regions, or portions thereof, of one or more of the recombinant laminin 10 chain DNA sequences disclosed herein (SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, and SEQ ID NO:35), or complementary sequences thereof; and/or (c) has at least 70% identity to one or more of the disclosed laminin 10 polypeptide chain amino acid sequences (SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:36), preferably at least 80% identity, and most preferably at least about 90% identity.

"Stringency of hybridization" is used herein to refer to conditions under which nucleic acid hybrids are stable. The invention also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of skill in the art, the stability of hybrids is reflected in the melting temperature ($T_M$) of the hybrids. $T_M$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein, high stringency refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are laminin 10-encoding nucleic acid sequences that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altschul (Proc. Natl. Acad. Sci. USA 87:2264 . 2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score 100, wordlength=12, to determine nucleotide sequences identity to the nucleic acid molecules of the invention. BLAST protein searches are performed with the XBLAST program, score=50, wordlength=3, to determine an amino acid sequence identity to a polypeptide of the invention. To obtain gapped alignments for comparison purposes, Gapped BLAST is utilized as described in Altschul et al. (Nucleic Acids. Res. 25:3389–3402, 1997). When utilizing BLAST and Gapped BLAST programs, the default parameters of the respective programs (e.g., XBLAST and NBLAST) are used.

Further embodiments of the present invention include polynucleotides encoding laminin 10 chain polypeptides having at least 70% identity, preferably at least 80% identity, and most preferably at least 90% identity to one or more of the polypeptide sequences contained in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:36.

As used herein, "α5 polynucleotide" refers to polynucleotides encoding an laminin α5 chain of the same name. Such polynucleotides can be characterized by one or more of the following: (a) polynucleotides that encode polypeptides which share at least 70% identity, preferably 80% identity, and most preferably at least 90% identity with one or more sequences selected from the group consisting of SEQ ID NO:2 and SEQ ID NO:4; (b) the α5 polynucleotides hybridize under low or high stringency conditions to one or more coding sequences selected from the group consisting of SEQ ID NO: 1 or SEQ ID NO:3; complementary sequences thereof; or (c) the α5 polynucleotides encode a laminin α5 chain polypeptide with a general structure selected from the group consisting of (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted α5 chain polypeptides.

As used herein, "β1 polynucleotides" refers to polynucleotides encoding a β1 laminin chain of the same name. Such polynucleotides can be characterized by one or more of the following: (a) polynucleotides that encode polypeptides which share at least 70% identity, preferably at least 80%, and most preferably at least 90% identity with one or more of the sequences selected from the group consisting of SEQ ID NO: 6, SEQ ID NO:8, SEQ ID NO:10, SEQ ID NO:12; (b) the β1 polynucleotides hybridize under low or high stringency conditions to one or more coding sequences selected from the group consisting of SEQ ID NO: 5, SEQ ID NO:7, SEQ ID NO:9, SEQ ID NO:11, or complementary sequences thereof; or (c) the β1 polynucleotides encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted β1 chain polypeptides.

As used herein, "γ1 polynucleotides" refers to polynucleotides encoding a γ1 laminin chain of the same name. Such polynucleotides can be characterized by one or more of the following: (a) polynucleotides that encode polypeptides which share at least 70% identity, preferably at least 80%, and most preferably at least 90% identity with one or more of the sequences selected from the group consisting of SEQ ID NO: 14, SEQ ID NO:16, SEQ ID NO:18, or SEQ ID NO:20; (b) the γ1 polynucleotides hybridize under low or high stringency conditions to one or more of the coding sequence selected from the group consisting of SEQ ID NO:13, SEQ ID NO:15, SEQ ID NO:17, SEQ ID NO:19 or complementary sequences thereof; or (c) the γ1 polynucleotides encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted γ1 chain polypeptides.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

In a preferred embodiment, cDNAs encoding the laminin α5, β1 and γ1 chains, or fragments thereof, are subcloned into an expression vector. Alternatively, laminin α5, β1 and/or γ1 gene sequences, including one or more introns, can be used for sub-cloning into an expression vector.

In another aspect, the present invention provides laminin 10 expressing-cells that have been transfected with an expression vector containing promoter sequences that are operatively linked to nucleic acid sequences encoding at least one polypeptide sequence comprising a sequence selected from the group consisting of the α5, β1 and γ1 chains of laminin 10, wherein the transfected cells secrete heterotrimeric laminin 10 containing the recombinant laminin chain. In a preferred embodiment, the cells are systematically transfected with recombinant expression vectors containing promoter sequences that are operatively linked to nucleic acid sequences encoding polypeptide sequences comprising the α5, β1 and γ1 chains of laminin 10, even more preferably, all human chains. After the multiple transfections, the cells express recombinant laminin 10 chains, which form the heterotrimeric r-laminin 10.

Transfection of the expression vectors into eukaryotic cells can be accomplished via any technique known in the art, including but not limited to calcium phosphate co-precipitation, electroporation, or liposome mediated-, DEAE dextran mediated-, polycationic mediated-, or viral mediated transfection. Transfection of bacterial cells can be done by standard methods.

In a preferred embodiment, the cells are stably transfected. Methods for stable transfection and selection of appropriate transfected cells are known in the art. In another preferred embodiment, a CMV promoter driven expression vector is used in a human kidney embryonic 293 cell line.

Any cell capable of expressing and secreting the r-laminin 10 can be used. Preferably, eukaryotic cells are used, and most preferably mammalian cells are used, including but not limited to kidney and epithelial cell lines. The promoter sequence used to drive expression of the individual chains or r-laminin 10 may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). Carbohydrate and disulfide post-translational modifications are believed to be required for laminin 10 protein folding and function. This makes the use of eukaryotic cells preferable for producing functional r-laminin 10, although other systems are useful for obtaining, for example, antigens for antibody production. In a most preferred embodiment, the mammalian cells do not express the laminin β2 chain endogenously. In another preferred embodiment, the cells do not express all of the laminin 10 chains endogenously.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals.

In one embodiment, at least one of the laminin chain polypeptide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to any of the polypeptide chains comprising r-laminin 10, so long as the resulting r-laminin 10 remains functional.

In another embodiment, one of the r-laminin 10 chains is expressed as a fusion protein with a first epitope tag, and at least one other r-laminin chain is expressed as a fusion protein with a second epitope tag. This permits multiple rounds of purification to be carried out. Alternatively, the same epitope tag can be used to create fusion proteins with more than one of the r-laminin chains.

In a further embodiment, the epitope tag can be engineered to be cleavable from the r-laminin 10 chain(s). Alternatively, no epitope tag is fused to any of the r-laminin 10 chains, and the r-laminin 10 is isolated by standard techniques, including but not limited to affinity chromatography using laminin 10 specific antibodies or other laminin 10 binding molecules.

Media from cells transfected with a single laminin chain are initially analyzed on Western blots using laminin chain-specific antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for r-laminin 10 secretion and/or activity, by any appropriate method, including Western blot analysis and cell binding assays. Activity of the r-laminin 10 is preferably analyzed in a cell adhesion assay.

In a preferred embodiment, purification of r-laminin 10 is accomplished by passing media from the transfected cells through an antibody affinity column. In one embodiment, antibodies against a peptide epitope expressed on at least one of the recombinant chains are attached to an affinity column, and bind the r-laminin 10 that has been secreted into the media. The r-laminin 10 is removed from the column by passing excess peptide over the column. Eluted fractions are analyzed by any appropriate method, including gel electrophoresis and Western blot analysis. In a further embodiment, the peptide epitope can be cleaved after purification. In other embodiments, two or three separate r-laminin chains are expressed as fusion proteins, each with a different epitope tag, permitting two or three rounds of purification and a doubly or triply isolated r-laminin 10. The epitope tag can be engineered so as to be cleavable from the r-laminin 10 chain(s) after purification. Alternatively, no epitope tag is fused to any of the r-laminin 10 chains, and the r-laminin 10 is isolated by standard techniques, including but not limited to affinity chromatography using laminin 10 specific antibodies or other laminin 10 binding molecules.

The laminin 10 polypeptide chains of the present invention also include (i) substitutions with one or more of the non-conserved amino acid residues, where the substituted amino acid residues may or may not be one encoded by the genetic code, or (ii) substitution with one or more amino acid residues having substituents groups, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

The present invention further provides pharmaceutical compositions comprising isolated laminin 10 and a pharmaceutically acceptable carrier. In a preferred embodiment, the pharmaceutical composition comprises isolated r-laminin 10. According to this aspect of the invention, other agents can be included in the pharmaceutical compositions, depending on the condition being treated. The pharmaceutical composition may further comprise one or more other compounds, including but not limited to any of the collagens, other laminin types, fibronectin, vitronectin, cadherins, integrins, α-dystroglycan, entactin/nidogen, α-dystroglycan, glycoproteins, proteoglycans, heparan sulfate proteoglycan, glycosaminoglycans, epidermal growth factor, vascular endothelial growth factor, fibroblast growth factor, or nerve growth factors, and peptide fragments thereof.

Pharmaceutical preparations comprising isolated laminin 10 can be prepared in any suitable form, and generally comprise the isolated laminin 10 in combination with any of the well known pharmaceutically acceptable carriers. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifingals, antioxidants, osmotic agents, and similar materials in composition and quantity as is conventional. Suitable solutions for use in accordance with the invention are sterile, are not harmful for the proposed application, and may be subjected to conventional pharmaceutical operations such as sterilization and/or may contain conventional adjuvants, such as preservatives, stabilizers, wetting agents, emulsifiers, buffers etc. For assistance in formulating the compositions of the present invention, one may refer to Remington's Pharmaceutical Sciences, 15th Ed., Mack Publishing Co., Easton, Pa. (1975).

In further aspect, the present invention provides methods and kits comprising isolated laminin 10, or pharmaceutical compositions thereof (and instructions for using the isolated laminin 10 in the kits) for accelerating the healing of injuries to vascular tissue, and for improving the biocompatibility of grafts used for treating such injuries. In a preferred embodiment of each of the methods disclosed below, isolated laminin 10 is used. In specific examples, isolated laminin 10, isolated r-laminin 10, or pharmaceutical compositions thereof are used to:

a. promote re-endothelialization at the site of vascular injuries;
  b. improve the "take" of grafts;
  c. improve the biocompatibility of medical devices;
  d. promote cell attachment and subsequent cell stasis, proliferation, differentiation, and/or migration by providing an amount effective of isolated laminin 10 or pharmaceutical compositions thereof for the various methods.

Endothelial cells normally rest on a subendothelium, composed of collagen type I/III, elastin, fibronectin, glycosaminoglycans, and a basement membrane, mainly consisting of laminin and type IV collagen. Several of the invasive treatments used in the repair of vascular occlusive diseases, or the disease itself, may cause large areas of endothelial cell-denudation in the vessel wall. Endothelialization is, in part, dependent upon the underlying matrix, as subendothelial proteins have been shown to be important modulators of endothelial cell function (Madri, J. A. et al., Am. J. Pathol. 132(1), 18–27 (1988); and Madri, J. A. et al., J. Cell Biochem. 45(2), 123–30 (1991). In an effort to enhance endothelialization of grafts in humans, extensive research has been devoted to identifying substances that promote endothelial cell migration. Endothelial cell migration is a key element of endothelialization of vascular grafts, whether by anastomotic ingrowth, transmural capillary ingrowth, adherence of circulating cells, or ex vivo cell seeding. Ultimately, it is desirable to encourage spontaneous migration in vivo because this would minimize the need for ex vivo graft and cell manipulation. In addition, retention of cells on the vascular surface is necessary prior to migration (Dixit, P. et al., J. Biomed. Mater. Res. 56(4), 545–55 (2001)). Pretreatment of the graft with an adhesive substrate significantly enhances endothelial cell attachment to graft samples.

Laminin-8 and laminin-10 are secreted by endothelial cells, and are major components of the subendothelial basement membrane (Sorokin, L. M. et al., Dev. Biol. 189(2), 285–300 (1997); Iivanainen, A. et al., J. Biol. Chem. 272 (44), 27862–8 (1997Patton, B. L. et al., J. Cell Biol. 139(6), 1507–21 (1997), Miner, J. H. et al., J. Cell Biol. 137(3), 685–701 (1997); Sorokin, L. et al., Eur. J. Biochem. 223(2), 603–10 (1994); and Tokida, Y. et al., J. Biol. Chem. 265(30), 18123–9 (1990)). The data presented below demonstrates that isolated laminin 10 promotes endothelial cell attachment and migration.

Thus, in one embodiment the isolated laminin 10 is used to promote re-endothelialization, and to thus inhibit abnormal smooth muscle cell proliferation, at the site of a vascular injury. In another embodiment, isolated laminin 10 is coated onto grafts to improve the "take" of grafts. As used herein the term "graft" refers to both natural and prosthetic grafts and implants.

In a further aspect, the present invention comprises medical devices with improved biocompatibility, wherein the devices are coated with isolated laminin 10 or pharmaceutical compositions thereof, alone or in combination with other proteins or agents that serve to increase the biocompatibility of the device surface. The coated device stimulates cell attachment (such as endothelial cell attachment), and provides for diminished inflammation and/or infection at the site of entry of the appliance.

Such medical devices can be of any material used for implantation into the body, and preferably are made of or coated with a biocompatible metal that may be either stainless steel or titanium. Alternatively, the device is made of or coated with a ceramic material, or a polymer including but not limited to polyester, polyglycolic acid or a polygalactose-polyglycolic acid copolymer.

One particular use of the present invention is to increase cell adhesion to target surfaces, including but not limited to endothelial cell adhesion. For example, vascular grafts and stents may be coated with isolated laminin 10 or pharmaceutical compositions thereof to stimulate endothelial cell attachment.

If the device is made of a natural or synthetic biodegradable material in the form of a mesh, sheet or fabric, isolated laminin 10 or pharmaceutical compositions thereof may be applied directly to the surface thereof. Appropriate cells may then be cultured on the matrix to form transplantable or implantable devices, including dental abutment pieces, needles, metal pins or rods, indwelling catheters, colostomy tubes, surgical meshes and any other appliance for which coating with isolated laminin 10 is desirable. Alternatively, the devices may be implanted and cells may be permitted to attach in vivo.

Coupling of the isolated laminin 10 may be non-covalent (such as by adsorption), or by covalent means. The device may be immersed in, incubated in, or sprayed with the isolated laminin 10 or pharmaceutical compositions thereof.

The dosage regimen for various treatments using the isolated laminin 10 of the present invention is based on a variety of factors, including the type of injury or condition, the age, weight, sex, medical condition of the individual, the severity of the condition, and the route of administration. Thus, the dosage regimen may vary widely, but can be determined routinely by a physician using standard methods. Laminins are extremely potent molecules, and one or a few molecules per cell could produce an effect. Thus, effective doses in the pico-gram per milliliter range are possible if the delivery is optimized. Laminins are sometimes present in an insoluble form in the basement membrane and have the capability of polymerizing at concentrations as low as about 50 µg/ml, depending on the laminin isoform and the conditions. Laminins can also polymerize into a gel at a concentration of about 2–3 mg/ml. Dosage levels of the order of between 1 ng/ml and 10 mg/ml are thus useful for all methods disclosed herein, preferably between about 1 µg/ml and about 3 mg/ml.

The present invention also provides a method for inducing cell attachment to the device (as disclosed above), comprising coating the appliance with isolated laminin 10 or pharmaceutical compositions thereof prior to incubation with cells appropriate for the desired application.

In another aspect of the present invention, isolated laminin 10 is used for the culture of cells, including but not limited to endothelial cells, by contacting the cells with an amount effective of isolated laminin 10 to stimulate cell attachment and subsequent cell stasis, proliferation, differentiation, and/or migration. The isolated laminin 10 can either be provided in the cell culture medium, or as a cell culture medium supplement, or may be coated on the surface of a cell growth substrate. In a preferred embodiment, the method further includes contacting the cells with other compounds, including but not limited to any of the collagens, other laminin types, fibronectin, α-dystroglycan, cadherins, integrins, entactin/nidogen, α-dystroglycan, glycoproteins, proteoglycans, heparan sulfate proteoglycan, glycosaminoglycans, epidermal growth factor or nerve growth factors, vascular endothelial growth factor, fibroblast growth factor, and peptide fragments thereof.

The cells may comprise primary cells or cell culture cell lines. The methods of this aspect of the invention can be used in vivo, or in vitro.

In a preferred embodiment, isolated laminin 10 is used to coat the surface of a substrate, to promote cell adhesion to the substrate. The substrate used herein may be any desired substrate. For laboratory use, the substrate may be as simple as glass or plastic. For use in vivo, the substrate may be any biologically compatible material capable of supporting cell adhesion. Suitable substrate materials include shaped articles made of or coated with such materials as collagen, regenerated collagen, polyglycolic acid, polygalactose, polylactic acid or derivatives thereof; biocompatible metals such as titanium and stainless steel; ceramic materials including prosthetic material such as hydroxylapatite; synthetic polymers including polyesters and nylons; polystyrene; polyacrylates; polytetrafluoroethylene and virtually any other material to which biological molecules can readily adhere. The determination of the ability of a particular material to support adhesion of the isolated laminin 10 of the invention requires only routine experimentation by the skilled artisan.

In a further aspect, the present invention provides cell growth substrates for adhesion and culturing of cells, by providing an amount effective of isolated laminin 10 for the attachment of cells to a cell culture device. The substrates may comprise any of the substrates discussed above.

In another aspect of the present invention, an improved cell culture medium is provided, wherein the improvement comprises addition to the cell culture medium of an effective amount of isolated laminin 10 to the cell culture medium to promote the adherence, proliferation, and/or maintenance of cells. Any cell culture media that can support the growth of cells can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, RPMI Medium, and Macrophage-SFM Medium or combinations thereof.

The improved cell culture medium can be supplied in either a concentrated (ie: 10×) or non-concentrated form, and may be supplied as either a liquid, a powder, or a lyophilizate. The cell culture may be either chemically defined, or may contain a serum supplement. Culture media is commercially available from many sources, such as GIBCO BRL (Gaithersburg, Md.) and Sigma (St. Louis, Mo.).In an alternative embodiment, the laminin 10 is used as a cell culture supplement.

The present invention may be better understood with reference to the accompanying examples that are intended for purposes of illustration only and should not be construed to limit the scope of the invention, as defined by the claims appended hereto.

EXAMPLES

Cloning of the Human Laminin α5 cDNA

The previously published mouse laminin α5 sequence (SEQ ID NO.:3) was used to search EST-databases. Based upon sequences of the identified ESTs, oligonucleotide primers were synthesized and used for PCR amplification of several human α5 specific probes with λgt11 cDNA library (Clontech) as template. These probes were used for screening of λgt11 cDNA libraries (Clontech) from human lung, fetal lung and fetal kidney. This resulted in the isolation of several clones, and further screening was performed with PCR amplified selected regions of these clones. This walk generated clones covering 2134 base pair of coding sequence and 195 base pairs of 3'UTR in the C-terminal part, and 5354 base pairs in the N-terminal part, but lacking a translation initiation start site. The center part, comprising base pairs 5582–9316, was obtained by PCR amplification from a Human Lung MARATHON READY™ cDNA-mix (Clontech). The remaining 296 base pairs of coding sequence and a 67 base pair 5'UTR end was obtained with SMART™ RACE cDNA Amplification Kit (Clontech) using poly-A RNA purified with QuickPrep mRNA Purification Kit (Pharmacia Biotech) from HEK293 cell lysate. The reverse transcription was performed with the MMLV reverse transcriptase SuperscriptII (Life Technologies), and subsequent PCR amplification was performed with Advantage®-GC 2 PCR kit (Clontech). This 363 base pair N-terminal sequence was confirmed by sequencing genomic P1-clone (GenomeSystems) obtained by screening with a PCR generated probe from nucleotides 344–452. This generated a full-length sequence, but most of the sequence was only covered by a single λ-clone or PCR fragment. To further confirm the sequence, we used PCR amplification of SMART™RACE-generated cDNA-mixes from HEK293 cells, human placenta total RNA and from Human Lung Marathon Ready™ cDNA-mix. This generated new clones so that all regions of the cDNA were covered by more than one clone from different sources. In the case of suspected polymorphisms, several clones from different sources were compared. Sequencing was performed on an ABI PRISM™ 310 Genetic Analyzer (Perkin Elmer) using ABI PRISM®BigDye™ Terminator Cycle Sequencing kit (PE Applied Biosystems). Sequence analysis was performed with AutoAssembler™ (PE Applied Biosystems) and sequence comparative analysis with the GCG-software (Group, G.C. et al., *Program for the GCG* Package, Version 10.1, Genetics Computer Group, Madison, Wis. (2000)).

Expression Constructs

For expression of the human laminin α5 chain containing a C-terminal FLAG epitope, the full-length cDNA was constructed as follows. To obtain overlapping cDNA clones, PCR amplification of SMART™ RACE-generated cDNA-mixes from HEK293 cells, human placenta total RNA, and Human Lung MARATHON READψ™ cDNA-mix was performed using ADVANTAGE®-GC 2 PCR kit and Pfu Turbo polymerase (Boeringer-Mannheim). All PCR derived cDNA fragments were cloned into the pCR2.1-TOPO vector (Invitrogen) and sequenced (AmpliTaq FS on an ABI310 sequencer, Perkin-Elmer) to ensure that no mutations had occurred during amplification. All primers for PCR and pCR2.1-TOPO™ plasmids into which the PCR derived cDNA fragments were cloned are shown in Table I. To ensure efficient and correct translation initiation, the Kozak sequence (accgcc, (Kozak, M., *J. Cell Biol.* 115(4), 997–903 (1991)) was edited to match the consensus. Primer KZK1 contained modified Kozak sequence and primer FLAG1 contained the FLAG sequence encoding the FLAG epitope (N-Asp-Tyr-Lys-Asp-Asp-Asp-Asp-Lys-C). (SEQ ID NO:37)

The EcoRI-BamHI insert from KBX3 was cloned into EcoRI-BamHI digested pUC18 vector to make KBX4. The BamHI-XbaI fragment from BBL3 was ligated into BamHI-XbaI sites of KBX4 to make KBY1'. The BNK2' BclI-NotI fragment was cloned into KBY1' BclI-NotI sites to make KNX3. The 1.2 kilobase Bpu10I-NotI fragment of KNX3, which contained unwanted mutation was corrected by replacing the mutated fragment with non-mutated Bpu10I-NotI fragment from BNL12 to make KNX4'. The 1.8 kilobase BbvCI-SalI fragment of NSK5 was replaced by D29D301II BbvCI-SalI fragment to make NSX1. The NotI-SalI fragment from NSX1 and AscI-EcoRI fragment containing FLAG epitope from SFK2 were cloned into SFL12 to make NFX4. The 5.3 kilobase NotI-HindIII fragment from NFX4 was ligated into NotI-HindIII sites of KNX4' to make KFX5 with full-length cDNA. The final expression construct named HLN5Full.pcDNA was made by inserting the KFX5 EcoRI fragment into the EcoRI sites of pcDNA3.1/Zeo(-) mammalian expression vector (Invitrogen) in correct orientation. The construct used for expression of human laminin β1 was constructed from a baculovirus expression vector (Pikkarainen, T. et al., *Eur. J. Biochem.* 209(2), 571–82 (1992)) by ligation of the insert into pIRES-vector (Clontech). The construct used for expression of laminin γ1 (HG1) has been described previously (Kortesmaa, J. et al., *J. Biol. Chem.* 275(20), 14853–9 (2000)).

Antibodies and Control Proteins

Anti-laminin α5 (15H5, (Kikkawa, Y. et al., *J. Bio. Chem.* 273(25), 15854–9 (1998)) monoclonal antibody (mAb) was kindly provided by Dr. K. Sekiguchi. Anti-laminin β1 (DG10,Virtanen, I. et al., Am. J. Pathol. 150(4), 1421–31 (1997)) mAb was kindly provided by Dr. I. Virtanen. Anti-laminin β1 (2E8, Engvall, E. et al., J. Cell Biol. 103(6 Pt 1), 2457–65 (1986)) mAb was kindly provided by Dr. E. Engvall. Anti-FLAG M2 mAb, purified control mouse IgG, collagen type I from calfskin, collagen type IV (Col IV) from mouse-EHS- tumor and heparin (grade I-A) were purchased from Sigma. Anti-laminin γ1 (clone 22) mAb was purchased from Transduction Laboratories. Mouse mAb against integrin α6 (BQ16) was purchased from Alexis Biochemicals. Mouse function blocking mAbs against integrin α1 (FB12), α2 (P1E6), α3 (P1B5), αv (NKI-M9), αωβ3 (ΛM609), mouse mAb against integrin β4 (ASC-3) and control rat IgG2a were obtained from Chemicon. Rat function blocking mAbs against integrin α6 (GoH3), mouse function blocking mAbs against integrin β1 (4B4) and mouse mAbs against integrin α4 (HP2/1), αv (AMF-7), and β3 (SZ-21) were obtained from Coulter. Secondary Ab conjugates anti-mouse IgG-horseradish peroxidase (HRP) and FITC-conjugated F(ab)2 fragments of rabbit anti-mouse immunoglobulin were purchased from Dako. RGDS-peptide, cyclical RGDS-peptide, control RAGS-peptide, mouse mAb against integrin α5 (P1D6) and human vitronectin from plasma were purchased from Life Technologies. Human fibronectin (FN) from plasma was obtained from Roche. EHS-derived laminin-1/nidogen complex (laminin-1/Nd) was kindly provided by Dr. J. Engel.

Production and Purification of Recombinant Laminin-10 r-laminin-10 was produced in human embryonic kidney cells (HEK293, ATCC CRL-1573) cultured in DMEM, pyruvate, 10% FCS in humidified 5% $CO_2$ atmosphere at 37° C. Wild-type cells were transfected using the standard calcium-phosphate method with the HG1 construct and stable colonies were selected using 100 mg/ml hygromycin (Cayla). All further cell culture and clonal expansion was carried out in continuous presence of relevant selection antibiotics. A highly expressing clone was then transfected with the human laminin β1 construct and stable clones were selected using 500 mg/ml G418 (Life Technologies). A clone highly expressing both laminin γ1 and laminin β1 was finally transfected with HLN5Full.pcDNA and stable colonies were selected using 200 mg/ml zeocin (Cayla). The clones showing the highest secretion were expanded further.

For production of r-laminin-10, confluent cells were cultured in DMEM supplemented with 1 mM pyruvate and insulin-transferrin-selen supplement (Sigma) for up to five days. r-laminin-10 was affinity purified using anti-FLAG M2 matrix (Sigma). The collected medium was incubated in batch mode with the matrix overnight at 4° C. with agitation. Bound r-laminin-10 was competitively eluted with 50 mg/ml FLAG peptide (Sigma) in TBS/E (50 mM Tris-Cl, pH 7.5, 150 mM NaCl, 1 mM EDTA) at room temperature. The elute was concentrated and the buffer was replaced by PBS using 30 kD cut-off ultrafiltration (Millipore). Finally the concentrated solution was passed through 0.2 mm filter to remove self-aggregated polymers. Recombinant human laminin-8 (r-laminin -8) was produced in HEK293 cells and isolated using anti-FLAG matrix and ion-exchange chromatography.

Characterization of Recombinant Laminin-10

Secreted laminin in medium and after purification was characterized using 5% SDS-PAGE and 4–15% gradient SDS-PAGE. Proteins were visualized using silver staining or transferred onto PVDF. The membranes were probed with mAbs described above. After washing, the membranes were incubated with HRP-conjugated goat anti-mouse antibody. The immunoreactivity was detected by a chemiluminescent kit (Life Science Products) according to the manufacturer's instructions.

Electron microscopy was performed by the rotary shadowing technique as described previously (Engel, J., Methods Enzymol. 245, 469–88 (1994)). Briefly, protein (25–50 mg/ml) in 0.2 M ammonium bicarbonate, pH 7.4, or 0.1 M acetic acid was mixed with an equal volume of glycerol and sprayed onto freshly cleaved mica discs. These were dried in high vacuum, shadowed with platinum/carbon at an angle of 9° and replicated. Negative staining was performed at neutral pH in order to avoid dissociation of aggregates by the acid pH in the routine procedure. Ten ml of a solution in PBS was put on a glow discharged collodium and carbon grid and 5 ml of a 2% sodium phosphotungstate solution of pH 7 was added. After removal of the first stain, incubation was repeated for 2 min.

Cell Culture and HSVEC Isolation

Human fibrosarcoma HT-1080 (CCL-121) cells were from ATCC. Immortomouse brain capillary endothelial (Kanda, S. et al Exp. Cell Res. 248(1), 203–13 (1999)) cells were kindly provided by Dr. L. Claesson-Welsh. All cells were cultured in humidified 5% $CO_2$ atmosphere. HT-1080 cells were cultured in DMEM, 10% FCS, pyruvate at 37° C. IBE cells were cultured in F-12, 10% FCS, 2 units/ml γ-interferon on gelatin-coated plastic at 33° C. Prior to assay, the IBE cells were cultured in serum-free F-12 at 37° C. without γ-interferon for 24 hours.

As approved by the ethical committee at the Karolinska Hospital, Stockholm, Sweden, residual segments of the great saphenous vein were collected from patients undergoing coronary bypass surgery. HSVECs were isolated as previously described (Haegerstrand, A. et al., J. Vasc. Surg. 16(2), 280–5 (1992)). Briefly, veins were rinsed with MEM (Life Technologies) and filled with 0.1% collagenase and 0.16% dispase (Boehringer Mannheim) in MEM for 20 min at 37° C. in an 8% $CO_2$-humidified atmosphere. Cells were cultured in MEM containing 40% heat-inactivated pooled human serum (HS), 1 nmol/L choleratoxin (CT; Sigma), 33 mmol/L isobutylmethylxantine (IBMX; Sigma), and antibiotics. HSVECs were seeded on gelatin-coated plates and passaged (1:3). HSVECs were characterized with monoclonal anti-human von Willebrand factor-related antigen (Dako) and HSVECs between passages 4 and 7 were used in the experiments.

Cell Adhesion Assays

Adhesion assay was performed as described previously (Kortesmaa, J. et al., J. Biol. Chem. 275(20), 14853–9 (2000)). Briefly, 96-well plates (Maxi-Sorp, Nunc) were coated with proteins overnight at 4° C. The remaining protein binding capacity was saturated by addition of 2% heat-inactivated BSA in PBS.

For the assay, cells were suspended in buffered serum-free medium at $3 \times 10^4$ cells/well. DMEM, 25 mM Hepes, pyruvate was used for HT-1080 cells, F-12, 25 mM Hepes, 0.25% BSA for others. Antibodies or other test compounds were added to the cell suspension and the cells were allowed to recover at 37° C. for 30 min. Integrin mAbs were used at 10 mg/ml, RGD-peptides at 0.25 mg/ml, heparin at 5 mg/ml, and EDTA at 5 mM. The cells were then allowed to adhere for 60 min at 37° C. Bound cells were quantitated by crystal violet staining. None of the cell lines bound appreciably to BSA. When the quantitative results were calculated, binding to BSA was given a value of zero, while the relevant control was given the value 100. The mean and standard deviation (S.D.) were calculated from results obtained from parallel wells.

Immunofluorescence Flow Cytometry

Briefly, suspended HSVECs were incubated in PBS containing anti-integrin mAbs against α1–6, αv, β1, β3, and β4 for 30 min at 4° C. Following washing, cells were incubated with FITC-conjugated F(ab)2 fragments of rabbit anti-mouse immunoglobulin for 30 min at 4° C. Cells were then analyzed in a FACS can flow cytometer (Becton Dickinson). Mouse IgG was used as a negative control.

Cell Migration Assays

Cell migration assay was performed as described previously (Jansson, K. et al., Eur. J. Vasc. Endovasc. Surg. 16(4), 334–41 (1998)). Flat-bottom 24-well culture plates (Corning) were coated with proteins overnight at 4° C. The remaining protein binding capacity was saturated by addition of 2% heat-inactivated BSA in PBS. Thereafter a 4×10 mm stainless steel-weight was put on the center of well, before seeding HSVECs at $2 \times 10^5$ cells/well. After adhesion for 2 days in MEM with 30% HS, the steel-weight was removed. A gap devoid of HSVECs was thus created, with two broad (10 mm) EC-edges facing each other at a distance of 4 mm. During endothelialization, HSVECs were incubated in MEM with 40% HS, CT and IBMX for 2 days after removing the steel-weight. The cells were visualized by 0.1% crystal violet staining.

Results

Sequence of Human Laminin Alpha 5 Chain

Figure 1A:
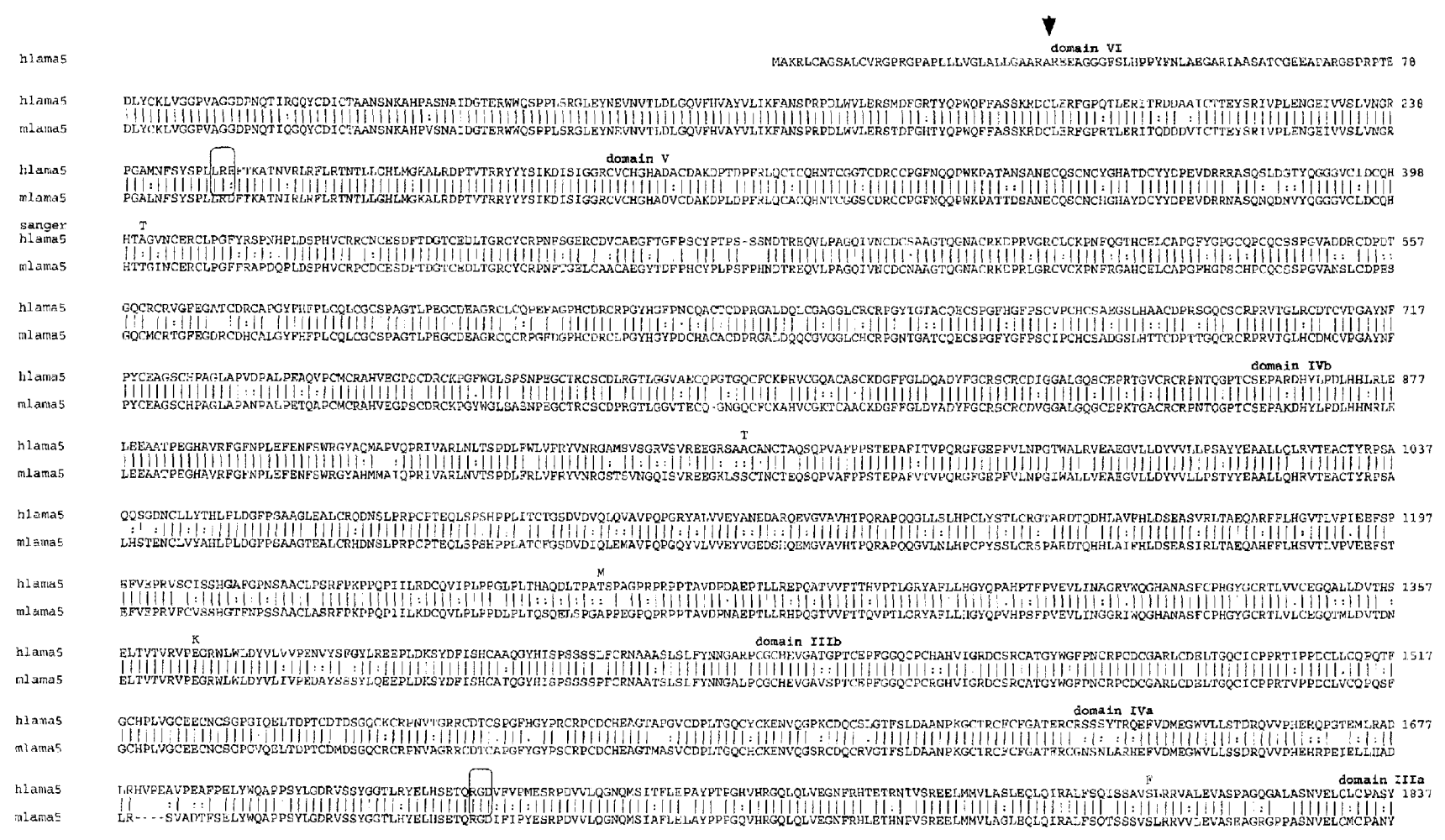
Figure 1B:
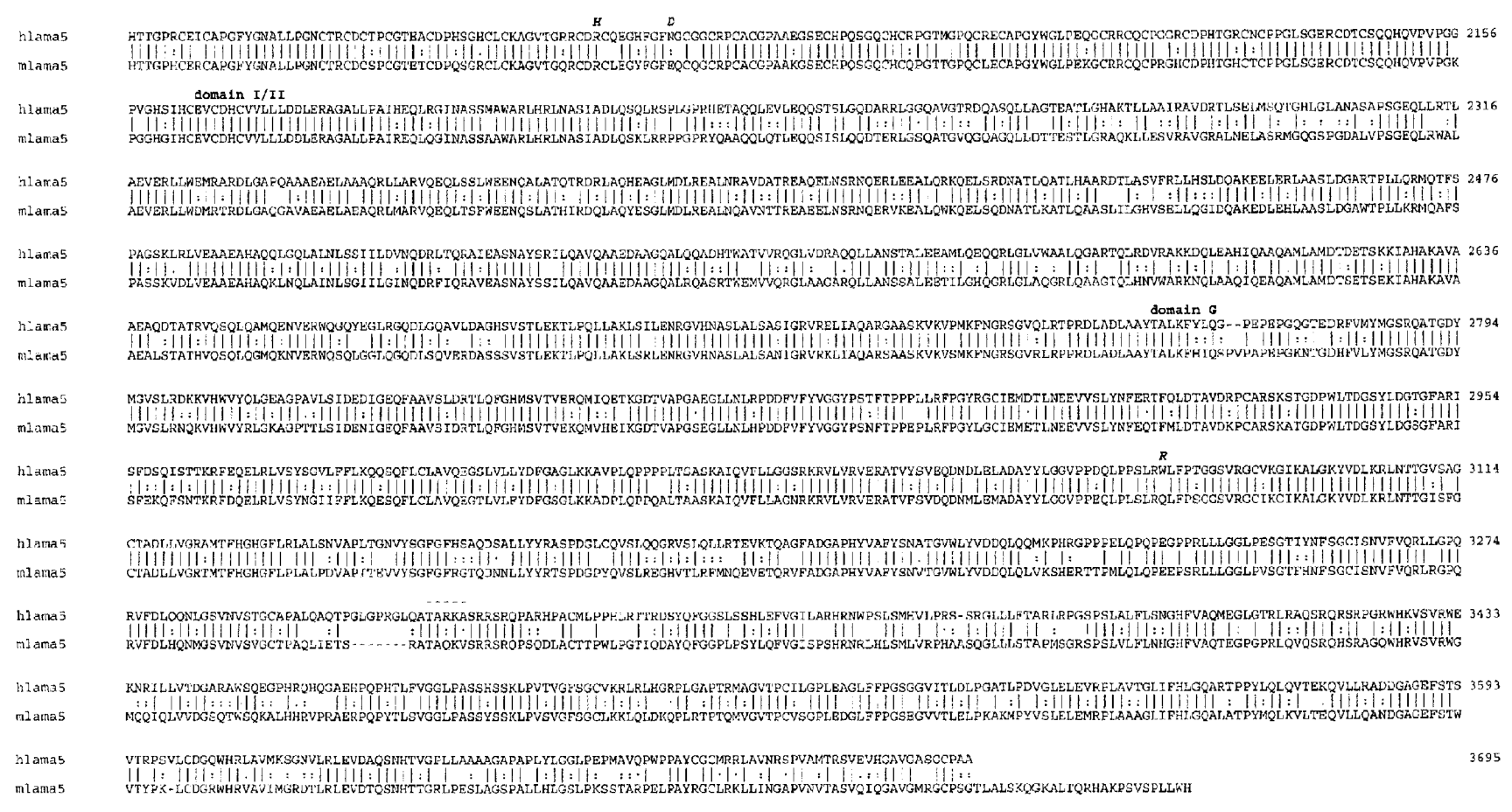

The full-length laminin α5 cDNA coding sequence (FIG. 1) (SEQ ID NO:1) consisted of 11,088 base pair with an open reading frame encoding 3696 amino acids (SEQ ID NO.:2). Compared to the previously reported mouse laminin α5 sequence (GENBANK™ accession number U37501; Miner, J. H. et al., J. Biol. Chem. 270(48), 28523–6 (1995)) (SEQ ID NO.:4), we obtained an additional 79 amino acids in the N-terminal end. The mouse sequence has an additional stretch of 20 amino acids in the C-terminus, compared to the human sequence. Alignment of mouse and human laminin LG5-modules with other published sequences (not shown) revealed similar C-terminal length in all cases except for the mouse α5. Comparison with the mouse laminin α5 showed an overall amino-acid identity of 79%. The previously reported adhesive tripeptide sequence LRE (Hunter, D. D. et al., Cell 59(5), 905–13 (1989)) was not conserved in the human chain (amino acid residues; 3176–3178 LQQ), while the two RGD-sequences were conserved (FIG. 1) . The human sequence contained two extra cysteines (amino acid residues; 3173 and 3663) and a hinge region between LG 3 and LG 4 that is seven residues longer than the mouse sequence. In addition, there was a stretch of four extra amino acids in domain IV (amino acid residues; 1680–1683) in the human sequence. We generated cDNAs from four different sources (placenta, HEK293 cells, and lung-marathon-ready-cDNA from two sources) and thereby detected four possible polymorphisms in domain IIIa; 5698:A-G (1900: Met-Val), 5722: G-A (1908: Ala-Thr), 6158: G-A (2053: Arg-Thr), 6184: A-G (2062: Asn-Asp) and one in the G domain; 9235:T-C (3079: Trp-Arg). The amino acids chosen for the r-laminin-10 construct at these possible polymorphic sites are those shown in FIG. 1.

Production and Characterization of Recombinant Laminin-10

Conditioned medium from wild-type HEK293 cells did not react in western blotting with the anti-laminin α5, anti-laminin β1, anti-laminin γ1, or anti-FLAG Abs, indicating that these cells express endogenous laminins at very low amounts if at all (data not shown). After triple transfection, the best cell clone produced 2–3 mg of r-laminin-10 per liter of medium, which is quite high considering the size and complexity of the protein.

Figure 2B:
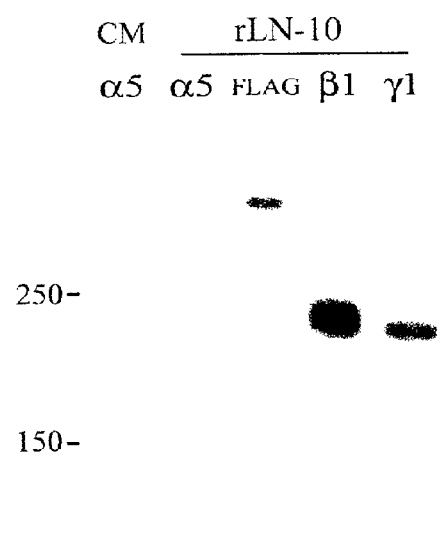
Figure 2C:
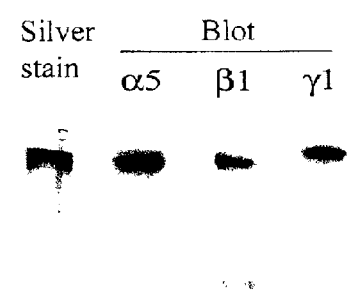

Immunoaffinity purification with anti-FLAG M2 matrix followed by competitive elution with FLAG-peptide resulted in highly purified protein as seen in silver stained SDS-PAGE gels (FIG. 2a). Under reducing conditions, two bands were seen, a 400 kD band corresponding to the laminin α5 chain and a 200 kD band corresponding to the laminin β1 and γ1 chains, which have similar molecular weights (FIG. 2a). In western blotting of the conditioned medium, two bands of approximately 350 and 400 kD could be seen with the laminin α5 mAb (FIG. 2b). The anti-FLAG antibody reacted with a 400 kD and a 40 kD fragment (FIG. 2b and not shown). Taken together, these data indicate that the 400 kD fragment is the intact laminin α5, the 350 kD is a N-terminal fragment and the 40 kD is a C-terminal fragment harboring the FLAG epitope. Under non-reducing conditions, most of the protein appeared at the top of the gel as a very high molecular weight band, which was immunoreactive with α5, FLAG, β1 and γ1 mAbs, showing that the r-laminin-10 was produced as disulfide-crosslinked heterotrimer (FIG. 2c). A minor band of approximately 400 kD was also seen in silver staining and in western blotting with α5, FLAG, β1 and γ1 mAbs. The non-covalently associated α5 chain had an apparent molecular weight similar to the β1/γ1 dimer, which explains the immunoreactivity of the minor band with α5 and FLAG mAbs.

Rotary shadowing EM revealed the r-laminin-10 protein as having three short arms and one long arm in accordance with the expected structure. Some monomers were shown to have an elongated globular domain in one of the short arms, which could be domain IVb. Oligomers dominated the preparation.

Cell Binding to r-laminin-10

Vascular endothelial cells undergo drastic morphological and functional changes during angiogenesis, and it is well established that the behavior of the cell is critically influenced by its interaction with components of the extracellular matrix. Because of this fact, endothelial cell attachment and migration on grafts used in vascular surgery might be improved if the surfaces of these non-biological materials would be pre-coated with ECM proteins, e. g. laminins. The ingrowth of endothelial cells on the surfaces of grafts, a process known as endothelialization, has been shown to be of critical importance for preventing thrombus formation on the graft material, and for reducing neointimal hyperplasia. Many adhesive substrate coatings to enhance endothelial cell attachment have been tested (Dixit, P., et al. (2001) *J. Biomed. Mater. Res.* 56(4), 545–55), but the long term patency of small-diameter vascular grafts is still disappointing, primarily due to stenosis and thrombus formation (Pevec, W. C., et al. (1992) *J. Vasc. Surg.* 16(1), 60–5; Watelet, J., et al. (1997) *Ann. Vasc. Surg.* 11(5), 510–9).

Figure 3A:
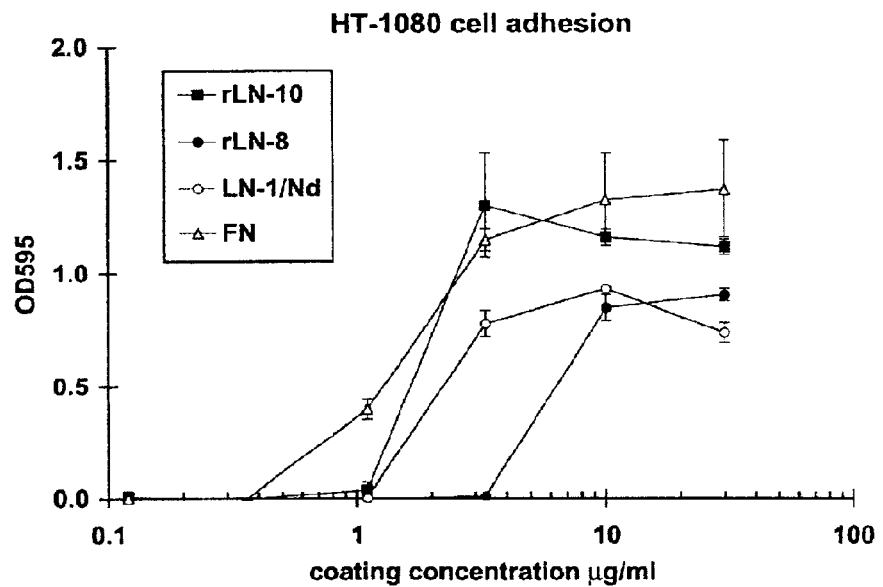
FIGS. 3A, 3B, and 3C. Cell adhesion activity of recombinant laminin-10 (rLN-10) and other proteins. (A) HT-1080 cell adhesion to rLN-10, recombinant laminin-8 (rLN-8), laminin-1/nidogen complex (LN-1/Nd), and fibronectin (FN) coated at increasing concentrations.; (B) IBE cell adhesion to rLN-10, rLN-8, LN-1/Nd, and FN coated at increasing concentrations.; (C) HSVEC adhesion to rLN-10 and rLN-8 coated at 3 and 10 mg/ml, and LN-1/Nd, commercial laminin-10/11 (LN-10/11), collagen type IV (Col IV) and FN coated at 10 mg/ml. N.T. means not-tested. Bound cells were quantitated spectrophometrically using adhesion to BSA as blank. Error bars indicate S.D.
Figure 3B:
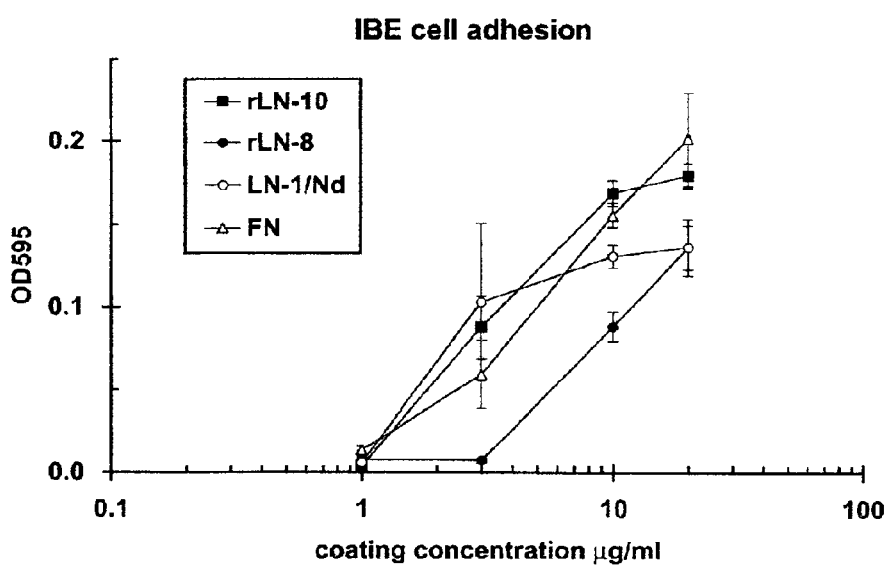

To investigate the biological activity of r-laminin-10, we assayed it for cell adhesion properties. Cell adhesion onto the laminin coated substratum is mediated predominantly by the integrin family of adhesion receptors. Several integrins have been implicated as receptors for laminin-10 or laminin-10/11, including α2β1, α3β1, α6β1, and α6β4 (Kikkawa, Y. et al., J. Biol. Chem. 273(25), 15854–9 (1998); Kikkawa, Y. et al., J. Cell Sci. 113(Pt 5), 869–76 (2000); Ferletta, M. et al., J. Cell Sci. 112 (Pt 1), 1–10 (1999); Gu, Y. et al., Blood 93(8), 2533–42 (1999); Pouliot, N. et al., Exp. Cell Res. 261(2), 360–71 (2000); and Tani, T. et al., Exp. Cell Res. 248(1), 115–21 (1999)). In addition, Nielsen and co-workers recently demonstrated that domain IV of the laminin α5 chain is a binding site for integrin α2β1, α3β1, α4β1 and α6β1 (Nielsen, P.K. et al., J. Biol. Chem. 276(14), 10906–12 (2001)). As a general model, we used the HT-1080 fibrosarcoma cell line, which expresses a wide variety of integrin receptors such as α2, α3, α5, α6 and β1 (Wayner, E. A. et al., J. Cell Biol. 121(5), 1141–52 (1993)). Different blocking anti-integrin antibodies were used to identify the integrin receptors mediating cell binding to r-laminin-10. Two endothelial cell types were also studied: HSVECs were used as model for macrovascular endothelial cells and IBE cells for microvascular endothelial cells. HT-1080 cells adhered to fibronectin equally strongly as to r-laminin-10 (FIG. 3a) while laminin-1 and r-laminin-8 were less effective in promoting cell adhesion (FIG. 3a). Similar results were obtained with IBE cells and HSVECs (FIG. 3b and c). Based on these results, further experiments with blocking integrin mAbs were performed using a coating concentration of 10 mg/ml.

Figure 4:
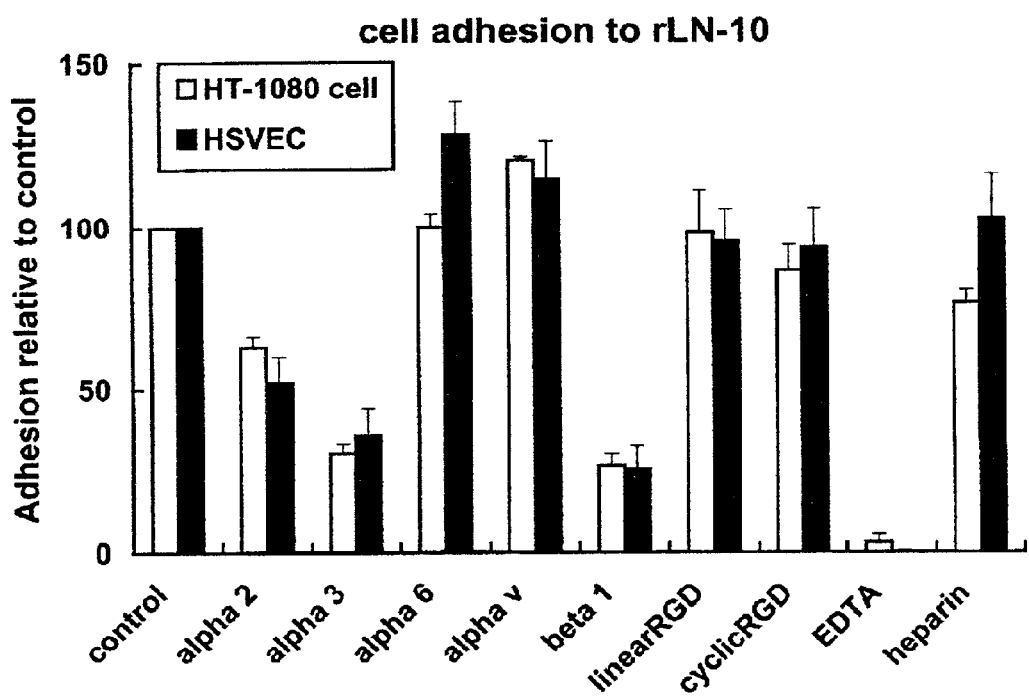
FIG. 4. HT-1080 cell and HSVEC adhesion assays on laminins coated at 10 g/ml. Text under columns indicate the integrin subunit mAbs used or other added substances. Adhesion shown is relative to control, designated 100. Adhesion to BSA was designated zero. Error bars indicate S.D.

Monoclonal Abs against either α3 or β1 inhibited HT-1080 cell binding to r-laminin-10 by approximately 80%, indicating that integrin α3β1 was a major mediator of adhesion to r-laminin-10 (FIG. 4). In addition, mAbs against integrin α2 had partial inhibitory effect on adhesion to r-laminin-10 (FIG. 4). Since some adhesion remained after blocking of the integrin β1, other receptor classes besides β1 could be involved in the cell adhesion. Monoclonal Abs against integrins α6 and αv had no effects on the adhesion of HT-1080 cells to r-laminin-10 either alone (FIG. 4) or in various combinations (α3+α6, β1+α6, β1+αvβ3, β1+α6+αvβ3, β1+α6+αv; not shown). This indicates that α6 integrins (α6β1, α6β4) or αv integrins (αvβ1, αvβ3 or αvβ5) were not mediating the cell adhesion.

HSVEC binding to the r-laminin-10 was also studied. To determine which integrins were present on the cell surface, we performed fluorescent cell sorting assay using mAbs against integrin subunits α1, α2, α3, α4, α5, α6, αv, β1, β3 and β4. From these results it can be concluded that HSVEC express large amounts of α2β1, α5β1 and αvβ3, moderate amounts of α3β1, and small amounts of α1β1, α6β1 and α6β4, but integrin α4β1 was not detected. The HSVEC binding was most efficiently inhibited by mAbs against integrin α3 and β1, but also against α2 (FIG. 3) had partial effect, in a fashion similar to that observed for HT-1080 cells. Integrin α6 was only weakly expressed on HSVECs and, consequently, mAbs against this integrin did not inhibit binding to r-laminin-10.

Figure 3C:
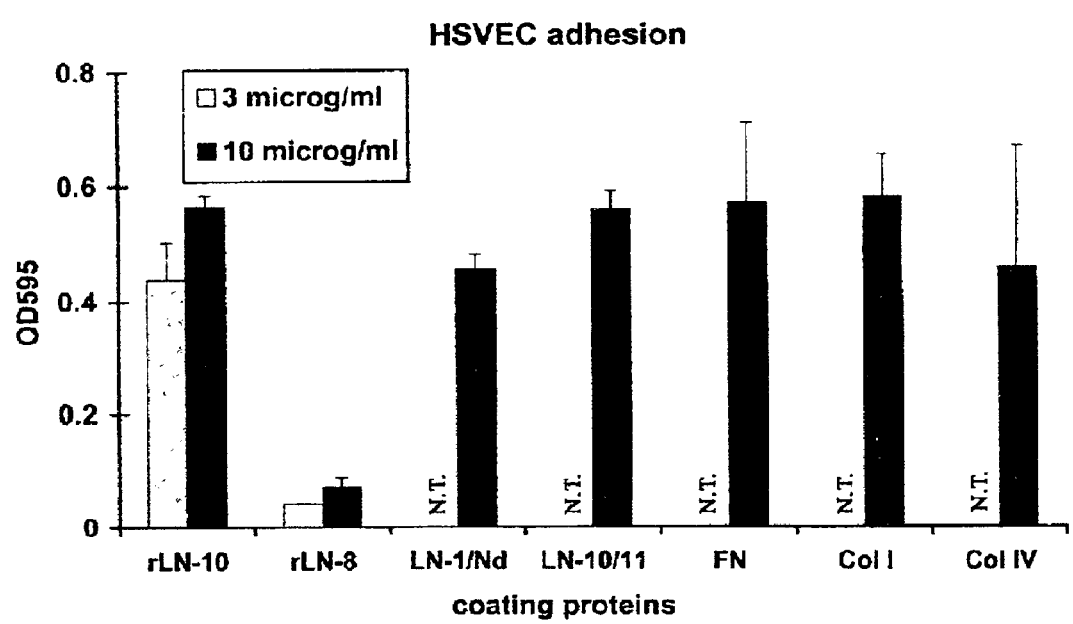

Cell adhesion to r-laminin-10 was found to be dependent of divalent cations since it could be abolished by 5 mM EDTA in both HT-1080 cells and HSVECs (FIG. 3). Heparin, when used at 5 mg/ml, had no effect on the adhesion of either cell type (FIG. 3). Since the α5-chain has conserved RGD-sequences, we tested the effect of RGD peptides, which are reported to block the function of various RGD-dependent integrins (such as α5β1 and the αv family) (Pierschbacher, M.D. et al., Nature 309(5963), 30–3 (1984)). Neither linear nor cyclic RGD-peptides had any effect at 0.25 mg/ml concentration on adhesion of either HT-1080 cells or HSVECs to r-laminin-10 (FIG. 4). It was, furthermore, observed that the cell binding activity of r-laminin-10 was sensitive to air-drying, as we have previously reported for r-laminin-8 (Kortesmaa, J. et al., J. Biol. Chem. 275(20), 14853–9 (2000)). When the coated protein was allowed to air dry for 20 min at room temperature before adding the cells, the cell binding activity of r-laminin-10 was completely lost (data not shown).

Cell Migration

Laminins have been shown to stimulate cell migration during development, and in many pathological processes. We examined the ability to promote HSVEC migration on dishes coated with 10 mg/ml of r-laminin-10 or other adhesive proteins. The migration assay was repeated three times using HSVEC obtained from three different donors. Among the seven different adhesive proteins examined, r-laminin-10 was the most potent in promoting HSVEC migration in vitro. In addition to r-laminin-10, type IV collagen was also quite potent in promoting HSVEC migration. Laminin N-1 and gelatin were of roughly equal potency but significantly lower than r-laminin-10, and r-laminin-8 was the least potent among the proteins examined.

Discussion

Several cell types have been tested for identification of the integrin receptors for laminin-10, but no report exists concerning endothelial cells. In this study, we demonstrated that HSVECs use integrins α2β1 and α3β1 to mediate cell adhesion to r laminin-10, and similar results were obtained for HT-1080 cells. An antibody against the integrin α6 subunit, either alone or combination with other mAbs (α3+α6, β1+α6, β1+α6+αvβ3, β1+α6+αv), did not inhibit cell adhesion (FIG. 4 and not shown), indicating that integrin α6 is not an important receptor in these cells for r laminin-10, although the α6 integrins have previously been implicated as receptors for laminins in general and laminin-10 in particular (Kikkawa, Y. et al., J. Cell Sci. 113(Pt 5), 869–76 (2000)).

HSVECs, as well as HT-1080 and IBE cells, attached to r-10 more strongly than to laminin-1 and r laminin-8. Poor adhesion of HSVECs to r laminin-8 is not surprising considering the fluorescent cell sorting data showing that the cells have little α6 integrins, which have previously been shown to be receptors for r-laminin-8 (Kortesmaa, J. et al., J. Biol. Chem. 275(20), 14853–9 (2000)). We can, therefore, conclude that the integrin-binding is distinctly different between the two main forms of endothelial laminins, as well as between different endothelial cell types, as we have previously shown that IBE and bovine capillary endothelial cell adhesion onto r-laminin-8 is mediated predominantly by α6 integrins (Kortesmaa, J. et al., J. Biol. Chem. 275(20), 14853–9 (2000)).

Figure 5:
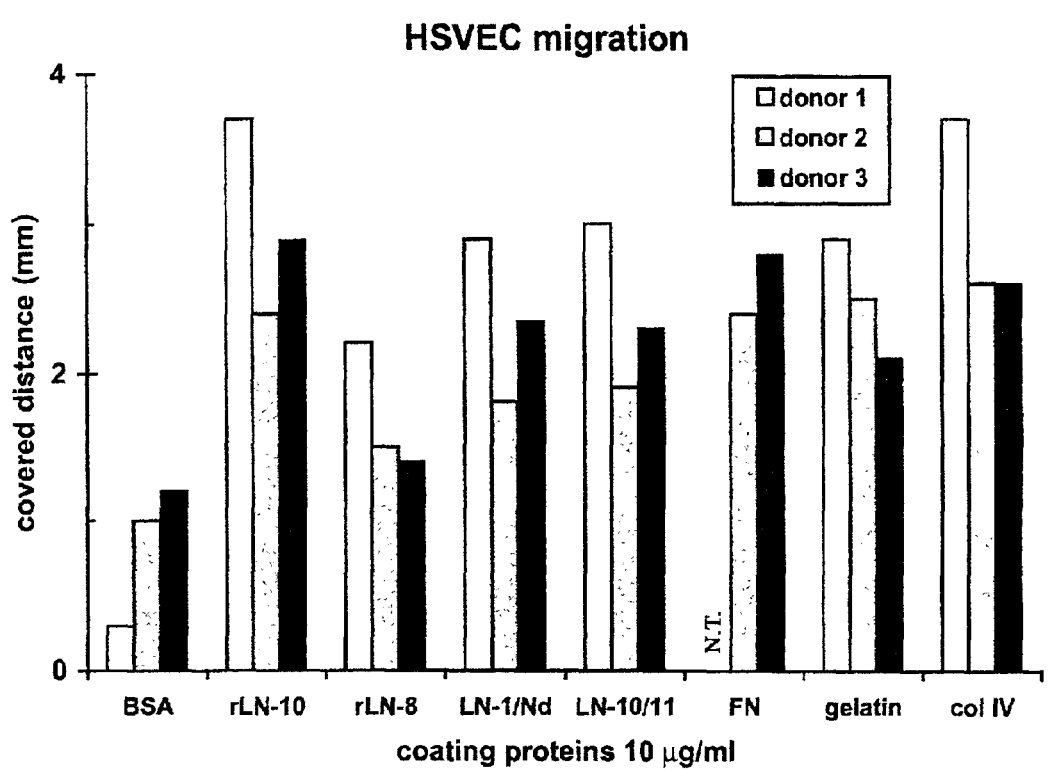
FIG. 5. HSVEC migration (endothelialization) on plastic coated with laminin-10 and other proteins. Migration of HSVECs into the cell free area coated with BSA, laminin-1/nidogen complex (LN-1/Nd), recombinant laminin-8 (rLN-8), recombinant laminin-10 (rLN-10), fibronectin (FN), commercial laminin-10/11 (LN-10/11), gelatin, and collagen type IV (Col IV) was measured. The distance covered by cells from three different donors. N.T. means not-tested.

Cell migration-promoting activities of different laminins appear to be dependent on cell specific factors. Human glioblastoma cell line T98G showed best migration on laminin-8 (Fujiwara, H. et al., J. Biol. Chem. 276(20), 17550–8 (2001)) compared to laminin-2/4, laminin-5, laminin-10/11 and fibronectin, while LIM1215 carcinoma cells migrate more efficiently on laminin-10 than on collagen type I, type IV or laminin-1 (Pouliot, N. et al., Exp. Cell Res. 266(1), 1–10 (2001)). Here, we demonstrated that r-laminin 10 was the most potent matrix of the components tested in promoting endothelial cell (HSVEC) migration in vitro (FIG. 5). Interestingly, HSVEC adhesion to commercial laminin-10/11 and to r-laminin-10 was equally strong, but the potency of laminin-10/11 in promoting HSVEC migration was much lower than that of r-laminin-10.

We claim:

1. An isolated laminin α5 polypeptide, consisting of the amino acid sequence of SEQ ID NO:2.

2. Isolated recombinant laminin 10 produced by a method comprising
   a. providing recombinant laminin 10-expressing host cells, wherein the recombinant laminin 10 comprises:
   a first chain comprising a polypeptide with at least 80% identity to a polypeptide sequence of SEQ ID NO:2;
   a second chain comprising a polypeptide at least 70% identity to one or more polypeptide sequences selected from the group consisting of SEQ ID NO:6, SEQ ID NO:8, SEQ ID NO:10, and SEQ ID NO:12; and
   a third chain comprising a polypeptide at least 70% identity to one or more polypeptide sequences selected from the group consisting of SEQ ID NO:14, SEQ ID NO:16, SEQ ID NO:18, and SEQ ID NO:20;
   wherein the first, second, and third chains are assembled into recombinant laminin 10;
   b. growing the cells in cell culture medium under conditions to stimulate expression of the recombinant laminin 10 chains;
   c. passing the cell culture medium through an affinity chromatography column, wherein the column contains a compound that binds to the recombinant laminin 10;
   d. washing the affinity column to remove unbound materials; and
   e. eluting the bound recombinant laminin 10 from the column.

3. Isolated recombinant laminin 10 comprising:
   a first chain comprising a polypeptide with at least 80% identity to a polypeptide sequence of SEQ ID NO:2;
   a second chain comprising a polypeptide at least 70% identity to one or more polypeptide sequences selected from the group consisting of SEQ ID NO:6, SEQ ID NO:8, SEQ ID NO:10, and SEQ ID NO:12; and
   a third chain comprising a polypeptide at least 70% identity to one or more polypeptide sequences selected from the group consisting of SEQ ID NO:14, SEQ ID NO:16, SEQ ID NO:18, and SEQ ID NO:20;
   wherein the first, second, and third chains are assembled into recombinant laminin 10.

4. The isolated laminin 10 of claim 3 wherein the first chain comprises a polypeptide with at least 90% identity to the polypeptide sequence of SEQ ID NO:2.

5. The isolated laminin 10 of claim 4 wherein the second chain comprises a polypeptide with at least 90% identity to one or more polypeptide sequences selected from the group consisting of SEQ ID NO:6 and SEQ ID NO:8.

6. The isolated laminin 10 of claim 5 wherein the third chain comprises a polypeptide with at least 90% identity to one or more polypeptide sequences selected from the group consisting of SEQ ID NO:14 and SEQ ID NO:16.

7. The isolated laminin 10 of claim 3 wherein the first chain comprises the polypeptide sequence of SEQ ID NO:2.

8. The isolated laminin 10 of claim 7 wherein the second chain comprises a polypeptide sequence selected from the group consisting of SEQ ID NO:6 and SEQ ID NO:8.

9. The isolated laminin 10 of claim 8 wherein the third chain comprises a polypeptide sequence selected from the group consisting of SEQ ID NO:14 and SEQ ID NO:16.

10. The isolated laminin 10 of claim 3 wherein the second chain comprises a polypeptide with at least 70% identity to one or more polypeptide sequences selected from the group consisting of SEQ ID NO:6 and SEQ ID NO:8.

11. The isolated laminin 10 of claim 10 wherein the third chain comprises a polypeptide with at least 70% identity to one or more polypeptide sequences selected from the group consisting of SEQ ID NO:14 and SEQ ID NO:16.

12. The isolated laminin 10 of claim 3 wherein the second chain comprises a polypeptide with at least 80% identity to one or more polypeptide sequences selected from the group consisting of SEQ ID NO:6 and SEQ ID NO:8.

13. The isolated laminin 10 of claim 12 wherein the third chain comprises a polypeptide at least 80% identical to one or more polypeptide sequences selected from the group consisting of SEQ ID NO:14 and SEQ ID NO:16.

14. A pharmaceutical composition comprising:
   a) the isolated laminin 10 of claim 3; and
   b) a pharmaceutically acceptable carrier.

15. A pharmaceutical composition comprising:
   a) the isolated laminin 10 of any one of claims 7–9; and
   b) a pharmaceutically acceptable carrier.

* * * * *

SEQUENCE LISTING

```
<160> NUMBER OF SEQ ID NOS: 36

<210> SEQ ID NO 1
<211> LENGTH: 11350
<212> TYPE: DNA
<213> ORGANISM: Homo sapiens
<220> FEATURE:
<221> NAME/KEY: CDS
<222> LOCATION: (68)..(11152)
<221> NAME/KEY: sig_peptide
<222> LOCATION: (68)..(173)

<400> SEQUENCE: 1
agacccgccg ggctcccgcc gcgcgcgctg tccctggagc tcggggacgc ggcccggagc      60 cgggaag atg gcg aag cgg ctc tgc gcg ggg agc gca ctg tgt gtt cgc     109
        Met Ala Lys Arg Leu Cys Ala Gly Ser Ala Leu Cys Val Arg
        1               5                  10 ggc ccc cgg ggc ccc gcg ccg ctg ctg ctg gtc ggg ctg gcg ctg ctg     157
Gly Pro Arg Gly Pro Ala Pro Leu Leu Leu Val Gly Leu Ala Leu Leu
 15                  20                  25                  30 ggc gcg gcg cgg gcg cgg gag gag gcg ggc ggc ggc ttc agc ctg cac     205
Gly Ala Ala Arg Ala Arg Glu Glu Ala Gly Gly Gly Phe Ser Leu His
                 35                  40                  45 ccg ccc tac ttc aac ctg gcc gag ggc gcc cgc atc gcc gcc tcc gcg     253
Pro Pro Tyr Phe Asn Leu Ala Glu Gly Ala Arg Ile Ala Ala Ser Ala
             50                  55                  60 acc tgc gga gag gag gcc ccg gcg cgc ggc tcc ccg cgc ccc acc gag     301
Thr Cys Gly Glu Glu Ala Pro Ala Arg Gly Ser Pro Arg Pro Thr Glu
 65                  70                  75 gac ctt tac tgc aag ctg gta ggg ggc ccc gtg gcc ggc ggc gac ccc     349
Asp Leu Tyr Cys Lys Leu Val Gly Gly Pro Val Ala Gly Gly Asp Pro
         80                  85                  90 aac cag acc atc cgg ggc cag tac tgc gac atc tgc acg gct gcc aac      397
```

```
        Asn Gln Thr Ile Arg Gly Gln Tyr Cys Asp Ile Cys Thr Ala Ala Asn
         95                 100                 105                 110 agc aac aag gca cac ccc gcg agc aat gcc atc gat ggc acg gag cgc         445
Ser Asn Lys Ala His Pro Ala Ser Asn Ala Ile Asp Gly Thr Glu Arg
                115                 120                 125 tgg tgg cag agt cca ccg ctg tcc cgc ggc ctg gag tac aac gag gtc         493
Trp Trp Gln Ser Pro Pro Leu Ser Arg Gly Leu Glu Tyr Asn Glu Val
        130                 135                 140 aac gtc acc ctg gac ctg ggc cag gtc ttc cac gtg gcc tac gtc ctc         541
Asn Val Thr Leu Asp Leu Gly Gln Val Phe His Val Ala Tyr Val Leu
            145                 150                 155 atc aag ttt gcc aac tca ccc cgg ccg gac ctc tgg gtg ctg gag cgg         589
Ile Lys Phe Ala Asn Ser Pro Arg Pro Asp Leu Trp Val Leu Glu Arg
160                 165                 170 tcc atg gac ttc ggc cgc acc tac cag ccc tgg cag ttc ttt gcc tcc         637
Ser Met Asp Phe Gly Arg Thr Tyr Gln Pro Trp Gln Phe Phe Ala Ser
175                 180                 185                 190 tct aag agg gac tgt ctg gag cgg ttc ggg cca cag acg ctg gag cgc         685
Ser Lys Arg Asp Cys Leu Glu Arg Phe Gly Pro Gln Thr Leu Glu Arg
                195                 200                 205 atc aca cgg gac gac gca gcc atc tgc acc acc gag tac tca cgc atc         733
Ile Thr Arg Asp Asp Ala Ala Ile Cys Thr Thr Glu Tyr Ser Arg Ile
            210                 215                 220 gtg ccc ctg gag aac gga gag atc gtg gtg tcc ctg gtg aac gga cgt         781
Val Pro Leu Glu Asn Gly Glu Ile Val Val Ser Leu Val Asn Gly Arg
        225                 230                 235 ccg ggc gcc atg aat ttc tcc tac tcg ccg ctg cta cgt gag ttc acc         829
Pro Gly Ala Met Asn Phe Ser Tyr Ser Pro Leu Leu Arg Glu Phe Thr
240                 245                 250 aag gcc acc aac gtc cgc ctg cgc ttc ctg cgt acc aac acg ctg ctg         877
Lys Ala Thr Asn Val Arg Leu Arg Phe Leu Arg Thr Asn Thr Leu Leu
255                 260                 265                 270 ggc cat ctc atg ggg aag gcg ctg cgg gac ccc acg gtc acc cgc cgg         925
Gly His Leu Met Gly Lys Ala Leu Arg Asp Pro Thr Val Thr Arg Arg
                275                 280                 285 tat tat tac agc atc aag gat atc agc atc gga ggc cgc tgt gtc tgc         973
Tyr Tyr Tyr Ser Ile Lys Asp Ile Ser Ile Gly Gly Arg Cys Val Cys
            290                 295                 300 cac ggc cac gcg gat gcc tgc gat gcc aaa gac ccc acg gac ccg ttc        1021
His Gly His Ala Asp Ala Cys Asp Ala Lys Asp Pro Thr Asp Pro Phe
        305                 310                 315 agg ctg cag tgc acc tgc cag cac aac acc tgc ggg ggc acc tgc gac        1069
Arg Leu Gln Cys Thr Cys Gln His Asn Thr Cys Gly Gly Thr Cys Asp
320                 325                 330 cgc tgc tgc ccc ggc ttc aat cag cag ccg tgg aag cct gcg act gcc        1117
Arg Cys Cys Pro Gly Phe Asn Gln Gln Pro Trp Lys Pro Ala Thr Ala
335                 340                 345                 350 aac agt gcc aac gag tgc cag tcc tgt aac tgc tac ggc cat gcc acc        1165
Asn Ser Ala Asn Glu Cys Gln Ser Cys Asn Cys Tyr Gly His Ala Thr
                355                 360                 365 gac tgt tac tac gac cct gag gtg gac cgg cgc cgc gcc agc cag agc        1213
Asp Cys Tyr Tyr Asp Pro Glu Val Asp Arg Arg Arg Ala Ser Gln Ser
            370                 375                 380 ctg gat ggc acc tat cag ggt ggg ggt gtc tgt atc gac tgc cag cac        1261
Leu Asp Gly Thr Tyr Gln Gly Gly Gly Val Cys Ile Asp Cys Gln His
        385                 390                 395 cac acc gcc ggc gtc aac tgt gag cgc tgc ctg ccc ggc ttc tac cgc        1309
His Thr Ala Gly Val Asn Cys Glu Arg Cys Leu Pro Gly Phe Tyr Arg
400                 405                 410
```

-continued

| | |
|---|---|
| tct ccc aac cac cct ctc gac tcg ccc cac gtc tgc cgc cgc tgc aac<br>Ser Pro Asn His Pro Leu Asp Ser Pro His Val Cys Arg Arg Cys Asn<br>415                       420                       425                   430 | 1357 |
| tgc gag tcc gac ttc acg gat ggc acc tgc gag gac ctg acg ggt cga<br>Cys Glu Ser Asp Phe Thr Asp Gly Thr Cys Glu Asp Leu Thr Gly Arg<br>                     435                       440                     445 | 1405 |
| tgc tac tgc cgg ccc aac ttc tct ggg gag cgg tgt gac gtg tgt gcc<br>Cys Tyr Cys Arg Pro Asn Phe Ser Gly Glu Arg Cys Asp Val Cys Ala<br>           450                       455                       460 | 1453 |
| gag ggc ttc acg ggc ttc cca agc tgc tac ccg acg ccc tcg tcc tcc<br>Glu Gly Phe Thr Gly Phe Pro Ser Cys Tyr Pro Thr Pro Ser Ser Ser<br>         465                     470                     475 | 1501 |
| aat gac acc agg gag cag gtg ctg cca gct ggc cag att gtg aat tgt<br>Asn Asp Thr Arg Glu Gln Val Leu Pro Ala Gly Gln Ile Val Asn Cys<br>480                       485                       490 | 1549 |
| gac tgc agc gcg gca ggg acc cag ggc aac gcc tgc cgg aag gac cca<br>Asp Cys Ser Ala Ala Gly Thr Gln Gly Asn Ala Cys Arg Lys Asp Pro<br>495                       500                     505                   510 | 1597 |
| agg gtg gga cgc tgt ctg tgc aaa ccc aac ttc caa ggc acc cat tgt<br>Arg Val Gly Arg Cys Leu Cys Lys Pro Asn Phe Gln Gly Thr His Cys<br>                     515                       520                     525 | 1645 |
| gag ctc tgc gcg cca ggg ttc tac ggc ccc ggc tgc cag ccc tgc cag<br>Glu Leu Cys Ala Pro Gly Phe Tyr Gly Pro Gly Cys Gln Pro Cys Gln<br>         530                     535                     540 | 1693 |
| tgt tcc agc cct gga gtg gcc gat gac cgc tgt gac cct gac aca ggc<br>Cys Ser Ser Pro Gly Val Ala Asp Asp Arg Cys Asp Pro Asp Thr Gly<br>               545                     550                     555 | 1741 |
| cag tgc agg tgc cga gtg ggc ttc gag ggg gcc aca tgt gat cgc tgt<br>Gln Cys Arg Cys Arg Val Gly Phe Glu Gly Ala Thr Cys Asp Arg Cys<br>560                       565                       570 | 1789 |
| gcc ccc ggc tac ttt cac ttc cct ctc tgc cag ttg tgt ggc tgc agc<br>Ala Pro Gly Tyr Phe His Phe Pro Leu Cys Gln Leu Cys Gly Cys Ser<br>575                       580                     585                   590 | 1837 |
| cct gca gga acc ttg ccc gag ggc tgc gat gag gcc ggc cgc tgc cta<br>Pro Ala Gly Thr Leu Pro Glu Gly Cys Asp Glu Ala Gly Arg Cys Leu<br>               595                     600                     605 | 1885 |
| tgc cag cct gag ttt gct gga cct cat tgt gac cgg tgc cgc cct ggc<br>Cys Gln Pro Glu Phe Ala Gly Pro His Cys Asp Arg Cys Arg Pro Gly<br>         610                     615                     620 | 1933 |
| tac cat ggt ttc ccc aac tgc caa gca tgc acc tgc gac cct cgg gga<br>Tyr His Gly Phe Pro Asn Cys Gln Ala Cys Thr Cys Asp Pro Arg Gly<br>               625                     630                     635 | 1981 |
| gcc ctg gac cag ctc tgt ggg gcg gga ggt ttg tgc cgc tgc cgc ccc<br>Ala Leu Asp Gln Leu Cys Gly Ala Gly Gly Leu Cys Arg Cys Arg Pro<br>640                       645                     650 | 2029 |
| ggc tac aca ggc act gcc tgc cag gaa tgc agc ccc ggc ttt cac ggc<br>Gly Tyr Thr Gly Thr Ala Cys Gln Glu Cys Ser Pro Gly Phe His Gly<br>655                       660                     665                   670 | 2077 |
| ttc ccc agc tgt gtc ccc tgc cac tgc tct gct gaa ggc tcc ctg cac<br>Phe Pro Ser Cys Val Pro Cys His Cys Ser Ala Glu Gly Ser Leu His<br>                     675                     680                   685 | 2125 |
| gca gcc tgt gac ccc cgg agt ggg cag tgc agc tgc cgg ccc cgt gtg<br>Ala Ala Cys Asp Pro Arg Ser Gly Gln Cys Ser Cys Arg Pro Arg Val<br>         690                     695                       700 | 2173 |
| acg ggg ctg cgg tgt gac acg tgt gtg ccc ggt gcc tac aac ttc ccc<br>Thr Gly Leu Arg Cys Asp Thr Cys Val Pro Gly Ala Tyr Asn Phe Pro<br>               705                     710                     715 | 2221 |
| tac tgc gaa gct ggc tct tgc cac cct gcc ggt ctg gcc cca gtg gat<br>Tyr Cys Glu Ala Gly Ser Cys His Pro Ala Gly Leu Ala Pro Val Asp<br>720                       725                     730 | 2269 |

-continued

```
cct gcc ctt cct gag gca cag gtt ccc tgt atg tgc cgg gct cac gtg    2317
Pro Ala Leu Pro Glu Ala Gln Val Pro Cys Met Cys Arg Ala His Val
735                 740                 745                 750 gag ggg ccg agc tgt gac cgc tgc aaa cct ggg ttc tgg gga ctg agc    2365
Glu Gly Pro Ser Cys Asp Arg Cys Lys Pro Gly Phe Trp Gly Leu Ser
                755                 760                 765 ccc agc aac ccc gag ggc tgt acc cgc tgc agc tgc gac ctc agg ggc    2413
Pro Ser Asn Pro Glu Gly Cys Thr Arg Cys Ser Cys Asp Leu Arg Gly
            770                 775                 780 aca ctg ggt gga gtt gct gag tgc cag ccg ggc acc ggc cag tgc ttc    2461
Thr Leu Gly Gly Val Ala Glu Cys Gln Pro Gly Thr Gly Gln Cys Phe
        785                 790                 795 tgc aag ccc cac gtg tgc ggc cag gcc tgc gcg tcc tgc aag gat ggc    2509
Cys Lys Pro His Val Cys Gly Gln Ala Cys Ala Ser Cys Lys Asp Gly
800                 805                 810 ttc ttt gga ctg gat cag gct gac tat ttt ggc tgc cgc agc tgc cgg    2557
Phe Phe Gly Leu Asp Gln Ala Asp Tyr Phe Gly Cys Arg Ser Cys Arg
815                 820                 825                 830 tgt gac att ggc ggt gca ctg ggc cag agc tgt gaa ccg agg acg ggc    2605
Cys Asp Ile Gly Gly Ala Leu Gly Gln Ser Cys Glu Pro Arg Thr Gly
                835                 840                 845 gtc tgc cgg tgc cgc ccc aac acc cag ggc ccc acc tgc agc gag cct    2653
Val Cys Arg Cys Arg Pro Asn Thr Gln Gly Pro Thr Cys Ser Glu Pro
            850                 855                 860 gcg agg gac cac tac ctc ccg gac ctg cac cac ctg cgc ctg gag ctg    2701
Ala Arg Asp His Tyr Leu Pro Asp Leu His His Leu Arg Leu Glu Leu
        865                 870                 875 gag gag gct gcc aca cct gag ggt cac gcc gtg cgc ttt ggc ttc aac    2749
Glu Glu Ala Ala Thr Pro Glu Gly His Ala Val Arg Phe Gly Phe Asn
880                 885                 890 ccc ctc gag ttc gag aac ttc agc tgg agg ggc tac gcg cag atg gca    2797
Pro Leu Glu Phe Glu Asn Phe Ser Trp Arg Gly Tyr Ala Gln Met Ala
895                 900                 905                 910 cct gtc cag ccc agg atc gtg gcc agg ctg aac ctg acc tcc ccc gac    2845
Pro Val Gln Pro Arg Ile Val Ala Arg Leu Asn Leu Thr Ser Pro Asp
                915                 920                 925 ctt ttc tgg ctc gtc ttc cga tac gtc aac cgg ggg gcc atg agt gtg    2893
Leu Phe Trp Leu Val Phe Arg Tyr Val Asn Arg Gly Ala Met Ser Val
            930                 935                 940 agc ggg cgg gtc tct gtg cga gag gag ggc agg tcg gcc gcc tgt gcc    2941
Ser Gly Arg Val Ser Val Arg Glu Glu Gly Arg Ser Ala Ala Cys Ala
        945                 950                 955 aac tgc aca gca cag agt cag ccc gtg gcc ttc cca ccc agc acg gag    2989
Asn Cys Thr Ala Gln Ser Gln Pro Val Ala Phe Pro Pro Ser Thr Glu
960                 965                 970 cct gcc ttc atc acc gtg ccc cag agg ggc ttc gga gag ccc ttt gtg    3037
Pro Ala Phe Ile Thr Val Pro Gln Arg Gly Phe Gly Glu Pro Phe Val
975                 980                 985                 990 ctg aac cct ggc acc tgg gcc ctg cgt gtg gag gcc gaa ggg gtg ctc    3085
Leu Asn Pro Gly Thr Trp Ala Leu Arg Val Glu Ala Glu Gly Val Leu
                995                 1000                1005 ctg gac tac gtg gtt ctg ctg cct agc gca tac tac gag gcg gcg ctc    3133
Leu Asp Tyr Val Val Leu Leu Pro Ser Ala Tyr Tyr Glu Ala Ala Leu
            1010                1015                1020 ctg cag ctg cgg gtg act gag gcc tgc aca tac cgt ccc tct gcc cag    3181
Leu Gln Leu Arg Val Thr Glu Ala Cys Thr Tyr Arg Pro Ser Ala Gln
        1025                1030                1035 cag tct ggc gac aac tgc ctc ctc tac aca cac ctc ccc ctg gat ggc    3229
Gln Ser Gly Asp Asn Cys Leu Leu Tyr Thr His Leu Pro Leu Asp Gly
```

```
                                                              -continued
      1040              1045              1050
ttc ccc tcg gcc gcc ggg ctg gag gcc ctg tgt cgc cag gac aac agc    3277
Phe Pro Ser Ala Ala Gly Leu Glu Ala Leu Cys Arg Gln Asp Asn Ser
1055              1060              1065              1070 ctg ccc cgg ccc tgc ccc acg gag cag ctc agc ccg tcg cac ccg cca    3325
Leu Pro Arg Pro Cys Pro Thr Glu Gln Leu Ser Pro Ser His Pro Pro
         1075              1080              1085 ctg atc acc tgc acg ggc agt gat gtg gac gtc cag ctt caa gtg gca    3373
Leu Ile Thr Cys Thr Gly Ser Asp Val Asp Val Gln Leu Gln Val Ala
         1090              1095              1100 gtg cca cag cca ggc cgc tat gcc cta gtg gtg gag tac gcc aat gag    3421
Val Pro Gln Pro Gly Arg Tyr Ala Leu Val Val Glu Tyr Ala Asn Glu
    1105              1110              1115 gat gcc cgc cag gag gtg ggc gtg gct gtg cac acc cca cag cgg gcc    3469
Asp Ala Arg Gln Glu Val Gly Val Ala Val His Thr Pro Gln Arg Ala
    1120              1125              1130 ccc cag cag ggg ctg ctc tcc ctg cac ccc tgc ctg tac agc acc ctg    3517
Pro Gln Gln Gly Leu Leu Ser Leu His Pro Cys Leu Tyr Ser Thr Leu
1135              1140              1145              1150 tgc cgg ggc act gcc cgg gat acc cag gac cac ctg gct gtc ttc cac    3565
Cys Arg Gly Thr Ala Arg Asp Thr Gln Asp His Leu Ala Val Phe His
         1155              1160              1165 ctg gac tcg gag gcc agc gtg agg ctc aca gcc gag cag gca cgc ttc    3613
Leu Asp Ser Glu Ala Ser Val Arg Leu Thr Ala Glu Gln Ala Arg Phe
         1170              1175              1180 ttc ctg cac ggg gtc act ctg gtg ccc att gag gag ttc agc ccg gag    3661
Phe Leu His Gly Val Thr Leu Val Pro Ile Glu Glu Phe Ser Pro Glu
         1185              1190              1195 ttc gtg gag ccc cgg gtc agc tgc atc agc agc cac ggc gcc ttt ggc    3709
Phe Val Glu Pro Arg Val Ser Cys Ile Ser Ser His Gly Ala Phe Gly
    1200              1205              1210 ccc aac agt gcc gcc tgt ctg ccc tcg cgc ttc cca aag ccg ccc cag    3757
Pro Asn Ser Ala Ala Cys Leu Pro Ser Arg Phe Pro Lys Pro Pro Gln
1215              1220              1225              1230 ccc atc atc ctc agg gac tgc cag gtg atc ccg ctg ccg ccc ggc ctc    3805
Pro Ile Ile Leu Arg Asp Cys Gln Val Ile Pro Leu Pro Pro Gly Leu
         1235              1240              1245 ccg ctg acc cac gcg cag gat ctc act cca gcc acg tcc cca gct gga    3853
Pro Leu Thr His Ala Gln Asp Leu Thr Pro Ala Thr Ser Pro Ala Gly
         1250              1255              1260 ccc cga cct cgg ccc ccc acc gct gtg gac cct gat gca gag ccc acc    3901
Pro Arg Pro Arg Pro Pro Thr Ala Val Asp Pro Asp Ala Glu Pro Thr
    1265              1270              1275 ctg ctg cgt gag ccc cag gcc acc gtg gtc ttc acc acc cat gtg ccc    3949
Leu Leu Arg Glu Pro Gln Ala Thr Val Val Phe Thr Thr His Val Pro
    1280              1285              1290 acg ctg ggc cgc tat gcc ttc ctg ctg cac ggc tac cag cca gcc cac    3997
Thr Leu Gly Arg Tyr Ala Phe Leu Leu His Gly Tyr Gln Pro Ala His
1295              1300              1305              1310 ccc acc ttc ccc gtg gaa gtc ctc atc aac gcc ggc cgc gtg tgg cag    4045
Pro Thr Phe Pro Val Glu Val Leu Ile Asn Ala Gly Arg Val Trp Gln
         1315              1320              1325 ggc cac gcc aac gcc agc ttc tgt cca cat ggc tac ggc tgc cgc acc    4093
Gly His Ala Asn Ala Ser Phe Cys Pro His Gly Tyr Gly Cys Arg Thr
         1330              1335              1340 ctg gtg gtg tgt gag ggc cag gcc ctg ctg gac gtg acc cac agc gag    4141
Leu Val Val Cys Glu Gly Gln Ala Leu Leu Asp Val Thr His Ser Glu
         1345              1350              1355 ctc act gtg acc gtg cgt gtg ccc gag ggc cgg tgg ctc tgg ctg gat    4189
```

-continued

```
Leu Thr Val Thr Val Arg Val Pro Glu Gly Arg Trp Leu Trp Leu Asp
    1360                1365                1370 tat gta ctc gtg gtc cct gag aac gtc tac agc ttt ggc tac ctc cgg         4237
Tyr Val Leu Val Val Pro Glu Asn Val Tyr Ser Phe Gly Tyr Leu Arg
1375                1380                1385                1390 gag gag ccc ctg gat aaa tcc tat gac ttc atc agc cac tgc gca gcc         4285
Glu Glu Pro Leu Asp Lys Ser Tyr Asp Phe Ile Ser His Cys Ala Ala
                1395                1400                1405 cag ggc tac cac atc agc ccc agc agc tca tcc ctg ttc tgc cga aac         4333
Gln Gly Tyr His Ile Ser Pro Ser Ser Ser Ser Leu Phe Cys Arg Asn
        1410                1415                1420 gct gct gct tcc ctc tcc ctc ttc tat aac aac gga gcc cgt cca tgt         4381
Ala Ala Ala Ser Leu Ser Leu Phe Tyr Asn Asn Gly Ala Arg Pro Cys
    1425                1430                1435 ggc tgc cac gaa gta ggt gct aca ggc ccc acg tgt gag ccc ttc ggg         4429
Gly Cys His Glu Val Gly Ala Thr Gly Pro Thr Cys Glu Pro Phe Gly
1440                1445                1450 ggc cag tgt ccc tgc cat gcc cat gtc att ggc cgt gac tgc tcc cgc         4477
Gly Gln Cys Pro Cys His Ala His Val Ile Gly Arg Asp Cys Ser Arg
1455                1460                1465                1470 tgt gcc acc gga tac tgg ggc ttc ccc aac tgc agg ccc tgt gac tgc         4525
Cys Ala Thr Gly Tyr Trp Gly Phe Pro Asn Cys Arg Pro Cys Asp Cys
                1475                1480                1485 ggt gcc cgc ctc tgt gac gag ctc acg ggc cag tgc atc tgc ccg cca         4573
Gly Ala Arg Leu Cys Asp Glu Leu Thr Gly Gln Cys Ile Cys Pro Pro
        1490                1495                1500 cgc acc atc ccg ccc gac tgc ctg ctg tgc cag ccc cag acc ttt ggc         4621
Arg Thr Ile Pro Pro Asp Cys Leu Leu Cys Gln Pro Gln Thr Phe Gly
    1505                1510                1515 tgc cac ccc ctg gtc ggc tgt gag gag tgt aac tgc tca ggc ccc ggc         4669
Cys His Pro Leu Val Gly Cys Glu Glu Cys Asn Cys Ser Gly Pro Gly
    1520                1525                1530 atc cag gag ctc aca gac cct acc tgt gac aca gac agc ggc cag tgc         4717
Ile Gln Glu Leu Thr Asp Pro Thr Cys Asp Thr Asp Ser Gly Gln Cys
1535                1540                1545                1550 aag tgc aga ccc aac gtg act ggg cgc cgc tgt gat acc tgc tct ccg         4765
Lys Cys Arg Pro Asn Val Thr Gly Arg Arg Cys Asp Thr Cys Ser Pro
                1555                1560                1565 ggc ttc cat ggc tac ccc cgc tgc cgc ccc tgt gac tgt cac gag gcg         4813
Gly Phe His Gly Tyr Pro Arg Cys Arg Pro Cys Asp Cys His Glu Ala
        1570                1575                1580 ggc act gcg cct ggc gtg tgt gac ccc ctc aca ggg cag tgc tac tgt         4861
Gly Thr Ala Pro Gly Val Cys Asp Pro Leu Thr Gly Gln Cys Tyr Cys
    1585                1590                1595 aag gag aac gtg cag ggc ccc aaa tgt gac cag tgc agc ctt ggg acc         4909
Lys Glu Asn Val Gln Gly Pro Lys Cys Asp Gln Cys Ser Leu Gly Thr
    1600                1605                1610 ttc tca ctg gat gct gcc aac ccc aaa ggt tgc acc cgc tgc ttc tgc         4957
Phe Ser Leu Asp Ala Ala Asn Pro Lys Gly Cys Thr Arg Cys Phe Cys
1615                1620                1625                1630 ttt ggg gcc acg gag cgc tgc cgg agc tcg tcc tac acc cgc cag gag         5005
Phe Gly Ala Thr Glu Arg Cys Arg Ser Ser Ser Tyr Thr Arg Gln Glu
                1635                1640                1645 ttc gtg gat atg gag gga tgg gtg ctg ctg agc act gac cgg cag gtg         5053
Phe Val Asp Met Glu Gly Trp Val Leu Leu Ser Thr Asp Arg Gln Val
        1650                1655                1660 gtg ccc cac gag cgg cag cca ggg acg gag atg ctc cgt gca gac ctg         5101
Val Pro His Glu Arg Gln Pro Gly Thr Glu Met Leu Arg Ala Asp Leu
    1665                1670                1675
```

```
                                                       -continued cgg cac gtg cct gag gct gtg ccc gag gct ttc ccc gag ctg tac tgg     5149
Arg His Val Pro Glu Ala Val Pro Glu Ala Phe Pro Glu Leu Tyr Trp
         1680             1685             1690 cag gcc cca ccc tcc tac ctg ggg gac cgg gtg tca tcc tac ggt ggg     5197
Gln Ala Pro Pro Ser Tyr Leu Gly Asp Arg Val Ser Ser Tyr Gly Gly
1695             1700             1705             1710 acc ctc cgt tat gaa ctg cac tca gag acc cag cgg gga gat gtc ttt     5245
Thr Leu Arg Tyr Glu Leu His Ser Glu Thr Gln Arg Gly Asp Val Phe
             1715             1720             1725 gtc ccc atg gag agc agg ccg gat gtg gtg ctg cag ggc aac cag atg     5293
Val Pro Met Glu Ser Arg Pro Asp Val Val Leu Gln Gly Asn Gln Met
         1730             1735             1740 agc atc aca ttc ctg gag ccg gca tac ccc acg cct ggc cac gtt cac     5341
Ser Ile Thr Phe Leu Glu Pro Ala Tyr Pro Thr Pro Gly His Val His
     1745             1750             1755 cgt ggg cag ctg cag ctg gtg gag ggg aac ttc cgg cat acg gag act     5389
Arg Gly Gln Leu Gln Leu Val Glu Gly Asn Phe Arg His Thr Glu Thr
 1760             1765             1770 cgc aac act gtg tcc cgc gag gag ctc atg atg gtg ctg gcc agc ctg     5437
Arg Asn Thr Val Ser Arg Glu Glu Leu Met Met Val Leu Ala Ser Leu
1775             1780             1785             1790 gag cag ctg cag atc cgt gcc ctc ttc tca cag atc tcc tcg gct gtc     5485
Glu Gln Leu Gln Ile Arg Ala Leu Phe Ser Gln Ile Ser Ser Ala Val
             1795             1800             1805 tcc ctg cgc agg gtg gca ctg gag gtg gcc agc cca gca ggc cag ggg     5533
Ser Leu Arg Arg Val Ala Leu Glu Val Ala Ser Pro Ala Gly Gln Gly
         1810             1815             1820 gcc ctg gcc agc aat gtg gag ctg tgc ctg tgc ccc gcc agc tac cgg     5581
Ala Leu Ala Ser Asn Val Glu Leu Cys Leu Cys Pro Ala Ser Tyr Arg
     1825             1830             1835 ggg gac tca tgc cag gaa tgt gcc ccc ggc ttc tat cgg gac gtc aaa     5629
Gly Asp Ser Cys Gln Glu Cys Ala Pro Gly Phe Tyr Arg Asp Val Lys
 1840             1845             1850 ggt ctc ttc ctg ggc cga tgt gtc cct tgt cag tgc cat gga cac tca     5677
Gly Leu Phe Leu Gly Arg Cys Val Pro Cys Gln Cys His Gly His Ser
1855             1860             1865             1870 gac cgc tgc ctc cct ggc tct ggc gtc tgt gtg gac tgc cag cac aac     5725
Asp Arg Cys Leu Pro Gly Ser Gly Val Cys Val Asp Cys Gln His Asn
             1875             1880             1885 acc gaa ggg gcc cac tgt gag cgc tgc cag gct ggc ttc atg agc agc     5773
Thr Glu Gly Ala His Cys Glu Arg Cys Gln Ala Gly Phe Met Ser Ser
         1890             1895             1900 agg gac gac ccc agc gcc ccc tgt gtc agc tgc ccc tgc ccc ctc tca     5821
Arg Asp Asp Pro Ser Ala Pro Cys Val Ser Cys Pro Cys Pro Leu Ser
     1905             1910             1915 gtg cct tcc aac aac ttc gcc gag ggc tgt gtc ctg cga ggc ggc cgc     5869
Val Pro Ser Asn Asn Phe Ala Glu Gly Cys Val Leu Arg Gly Gly Arg
 1920             1925             1930 acc cag tgc ctc tgc aaa cct ggt tat gca ggt gcc tcc tgc gag cgg     5917
Thr Gln Cys Leu Cys Lys Pro Gly Tyr Ala Gly Ala Ser Cys Glu Arg
1935             1940             1945             1950 tgt gcg ccc gga ttc ttt ggg aac cca ctg gtg ctg ggc agc tcc tgc     5965
Cys Ala Pro Gly Phe Phe Gly Asn Pro Leu Val Leu Gly Ser Ser Cys
             1955             1960             1965 cag cca tgc gac tgc agc ggc aac ggt gac ccc aac ttg ctc ttc agc     6013
Gln Pro Cys Asp Cys Ser Gly Asn Gly Asp Pro Asn Leu Leu Phe Ser
         1970             1975             1980 gac tgc gac ccc ctg acg ggc gcc tgc cgt ggc tgc ctg cgc cac acc     6061
Asp Cys Asp Pro Leu Thr Gly Ala Cys Arg Gly Cys Leu Arg His Thr
     1985             1990             1995
```

```
act ggg ccc cgc tgc gag atc tgt gcc ccc ggc ttc tac ggc aac gcc      6109
Thr Gly Pro Arg Cys Glu Ile Cys Ala Pro Gly Phe Tyr Gly Asn Ala
    2000                2005                2010 ctg ctg ccc gga aac tgc acc cgg tgc gac tgt acc cca tgt ggg aca      6157
Leu Leu Pro Gly Asn Cys Thr Arg Cys Asp Cys Thr Pro Cys Gly Thr
2015                2020                2025                2030 gag gcc tgc gac ccc cac agc ggg cac tgc ctg tgc aag gcg ggc gtg      6205
Glu Ala Cys Asp Pro His Ser Gly His Cys Leu Cys Lys Ala Gly Val
            2035                2040                2045 act ggg cgg cgc tgt gac cgc tgc cag gag gga cat ttt ggt ttc aat      6253
Thr Gly Arg Arg Cys Asp Arg Cys Gln Glu Gly His Phe Gly Phe Asn
        2050                2055                2060 ggc tgc ggg ggc tgc cgc ccg tgt gct tgt gga ccg gcc gcc gag ggc      6301
Gly Cys Gly Gly Cys Arg Pro Cys Ala Cys Gly Pro Ala Ala Glu Gly
    2065                2070                2075 tcc gag tgc cac ccc cag agc gga cag tgc cac tgc cga cca ggg acc      6349
Ser Glu Cys His Pro Gln Ser Gly Gln Cys His Cys Arg Pro Gly Thr
2080                2085                2090 atg gga ccc cag tgc cgc gag tgt gcc cct ggc tac tgg ggg ctc cct      6397
Met Gly Pro Gln Cys Arg Glu Cys Ala Pro Gly Tyr Trp Gly Leu Pro
2095                2100                2105                2110 gag cag ggc tgc agg cgc tgc cag tgc cct ggg ggc cgc tgt gac cct      6445
Glu Gln Gly Cys Arg Arg Cys Gln Cys Pro Gly Gly Arg Cys Asp Pro
            2115                2120                2125 cac acg ggc cgc tgc aac tgc ccc ccg ggg ctc agc ggg gag cgc tgc      6493
His Thr Gly Arg Cys Asn Cys Pro Pro Gly Leu Ser Gly Glu Arg Cys
        2130                2135                2140 gac acc tgc agc cag cag cat cag gtg cct gtt cca ggc ggg cct gtg      6541
Asp Thr Cys Ser Gln Gln His Gln Val Pro Val Pro Gly Gly Pro Val
    2145                2150                2155 ggc cac agc atc cac tgt gaa gtg tgt gac cac tgt gtg gtc ctg ctc      6589
Gly His Ser Ile His Cys Glu Val Cys Asp His Cys Val Val Leu Leu
2160                2165                2170 ctg gat gac ctg gaa cgg gcc ggc gcc ctc ctc ccc gcc att cac gag      6637
Leu Asp Asp Leu Glu Arg Ala Gly Ala Leu Leu Pro Ala Ile His Glu
2175                2180                2185                2190 caa ctg cgt ggc atc aat gcc agc tcc atg gcc tgg gcc cgt ctg cac      6685
Gln Leu Arg Gly Ile Asn Ala Ser Ser Met Ala Trp Ala Arg Leu His
            2195                2200                2205 agg ctg aac gcc tcc atc gct gac ctg cag agc cag ctc cgg agc ccc      6733
Arg Leu Asn Ala Ser Ile Ala Asp Leu Gln Ser Gln Leu Arg Ser Pro
        2210                2215                2220 ctg ggc ccc cgc cat gag acg gca cag cag ctg gag gtg ctg gag cag      6781
Leu Gly Pro Arg His Glu Thr Ala Gln Gln Leu Glu Val Leu Glu Gln
    2225                2230                2235 cag agc aca agc ctc ggg cag gac gca cgg cgg cta ggc ggc cag gcc      6829
Gln Ser Thr Ser Leu Gly Gln Asp Ala Arg Arg Leu Gly Gly Gln Ala
2240                2245                2250 gtg ggg acc cga gac cag gcg agc caa ttg ctg gcc ggc acc gag gcc      6877
Val Gly Thr Arg Asp Gln Ala Ser Gln Leu Leu Ala Gly Thr Glu Ala
2255                2260                2265                2270 aca ctg ggc cat gcg aag acg ctg ttg gcg gcc atc cgg gct gtg gac      6925
Thr Leu Gly His Ala Lys Thr Leu Leu Ala Ala Ile Arg Ala Val Asp
            2275                2280                2285 cgc acc ctg agc gag ctc atg tcc cag acg ggc cac ctg ggg ctg gcc      6973
Arg Thr Leu Ser Glu Leu Met Ser Gln Thr Gly His Leu Gly Leu Ala
        2290                2295                2300 aat gcc tcg gct cca tca ggt gag cag ctg ctc cgg aca ctg gcc gag      7021
Asn Ala Ser Ala Pro Ser Gly Glu Gln Leu Leu Arg Thr Leu Ala Glu
```

-continued

| | | |
|---|---|---|
| gtg gag cgg ctg ctc tgg gag atg cgg gcc cgg gac ctg ggg gcc ccg<br>Val Glu Arg Leu Leu Trp Glu Met Arg Ala Arg Asp Leu Gly Ala Pro<br>2320                       2325                       2330 | 7069 |
| cag gca gca gct gag gct gag ttg gct gca gca cag aga ttg ctg gcc<br>Gln Ala Ala Ala Glu Ala Glu Leu Ala Ala Ala Gln Arg Leu Leu Ala<br>2335                       2340                       2345                       2350 | 7117 |
| cgg gtg cag gag cag ctg agc agc ctc tgg gag gag aac cag gca ctg<br>Arg Val Gln Glu Gln Leu Ser Ser Leu Trp Glu Glu Asn Gln Ala Leu<br>             2355                       2360                       2365 | 7165 |
| gcc aca caa acc cgc gac cgg ctg gcc cag cac gag gcc ggc ctc atg<br>Ala Thr Gln Thr Arg Asp Arg Leu Ala Gln His Glu Ala Gly Leu Met<br>             2370                       2375                       2380 | 7213 |
| gac ctg cga gag gct ttg aac cgg gca gtg gac gcc aca cgg gag gcc<br>Asp Leu Arg Glu Ala Leu Asn Arg Ala Val Asp Ala Thr Arg Glu Ala<br>2385                       2390                       2395 | 7261 |
| cag gag ctc aac agc cgc aac cag gag cgc ctg gag gaa gcc ctg caa<br>Gln Glu Leu Asn Ser Arg Asn Gln Glu Arg Leu Glu Glu Ala Leu Gln<br>             2400                       2405                       2410 | 7309 |
| agg aag cag gag ctg tcc cgg gac aat gcc acc ctg cag gcc act ctg<br>Arg Lys Gln Glu Leu Ser Arg Asp Asn Ala Thr Leu Gln Ala Thr Leu<br>2415                       2420                       2425                       2430 | 7357 |
| cat gcg gct agg gac acc ctg gcc agc gtc ttc aga ttg ctg cac agc<br>His Ala Ala Arg Asp Thr Leu Ala Ser Val Phe Arg Leu Leu His Ser<br>             2435                       2440                       2445 | 7405 |
| ctg gac cag gct aag gag gag ctg gag cgc ctc gcc gcc agc ctg gac<br>Leu Asp Gln Ala Lys Glu Glu Leu Glu Arg Leu Ala Ala Ser Leu Asp<br>             2450                       2455                       2460 | 7453 |
| ggg gct cgg acc cca ctg ctg cag agg atg cag acc ttc tcc ccg gcg<br>Gly Ala Arg Thr Pro Leu Leu Gln Arg Met Gln Thr Phe Ser Pro Ala<br>2465                       2470                       2475 | 7501 |
| ggc agc aag ctg cgt cta gtg gag gcc gcc gag gcc cac gca cag cag<br>Gly Ser Lys Leu Arg Leu Val Glu Ala Ala Glu Ala His Ala Gln Gln<br>             2480                       2485                       2490 | 7549 |
| ctg ggc cag ctg gca ctc aat ctg tcc agc atc atc ctg gac gtc aac<br>Leu Gly Gln Leu Ala Leu Asn Leu Ser Ser Ile Ile Leu Asp Val Asn<br>2495                       2500                       2505                       2510 | 7597 |
| cag gac cgc ctc acc cag agg gcc atc gag gcc tcc aac gcc tac agc<br>Gln Asp Arg Leu Thr Gln Arg Ala Ile Glu Ala Ser Asn Ala Tyr Ser<br>             2515                       2520                       2525 | 7645 |
| cgc atc ctg cag gcc gtg cag gct gcc gag gat gct gct ggc cag gcc<br>Arg Ile Leu Gln Ala Val Gln Ala Ala Glu Asp Ala Ala Gly Gln Ala<br>             2530                       2535                       2540 | 7693 |
| ctg cag cag gcg gac cac acg tgg gcg acg gtg gtg cgg cag ggc ctg<br>Leu Gln Gln Ala Asp His Thr Trp Ala Thr Val Val Arg Gln Gly Leu<br>2545                       2550                       2555 | 7741 |
| gtg gac cga gcc cag cag ctc ctg gcc aac agc act gca cta gaa gag<br>Val Asp Arg Ala Gln Gln Leu Leu Ala Asn Ser Thr Ala Leu Glu Glu<br>             2560                       2565                       2570 | 7789 |
| gcc atg ctc cag gaa cag cag agg ctg ggc ctt gtg tgg gct gcc ctc<br>Ala Met Leu Gln Glu Gln Gln Arg Leu Gly Leu Val Trp Ala Ala Leu<br>2575                       2580                       2585                       2590 | 7837 |
| cag ggt gcc agg acc cag ctc cga gat gtc cgg gcc aag aag gac cag<br>Gln Gly Ala Arg Thr Gln Leu Arg Asp Val Arg Ala Lys Lys Asp Gln<br>             2595                       2600                       2605 | 7885 |
| ctg gag gcg cac atc cag gcg gcg cag gcc atg ctt gcc atg gac aca<br>Leu Glu Ala His Ile Gln Ala Ala Gln Ala Met Leu Ala Met Asp Thr<br>             2610                       2615                       2620 | 7933 |
| gac gag aca agc aag aag atc gca cat gcc aag gct gtg gct gct gaa | 7981 |

```
                                                                      -continued Asp Glu Thr Ser Lys Lys Ile Ala His Ala Lys Ala Val Ala Ala Glu
        2625                2630                2635 gcc cag gac acc gcc acc cgt gtg cag tcc cag ctg cag gcc atg cag        8029
Ala Gln Asp Thr Ala Thr Arg Val Gln Ser Gln Leu Gln Ala Met Gln
2640                2645                2650 gag aat gtg gag cgg tgg cag ggc cag tac gag ggc ctg cgg ggc cag        8077
Glu Asn Val Glu Arg Trp Gln Gly Gln Tyr Glu Gly Leu Arg Gly Gln
2655                2660                2665                2670 gac ctg ggc cag gca gtg ctt gac gca ggc cac tca gtg tcc acc ctg        8125
Asp Leu Gly Gln Ala Val Leu Asp Ala Gly His Ser Val Ser Thr Leu
        2675                2680                2685 gag aag acg ctg ccc cag ctg ctg gcc aag ctg agc atc ctg gag aac        8173
Glu Lys Thr Leu Pro Gln Leu Leu Ala Lys Leu Ser Ile Leu Glu Asn
    2690                2695                2700 cgt ggg gtg cac aac gcc agc ctg gcc ctg tcc gcc agc att ggc cgc        8221
Arg Gly Val His Asn Ala Ser Leu Ala Leu Ser Ala Ser Ile Gly Arg
2705                2710                2715 gtg cga gag ctc att gcc cag gcc cgg ggg gct gcc agt aag gtc aag        8269
Val Arg Glu Leu Ile Ala Gln Ala Arg Gly Ala Ala Ser Lys Val Lys
        2720                2725                2730 gtg ccc atg aag ttc aac ggg cgc tca ggg gtg cag ctg cgc acc cca        8317
Val Pro Met Lys Phe Asn Gly Arg Ser Gly Val Gln Leu Arg Thr Pro
2735                2740                2745                2750 cgg gat ctt gcc gac ctt gct gcc tac act gcc ctc aag ttc tac ctg        8365
Arg Asp Leu Ala Asp Leu Ala Ala Tyr Thr Ala Leu Lys Phe Tyr Leu
        2755                2760                2765 cag ggc cca gag cct gag cct ggg cag ggt acc gag gat cgc ttt gtg        8413
Gln Gly Pro Glu Pro Glu Pro Gly Gln Gly Thr Glu Asp Arg Phe Val
    2770                2775                2780 atg tac atg ggc agc cgc cag gcc act ggg gac tac atg ggt gtg tct        8461
Met Tyr Met Gly Ser Arg Gln Ala Thr Gly Asp Tyr Met Gly Val Ser
        2785                2790                2795 ctg cgt gac aag aag gtg cac tgg gtg tat cag ctg ggt gag gcg ggc        8509
Leu Arg Asp Lys Lys Val His Trp Val Tyr Gln Leu Gly Glu Ala Gly
    2800                2805                2810 cct gca gtc cta agc atc gat gag gac att ggg gag cag ttc gca gct        8557
Pro Ala Val Leu Ser Ile Asp Glu Asp Ile Gly Glu Gln Phe Ala Ala
2815                2820                2825                2830 gtc agc ctg gac agg act ctc cag ttt ggc cac atg tcc gtc aca gtg        8605
Val Ser Leu Asp Arg Thr Leu Gln Phe Gly His Met Ser Val Thr Val
        2835                2840                2845 gag aga cag atg atc cag gaa acc aag ggt gac acg gtg gcc cct ggg        8653
Glu Arg Gln Met Ile Gln Glu Thr Lys Gly Asp Thr Val Ala Pro Gly
    2850                2855                2860 gca gag ggg ctg ctc aac ctg cgg cca gac gac ttc gtc ttc tac gtc        8701
Ala Glu Gly Leu Leu Asn Leu Arg Pro Asp Asp Phe Val Phe Tyr Val
2865                2870                2875 ggg ggg tac ccc agt acc ttc acg ccc cct ccc ctg ctt cgc ttc ccc        8749
Gly Gly Tyr Pro Ser Thr Phe Thr Pro Pro Pro Leu Leu Arg Phe Pro
        2880                2885                2890 ggc tac cgg ggc tgc atc gag atg gac acg ctg aat gag gag gtg gtc        8797
Gly Tyr Arg Gly Cys Ile Glu Met Asp Thr Leu Asn Glu Glu Val Val
2895                2900                2905                2910 agc ctc tac aac ttc gag agg acc ttc cag ctg gac acg gct gtg gac        8845
Ser Leu Tyr Asn Phe Glu Arg Thr Phe Gln Leu Asp Thr Ala Val Asp
        2915                2920                2925 agg cct tgt gcc cgc tcc aag tcg acc ggg gac ccg tgg ctc acg gac        8893
Arg Pro Cys Ala Arg Ser Lys Ser Thr Gly Asp Pro Trp Leu Thr Asp
    2930                2935                2940
```

```
ggc tcc tac ctg gac ggc acc ggc ttc gcc cgc atc agc ttc gac agt    8941
Gly Ser Tyr Leu Asp Gly Thr Gly Phe Ala Arg Ile Ser Phe Asp Ser
        2945                2950                2955 cag atc agc acc acc aag cgc ttc gag cag gag ctg cgg ctc gtg tcc    8989
Gln Ile Ser Thr Thr Lys Arg Phe Glu Gln Glu Leu Arg Leu Val Ser
        2960                2965                2970 tac agc ggg gtg ctc ttc ttc ctg aag cag cag agc cag ttc ctg tgc    9037
Tyr Ser Gly Val Leu Phe Phe Leu Lys Gln Gln Ser Gln Phe Leu Cys
2975                2980                2985                2990 ttg gcc gtg caa gaa ggc agc ctc gtg ctg ttg tat gac ttt ggg gct    9085
Leu Ala Val Gln Glu Gly Ser Leu Val Leu Leu Tyr Asp Phe Gly Ala
            2995                3000                3005 ggc ctg aaa aag gcc gtc cca ctg cag ccc cca ccg ccc ctg acc tcg    9133
Gly Leu Lys Lys Ala Val Pro Leu Gln Pro Pro Pro Pro Leu Thr Ser
        3010                3015                3020 gcc agc aag gcg atc cag gtg ttc ctg ctg ggg ggc agc cgc aag cgt    9181
Ala Ser Lys Ala Ile Gln Val Phe Leu Leu Gly Gly Ser Arg Lys Arg
        3025                3030                3035 gtg ctg gtg cgt gtg gag cgg gcc acg gtg tac agc gtg gag cag gac    9229
Val Leu Val Arg Val Glu Arg Ala Thr Val Tyr Ser Val Glu Gln Asp
    3040                3045                3050 aat gat ctg gag ctg gcc gac gcc tac tac ctg ggg ggc gtg ccg ccc    9277
Asn Asp Leu Glu Leu Ala Asp Ala Tyr Tyr Leu Gly Gly Val Pro Pro
3055                3060                3065                3070 gac cag ctg ccc ccg agc ctg cga tgg ctc ttc ccc acc gga ggc tca    9325
Asp Gln Leu Pro Pro Ser Leu Arg Trp Leu Phe Pro Thr Gly Gly Ser
            3075                3080                3085 gtc cgt ggc tgc gtc aaa ggc atc aag gcc ctg ggc aag tat gtg gac    9373
Val Arg Gly Cys Val Lys Gly Ile Lys Ala Leu Gly Lys Tyr Val Asp
        3090                3095                3100 ctc aag cgg ctg aac acg aca ggc gtg agc gcc ggc tgc acc gcc gac    9421
Leu Lys Arg Leu Asn Thr Thr Gly Val Ser Ala Gly Cys Thr Ala Asp
        3105                3110                3115 ctg ctg gtg ggg cgc gcc atg act ttc cat ggc cac ggc ttc ctt cgc    9469
Leu Leu Val Gly Arg Ala Met Thr Phe His Gly His Gly Phe Leu Arg
    3120                3125                3130 ctg gcg ctc tcg aac gtg gca ccg ctc act ggc aac gtc tac tcc ggc    9517
Leu Ala Leu Ser Asn Val Ala Pro Leu Thr Gly Asn Val Tyr Ser Gly
3135                3140                3145                3150 ttc ggc ttc cac agc gcc cag gac agt gcc ctg ctc tac tac cgg gcg    9565
Phe Gly Phe His Ser Ala Gln Asp Ser Ala Leu Leu Tyr Tyr Arg Ala
            3155                3160                3165 tcc ccg gat ggg cta tgc cag gtg tcc ctg cag cag ggc cgt gtg agc    9613
Ser Pro Asp Gly Leu Cys Gln Val Ser Leu Gln Gln Gly Arg Val Ser
        3170                3175                3180 cta cag ctc ctg agg act gaa gtg aaa act caa gcg ggc ttc gcc gat    9661
Leu Gln Leu Leu Arg Thr Glu Val Lys Thr Gln Ala Gly Phe Ala Asp
        3185                3190                3195 ggt gcc ccc cat tac gtc gcc ttc tac agc aat gcc acg gga gtc tgg    9709
Gly Ala Pro His Tyr Val Ala Phe Tyr Ser Asn Ala Thr Gly Val Trp
    3200                3205                3210 ctg tat gtc gat gac cag ctc cag cag atg aag ccc cac cgg gga cca    9757
Leu Tyr Val Asp Asp Gln Leu Gln Gln Met Lys Pro His Arg Gly Pro
3215                3220                3225                3230 ccc ccc gag ctc cag ccg cag cct gag ggg ccc ccg agg ctc ctc ctg    9805
Pro Pro Glu Leu Gln Pro Gln Pro Glu Gly Pro Pro Arg Leu Leu Leu
            3235                3240                3245 gga ggc ctg cct gag tct ggc acc att tac aac ttc agt ggc tgc atc    9853
Gly Gly Leu Pro Glu Ser Gly Thr Ile Tyr Asn Phe Ser Gly Cys Ile
        3250                3255                3260
```

```
agc aac gtc ttc gtg cag cgg ctc ctg ggc cca cag cgc gta ttt gat    9901
Ser Asn Val Phe Val Gln Arg Leu Leu Gly Pro Gln Arg Val Phe Asp
    3265                3270                3275 ctg cag cag aac ctg ggc agc gtc aat gtg agc acg ggc tgt gca ccc    9949
Leu Gln Gln Asn Leu Gly Ser Val Asn Val Ser Thr Gly Cys Ala Pro
3280                3285                3290 gcc ctg caa gcc cag acc ccg ggc ctg ggg cct aga gga ctc cag gcc    9997
Ala Leu Gln Ala Gln Thr Pro Gly Leu Gly Pro Arg Gly Leu Gln Ala
3295                3300                3305                3310 acc gcc cgg aag gcc tcc cgc cgc agc cgt cag ccc gcc cgg cat cct    10045
Thr Ala Arg Lys Ala Ser Arg Arg Ser Arg Gln Pro Ala Arg His Pro
            3315                3320                3325 gcc tgc atg ctg ccc cca cac ctc agg acc acc cga gac tcc tac cag    10093
Ala Cys Met Leu Pro Pro His Leu Arg Thr Thr Arg Asp Ser Tyr Gln
        3330                3335                3340 ttt ggg ggt tcc ctg tcc agt cac ctg gag ttt gtg ggc atc ctg gcc    10141
Phe Gly Gly Ser Leu Ser Ser His Leu Glu Phe Val Gly Ile Leu Ala
    3345                3350                3355 cga cat agg aac tgg ccc agt ctc tcc atg cac gtc ctc ccg cga agc    10189
Arg His Arg Asn Trp Pro Ser Leu Ser Met His Val Leu Pro Arg Ser
3360                3365                3370 tcc cga ggc ctc ctc ctc ttc act gcc cgt ctg agg ccc ggc agc ccc    10237
Ser Arg Gly Leu Leu Leu Phe Thr Ala Arg Leu Arg Pro Gly Ser Pro
3375                3380                3385                3390 tcc ctg gcg ctc ttc ctg agc aat ggc cac ttc gtt gca cag atg gaa    10285
Ser Leu Ala Leu Phe Leu Ser Asn Gly His Phe Val Ala Gln Met Glu
            3395                3400                3405 ggc ctc ggg act cgg ctc cgc gcc cag agc cgc cag cgc tcc cgg cct    10333
Gly Leu Gly Thr Arg Leu Arg Ala Gln Ser Arg Gln Arg Ser Arg Pro
        3410                3415                3420 ggc cgc tgg cac aag gtc tcc gtg cgc tgg gag aag aac cgg atc ctg    10381
Gly Arg Trp His Lys Val Ser Val Arg Trp Glu Lys Asn Arg Ile Leu
    3425                3430                3435 ctg gtg acg gac ggg gcc cgg gcc tgg agc cag gag ggg ccg cac cgg    10429
Leu Val Thr Asp Gly Ala Arg Ala Trp Ser Gln Glu Gly Pro His Arg
3440                3445                3450 cag cac cag ggg gca gag cac ccc cag ccc cac acc ctc ttt gtg ggc    10477
Gln His Gln Gly Ala Glu His Pro Gln Pro His Thr Leu Phe Val Gly
3455                3460                3465                3470 ggc ctc ccg gcc agc agc cac agc tcc aaa ctt ccg gtg acc gtc ggg    10525
Gly Leu Pro Ala Ser Ser His Ser Ser Lys Leu Pro Val Thr Val Gly
            3475                3480                3485 ttc agc ggc tgt gtg aag aga ctg agg ctg cac ggg agg ccc ctg ggg    10573
Phe Ser Gly Cys Val Lys Arg Leu Arg Leu His Gly Arg Pro Leu Gly
        3490                3495                3500 gcc ccc aca cgg atg gca ggg gtc aca ccc tgc atc ttg ggc ccc ctg    10621
Ala Pro Thr Arg Met Ala Gly Val Thr Pro Cys Ile Leu Gly Pro Leu
    3505                3510                3515 gag gcg ggc ctg ttc ttc cca ggc agc ggg gga gtt atc act tta gac    10669
Glu Ala Gly Leu Phe Phe Pro Gly Ser Gly Gly Val Ile Thr Leu Asp
3520                3525                3530 ctc cca gga gct aca ctg cct gat gtg ggc ctg gaa ctg gag gtg cgg    10717
Leu Pro Gly Ala Thr Leu Pro Asp Val Gly Leu Glu Leu Glu Val Arg
3535                3540                3545                3550 ccc ctg gca gtc acc gga ctg atc ttc cac ttg ggc cag gcc cgg acg    10765
Pro Leu Ala Val Thr Gly Leu Ile Phe His Leu Gly Gln Ala Arg Thr
            3555                3560                3565 ccc ccc tac ttg cag ttg cag gtg acc gag aag caa gtc ctg ctg cgg    10813
Pro Pro Tyr Leu Gln Leu Gln Val Thr Glu Lys Gln Val Leu Leu Arg
```

```
                       3570                3575                3580
gcg gat gac gga gca ggg gag ttc tcc acg tca gtg acc cgc ccc tca    10861
Ala Asp Asp Gly Ala Gly Glu Phe Ser Thr Ser Val Thr Arg Pro Ser
    3585                3590                3595 gtg ctg tgt gat ggc cag tgg cac cgg cta gcg gtg atg aaa agc ggg    10909
Val Leu Cys Asp Gly Gln Trp His Arg Leu Ala Val Met Lys Ser Gly
3600                3605                3610 aat gtg ctc cgg ctg gag gtg gac gcg cag agc aac cac acc gtg ggc    10957
Asn Val Leu Arg Leu Glu Val Asp Ala Gln Ser Asn His Thr Val Gly
3615                3620                3625                3630 ccc ttg ctg gcg gct gca gct ggt gcc cca gcc cct ctg tac ctc ggg    11005
Pro Leu Leu Ala Ala Ala Ala Gly Ala Pro Ala Pro Leu Tyr Leu Gly
                3635                3640                3645 ggc ctg cct gag ccc atg gcc gtg cag ccc tgg ccc ccc gcc tac tgc    11053
Gly Leu Pro Glu Pro Met Ala Val Gln Pro Trp Pro Pro Ala Tyr Cys
                3650                3655                3660 ggc tgc atg agg agg ctg gcg gtg aac cgg tcc ccc gtc gcc atg act    11101
Gly Cys Met Arg Arg Leu Ala Val Asn Arg Ser Pro Val Ala Met Thr
        3665                3670                3675 cgc tct gtg gag gtc cac ggg gca gtg ggg gcc agt ggc tgc cca gcc    11149
Arg Ser Val Glu Val His Gly Ala Val Gly Ala Ser Gly Cys Pro Ala
    3680                3685                3690 gcc taggacacag ccaaccccgg cccctggtca ggcccctgca gctgcctcac         11202
Ala
3695 accgccccct tgtgctcgcct cataggtgtc tatttggact ctaagctcta cgggtgacag  11262 atcttgtttc tgaagatggt ttaagttata gcttcttaaa cgaaagaata aaatactgca  11322 aaatgccgga attcgatatc aagcttat                                    11350

<210> SEQ ID NO 2
<211> LENGTH: 3695
<212> TYPE: PRT
<213> ORGANISM: Homo sapiens

<400> SEQUENCE: 2

Met Ala Lys Arg Leu Cys Ala Gly Ser Ala Leu Cys Val Arg Gly Pro
1               5                   10                  15

Arg Gly Pro Ala Pro Leu Leu Val Gly Leu Ala Leu Leu Gly Ala
            20                  25                  30

Ala Arg Ala Arg Glu Glu Ala Gly Gly Gly Phe Ser Leu His Pro Pro
        35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Gly Asp Pro Asn Gln
                85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
        115                 120                 125

Gln Ser Pro Pro Leu Ser Arg Gly Leu Glu Tyr Asn Glu Val Asn Val
    130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
```

-continued

```
                165                 170                 175
Asp Phe Gly Arg Thr Tyr Gln Pro Trp Gln Phe Ala Ser Ser Lys
            180                 185                 190
Arg Asp Cys Leu Glu Arg Phe Gly Pro Gln Thr Leu Glu Arg Ile Thr
        195                 200                 205
Arg Asp Asp Ala Ala Ile Cys Thr Thr Glu Tyr Ser Arg Ile Val Pro
    210                 215                 220
Leu Glu Asn Gly Glu Ile Val Val Ser Leu Val Asn Gly Arg Pro Gly
225                 230                 235                 240
Ala Met Asn Phe Ser Tyr Ser Pro Leu Leu Arg Glu Phe Thr Lys Ala
            245                 250                 255
Thr Asn Val Arg Leu Arg Phe Leu Arg Thr Asn Thr Leu Leu Gly His
        260                 265                 270
Leu Met Gly Lys Ala Leu Arg Asp Pro Thr Val Thr Arg Arg Tyr Tyr
    275                 280                 285
Tyr Ser Ile Lys Asp Ile Ser Ile Gly Gly Arg Cys Val Cys His Gly
    290                 295                 300
His Ala Asp Ala Cys Asp Ala Lys Asp Pro Thr Asp Pro Phe Arg Leu
305                 310                 315                 320
Gln Cys Thr Cys Gln His Asn Thr Cys Gly Gly Thr Cys Asp Arg Cys
            325                 330                 335
Cys Pro Gly Phe Asn Gln Gln Pro Trp Lys Pro Ala Thr Ala Asn Ser
            340                 345                 350
Ala Asn Glu Cys Gln Ser Cys Asn Cys Tyr Gly His Ala Thr Asp Cys
            355                 360                 365
Tyr Tyr Asp Pro Glu Val Asp Arg Arg Arg Ala Ser Gln Ser Leu Asp
    370                 375                 380
Gly Thr Tyr Gln Gly Gly Gly Val Cys Ile Asp Cys Gln His His Thr
385                 390                 395                 400
Ala Gly Val Asn Cys Glu Arg Cys Leu Pro Gly Phe Tyr Arg Ser Pro
            405                 410                 415
Asn His Pro Leu Asp Ser Pro His Val Cys Arg Arg Cys Asn Cys Glu
            420                 425                 430
Ser Asp Phe Thr Asp Gly Thr Cys Glu Asp Leu Thr Gly Arg Cys Tyr
        435                 440                 445
Cys Arg Pro Asn Phe Ser Gly Glu Arg Cys Asp Val Cys Ala Glu Gly
    450                 455                 460
Phe Thr Gly Phe Pro Ser Cys Tyr Pro Thr Pro Ser Ser Ser Asn Asp
465                 470                 475                 480
Thr Arg Glu Gln Val Leu Pro Ala Gly Gln Ile Val Asn Cys Asp Cys
            485                 490                 495
Ser Ala Ala Gly Thr Gln Gly Asn Ala Cys Arg Lys Asp Pro Arg Val
            500                 505                 510
Gly Arg Cys Leu Cys Lys Pro Asn Phe Gln Gly Thr His Cys Glu Leu
        515                 520                 525
Cys Ala Pro Gly Phe Tyr Gly Pro Gly Cys Gln Pro Cys Gln Cys Ser
    530                 535                 540
Ser Pro Gly Val Ala Asp Asp Arg Cys Asp Pro Asp Thr Gly Gln Cys
545                 550                 555                 560
Arg Cys Arg Val Gly Phe Glu Gly Ala Thr Cys Asp Arg Cys Ala Pro
            565                 570                 575
Gly Tyr Phe His Phe Pro Leu Cys Gln Leu Cys Gly Cys Ser Pro Ala
            580                 585                 590
```

-continued

Gly Thr Leu Pro Glu Gly Cys Asp Glu Ala Gly Arg Cys Leu Cys Gln
            595                 600                 605
Pro Glu Phe Ala Gly Pro His Cys Asp Arg Cys Arg Pro Gly Tyr His
        610                 615                 620
Gly Phe Pro Asn Cys Gln Ala Cys Thr Cys Asp Pro Arg Gly Ala Leu
625                 630                 635                 640
Asp Gln Leu Cys Gly Ala Gly Leu Cys Arg Cys Arg Pro Gly Tyr
                645                 650                 655
Thr Gly Thr Ala Cys Gln Glu Cys Ser Pro Gly Phe His Gly Phe Pro
            660                 665                 670
Ser Cys Val Pro Cys His Cys Ser Ala Glu Gly Ser Leu His Ala Ala
        675                 680                 685
Cys Asp Pro Arg Ser Gly Gln Cys Ser Cys Arg Pro Arg Val Thr Gly
690                 695                 700
Leu Arg Cys Asp Thr Cys Val Pro Gly Ala Tyr Asn Phe Pro Tyr Cys
705                 710                 715                 720
Glu Ala Gly Ser Cys His Pro Ala Gly Leu Ala Pro Val Asp Pro Ala
                725                 730                 735
Leu Pro Glu Ala Gln Val Pro Cys Met Cys Arg Ala His Val Glu Gly
            740                 745                 750
Pro Ser Cys Asp Arg Cys Lys Pro Gly Phe Trp Gly Leu Ser Pro Ser
        755                 760                 765
Asn Pro Glu Gly Cys Thr Arg Cys Ser Cys Asp Leu Arg Gly Thr Leu
770                 775                 780
Gly Gly Val Ala Glu Cys Gln Pro Gly Thr Gly Gln Cys Phe Cys Lys
785                 790                 795                 800
Pro His Val Cys Gly Gln Ala Cys Ala Ser Cys Lys Asp Gly Phe Phe
                805                 810                 815
Gly Leu Asp Gln Ala Asp Tyr Phe Gly Cys Arg Ser Cys Arg Cys Asp
            820                 825                 830
Ile Gly Gly Ala Leu Gly Gln Ser Cys Glu Pro Arg Thr Gly Val Cys
        835                 840                 845
Arg Cys Arg Pro Asn Thr Gln Gly Pro Thr Cys Ser Glu Pro Ala Arg
850                 855                 860
Asp His Tyr Leu Pro Asp Leu His His Leu Arg Leu Glu Leu Glu Glu
865                 870                 875                 880
Ala Ala Thr Pro Glu Gly His Ala Val Arg Phe Gly Phe Asn Pro Leu
                885                 890                 895
Glu Phe Glu Asn Phe Ser Trp Arg Gly Tyr Ala Gln Met Ala Pro Val
            900                 905                 910
Gln Pro Arg Ile Val Ala Arg Leu Asn Leu Thr Ser Pro Asp Leu Phe
        915                 920                 925
Trp Leu Val Phe Arg Tyr Val Asn Arg Gly Ala Met Ser Val Ser Gly
        930                 935                 940
Arg Val Ser Val Arg Glu Glu Gly Arg Ser Ala Ala Cys Ala Asn Cys
945                 950                 955                 960
Thr Ala Gln Ser Gln Pro Val Ala Phe Pro Pro Ser Thr Glu Pro Ala
                965                 970                 975
Phe Ile Thr Val Pro Gln Arg Gly Phe Gly Glu Pro Phe Val Leu Asn
            980                 985                 990
Pro Gly Thr Trp Ala Leu Arg Val Glu Ala Glu Gly Val Leu Leu Asp
        995                 1000                1005

-continued

```
Tyr Val Leu Leu Pro Ser Ala Tyr Tyr Glu Ala Ala Leu Leu Gln
1010                1015                1020

Leu Arg Val Thr Glu Ala Cys Thr Tyr Arg Pro Ser Ala Gln Gln Ser
1025                1030                1035                1040

Gly Asp Asn Cys Leu Leu Tyr Thr His Leu Pro Leu Asp Gly Phe Pro
                1045                1050                1055

Ser Ala Ala Gly Leu Glu Ala Leu Cys Arg Gln Asp Asn Ser Leu Pro
                1060                1065                1070

Arg Pro Cys Pro Thr Glu Gln Leu Ser Pro Ser His Pro Pro Leu Ile
                1075                1080                1085

Thr Cys Thr Gly Ser Asp Val Asp Val Gln Leu Gln Val Ala Val Pro
                1090                1095                1100

Gln Pro Gly Arg Tyr Ala Leu Val Val Glu Tyr Ala Asn Glu Asp Ala
1105                1110                1115                1120

Arg Gln Glu Val Gly Val Ala Val His Thr Pro Gln Arg Ala Pro Gln
                1125                1130                1135

Gln Gly Leu Leu Ser Leu His Pro Cys Leu Tyr Ser Thr Leu Cys Arg
                1140                1145                1150

Gly Thr Ala Arg Asp Thr Gln Asp His Leu Ala Val Phe His Leu Asp
                1155                1160                1165

Ser Glu Ala Ser Val Arg Leu Thr Ala Glu Gln Ala Arg Phe Phe Leu
                1170                1175                1180

His Gly Val Thr Leu Val Pro Ile Glu Glu Phe Ser Pro Glu Phe Val
1185                1190                1195                1200

Glu Pro Arg Val Ser Cys Ile Ser Ser His Gly Ala Phe Gly Pro Asn
                1205                1210                1215

Ser Ala Ala Cys Leu Pro Ser Arg Phe Pro Lys Pro Pro Gln Pro Ile
                1220                1225                1230

Ile Leu Arg Asp Cys Gln Val Ile Pro Leu Pro Pro Gly Leu Pro Leu
                1235                1240                1245

Thr His Ala Gln Asp Leu Thr Pro Ala Thr Ser Pro Ala Gly Pro Arg
                1250                1255                1260

Pro Arg Pro Pro Thr Ala Val Asp Pro Asp Ala Glu Pro Thr Leu Leu
1265                1270                1275                1280

Arg Glu Pro Gln Ala Thr Val Val Phe Thr Thr His Val Pro Thr Leu
                1285                1290                1295

Gly Arg Tyr Ala Phe Leu Leu His Gly Tyr Gln Pro Ala His Pro Thr
                1300                1305                1310

Phe Pro Val Glu Val Leu Ile Asn Ala Gly Arg Val Trp Gln Gly His
                1315                1320                1325

Ala Asn Ala Ser Phe Cys Pro His Gly Tyr Gly Cys Arg Thr Leu Val
                1330                1335                1340

Val Cys Glu Gly Gln Ala Leu Leu Asp Val Thr His Ser Glu Leu Thr
1345                1350                1355                1360

Val Thr Val Arg Val Pro Glu Gly Arg Trp Leu Trp Leu Asp Tyr Val
                1365                1370                1375

Leu Val Val Pro Glu Asn Val Tyr Ser Phe Gly Tyr Leu Arg Glu Glu
                1380                1385                1390

Pro Leu Asp Lys Ser Tyr Asp Phe Ile Ser His Cys Ala Ala Gln Gly
                1395                1400                1405

Tyr His Ile Ser Pro Ser Ser Ser Leu Phe Cys Arg Asn Ala Ala
                1410                1415                1420

Ala Ser Leu Ser Leu Phe Tyr Asn Asn Gly Ala Arg Pro Cys Gly Cys
```

-continued

```
        1425                1430                1435                1440
His Glu Val Gly Ala Thr Gly Pro Thr Cys Glu Pro Phe Gly Gly Gln
                1445                1450                1455
Cys Pro Cys His Ala His Val Ile Gly Arg Asp Cys Ser Arg Cys Ala
                1460                1465                1470
Thr Gly Tyr Trp Gly Phe Pro Asn Cys Arg Pro Cys Asp Cys Gly Ala
            1475                1480                1485
Arg Leu Cys Asp Glu Leu Thr Gly Gln Cys Ile Cys Pro Pro Arg Thr
        1490                1495                1500
Ile Pro Pro Asp Cys Leu Leu Cys Gln Pro Gln Thr Phe Gly Cys His
1505                1510                1515                1520
Pro Leu Val Gly Cys Glu Glu Cys Asn Cys Ser Gly Pro Gly Ile Gln
                1525                1530                1535
Glu Leu Thr Asp Pro Thr Cys Asp Thr Asp Ser Gly Gln Cys Lys Cys
            1540                1545                1550
Arg Pro Asn Val Thr Gly Arg Arg Cys Asp Thr Cys Ser Pro Gly Phe
        1555                1560                1565
His Gly Tyr Pro Arg Cys Arg Pro Cys Asp Cys His Glu Ala Gly Thr
    1570                1575                1580
Ala Pro Gly Val Cys Asp Pro Leu Thr Gly Gln Cys Tyr Cys Lys Glu
1585                1590                1595                1600
Asn Val Gln Gly Pro Lys Cys Asp Gln Cys Ser Leu Gly Thr Phe Ser
                1605                1610                1615
Leu Asp Ala Ala Asn Pro Lys Gly Cys Thr Arg Cys Phe Cys Phe Gly
            1620                1625                1630
Ala Thr Glu Arg Cys Arg Ser Ser Tyr Thr Arg Gln Glu Phe Val
        1635                1640                1645
Asp Met Glu Gly Trp Val Leu Leu Ser Thr Asp Arg Gln Val Val Pro
    1650                1655                1660
His Glu Arg Gln Pro Gly Thr Glu Met Leu Arg Ala Asp Leu Arg His
1665                1670                1675                1680
Val Pro Glu Ala Val Pro Glu Ala Phe Pro Glu Leu Tyr Trp Gln Ala
                1685                1690                1695
Pro Pro Ser Tyr Leu Gly Asp Arg Val Ser Ser Tyr Gly Gly Thr Leu
            1700                1705                1710
Arg Tyr Glu Leu His Ser Glu Thr Gln Arg Gly Asp Val Phe Val Pro
        1715                1720                1725
Met Glu Ser Arg Pro Asp Val Val Leu Gln Gly Asn Gln Met Ser Ile
    1730                1735                1740
Thr Phe Leu Glu Pro Ala Tyr Pro Thr Pro Gly His Val His Arg Gly
1745                1750                1755                1760
Gln Leu Gln Leu Val Glu Gly Asn Phe Arg His Thr Glu Thr Arg Asn
                1765                1770                1775
Thr Val Ser Arg Glu Glu Leu Met Met Val Leu Ala Ser Leu Glu Gln
            1780                1785                1790
Leu Gln Ile Arg Ala Leu Phe Ser Gln Ile Ser Ser Ala Val Ser Leu
        1795                1800                1805
Arg Arg Val Ala Leu Glu Val Ala Ser Pro Ala Gly Gln Gly Ala Leu
    1810                1815                1820
Ala Ser Asn Val Glu Leu Cys Leu Cys Pro Ala Ser Tyr Arg Gly Asp
1825                1830                1835                1840
Ser Cys Gln Glu Cys Ala Pro Gly Phe Tyr Arg Asp Val Lys Gly Leu
                1845                1850                1855
```

-continued

Phe Leu Gly Arg Cys Val Pro Cys Gln Cys His Gly His Ser Asp Arg
        1860                1865                1870

Cys Leu Pro Gly Ser Gly Val Cys Val Asp Cys Gln His Asn Thr Glu
        1875                1880                1885

Gly Ala His Cys Glu Arg Cys Gln Ala Gly Phe Met Ser Ser Arg Asp
        1890                1895                1900

Asp Pro Ser Ala Pro Cys Val Ser Cys Pro Cys Pro Leu Ser Val Pro
1905                1910                1915                1920

Ser Asn Asn Phe Ala Glu Gly Cys Val Leu Arg Gly Arg Thr Gln
            1925                1930                1935

Cys Leu Cys Lys Pro Gly Tyr Ala Gly Ala Ser Cys Glu Arg Cys Ala
        1940                1945                1950

Pro Gly Phe Phe Gly Asn Pro Leu Val Leu Gly Ser Ser Cys Gln Pro
            1955                1960                1965

Cys Asp Cys Ser Gly Asn Gly Asp Pro Asn Leu Leu Phe Ser Asp Cys
        1970                1975                1980

Asp Pro Leu Thr Gly Ala Cys Arg Gly Cys Leu Arg His Thr Thr Gly
1985                1990                1995                2000

Pro Arg Cys Glu Ile Cys Ala Pro Gly Phe Tyr Gly Asn Ala Leu Leu
            2005                2010                2015

Pro Gly Asn Cys Thr Arg Cys Asp Cys Thr Pro Cys Gly Thr Glu Ala
            2020                2025                2030

Cys Asp Pro His Ser Gly His Cys Leu Cys Lys Ala Gly Val Thr Gly
        2035                2040                2045

Arg Arg Cys Asp Arg Cys Gln Glu Gly His Phe Gly Phe Asn Gly Cys
2050                2055                2060

Gly Gly Cys Arg Pro Cys Ala Cys Gly Pro Ala Ala Glu Gly Ser Glu
2065                2070                2075                2080

Cys His Pro Gln Ser Gly Gln Cys His Cys Arg Pro Gly Thr Met Gly
            2085                2090                2095

Pro Gln Cys Arg Glu Cys Ala Pro Gly Tyr Trp Gly Leu Pro Glu Gln
            2100                2105                2110

Gly Cys Arg Arg Cys Gln Cys Pro Gly Gly Arg Cys Asp Pro His Thr
        2115                2120                2125

Gly Arg Cys Asn Cys Pro Pro Gly Leu Ser Gly Glu Arg Cys Asp Thr
        2130                2135                2140

Cys Ser Gln Gln His Gln Val Pro Val Pro Gly Gly Pro Val Gly His
2145                2150                2155                2160

Ser Ile His Cys Glu Val Cys Asp His Cys Val Val Leu Leu Leu Asp
            2165                2170                2175

Asp Leu Glu Arg Ala Gly Ala Leu Leu Pro Ala Ile His Glu Gln Leu
        2180                2185                2190

Arg Gly Ile Asn Ala Ser Ser Met Ala Trp Ala Arg Leu His Arg Leu
        2195                2200                2205

Asn Ala Ser Ile Ala Asp Leu Gln Ser Gln Leu Arg Ser Pro Leu Gly
        2210                2215                2220

Pro Arg His Glu Thr Ala Gln Gln Leu Glu Val Leu Glu Gln Gln Ser
2225                2230                2235                2240

Thr Ser Leu Gly Gln Asp Ala Arg Arg Leu Gly Gly Gln Ala Val Gly
            2245                2250                2255

Thr Arg Asp Gln Ala Ser Gln Leu Leu Ala Gly Thr Glu Ala Thr Leu
        2260                2265                2270

-continued

```
Gly His Ala Lys Thr Leu Leu Ala Ala Ile Arg Ala Val Asp Arg Thr
    2275                2280                2285

Leu Ser Glu Leu Met Ser Gln Thr Gly His Leu Gly Leu Ala Asn Ala
    2290                2295                2300

Ser Ala Pro Ser Gly Glu Gln Leu Leu Arg Thr Leu Ala Glu Val Glu
2305                2310                2315                2320

Arg Leu Leu Trp Glu Met Arg Ala Arg Asp Leu Gly Ala Pro Gln Ala
            2325                2330                2335

Ala Ala Glu Ala Glu Leu Ala Ala Gln Arg Leu Leu Ala Arg Val
            2340                2345                2350

Gln Glu Gln Leu Ser Ser Leu Trp Glu Glu Asn Gln Ala Leu Ala Thr
            2355                2360                2365

Gln Thr Arg Asp Arg Leu Ala Gln His Glu Ala Gly Leu Met Asp Leu
    2370                2375                2380

Arg Glu Ala Leu Asn Arg Ala Val Asp Ala Thr Arg Glu Ala Gln Glu
2385                2390                2395                2400

Leu Asn Ser Arg Asn Gln Glu Arg Leu Glu Glu Ala Leu Gln Arg Lys
            2405                2410                2415

Gln Glu Leu Ser Arg Asp Asn Ala Thr Leu Gln Ala Thr Leu His Ala
            2420                2425                2430

Ala Arg Asp Thr Leu Ala Ser Val Phe Arg Leu Leu His Ser Leu Asp
    2435                2440                2445

Gln Ala Lys Glu Glu Leu Glu Arg Leu Ala Ala Ser Leu Asp Gly Ala
    2450                2455                2460

Arg Thr Pro Leu Leu Gln Arg Met Gln Thr Phe Ser Pro Ala Gly Ser
2465                2470                2475                2480

Lys Leu Arg Leu Val Glu Ala Ala Glu Ala His Ala Gln Gln Leu Gly
            2485                2490                2495

Gln Leu Ala Leu Asn Leu Ser Ser Ile Ile Leu Asp Val Asn Gln Asp
            2500                2505                2510

Arg Leu Thr Gln Arg Ala Ile Glu Ala Ser Asn Ala Tyr Ser Arg Ile
    2515                2520                2525

Leu Gln Ala Val Gln Ala Ala Glu Asp Ala Ala Gly Gln Ala Leu Gln
    2530                2535                2540

Gln Ala Asp His Thr Trp Ala Thr Val Val Arg Gln Gly Leu Val Asp
2545                2550                2555                2560

Arg Ala Gln Gln Leu Leu Ala Asn Ser Thr Ala Leu Glu Glu Ala Met
            2565                2570                2575

Leu Gln Glu Gln Gln Arg Leu Gly Leu Val Trp Ala Ala Leu Gln Gly
            2580                2585                2590

Ala Arg Thr Gln Leu Arg Asp Val Arg Ala Lys Lys Asp Gln Leu Glu
    2595                2600                2605

Ala His Ile Gln Ala Ala Gln Ala Met Leu Ala Met Asp Thr Asp Glu
    2610                2615                2620

Thr Ser Lys Lys Ile Ala His Ala Lys Ala Val Ala Ala Glu Ala Gln
2625                2630                2635                2640

Asp Thr Ala Thr Arg Val Gln Ser Gln Leu Gln Ala Met Gln Glu Asn
            2645                2650                2655

Val Glu Arg Trp Gln Gly Gln Tyr Glu Gly Leu Arg Gly Gln Asp Leu
            2660                2665                2670

Gly Gln Ala Val Leu Asp Ala Gly His Ser Val Ser Thr Leu Glu Lys
    2675                2680                2685

Thr Leu Pro Gln Leu Leu Ala Lys Leu Ser Ile Leu Glu Asn Arg Gly
```

-continued

```
               2690                2695                 2700
Val His Asn Ala Ser Leu Ala Leu Ser Ala Ser Ile Gly Arg Val Arg
2705                2710                2715                2720

Glu Leu Ile Ala Gln Ala Arg Gly Ala Ala Ser Lys Val Lys Val Pro
                2725                2730                2735

Met Lys Phe Asn Gly Arg Ser Gly Val Gln Leu Arg Thr Pro Arg Asp
            2740                2745                2750

Leu Ala Asp Leu Ala Ala Tyr Thr Ala Leu Lys Phe Tyr Leu Gln Gly
        2755                2760                2765

Pro Glu Pro Glu Pro Gly Gln Gly Thr Glu Asp Arg Phe Val Met Tyr
    2770                2775                2780

Met Gly Ser Arg Gln Ala Thr Gly Asp Tyr Met Gly Val Ser Leu Arg
2785                2790                2795                2800

Asp Lys Lys Val His Trp Val Tyr Gln Leu Gly Glu Ala Gly Pro Ala
                2805                2810                2815

Val Leu Ser Ile Asp Glu Asp Ile Gly Glu Gln Phe Ala Ala Val Ser
            2820                2825                2830

Leu Asp Arg Thr Leu Gln Phe Gly His Met Ser Val Thr Val Glu Arg
        2835                2840                2845

Gln Met Ile Gln Glu Thr Lys Gly Asp Thr Val Ala Pro Gly Ala Glu
    2850                2855                2860

Gly Leu Leu Asn Leu Arg Pro Asp Asp Phe Val Phe Tyr Val Gly Gly
2865                2870                2875                2880

Tyr Pro Ser Thr Phe Thr Pro Pro Leu Leu Arg Phe Pro Gly Tyr
                2885                2890                2895

Arg Gly Cys Ile Glu Met Asp Thr Leu Asn Glu Glu Val Val Ser Leu
            2900                2905                2910

Tyr Asn Phe Glu Arg Thr Phe Gln Leu Asp Thr Ala Val Asp Arg Pro
        2915                2920                2925

Cys Ala Arg Ser Lys Ser Thr Gly Asp Pro Trp Leu Thr Asp Gly Ser
    2930                2935                2940

Tyr Leu Asp Gly Thr Gly Phe Ala Arg Ile Ser Phe Asp Ser Gln Ile
2945                2950                2955                2960

Ser Thr Thr Lys Arg Phe Glu Gln Glu Leu Arg Leu Val Ser Tyr Ser
                2965                2970                2975

Gly Val Leu Phe Phe Leu Lys Gln Gln Ser Gln Phe Leu Cys Leu Ala
            2980                2985                2990

Val Gln Glu Gly Ser Leu Val Leu Leu Tyr Asp Phe Gly Ala Gly Leu
        2995                3000                3005

Lys Lys Ala Val Pro Leu Gln Pro Pro Pro Leu Thr Ser Ala Ser
    3010                3015                3020

Lys Ala Ile Gln Val Phe Leu Leu Gly Gly Ser Arg Lys Arg Val Leu
3025                3030                3035                3040

Val Arg Val Glu Arg Ala Thr Val Tyr Ser Val Glu Gln Asp Asn Asp
                3045                3050                3055

Leu Glu Leu Ala Asp Ala Tyr Tyr Leu Gly Gly Val Pro Pro Asp Gln
            3060                3065                3070

Leu Pro Pro Ser Leu Arg Trp Leu Phe Pro Thr Gly Gly Ser Val Arg
        3075                3080                3085

Gly Cys Val Lys Gly Ile Lys Ala Leu Gly Lys Tyr Val Asp Leu Lys
    3090                3095                3100

Arg Leu Asn Thr Thr Gly Val Ser Ala Gly Cys Thr Ala Asp Leu Leu
3105                3110                3115                3120
```

-continued

```
Val Gly Arg Ala Met Thr Phe His Gly His Gly Phe Leu Arg Leu Ala
            3125                3130                3135

Leu Ser Asn Val Ala Pro Leu Thr Gly Asn Val Tyr Ser Gly Phe Gly
            3140                3145                3150

Phe His Ser Ala Gln Asp Ser Ala Leu Leu Tyr Tyr Arg Ala Ser Pro
            3155                3160                3165

Asp Gly Leu Cys Gln Val Ser Leu Gln Gln Gly Arg Val Ser Leu Gln
            3170                3175                3180

Leu Leu Arg Thr Glu Val Lys Thr Gln Ala Gly Phe Ala Asp Gly Ala
3185                3190                3195                3200

Pro His Tyr Val Ala Phe Tyr Ser Asn Ala Thr Gly Val Trp Leu Tyr
            3205                3210                3215

Val Asp Asp Gln Leu Gln Gln Met Lys Pro His Arg Gly Pro Pro Pro
            3220                3225                3230

Glu Leu Gln Pro Gln Pro Glu Gly Pro Pro Arg Leu Leu Leu Gly Gly
            3235                3240                3245

Leu Pro Glu Ser Gly Thr Ile Tyr Asn Phe Ser Gly Cys Ile Ser Asn
            3250                3255                3260

Val Phe Val Gln Arg Leu Leu Gly Pro Gln Arg Val Phe Asp Leu Gln
3265                3270                3275                3280

Gln Asn Leu Gly Ser Val Asn Val Ser Thr Gly Cys Ala Pro Ala Leu
            3285                3290                3295

Gln Ala Gln Thr Pro Gly Leu Gly Pro Arg Gly Leu Gln Ala Thr Ala
            3300                3305                3310

Arg Lys Ala Ser Arg Arg Ser Arg Gln Pro Ala Arg His Pro Ala Cys
            3315                3320                3325

Met Leu Pro Pro His Leu Arg Thr Thr Arg Asp Ser Tyr Gln Phe Gly
            3330                3335                3340

Gly Ser Leu Ser Ser His Leu Glu Phe Val Gly Ile Leu Ala Arg His
3345                3350                3355                3360

Arg Asn Trp Pro Ser Leu Ser Met His Val Leu Pro Arg Ser Ser Arg
            3365                3370                3375

Gly Leu Leu Leu Phe Thr Ala Arg Leu Arg Pro Gly Ser Pro Ser Leu
            3380                3385                3390

Ala Leu Phe Leu Ser Asn Gly His Phe Val Ala Gln Met Glu Gly Leu
            3395                3400                3405

Gly Thr Arg Leu Arg Ala Gln Ser Arg Gln Arg Ser Arg Pro Gly Arg
            3410                3415                3420

Trp His Lys Val Ser Val Arg Trp Glu Lys Asn Arg Ile Leu Leu Val
3425                3430                3435                3440

Thr Asp Gly Ala Arg Ala Trp Ser Gln Glu Gly Pro His Arg Gln His
            3445                3450                3455

Gln Gly Ala Glu His Pro Gln Pro His Thr Leu Phe Val Gly Gly Leu
            3460                3465                3470

Pro Ala Ser Ser His Ser Ser Lys Leu Pro Val Thr Val Gly Phe Ser
            3475                3480                3485

Gly Cys Val Lys Arg Leu Arg Leu His Gly Arg Pro Leu Gly Ala Pro
            3490                3495                3500

Thr Arg Met Ala Gly Val Thr Pro Cys Ile Leu Gly Pro Leu Glu Ala
3505                3510                3515                3520

Gly Leu Phe Phe Pro Gly Ser Gly Gly Val Ile Thr Leu Asp Leu Pro
            3525                3530                3535
```

-continued

```
Gly Ala Thr Leu Pro Asp Val Gly Leu Glu Leu Glu Val Arg Pro Leu
            3540                3545                3550

Ala Val Thr Gly Leu Ile Phe His Leu Gly Gln Ala Arg Thr Pro Pro
            3555                3560                3565

Tyr Leu Gln Leu Gln Val Thr Glu Lys Gln Val Leu Leu Arg Ala Asp
            3570                3575                3580

Asp Gly Ala Gly Glu Phe Ser Thr Ser Val Thr Arg Pro Ser Val Leu
3585                3590                3595                3600

Cys Asp Gly Gln Trp His Arg Leu Ala Val Met Lys Ser Gly Asn Val
            3605                3610                3615

Leu Arg Leu Glu Val Asp Ala Gln Ser Asn His Thr Val Gly Pro Leu
            3620                3625                3630

Leu Ala Ala Ala Gly Ala Pro Ala Pro Leu Tyr Leu Gly Gly Leu
            3635                3640                3645

Pro Glu Pro Met Ala Val Gln Pro Trp Pro Ala Tyr Cys Gly Cys
            3650                3655                3660

Met Arg Arg Leu Ala Val Asn Arg Ser Pro Val Ala Met Thr Arg Ser
3665                3670                3675                3680

Val Glu Val His Gly Ala Val Gly Ala Ser Gly Cys Pro Ala Ala
            3685                3690                3695
```

<210> SEQ ID NO 3
<211> LENGTH: 11009
<212> TYPE: DNA
<213> ORGANISM: Mus musculus
<220> FEATURE:
<221> NAME/KEY: CDS
<222> LOCATION: (1)..(10905)

<400> SEQUENCE: 3

```
gac ctc tac tgc aag ctg gtt ggg ggt ccg gtg gct ggc gga gat ccc     48
Asp Leu Tyr Cys Lys Leu Val Gly Gly Pro Val Ala Gly Gly Asp Pro
  1               5                  10                  15 aat cag aca atc cag ggc cag tac tgt gac atc tgt aca gct gcc aac     96
Asn Gln Thr Ile Gln Gly Gln Tyr Cys Asp Ile Cys Thr Ala Ala Asn
             20                  25                  30 agc aac aag gca cac cct gtg agc aac gcc atc gat ggc acg gag cgc    144
Ser Asn Lys Ala His Pro Val Ser Asn Ala Ile Asp Gly Thr Glu Arg
         35                  40                  45 tgg tgg cag agc cca ccc ctg tcc cgt ggc ctg gag tac aat gag gtc    192
Trp Trp Gln Ser Pro Pro Leu Ser Arg Gly Leu Glu Tyr Asn Glu Val
     50                  55                  60 aac gtc aca ctg gac ctg ggc cag gtg ttc cat gtg gcc tat gtg ctc    240
Asn Val Thr Leu Asp Leu Gly Gln Val Phe His Val Ala Tyr Val Leu
 65                  70                  75                  80 atc aag ttt gcc aac tca cct cgg cct gac ctc tgg gtg ctg gag cgg    288
Ile Lys Phe Ala Asn Ser Pro Arg Pro Asp Leu Trp Val Leu Glu Arg
                 85                  90                  95 tcc aca gac ttc ggt cac act tat cag ccg tgg cag ttc ttt gcc tcc    336
Ser Thr Asp Phe Gly His Thr Tyr Gln Pro Trp Gln Phe Phe Ala Ser
            100                 105                 110 tcc aag agg gat tgt ttg gag cgg ttt gga cct cgg act cta gag cgc    384
Ser Lys Arg Asp Cys Leu Glu Arg Phe Gly Pro Arg Thr Leu Glu Arg
        115                 120                 125 atc acg cag gac gac gac gtc atc tgc acc aca gaa tac tcg cga ata    432
Ile Thr Gln Asp Asp Asp Val Ile Cys Thr Thr Glu Tyr Ser Arg Ile
    130                 135                 140 gtg cct ttg gag aat ggc gag att gtg gtg tcc ttg gta aat ggg cgc    480
Val Pro Leu Glu Asn Gly Glu Ile Val Val Ser Leu Val Asn Gly Arg
```

-continued

```
            145                 150                 155                 160
cct ggg gcc ttg aac ttc tcc tac tca ccg tta ctt cga gac ttc acc          528
Pro Gly Ala Leu Asn Phe Ser Tyr Ser Pro Leu Leu Arg Asp Phe Thr
                    165                 170                 175 aaa gcc acc aac atc cgc ttg cgg ttt ctg cga acc aac acg cta ctg          576
Lys Ala Thr Asn Ile Arg Leu Arg Phe Leu Arg Thr Asn Thr Leu Leu
                180                 185                 190 ggc cac ctc atg ggc aag gcg ctg cgg gac ccc aca gtc acc cgc agg          624
Gly His Leu Met Gly Lys Ala Leu Arg Asp Pro Thr Val Thr Arg Arg
            195                 200                 205 tat tat tac agc atc aaa gac atc agc att ggt ggg cgc tgt gtc tgt          672
Tyr Tyr Tyr Ser Ile Lys Asp Ile Ser Ile Gly Gly Arg Cys Val Cys
        210                 215                 220 cat ggc cac gca gat gtc tgt gac gcc aag gac cca ttg gat cct ttc          720
His Gly His Ala Asp Val Cys Asp Ala Lys Asp Pro Leu Asp Pro Phe
225                 230                 235                 240 agg ctg cag tgt gcc tgc cag cac aat aca tgt gga ggc tct tgt gac          768
Arg Leu Gln Cys Ala Cys Gln His Asn Thr Cys Gly Gly Ser Cys Asp
                    245                 250                 255 cga tgc tgt cca ggc ttc aac cag cag ccg tgg aag ccc gcc acc acg          816
Arg Cys Cys Pro Gly Phe Asn Gln Gln Pro Trp Lys Pro Ala Thr Thr
                260                 265                 270 gac agc gcc aat gag tgc cag tcc tgc aat tgc cac ggc cat gcc tac          864
Asp Ser Ala Asn Glu Cys Gln Ser Cys Asn Cys His Gly His Ala Tyr
            275                 280                 285 gac tgt tac tac gac cct gag gtg gat cgg cgc aat gcc agc cag aac          912
Asp Cys Tyr Tyr Asp Pro Glu Val Asp Arg Arg Asn Ala Ser Gln Asn
        290                 295                 300 cag gac aac gtg tac cag ggt gga ggt gtc tgc ctg gat tgc cag cat          960
Gln Asp Asn Val Tyr Gln Gly Gly Gly Val Cys Leu Asp Cys Gln His
305                 310                 315                 320 cac act acg ggt atc aac tgt gag cgt tgt ctg cct ggc ttc ttc cgt         1008
His Thr Thr Gly Ile Asn Cys Glu Arg Cys Leu Pro Gly Phe Phe Arg
                    325                 330                 335 gcc cct gac cag cct ctc gac tca cct cat gtc tgt cgg ccc tgc gac         1056
Ala Pro Asp Gln Pro Leu Asp Ser Pro His Val Cys Arg Pro Cys Asp
                340                 345                 350 tgt gag tca gac ttc acg gat ggg acc tgt gaa gac ttg acg ggc cgc         1104
Cys Glu Ser Asp Phe Thr Asp Gly Thr Cys Glu Asp Leu Thr Gly Arg
            355                 360                 365 tgt tac tgc agg ccg aac ttc aca gga gag cta tgt gct gcc tgc gct         1152
Cys Tyr Cys Arg Pro Asn Phe Thr Gly Glu Leu Cys Ala Ala Cys Ala
        370                 375                 380 gag ggc tac acg gac ttc cca cac tgc tac cct ctg cct tca ttt cct         1200
Glu Gly Tyr Thr Asp Phe Pro His Cys Tyr Pro Leu Pro Ser Phe Pro
385                 390                 395                 400 cac aat gac acg aga gaa cag gtg ctt ccc gct gga caa atc gtg aac         1248
His Asn Asp Thr Arg Glu Gln Val Leu Pro Ala Gly Gln Ile Val Asn
                    405                 410                 415 tgt gat tgc aat gct gca ggg acc cag ggc aat gcc tgc cgg aag gac         1296
Cys Asp Cys Asn Ala Ala Gly Thr Gln Gly Asn Ala Cys Arg Lys Asp
                420                 425                 430 cca agg ttg gga cgg tgt gtc tgc aaa ccc aac ttc cgg ggt gcc cac         1344
Pro Arg Leu Gly Arg Cys Val Cys Lys Pro Asn Phe Arg Gly Ala His
            435                 440                 445 tgt gag ctc tgt gct cct gga ttc cac ggg cct agc tgc cac cca tgc         1392
Cys Glu Leu Cys Ala Pro Gly Phe His Gly Pro Ser Cys His Pro Cys
        450                 455                 460 cag tgt tcc agc cct ggg gta gcc aac agc ctc tgt gac cca gag tct         1440
```

-continued

| | |
|---|---|
| Gln Cys Ser Ser Pro Gly Val Ala Asn Ser Leu Cys Asp Pro Glu Ser<br>465                    470                    475                    480 | |
| ggc cag tgc atg tgc cgc acc ggc ttt gag ggg gac agg tgt gac cac<br>Gly Gln Cys Met Cys Arg Thr Gly Phe Glu Gly Asp Arg Cys Asp His<br>                         485                    490                    495 | 1488 |
| tgt gcc ctt ggc tat ttc cac ttc cct ctc tgt cag ctg tgt ggc tgc<br>Cys Ala Leu Gly Tyr Phe His Phe Pro Leu Cys Gln Leu Cys Gly Cys<br>                500                    505                    510 | 1536 |
| agc cca gca ggg acc ctg cct gaa ggc tgt gac gag gct ggc cgc tgc<br>Ser Pro Ala Gly Thr Leu Pro Glu Gly Cys Asp Glu Ala Gly Arg Cys<br>            515                    520                    525 | 1584 |
| cag tgc cga cct ggc ttt gac ggt cct cac tgt gac cga tgc ctt cca<br>Gln Cys Arg Pro Gly Phe Asp Gly Pro His Cys Asp Arg Cys Leu Pro<br>530                    535                    540 | 1632 |
| gga tac cat ggg tat ccc gac tgt cac gct tgt gcc tgt gac cct cgg<br>Gly Tyr His Gly Tyr Pro Asp Cys His Ala Cys Ala Cys Asp Pro Arg<br>545                    550                    555                    560 | 1680 |
| ggg gcc ctg gat caa cag tgt gga gtg ggc ggt ttg tgc cac tgc cgt<br>Gly Ala Leu Asp Gln Gln Cys Gly Val Gly Gly Leu Cys His Cys Arg<br>                    565                    570                    575 | 1728 |
| cct ggc aac aca ggt gcc act tgt cag gaa tgt agc ccc ggc ttc tac<br>Pro Gly Asn Thr Gly Ala Thr Cys Gln Glu Cys Ser Pro Gly Phe Tyr<br>                580                    585                    590 | 1776 |
| ggc ttc ccc agc tgc atc ccc tgc cac tgc tct gcc gat ggc tcc ttg<br>Gly Phe Pro Ser Cys Ile Pro Cys His Cys Ser Ala Asp Gly Ser Leu<br>            595                    600                    605 | 1824 |
| cat aca acc tgt gac ccg aca acc ggc cag tgt agg tgt cga ccc cga<br>His Thr Thr Cys Asp Pro Thr Thr Gly Gln Cys Arg Cys Arg Pro Arg<br>610                    615                    620 | 1872 |
| gtg aca gga cta cat tgt gat atg tgt gta cca ggc gcc tat aac ttc<br>Val Thr Gly Leu His Cys Asp Met Cys Val Pro Gly Ala Tyr Asn Phe<br>625                    630                    635                    640 | 1920 |
| ccc tac tgt gaa gct ggc tct tgt cat cct gct ggt ctg gcc cca gcc<br>Pro Tyr Cys Glu Ala Gly Ser Cys His Pro Ala Gly Leu Ala Pro Ala<br>                    645                    650                    655 | 1968 |
| aat cct gcc ctt cct gag aca cag gct ccc tgt atg tgc cgg gct cac<br>Asn Pro Ala Leu Pro Glu Thr Gln Ala Pro Cys Met Cys Arg Ala His<br>                660                    665                    670 | 2016 |
| gtg gaa ggg cca agc tgt gat cgc tgt aaa cct ggg tac tgg ggc ctg<br>Val Glu Gly Pro Ser Cys Asp Arg Cys Lys Pro Gly Tyr Trp Gly Leu<br>            675                    680                    685 | 2064 |
| agc gcc agc aac cct gaa ggc tgc aca cgc tgc agc tgt gac cca cga<br>Ser Ala Ser Asn Pro Glu Gly Cys Thr Arg Cys Ser Cys Asp Pro Arg<br>690                    695                    700 | 2112 |
| ggc acc ctg ggt gga gtt act gag tgc cag ggc aat ggg cag tgc ttc<br>Gly Thr Leu Gly Gly Val Thr Glu Cys Gln Gly Asn Gly Gln Cys Phe<br>705                    710                    715                    720 | 2160 |
| tgc aag gct cac gtg tgt ggc aag acc tgt gca gcc tgc aag gat ggc<br>Cys Lys Ala His Val Cys Gly Lys Thr Cys Ala Ala Cys Lys Asp Gly<br>                    725                    730                    735 | 2208 |
| ttc ttt ggc ctg gat tat gct gac tac ttt ggc tgc cgt agc tgt agg<br>Phe Phe Gly Leu Asp Tyr Ala Asp Tyr Phe Gly Cys Arg Ser Cys Arg<br>                740                    745                    750 | 2256 |
| tgt gat gtt ggt ggt gcc ctg ggt cag ggc tgt gaa cca aag aca ggt<br>Cys Asp Val Gly Gly Ala Leu Gly Gln Gly Cys Glu Pro Lys Thr Gly<br>            755                    760                    765 | 2304 |
| gcc tgc agg tgc cgc cct aac acc caa gga ccc acc tgt agc gag cca<br>Ala Cys Arg Cys Arg Pro Asn Thr Gln Gly Pro Thr Cys Ser Glu Pro<br>770                    775                    780 | 2352 |

```
gcg aag gac cac tac ttg cca gac ctg cac cac atg cgg ctg gaa cta      2400
Ala Lys Asp His Tyr Leu Pro Asp Leu His His Met Arg Leu Glu Leu
785                 790                 795                 800 gag gag gcg gcc act ccc gag ggc cac gct gta cgc ttt ggc ttc aac      2448
Glu Glu Ala Ala Thr Pro Glu Gly His Ala Val Arg Phe Gly Phe Asn
            805                 810                 815 ccc ctg gag ttt gag aac ttt agc tgg aga ggc tac gca cac atg atg      2496
Pro Leu Glu Phe Glu Asn Phe Ser Trp Arg Gly Tyr Ala His Met Met
        820                 825                 830 gct atc cag ccc agg att gtg gcc agg ctg aac gtg acc tcc cct gac      2544
Ala Ile Gln Pro Arg Ile Val Ala Arg Leu Asn Val Thr Ser Pro Asp
    835                 840                 845 ctc ttt cga ctg gtt ttc cga tat gtc aac cgt gga tca acc agc gtg      2592
Leu Phe Arg Leu Val Phe Arg Tyr Val Asn Arg Gly Ser Thr Ser Val
850                 855                 860 aat ggg cag atc tct gtt cgt gaa gag ggc aag ctt tcc agc tgt acc      2640
Asn Gly Gln Ile Ser Val Arg Glu Glu Gly Lys Leu Ser Ser Cys Thr
865                 870                 875                 880 aac tgc aca gag cag agc cag cca gtg gct ttc cca ccc agc act gag      2688
Asn Cys Thr Glu Gln Ser Gln Pro Val Ala Phe Pro Pro Ser Thr Glu
            885                 890                 895 cct gcc ttt gtc act gtg ccc cag agg ggc ttt ggg gaa ccc ttt gtg      2736
Pro Ala Phe Val Thr Val Pro Gln Arg Gly Phe Gly Glu Pro Phe Val
        900                 905                 910 ctg aac ccc ggc atc tgg gcc ttg ctg gtc gag gct gaa ggt gta ctc      2784
Leu Asn Pro Gly Ile Trp Ala Leu Leu Val Glu Ala Glu Gly Val Leu
    915                 920                 925 ttg gac tac gtg gtc cta ctg ccc agc acc tac tat gag gca gct ctc      2832
Leu Asp Tyr Val Val Leu Leu Pro Ser Thr Tyr Tyr Glu Ala Ala Leu
930                 935                 940 cta cag cat cga gta acg gag gcc tgt acc tac cgt ccc tca gcc ctg      2880
Leu Gln His Arg Val Thr Glu Ala Cys Thr Tyr Arg Pro Ser Ala Leu
945                 950                 955                 960 cac tcc aca gag aac tgt ctt gtc tat gct cac cta ccc ctg gat ggc      2928
His Ser Thr Glu Asn Cys Leu Val Tyr Ala His Leu Pro Leu Asp Gly
            965                 970                 975 ttc cct tca gca gct gga act gag gcc ctg tgt cgc cat gac aac agc      2976
Phe Pro Ser Ala Ala Gly Thr Glu Ala Leu Cys Arg His Asp Asn Ser
        980                 985                 990 ctg ccc cgg ccc tgc ccc aca gag cag ctc agc ccc tca cac cca ccg      3024
Leu Pro Arg Pro Cys Pro Thr Glu Gln Leu Ser Pro Ser His Pro Pro
    995                 1000                1005 ctg gcg acc tgc ttc ggc agt gat gtg gac atc cag ctc gag atg gcc      3072
Leu Ala Thr Cys Phe Gly Ser Asp Val Asp Ile Gln Leu Glu Met Ala
    1010                1015                1020 gtg cct cag cct ggc caa tat gtt ctc gtg gtg gaa tat gtc ggt gag      3120
Val Pro Gln Pro Gly Gln Tyr Val Leu Val Val Glu Tyr Val Gly Glu
1025                1030                1035                1040 gat tca cac caa gag atg gga gtg gct gtg cac acc cct cag aga gcc      3168
Asp Ser His Gln Glu Met Gly Val Ala Val His Thr Pro Gln Arg Ala
                1045                1050                1055 ccc cag caa ggg gtg ctc aac ctc cac ccc tgc cca tac agc tcc ctg      3216
Pro Gln Gln Gly Val Leu Asn Leu His Pro Cys Pro Tyr Ser Ser Leu
            1060                1065                1070 tgc cgg agt ccg gct cgg gac acc cag cat cat cta gcc atc ttc cac      3264
Cys Arg Ser Pro Ala Arg Asp Thr Gln His His Leu Ala Ile Phe His
        1075                1080                1085 ctg gac tct gag gct agc atc cgg ctc aca gct gag caa gct cac ttc      3312
Leu Asp Ser Glu Ala Ser Ile Arg Leu Thr Ala Glu Gln Ala His Phe
    1090                1095                1100
```

```
ttc ctg cac agc gtc acc ctg gta cct gtg gag gag ttc agt act gag      3360
Phe Leu His Ser Val Thr Leu Val Pro Val Glu Glu Phe Ser Thr Glu
1105                1110                1115                1120 ttt gtg gag ccc cgg gtc ttc tgt gtg agc agt cat gga act ttc aac      3408
Phe Val Glu Pro Arg Val Phe Cys Val Ser Ser His Gly Thr Phe Asn
                1125                1130                1135 ccc agc agt gct gcc tgt cta gcc tcc cga ttc ccg aag cca ccg cag      3456
Pro Ser Ser Ala Ala Cys Leu Ala Ser Arg Phe Pro Lys Pro Pro Gln
            1140                1145                1150 ccc atc atc ctt aag gac tgc cag gtc ttg ccg ctg cct ccc gac ctg      3504
Pro Ile Ile Leu Lys Asp Cys Gln Val Leu Pro Leu Pro Pro Asp Leu
        1155                1160                1165 cct ctg act cag tct cag gag ctc tca cca ggt gca ccc ccc gag gga      3552
Pro Leu Thr Gln Ser Gln Glu Leu Ser Pro Gly Ala Pro Pro Glu Gly
    1170                1175                1180 cca cag cct cgg ccg cca act gcg gtg gat cct aat gca gaa ccc acc      3600
Pro Gln Pro Arg Pro Pro Thr Ala Val Asp Pro Asn Ala Glu Pro Thr
1185                1190                1195                1200 ttg ctg cgc cac ccc cag ggc acg gtg gtc ttc acc acc cag gtg ccc      3648
Leu Leu Arg His Pro Gln Gly Thr Val Val Phe Thr Thr Gln Val Pro
                1205                1210                1215 acc ctg ggc cgc tat gcc ttc ctg ctg cac ggc tac cag ccg gtc cac      3696
Thr Leu Gly Arg Tyr Ala Phe Leu Leu His Gly Tyr Gln Pro Val His
            1220                1225                1230 ccc tcc ttc cct gtg gag gta ctc att aat ggt ggc cgc atc tgg cag      3744
Pro Ser Phe Pro Val Glu Val Leu Ile Asn Gly Gly Arg Ile Trp Gln
        1235                1240                1245 ggc cac gcc aac gcc agc ttt tgt cct cat ggt tat ggc tgc cgt acc      3792
Gly His Ala Asn Ala Ser Phe Cys Pro His Gly Tyr Gly Cys Arg Thr
    1250                1255                1260 ctg gtg ttg tgt gag ggt cag acg atg ctg gat gtt aca gac aac gag      3840
Leu Val Leu Cys Glu Gly Gln Thr Met Leu Asp Val Thr Asp Asn Glu
1265                1270                1275                1280 ctc acc gtg act gtg cgt gtg cca gaa ggc cgg tgg ctc tgg ctg gac      3888
Leu Thr Val Thr Val Arg Val Pro Glu Gly Arg Trp Leu Trp Leu Asp
                1285                1290                1295 tac gta ctc att gtc cct gag gat gct tac agc tcc agt tac ctc caa      3936
Tyr Val Leu Ile Val Pro Glu Asp Ala Tyr Ser Ser Ser Tyr Leu Gln
            1300                1305                1310 gag gag cct ttg gac aaa tcc tat gac ttc atc agc cac tgt gcc acc      3984
Glu Glu Pro Leu Asp Lys Ser Tyr Asp Phe Ile Ser His Cys Ala Thr
        1315                1320                1325 cag ggc tac cac att agc ccc agc agc tca tct cca ttc tgc cgg aat      4032
Gln Gly Tyr His Ile Ser Pro Ser Ser Ser Ser Pro Phe Cys Arg Asn
    1330                1335                1340 gcc gcc acc tcc ttg tct ctc ttc tac aac aac ggg gcc ctc cct tgt      4080
Ala Ala Thr Ser Leu Ser Leu Phe Tyr Asn Asn Gly Ala Leu Pro Cys
1345                1350                1355                1360 ggc tgc cac gag gtg ggt gcc gta agc ccc acg tgc gaa ccc ttc ggg      4128
Gly Cys His Glu Val Gly Ala Val Ser Pro Thr Cys Glu Pro Phe Gly
                1365                1370                1375 ggc cag tgt ccc tgc cgg ggc cac gtt att ggc cgt gac tgt tcc cgc      4176
Gly Gln Cys Pro Cys Arg Gly His Val Ile Gly Arg Asp Cys Ser Arg
            1380                1385                1390 tgt gcc acc ggc tac tgg ggt ttc ccc aac tgc agg ccc tgt gac tgt      4224
Cys Ala Thr Gly Tyr Trp Gly Phe Pro Asn Cys Arg Pro Cys Asp Cys
        1395                1400                1405 gga gcc cgc ctg tgt gac gag ctc acg ggc cag tgt atc tgt cca cca      4272
Gly Ala Arg Leu Cys Asp Glu Leu Thr Gly Gln Cys Ile Cys Pro Pro
```

-continued

```
      1410              1415              1420
cgc act gtt ccc cct gac tgc ttg gtc tgc cag cca cag agc ttt ggt      4320
Arg Thr Val Pro Pro Asp Cys Leu Val Cys Gln Pro Gln Ser Phe Gly
1425              1430              1435              1440 tgc cac ccc ttg gtg ggc tgt gag gag tgt aac tgc tca ggg ccc ggc      4368
Cys His Pro Leu Val Gly Cys Glu Glu Cys Asn Cys Ser Gly Pro Gly
                  1445              1450              1455 gtc cag gag ctg acg gac cct acc tgt gac atg gac agc ggc cag tgc      4416
Val Gln Glu Leu Thr Asp Pro Thr Cys Asp Met Asp Ser Gly Gln Cys
        1460              1465              1470 aga tgc aga ccc aat gta gct gga cgt cgc tgt gat acc tgt gcc ccg      4464
Arg Cys Arg Pro Asn Val Ala Gly Arg Arg Cys Asp Thr Cys Ala Pro
1475              1480              1485 ggc ttc tat ggc tat cct agc tgt cgc ccc tgt gac tgc cat gag gca      4512
Gly Phe Tyr Gly Tyr Pro Ser Cys Arg Pro Cys Asp Cys His Glu Ala
          1490              1495              1500 ggc acc atg gct agc gtg tgt gac ccc ctc aca ggc caa tgc cat tgc      4560
Gly Thr Met Ala Ser Val Cys Asp Pro Leu Thr Gly Gln Cys His Cys
1505              1510              1515              1520 aag gag aac gtg cag ggc tca aga tgt gac cag tgt cgc gtg ggg acc      4608
Lys Glu Asn Val Gln Gly Ser Arg Cys Asp Gln Cys Arg Val Gly Thr
                  1525              1530              1535 ttc tcc ttg gat gct gct aac ccc aag ggc tgt acc cgc tgc ttc tgt      4656
Phe Ser Leu Asp Ala Ala Asn Pro Lys Gly Cys Thr Arg Cys Phe Cys
        1540              1545              1550 ttc ggg gcc aca gag cgc tgt ggg aac tct aac ctc gcc cgc cat gag      4704
Phe Gly Ala Thr Glu Arg Cys Gly Asn Ser Asn Leu Ala Arg His Glu
1555              1560              1565 ttc gtg gac atg gag ggc tgg gtg ctg ttg agc agt gac cgg cag gtg      4752
Phe Val Asp Met Glu Gly Trp Val Leu Leu Ser Ser Asp Arg Gln Val
          1570              1575              1580 gta ccc cac gag cat cgg cct gag ata gag ctg ctg cac gca gat ctg      4800
Val Pro His Glu His Arg Pro Glu Ile Glu Leu Leu His Ala Asp Leu
1585              1590              1595              1600 cgc tct gtg gct gac act ttc tca gag ctg tac tgg cag gct ccg ccc      4848
Arg Ser Val Ala Asp Thr Phe Ser Glu Leu Tyr Trp Gln Ala Pro Pro
                  1605              1610              1615 tcc tat ctg gga gac agg gtg tca tcc tac ggt gga acc ctc cac tat      4896
Ser Tyr Leu Gly Asp Arg Val Ser Ser Tyr Gly Gly Thr Leu His Tyr
        1620              1625              1630 gag ctg cac tca gag acc cag cga ggt gat atc ttc att ccc tac gag      4944
Glu Leu His Ser Glu Thr Gln Arg Gly Asp Ile Phe Ile Pro Tyr Glu
1635              1640              1645 agc cgg ccg gac gtc gtg ctg cag ggc aac caa atg agc atc gcc ttc      4992
Ser Arg Pro Asp Val Val Leu Gln Gly Asn Gln Met Ser Ile Ala Phe
                  1650              1655              1660 ctg gaa ctg gcg tac cct ccg cct ggc cag gtt cac cga gga cag cta      5040
Leu Glu Leu Ala Tyr Pro Pro Pro Gly Gln Val His Arg Gly Gln Leu
1665              1670              1675              1680 cag ctg gta gag ggg aac ttc cgg cac ttg gag act cac aac ccc gtg      5088
Gln Leu Val Glu Gly Asn Phe Arg His Leu Glu Thr His Asn Pro Val
                  1685              1690              1695 tcc cga gaa gaa ctc atg atg gtg ctg gcc ggc ctg gag cag ctg cag      5136
Ser Arg Glu Glu Leu Met Met Val Leu Ala Gly Leu Glu Gln Leu Gln
        1700              1705              1710 atc cgt gct ctc ttc tcg cag acc tct tcc agt gtc tcc ttg cgt aga      5184
Ile Arg Ala Leu Phe Ser Gln Thr Ser Ser Ser Val Ser Leu Arg Arg
1715              1720              1725 gtg gta ctg gag gtg gct agc gag gct ggt agg ggg cct cca gcc agc      5232
```

```
Val Val Leu Glu Val Ala Ser Glu Ala Gly Arg Gly Pro Pro Ala Ser
    1730                1735                1740 aat gtg gaa ctg tgt atg tgc cct gcc aac tac cgt ggg gac tcg tgc       5280
Asn Val Glu Leu Cys Met Cys Pro Ala Asn Tyr Arg Gly Asp Ser Cys
1745                1750                1755                1760 cag gaa tgt gcc cct ggc tat tac cgg gac acc aag ggt ctc ttc cta       5328
Gln Glu Cys Ala Pro Gly Tyr Tyr Arg Asp Thr Lys Gly Leu Phe Leu
                1765                1770                1775 ggc cga tgt gtc ccc tgt cag tgc cat ggc cat tca gat cgc tgc ctt       5376
Gly Arg Cys Val Pro Cys Gln Cys His Gly His Ser Asp Arg Cys Leu
            1780                1785                1790 cct ggc tct ggc att tgt gtg ggc tgc cag cac aac aca gaa ggg gac       5424
Pro Gly Ser Gly Ile Cys Val Gly Cys Gln His Asn Thr Glu Gly Asp
        1795                1800                1805 caa tgt gag cgc tgt agg cct ggc ttt gtc agc agt gat ccc agt aac       5472
Gln Cys Glu Arg Cys Arg Pro Gly Phe Val Ser Ser Asp Pro Ser Asn
    1810                1815                1820 cct gca tcc cca tgt gtg agc tgc cct tgc ccc ttg gca gtg ccc tcc       5520
Pro Ala Ser Pro Cys Val Ser Cys Pro Cys Pro Leu Ala Val Pro Ser
1825                1830                1835                1840 aat aat ttt gca gac ggt tgc gtc tta aga aat ggc cga acc cag tgc       5568
Asn Asn Phe Ala Asp Gly Cys Val Leu Arg Asn Gly Arg Thr Gln Cys
                1845                1850                1855 ctc tgc agg cca ggc tat gct ggt gcc tcc tgc gag cgg tgt gca cct       5616
Leu Cys Arg Pro Gly Tyr Ala Gly Ala Ser Cys Glu Arg Cys Ala Pro
            1860                1865                1870 ggc ttt ttt ggg aac ccc ctg gtg cta ggc agc tcc tgt cag ccc tgc       5664
Gly Phe Phe Gly Asn Pro Leu Val Leu Gly Ser Ser Cys Gln Pro Cys
        1875                1880                1885 gac tgc agc ggt aat gga gac ccc aac atg atc ttc agt gac tgc gac       5712
Asp Cys Ser Gly Asn Gly Asp Pro Asn Met Ile Phe Ser Asp Cys Asp
    1890                1895                1900 ccc ctg acg ggt gcc tgt cga ggc tgc ctc cgt cac acc act ggg ccc       5760
Pro Leu Thr Gly Ala Cys Arg Gly Cys Leu Arg His Thr Thr Gly Pro
1905                1910                1915                1920 cac tgt gaa cgc tgt gcc cca ggc ttc tat ggc aat gct ttg ttg cca       5808
His Cys Glu Arg Cys Ala Pro Gly Phe Tyr Gly Asn Ala Leu Leu Pro
                1925                1930                1935 ggc aac tgc acc cgg tgt gac tgt tcc cca tgt ggg aca gaa acc tgt       5856
Gly Asn Cys Thr Arg Cys Asp Cys Ser Pro Cys Gly Thr Glu Thr Cys
            1940                1945                1950 gat ccc cag agt gga cgc tgc ctg tgc aaa gca ggc gtg act gga caa       5904
Asp Pro Gln Ser Gly Arg Cys Leu Cys Lys Ala Gly Val Thr Gly Gln
        1955                1960                1965 cgt tgt gac cgc tgt ttg gaa gga tac ttc ggt ttt gag caa tgc cag       5952
Arg Cys Asp Arg Cys Leu Glu Gly Tyr Phe Gly Phe Glu Gln Cys Gln
    1970                1975                1980 ggc tgc cgc cct tgt gcc tgt gga cca gct gcc aag ggc tcc gag tgc       6000
Gly Cys Arg Pro Cys Ala Cys Gly Pro Ala Ala Lys Gly Ser Glu Cys
1985                1990                1995                2000 cac cct cag agc ggt cag tgt cac tgc cag cca ggg acc aca gga ccc       6048
His Pro Gln Ser Gly Gln Cys His Cys Gln Pro Gly Thr Thr Gly Pro
                2005                2010                2015 cag tgc ctc gag tgc gcc cct ggc tac tgg ggc ctc cca gag aag ggc       6096
Gln Cys Leu Glu Cys Ala Pro Gly Tyr Trp Gly Leu Pro Glu Lys Gly
            2020                2025                2030 tgc agg cgc tgc cag tgt ccc cga ggc cac tgt gac cca cac acg ggc       6144
Cys Arg Arg Cys Gln Cys Pro Arg Gly His Cys Asp Pro His Thr Gly
        2035                2040                2045
```

```
cac tgc acc tgt ccc ccg ggg ctc agc ggg gaa cgc tgt gac acc tgc    6192
His Cys Thr Cys Pro Pro Gly Leu Ser Gly Glu Arg Cys Asp Thr Cys
         2050                2055                2060 agc cag cag cac cag gtg cct gta ccg ggc aag cct ggg ggc cat ggc    6240
Ser Gln Gln His Gln Val Pro Val Pro Gly Lys Pro Gly Gly His Gly
2065                2070                2075                2080 ata cac tgt gaa gtg tgt gac cac tgt gtg gtt ctc ctt ctg gat gac    6288
Ile His Cys Glu Val Cys Asp His Cys Val Val Leu Leu Leu Asp Asp
             2085                2090                2095 ctc gag cgg gct ggt gcc ctc ctc ccc gct atc cgt gag cag ctg cag    6336
Leu Glu Arg Ala Gly Ala Leu Leu Pro Ala Ile Arg Glu Gln Leu Gln
         2100                2105                2110 ggt atc aat gcc agc tcc gcg gcc tgg gcc agg ctg cac agg ctg aat    6384
Gly Ile Asn Ala Ser Ser Ala Ala Trp Ala Arg Leu His Arg Leu Asn
         2115                2120                2125 gcc tcc att gct gac ctg cag agt aaa ctc cgg agg cca ccg gga ccc    6432
Ala Ser Ile Ala Asp Leu Gln Ser Lys Leu Arg Arg Pro Pro Gly Pro
         2130                2135                2140 cgc tac cag gca gca cag cag cta cag act cta gag cag cag agt ata    6480
Arg Tyr Gln Ala Ala Gln Gln Leu Gln Thr Leu Glu Gln Gln Ser Ile
2145                2150                2155                2160 agc ctt caa cag gac acg gag agg ctg ggc agt cag gcc aca ggg gtc    6528
Ser Leu Gln Gln Asp Thr Glu Arg Leu Gly Ser Gln Ala Thr Gly Val
             2165                2170                2175 caa ggt cag gca ggc cag cta ctg gac acc aca gag tcc aca ctg ggc    6576
Gln Gly Gln Ala Gly Gln Leu Leu Asp Thr Thr Glu Ser Thr Leu Gly
         2180                2185                2190 cgg gca cag aag ttg ttg gag tct gtg cga gct gtg ggc cgt gcc ctg    6624
Arg Ala Gln Lys Leu Leu Glu Ser Val Arg Ala Val Gly Arg Ala Leu
         2195                2200                2205 aat gag ctg gca tct cgc atg ggc caa gga tct cca ggc gat gcc ttg    6672
Asn Glu Leu Ala Ser Arg Met Gly Gln Gly Ser Pro Gly Asp Ala Leu
         2210                2215                2220 gta ccg tct ggc gag cag ctg cgc tgg gct ctg gct gaa gtg gag cgg    6720
Val Pro Ser Gly Glu Gln Leu Arg Trp Ala Leu Ala Glu Val Glu Arg
2225                2230                2235                2240 ctg ctc tgg gat atg cgg acg cgt gac ctg ggg gcc cag ggg gca gtg    6768
Leu Leu Trp Asp Met Arg Thr Arg Asp Leu Gly Ala Gln Gly Ala Val
             2245                2250                2255 gca gag gcc gaa ctg gcc gaa gcc cag agg ctg atg gct cgt gtc cag    6816
Ala Glu Ala Glu Leu Ala Glu Ala Gln Arg Leu Met Ala Arg Val Gln
         2260                2265                2270 gag cag ctg acc agc ttc tgg gag gag aac cag tca ttg gcc aca cac    6864
Glu Gln Leu Thr Ser Phe Trp Glu Glu Asn Gln Ser Leu Ala Thr His
         2275                2280                2285 att cgg gac cag ctg gct cag tat gag tct ggc ctc atg gat ctt cgt    6912
Ile Arg Asp Gln Leu Ala Gln Tyr Glu Ser Gly Leu Met Asp Leu Arg
         2290                2295                2300 gag gcc ctg aac cag gcc gtt aat acc acc cgg gag gct gag gaa ctc    6960
Glu Ala Leu Asn Gln Ala Val Asn Thr Thr Arg Glu Ala Glu Glu Leu
2305                2310                2315                2320 aac agc cgc aac cag gaa cgg gtg aag gaa gcc ctg caa tgg aaa cag    7008
Asn Ser Arg Asn Gln Glu Arg Val Lys Glu Ala Leu Gln Trp Lys Gln
             2325                2330                2335 gaa ctg tcc cag gac aat gcc acc ctg aag gcc act ctt caa gct gcc    7056
Glu Leu Ser Gln Asp Asn Ala Thr Leu Lys Ala Thr Leu Gln Ala Ala
         2340                2345                2350 agt ctc atc ttg ggc cat gtt tct gag ctt ctg cag ggc ata gac cag    7104
Ser Leu Ile Leu Gly His Val Ser Glu Leu Leu Gln Gly Ile Asp Gln
         2355                2360                2365
```

```
gct aag gag gac cta gag cac ctg gcg gcc agc ctg gat gga gcc tgg     7152
Ala Lys Glu Asp Leu Glu His Leu Ala Ala Ser Leu Asp Gly Ala Trp
   2370                2375                2380 aca ccc tta ctg aag agg atg cag gcc ttt tcc cct gcc agc agc aag     7200
Thr Pro Leu Leu Lys Arg Met Gln Ala Phe Ser Pro Ala Ser Ser Lys
2385                2390                2395                2400 gtg gac ttg gta gag gct gct gag gcc cac gct cag aag ctg aac cag     7248
Val Asp Leu Val Glu Ala Ala Glu Ala His Ala Gln Lys Leu Asn Gln
            2405                2410                2415 ctg gca atc aac ctg tct ggc atc atc ctt ggc atc aat cag gac cgc     7296
Leu Ala Ile Asn Leu Ser Gly Ile Ile Leu Gly Ile Asn Gln Asp Arg
        2420                2425                2430 ttc atc cag agg gct gtg gaa gcc tcc aat gcc tac agc agc atc ctt     7344
Phe Ile Gln Arg Ala Val Glu Ala Ser Asn Ala Tyr Ser Ser Ile Leu
    2435                2440                2445 cag gcc gtt cag gct gcc gag gat gcg gca ggc cag gca ctg agg cag     7392
Gln Ala Val Gln Ala Ala Glu Asp Ala Ala Gly Gln Ala Leu Arg Gln
2450                2455                2460 gcc agc cgc aca tgg gag atg gtg gtg cag cgg ggc cta gca gct gga     7440
Ala Ser Arg Thr Trp Glu Met Val Val Gln Arg Gly Leu Ala Ala Gly
2465                2470                2475                2480 gcc cgg cag ctg tta gcc aac agc agt gcc ctg gag gag acc atc ctt     7488
Ala Arg Gln Leu Leu Ala Asn Ser Ser Ala Leu Glu Glu Thr Ile Leu
            2485                2490                2495 gga cac cag ggg agg ctg ggc ctt gct cag ggc cgt ctg cag gct gcg     7536
Gly His Gln Gly Arg Leu Gly Leu Ala Gln Gly Arg Leu Gln Ala Ala
        2500                2505                2510 ggg atc cag ctt cat aat gtc tgg gcc agg aag aac cag cta gca gcc     7584
Gly Ile Gln Leu His Asn Val Trp Ala Arg Lys Asn Gln Leu Ala Ala
    2515                2520                2525 cag atc cag gag gca caa gcc atg ctg gcc atg gac acg agc gag acc     7632
Gln Ile Gln Glu Ala Gln Ala Met Leu Ala Met Asp Thr Ser Glu Thr
2530                2535                2540 agt gag aag att gct cac gcc aag gct gtg gct gcc gaa gcc ctc agt     7680
Ser Glu Lys Ile Ala His Ala Lys Ala Val Ala Ala Glu Ala Leu Ser
2545                2550                2555                2560 acg gcc acc cac gtg cag tct cag ctt cag ggt atg cag aag aat gtg     7728
Thr Ala Thr His Val Gln Ser Gln Leu Gln Gly Met Gln Lys Asn Val
            2565                2570                2575 gag agg tgg cag agc cag ctg gga ggc ctg caa ggc cag gac ctg agc     7776
Glu Arg Trp Gln Ser Gln Leu Gly Gly Leu Gln Gly Gln Asp Leu Ser
        2580                2585                2590 cag gtg gaa cgg gat gca agc agt tca gtg tcc acc ctg gag aag aca     7824
Gln Val Glu Arg Asp Ala Ser Ser Ser Val Ser Thr Leu Glu Lys Thr
    2595                2600                2605 ttg cca cag ctg ctg gcc aaa ctg agc cgt cta gag aac cgt gga gtt     7872
Leu Pro Gln Leu Leu Ala Lys Leu Ser Arg Leu Glu Asn Arg Gly Val
2610                2615                2620 cac aat gcc agc ctg gct ttg tct gcc aac att ggt cgt gtg cgc aag     7920
His Asn Ala Ser Leu Ala Leu Ser Ala Asn Ile Gly Arg Val Arg Lys
2625                2630                2635                2640 ctc att gcc caa gcc cgg agt gcc gcc agc aag gtc aag gtg tcc atg     7968
Leu Ile Ala Gln Ala Arg Ser Ala Ala Ser Lys Val Lys Val Ser Met
            2645                2650                2655 aag ttc aat ggg cgt tca ggg gta cga ctg cgt ccc cca cga gac ctt     8016
Lys Phe Asn Gly Arg Ser Gly Val Arg Leu Arg Pro Pro Arg Asp Leu
        2660                2665                2670 gcc gac ctt gct gcg tac act gcc ctc aag ttc cac atc cag agc cca     8064
Ala Asp Leu Ala Ala Tyr Thr Ala Leu Lys Phe His Ile Gln Ser Pro
```

-continued

| | | |
|---|---|---|
| gtg cca gcg ccc gaa cct ggc aag aac acg ggg gac cac ttt gtt ctg<br>Val Pro Ala Pro Glu Pro Gly Lys Asn Thr Gly Asp His Phe Val Leu<br>    2690                          2695                        2700 | 8112 |
| tac atg ggc agc cgc cag gcc act ggg gac tac atg gga gtg tct ctg<br>Tyr Met Gly Ser Arg Gln Ala Thr Gly Asp Tyr Met Gly Val Ser Leu<br>2705                      2710                       2715                        2720 | 8160 |
| cgt aat cag aag gtg cac tgg gtg tac agg cta gga aag gct ggc ccc<br>Arg Asn Gln Lys Val His Trp Val Tyr Arg Leu Gly Lys Ala Gly Pro<br>    2725                          2730                        2735 | 8208 |
| aca act ctc agc atc gac gag aac atc ggg gag cag ttt gca gcc gtc<br>Thr Thr Leu Ser Ile Asp Glu Asn Ile Gly Glu Gln Phe Ala Ala Val<br>        2740                          2745                        2750 | 8256 |
| agc atc gac agg acc ctc cag ttt ggc cac atg tct gtc acc gtg gag<br>Ser Ile Asp Arg Thr Leu Gln Phe Gly His Met Ser Val Thr Val Glu<br>2755                      2760                       2765 | 8304 |
| aaa cag atg gtt cat gag atc aag gga gac acg gtg gcc cct ggg agc<br>Lys Gln Met Val His Glu Ile Lys Gly Asp Thr Val Ala Pro Gly Ser<br>    2770                          2775                        2780 | 8352 |
| gag gga cta ctc aac ctg cat cct gac gat ttt gtc ttc tac gtg gga<br>Glu Gly Leu Leu Asn Leu His Pro Asp Asp Phe Val Phe Tyr Val Gly<br>2785                      2790                       2795                        2800 | 8400 |
| gga tac ccc agc aac ttc acg ccc cct gaa ccc ctc cga ttc cct ggc<br>Gly Tyr Pro Ser Asn Phe Thr Pro Pro Glu Pro Leu Arg Phe Pro Gly<br>        2805                          2810                        2815 | 8448 |
| tac ctg ggc tgc att gag atg gaa aca ctg aat gag gag gtg gtc agc<br>Tyr Leu Gly Cys Ile Glu Met Glu Thr Leu Asn Glu Glu Val Val Ser<br>                 2820                        2825                        2830 | 8496 |
| ctc tac aat ttt gag cag acc ttc atg ctg gac acg gca gta gat aaa<br>Leu Tyr Asn Phe Glu Gln Thr Phe Met Leu Asp Thr Ala Val Asp Lys<br>2835                      2840                       2845 | 8544 |
| cct tgt gct cgc tcc aag gcc acc ggt gac cca tgg ctc aca gat ggc<br>Pro Cys Ala Arg Ser Lys Ala Thr Gly Asp Pro Trp Leu Thr Asp Gly<br>    2850                          2855                        2860 | 8592 |
| tcc tac ctg gat ggc agt ggc ttt gcc cgc atc agc ttt gag aag cag<br>Ser Tyr Leu Asp Gly Ser Gly Phe Ala Arg Ile Ser Phe Glu Lys Gln<br>2865                      2870                       2875                        2880 | 8640 |
| ttc agc aac aca aaa cgc ttt gac cag gag ctg cgg ctt gtg tcc tac<br>Phe Ser Asn Thr Lys Arg Phe Asp Gln Glu Leu Arg Leu Val Ser Tyr<br>        2885                          2890                        2895 | 8688 |
| aat ggg atc atc ttt ttc ctc aag caa gag agc cag ttc ttg tgc ctg<br>Asn Gly Ile Ile Phe Phe Leu Lys Gln Glu Ser Gln Phe Leu Cys Leu<br>                 2900                        2905                        2910 | 8736 |
| gca gtg cag gaa ggc acc ctg gtg ctc ttc tat gac ttc ggc tct ggc<br>Ala Val Gln Glu Gly Thr Leu Val Leu Phe Tyr Asp Phe Gly Ser Gly<br>2915                      2920                       2925 | 8784 |
| ctg aag aag gcc gac cca ctg cag ccc cca caa gcc ttg acg gca gcc<br>Leu Lys Lys Ala Asp Pro Leu Gln Pro Pro Gln Ala Leu Thr Ala Ala<br>    2930                          2935                        2940 | 8832 |
| agc aag gcg atc caa gtg ttt cta ttg gct ggc aat cgc aaa cgt gtg<br>Ser Lys Ala Ile Gln Val Phe Leu Leu Ala Gly Asn Arg Lys Arg Val<br>2945                      2950                       2955                        2960 | 8880 |
| ttg gtg cgt gtg gag cgg gcc act gtg ttc agc gta gac cag gat aac<br>Leu Val Arg Val Glu Arg Ala Thr Val Phe Ser Val Asp Gln Asp Asn<br>        2965                        2970                        2975 | 8928 |
| atg ctg gag atg gct gat gcc tac tac ttg gga ggd gtg cca cct gaa<br>Met Leu Glu Met Ala Asp Ala Tyr Tyr Leu Gly Gly Val Pro Pro Glu<br>                 2980                        2985                        2990 | 8976 |
| cag ctg ccc ttg agc cta cgg cag ctc ttc ccc tcc gga ggc tct gtc | 9024 |

```
                Gln Leu Pro Leu Ser Leu Arg Gln Leu Phe Pro Ser Gly Gly Ser Val
                    2995                3000                3005 cgt ggy tgc atc aag ggt att aag gct ctg ggc aag tac gtg gac ctc          9072
Arg Gly Cys Ile Lys Gly Ile Lys Ala Leu Gly Lys Tyr Val Asp Leu
    3010                3015                3020 aaa cgg ttg aac acc acg ggc atc agt ttc ggc tgc acc gct gac ctg          9120
Lys Arg Leu Asn Thr Thr Gly Ile Ser Phe Gly Cys Thr Ala Asp Leu
3025                3030                3035                3040 cta gtg gga cgc acc atg act ttt cac ggc cac ggc ttc ctg ccc ctg          9168
Leu Val Gly Arg Thr Met Thr Phe His Gly His Gly Phe Leu Pro Leu
                3045                3050                3055 gca ctt cct gat gtg gca ccc atc acc gaa gtg gtc tat tct ggc ttt          9216
Ala Leu Pro Asp Val Ala Pro Ile Thr Glu Val Val Tyr Ser Gly Phe
            3060                3065                3070 ggc ttt cgt ggc acc cag gac aac aac ctg ctg tat tac cgt acc tcc          9264
Gly Phe Arg Gly Thr Gln Asp Asn Asn Leu Leu Tyr Tyr Arg Thr Ser
        3075                3080                3085 ccg gat ggg ccg tac cag gta tcc ctg agg gag ggc cac gtg aca ctc          9312
Pro Asp Gly Pro Tyr Gln Val Ser Leu Arg Glu Gly His Val Thr Leu
    3090                3095                3100 cgt ttt atg aac caa gag gtg gaa act caa agg gtc ttt gct gat ggt          9360
Arg Phe Met Asn Gln Glu Val Glu Thr Gln Arg Val Phe Ala Asp Gly
3105                3110                3115                3120 gct cct cac tat gtt gcc ttc tat agc aat gtc aca ggg gta tgg ctg          9408
Ala Pro His Tyr Val Ala Phe Tyr Ser Asn Val Thr Gly Val Trp Leu
                3125                3130                3135 tat gtg gat gac cag cta caa cta gta aag tct cat gag aga aca act          9456
Tyr Val Asp Asp Gln Leu Gln Leu Val Lys Ser His Glu Arg Thr Thr
            3140                3145                3150 ccc atg ctc caa cta cag ccc gag gaa ccc tca cgg ctt ctc ctg gga          9504
Pro Met Leu Gln Leu Gln Pro Glu Glu Pro Ser Arg Leu Leu Leu Gly
        3155                3160                3165 ggc ctg cct gtg tct ggt acc ttc cac aac ttc agt ggc tgc atc agc          9552
Gly Leu Pro Val Ser Gly Thr Phe His Asn Phe Ser Gly Cys Ile Ser
    3170                3175                3180 aat gtt ttt gta cag cga ctt cgg gga cca cag cgt gtg ttt gac cta          9600
Asn Val Phe Val Gln Arg Leu Arg Gly Pro Gln Arg Val Phe Asp Leu
3185                3190                3195                3200 cac cag aac atg ggg agt gtc aat gta agc gta ggc tgt aca cca gcc          9648
His Gln Asn Met Gly Ser Val Asn Val Ser Val Gly Cys Thr Pro Ala
                3205                3210                3215 caa ctc atc gag acc tca agg gcc acg gct cag aag gtt tcc cgc cgt          9696
Gln Leu Ile Glu Thr Ser Arg Ala Thr Ala Gln Lys Val Ser Arg Arg
            3220                3225                3230 agt cga caa ccc agc cag gac ctt gcc tgc acg aca ccc tgg ctc cct          9744
Ser Arg Gln Pro Ser Gln Asp Leu Ala Cys Thr Thr Pro Trp Leu Pro
        3235                3240                3245 ggg act att cag gat gca tac cag ttt ggg gga ccc ctg ccc agt tac          9792
Gly Thr Ile Gln Asp Ala Tyr Gln Phe Gly Gly Pro Leu Pro Ser Tyr
    3250                3255                3260 cta cag ttt gtg ggt atc tct ccg tcc cac agg aat agg ctc cac ctc          9840
Leu Gln Phe Val Gly Ile Ser Pro Ser His Arg Asn Arg Leu His Leu
3265                3270                3275                3280 tcc atg ctt gtc cgt cca cat gcg gct tcc cag ggc ctc ctg ctc tct          9888
Ser Met Leu Val Arg Pro His Ala Ala Ser Gln Gly Leu Leu Leu Ser
                3285                3290                3295 aca gcc ccc atg tcg ggc cgc agc cct tcg ttg gta ctc ttt cta aac          9936
Thr Ala Pro Met Ser Gly Arg Ser Pro Ser Leu Val Leu Phe Leu Asn
            3300                3305                3310
```

-continued

| | |
|---|---|
| cat gga cac ttt gtc gca cag act gag ggc cct ggg ccc cgg ctc cag<br>His Gly His Phe Val Ala Gln Thr Glu Gly Pro Gly Pro Arg Leu Gln<br>                3315                        3320                        3325 | 9984 |
| gtc cag agt cgc cag cac tca cgg gct ggc cag tgg cac agg gtg tcc<br>Val Gln Ser Arg Gln His Ser Arg Ala Gly Gln Trp His Arg Val Ser<br>        3330                        3335                        3340 | 10032 |
| gtc cgc tgg gga atg cag cag atc cag ctt gtg gtg gac ggc agc cag<br>Val Arg Trp Gly Met Gln Gln Ile Gln Leu Val Val Asp Gly Ser Gln<br>3345                        3350                        3355                        3360 | 10080 |
| acc tgg agc cag aag gct ctc cac cat cgg gtc ccc agg gca gag cga<br>Thr Trp Ser Gln Lys Ala Leu His His Arg Val Pro Arg Ala Glu Arg<br>                3365                        3370                        3375 | 10128 |
| cca cag ccc tac acc ctc tct gta gga ggt ctt cct gcc agc agt tac<br>Pro Gln Pro Tyr Thr Leu Ser Val Gly Gly Leu Pro Ala Ser Ser Tyr<br>        3380                        3385                        3390 | 10176 |
| agt tcc aag ctc cct gtg tct gtg ggg ttc agc ggc tgt ctg aag aaa<br>Ser Ser Lys Leu Pro Val Ser Val Gly Phe Ser Gly Cys Leu Lys Lys<br>                3395                        3400                        3405 | 10224 |
| tta cag ctg gat aag cag cca ctg agg acc cca acg caa atg gtg ggg<br>Leu Gln Leu Asp Lys Gln Pro Leu Arg Thr Pro Thr Gln Met Val Gly<br>     3410                        3415                        3420 | 10272 |
| gtc aca ccc tgt gtc tca ggc ccc ctg gaa gat ggc ctg ttc ttc cca<br>Val Thr Pro Cys Val Ser Gly Pro Leu Glu Asp Gly Leu Phe Phe Pro<br>3425                        3430                        3435                        3440 | 10320 |
| ggc agt gag gga gtt gtc aca tta gag ctc ccc aag gcc aag atg ccc<br>Gly Ser Glu Gly Val Val Thr Leu Glu Leu Pro Lys Ala Lys Met Pro<br>                3445                        3450                        3455 | 10368 |
| tat gtg agc ctg gag cta gag atg cgg ccc ttg gca gct gct ggc ctc<br>Tyr Val Ser Leu Glu Leu Glu Met Arg Pro Leu Ala Ala Ala Gly Leu<br>        3460                        3465                        3470 | 10416 |
| atc ttc cac ctg ggc cag gcc ctg gcc act ccc tac atg cag ctg aag<br>Ile Phe His Leu Gly Gln Ala Leu Ala Thr Pro Tyr Met Gln Leu Lys<br>                3475                        3480                        3485 | 10464 |
| gtg ctg aca gaa cag gtc ctg ctg cag gca aat gat ggg gca ggg gag<br>Val Leu Thr Glu Gln Val Leu Leu Gln Ala Asn Asp Gly Ala Gly Glu<br>     3490                        3495                        3500 | 10512 |
| ttt tcc acg tgg gtg acc tac ccc aag ctt tgt gat gga cgg tgg cac<br>Phe Ser Thr Trp Val Thr Tyr Pro Lys Leu Cys Asp Gly Arg Trp His<br>3505                        3510                        3515                        3520 | 10560 |
| cga gtg gca gtg atc atg ggc agg gac aca ctc cgg ctg gag gta gac<br>Arg Val Ala Val Ile Met Gly Arg Asp Thr Leu Arg Leu Glu Val Asp<br>                3525                        3530                        3535 | 10608 |
| aca cag agc aac cac acc aca ggc cgt ttg cca gag agc ttg gct ggt<br>Thr Gln Ser Asn His Thr Thr Gly Arg Leu Pro Glu Ser Leu Ala Gly<br>        3540                        3545                        3550 | 10656 |
| tct cca gca ctt ctg cac ctc ggg agc ctg ccc aag tct tca act gct<br>Ser Pro Ala Leu Leu His Leu Gly Ser Leu Pro Lys Ser Ser Thr Ala<br>                3555                        3560                        3565 | 10704 |
| cgg cca gag ctc cct gcc tac cga gga tgc ttg agg aag ctg ctg atc<br>Arg Pro Glu Leu Pro Ala Tyr Arg Gly Cys Leu Arg Lys Leu Leu Ile<br>     3570                        3575                        3580 | 10752 |
| aat ggg gcc cct gtc aac gtg act gct tct gta caa atc cag ggg gca<br>Asn Gly Ala Pro Val Asn Val Thr Ala Ser Val Gln Ile Gln Gly Ala<br>3585                        3590                        3595                        3600 | 10800 |
| gtg ggg atg cgc gga tgc ccc tca gga acc cta gca ctt tcc aag cag<br>Val Gly Met Arg Gly Cys Pro Ser Gly Thr Leu Ala Leu Ser Lys Gln<br>                3605                        3610                        3615 | 10848 |
| gga aag gca ctg acc cag agg cac gcc aag ccc agt gtc tcc ccg cta<br>Gly Lys Ala Leu Thr Gln Arg His Ala Lys Pro Ser Val Ser Pro Leu<br>     3620                        3625                        3630 | 10896 |

-continued

```
ctt tgg cat tgagggttcc cagaccttgg ggtttgccta cactttctat              10945
Leu Trp His
        3635 gaataacaag tcatttctgg tttacactgt cttttagagg aaaaggactc tgtagaacag    11005 atat                                                                 11009
```

<210> SEQ ID NO 4
<211> LENGTH: 3635
<212> TYPE: PRT
<213> ORGANISM: Mus musculus

<400> SEQUENCE: 4

```
Asp Leu Tyr Cys Lys Leu Val Gly Gly Pro Val Ala Gly Gly Asp Pro
 1               5                  10                  15

Asn Gln Thr Ile Gln Gly Gln Tyr Cys Asp Ile Cys Thr Ala Ala Asn
            20                  25                  30

Ser Asn Lys Ala His Pro Val Ser Asn Ala Ile Asp Gly Thr Glu Arg
        35                  40                  45

Trp Trp Gln Ser Pro Pro Leu Ser Arg Gly Leu Glu Tyr Asn Glu Val
    50                  55                  60

Asn Val Thr Leu Asp Leu Gly Gln Val Phe His Val Ala Tyr Val Leu
65                  70                  75                  80

Ile Lys Phe Ala Asn Ser Pro Arg Pro Asp Leu Trp Val Leu Glu Arg
                85                  90                  95

Ser Thr Asp Phe Gly His Thr Tyr Gln Pro Trp Gln Phe Phe Ala Ser
            100                 105                 110

Ser Lys Arg Asp Cys Leu Glu Arg Phe Gly Pro Arg Thr Leu Glu Arg
        115                 120                 125

Ile Thr Gln Asp Asp Val Ile Cys Thr Thr Glu Tyr Ser Arg Ile
    130                 135                 140

Val Pro Leu Glu Asn Gly Glu Ile Val Val Ser Leu Val Asn Gly Arg
145                 150                 155                 160

Pro Gly Ala Leu Asn Phe Ser Tyr Ser Pro Leu Leu Arg Asp Phe Thr
                165                 170                 175

Lys Ala Thr Asn Ile Arg Leu Arg Phe Leu Arg Thr Asn Thr Leu Leu
            180                 185                 190

Gly His Leu Met Gly Lys Ala Leu Arg Asp Pro Thr Val Thr Arg Arg
        195                 200                 205

Tyr Tyr Tyr Ser Ile Lys Asp Ile Ser Ile Gly Gly Arg Cys Val Cys
    210                 215                 220

His Gly His Ala Asp Val Cys Asp Ala Lys Asp Pro Leu Asp Pro Phe
225                 230                 235                 240

Arg Leu Gln Cys Ala Cys Gln His Asn Thr Cys Gly Gly Ser Cys Asp
                245                 250                 255

Arg Cys Cys Pro Gly Phe Asn Gln Gln Pro Trp Lys Pro Ala Thr Thr
            260                 265                 270

Asp Ser Ala Asn Glu Cys Gln Ser Cys Asn Cys His Gly His Ala Tyr
        275                 280                 285

Asp Cys Tyr Tyr Asp Pro Glu Val Asp Arg Arg Asn Ala Ser Gln Asn
    290                 295                 300

Gln Asp Asn Val Tyr Gln Gly Gly Val Cys Leu Asp Cys Gln His
305                 310                 315                 320

His Thr Thr Gly Ile Asn Cys Glu Arg Cys Leu Pro Gly Phe Phe Arg
                325                 330                 335
```

```
Ala Pro Asp Gln Pro Leu Asp Ser Pro His Val Cys Arg Pro Cys Asp
            340                 345                 350

Cys Glu Ser Asp Phe Thr Asp Gly Thr Cys Glu Asp Leu Thr Gly Arg
            355                 360                 365

Cys Tyr Cys Arg Pro Asn Phe Thr Gly Glu Leu Cys Ala Ala Cys Ala
            370                 375                 380

Glu Gly Tyr Thr Asp Phe Pro His Cys Tyr Pro Leu Pro Ser Phe Pro
385                 390                 395                 400

His Asn Asp Thr Arg Glu Gln Val Leu Pro Ala Gly Gln Ile Val Asn
                405                 410                 415

Cys Asp Cys Asn Ala Ala Gly Thr Gln Gly Asn Ala Cys Arg Lys Asp
            420                 425                 430

Pro Arg Leu Gly Arg Cys Val Cys Lys Pro Asn Phe Arg Gly Ala His
            435                 440                 445

Cys Glu Leu Cys Ala Pro Gly Phe His Gly Pro Ser Cys His Pro Cys
            450                 455                 460

Gln Cys Ser Ser Pro Gly Val Ala Asn Ser Leu Cys Asp Pro Glu Ser
465                 470                 475                 480

Gly Gln Cys Met Cys Arg Thr Gly Phe Glu Gly Asp Arg Cys Asp His
            485                 490                 495

Cys Ala Leu Gly Tyr Phe His Phe Pro Leu Cys Gln Leu Cys Gly Cys
            500                 505                 510

Ser Pro Ala Gly Thr Leu Pro Glu Gly Cys Asp Glu Ala Gly Arg Cys
            515                 520                 525

Gln Cys Arg Pro Gly Phe Asp Gly Pro His Cys Asp Arg Cys Leu Pro
            530                 535                 540

Gly Tyr His Gly Tyr Pro Asp Cys His Ala Cys Ala Cys Asp Pro Arg
545                 550                 555                 560

Gly Ala Leu Asp Gln Gln Cys Gly Val Gly Gly Leu Cys His Cys Arg
                565                 570                 575

Pro Gly Asn Thr Gly Ala Thr Cys Gln Glu Cys Ser Pro Gly Phe Tyr
            580                 585                 590

Gly Phe Pro Ser Cys Ile Pro Cys His Cys Ser Ala Asp Gly Ser Leu
            595                 600                 605

His Thr Thr Cys Asp Pro Thr Thr Gly Gln Cys Arg Cys Arg Pro Arg
            610                 615                 620

Val Thr Gly Leu His Cys Asp Met Cys Val Pro Gly Ala Tyr Asn Phe
625                 630                 635                 640

Pro Tyr Cys Glu Ala Gly Ser Cys His Pro Ala Gly Leu Ala Pro Ala
            645                 650                 655

Asn Pro Ala Leu Pro Glu Thr Gln Ala Pro Cys Met Cys Arg Ala His
            660                 665                 670

Val Glu Gly Pro Ser Cys Asp Arg Cys Lys Pro Gly Tyr Trp Gly Leu
            675                 680                 685

Ser Ala Ser Asn Pro Glu Gly Cys Thr Arg Cys Ser Cys Asp Pro Arg
            690                 695                 700

Gly Thr Leu Gly Gly Val Thr Glu Cys Gln Gly Asn Gly Gln Cys Phe
705                 710                 715                 720

Cys Lys Ala His Val Cys Gly Lys Thr Cys Ala Ala Cys Lys Asp Gly
            725                 730                 735

Phe Phe Gly Leu Asp Tyr Ala Asp Tyr Phe Gly Cys Arg Ser Cys Arg
            740                 745                 750
```

-continued

```
Cys Asp Val Gly Gly Ala Leu Gly Gln Gly Cys Glu Pro Lys Thr Gly
        755                 760                 765
Ala Cys Arg Cys Arg Pro Asn Thr Gln Gly Pro Thr Cys Ser Glu Pro
    770                 775                 780
Ala Lys Asp His Tyr Leu Pro Asp Leu His His Met Arg Leu Glu Leu
785                 790                 795                 800
Glu Glu Ala Ala Thr Pro Glu Gly His Ala Val Arg Phe Gly Phe Asn
                805                 810                 815
Pro Leu Glu Phe Glu Asn Phe Ser Trp Arg Gly Tyr Ala His Met Met
            820                 825                 830
Ala Ile Gln Pro Arg Ile Val Ala Arg Leu Asn Val Thr Ser Pro Asp
            835                 840                 845
Leu Phe Arg Leu Val Phe Arg Tyr Val Asn Arg Gly Ser Thr Ser Val
    850                 855                 860
Asn Gly Gln Ile Ser Val Arg Glu Gly Lys Leu Ser Ser Cys Thr
865                 870                 875                 880
Asn Cys Thr Glu Gln Ser Gln Pro Val Ala Phe Pro Pro Ser Thr Glu
                885                 890                 895
Pro Ala Phe Val Thr Val Pro Gln Arg Gly Phe Gly Glu Pro Phe Val
            900                 905                 910
Leu Asn Pro Gly Ile Trp Ala Leu Leu Val Glu Ala Glu Gly Val Leu
        915                 920                 925
Leu Asp Tyr Val Val Leu Leu Pro Ser Thr Tyr Tyr Glu Ala Ala Leu
    930                 935                 940
Leu Gln His Arg Val Thr Glu Ala Cys Thr Tyr Arg Pro Ser Ala Leu
945                 950                 955                 960
His Ser Thr Glu Asn Cys Leu Val Tyr Ala His Leu Pro Leu Asp Gly
                965                 970                 975
Phe Pro Ser Ala Ala Gly Thr Glu Ala Leu Cys Arg His Asp Asn Ser
            980                 985                 990
Leu Pro Arg Pro Cys Pro Thr Glu Gln Leu Ser Pro Ser His Pro Pro
        995                 1000                1005
Leu Ala Thr Cys Phe Gly Ser Asp Val Asp Ile Gln Leu Glu Met Ala
    1010                1015                1020
Val Pro Gln Pro Gly Gln Tyr Val Leu Val Val Glu Tyr Val Gly Glu
1025                1030                1035                1040
Asp Ser His Gln Glu Met Gly Val Ala Val His Thr Pro Gln Arg Ala
                1045                1050                1055
Pro Gln Gln Gly Val Leu Asn Leu His Pro Cys Pro Tyr Ser Ser Leu
            1060                1065                1070
Cys Arg Ser Pro Ala Arg Asp Thr Gln His His Leu Ala Ile Phe His
        1075                1080                1085
Leu Asp Ser Glu Ala Ser Ile Arg Leu Thr Ala Glu Gln Ala His Phe
    1090                1095                1100
Phe Leu His Ser Val Thr Leu Val Pro Val Glu Glu Phe Ser Thr Glu
1105                1110                1115                1120
Phe Val Glu Pro Arg Val Phe Cys Val Ser Ser His Gly Thr Phe Asn
                1125                1130                1135
Pro Ser Ser Ala Ala Cys Leu Ala Ser Arg Phe Pro Lys Pro Pro Gln
            1140                1145                1150
Pro Ile Ile Leu Lys Asp Cys Gln Val Leu Pro Leu Pro Pro Asp Leu
        1155                1160                1165
Pro Leu Thr Gln Ser Gln Glu Leu Ser Pro Gly Ala Pro Pro Glu Gly
```

```
                1170                1175                1180
Pro Gln Pro Arg Pro Pro Thr Ala Val Asp Pro Asn Ala Glu Pro Thr
1185                1190                1195                1200

Leu Leu Arg His Pro Gln Gly Thr Val Val Phe Thr Thr Gln Val Pro
                1205                1210                1215

Thr Leu Gly Arg Tyr Ala Phe Leu Leu His Gly Tyr Gln Pro Val His
                1220                1225                1230

Pro Ser Phe Pro Val Glu Val Leu Ile Asn Gly Gly Arg Ile Trp Gln
            1235                1240                1245

Gly His Ala Asn Ala Ser Phe Cys Pro His Gly Tyr Gly Cys Arg Thr
1250                1255                1260

Leu Val Leu Cys Glu Gly Gln Thr Met Leu Asp Val Thr Asp Asn Glu
1265                1270                1275                1280

Leu Thr Val Thr Val Arg Val Pro Glu Gly Arg Trp Leu Trp Leu Asp
                1285                1290                1295

Tyr Val Leu Ile Val Pro Glu Asp Ala Tyr Ser Ser Ser Tyr Leu Gln
                1300                1305                1310

Glu Glu Pro Leu Asp Lys Ser Tyr Asp Phe Ile Ser His Cys Ala Thr
        1315                1320                1325

Gln Gly Tyr His Ile Ser Pro Ser Ser Ser Pro Phe Cys Arg Asn
    1330                1335                1340

Ala Ala Thr Ser Leu Ser Leu Phe Tyr Asn Asn Gly Ala Leu Pro Cys
1345                1350                1355                1360

Gly Cys His Glu Val Gly Ala Val Ser Pro Thr Cys Glu Pro Phe Gly
                1365                1370                1375

Gly Gln Cys Pro Cys Arg Gly His Val Ile Gly Arg Asp Cys Ser Arg
            1380                1385                1390

Cys Ala Thr Gly Tyr Trp Gly Phe Pro Asn Cys Arg Pro Cys Asp Cys
        1395                1400                1405

Gly Ala Arg Leu Cys Asp Glu Leu Thr Gly Gln Cys Ile Cys Pro Pro
    1410                1415                1420

Arg Thr Val Pro Pro Asp Cys Leu Val Cys Gln Pro Gln Ser Phe Gly
1425                1430                1435                1440

Cys His Pro Leu Val Gly Cys Glu Glu Cys Asn Cys Ser Gly Pro Gly
                1445                1450                1455

Val Gln Glu Leu Thr Asp Pro Thr Cys Asp Met Asp Ser Gly Gln Cys
            1460                1465                1470

Arg Cys Arg Pro Asn Val Ala Gly Arg Arg Cys Asp Thr Cys Ala Pro
        1475                1480                1485

Gly Phe Tyr Gly Tyr Pro Ser Cys Arg Pro Cys Asp Cys His Glu Ala
    1490                1495                1500

Gly Thr Met Ala Ser Val Cys Asp Pro Leu Thr Gly Gln Cys His Cys
1505                1510                1515                1520

Lys Glu Asn Val Gln Gly Ser Arg Cys Asp Gln Cys Arg Val Gly Thr
                1525                1530                1535

Phe Ser Leu Asp Ala Ala Asn Pro Lys Gly Cys Thr Arg Cys Phe Cys
            1540                1545                1550

Phe Gly Ala Thr Glu Arg Cys Gly Asn Ser Asn Leu Ala Arg His Glu
        1555                1560                1565

Phe Val Asp Met Glu Gly Trp Val Leu Leu Ser Ser Asp Arg Gln Val
    1570                1575                1580

Val Pro His Glu His Arg Pro Glu Ile Glu Leu Leu His Ala Asp Leu
1585                1590                1595                1600
```

```
Arg Ser Val Ala Asp Thr Phe Ser Glu Leu Tyr Trp Gln Ala Pro Pro
            1605                1610                1615

Ser Tyr Leu Gly Asp Arg Val Ser Ser Tyr Gly Gly Thr Leu His Tyr
        1620                1625                1630

Glu Leu His Ser Glu Thr Gln Arg Gly Asp Ile Phe Ile Pro Tyr Glu
    1635                1640                1645

Ser Arg Pro Asp Val Val Leu Gln Gly Asn Gln Met Ser Ile Ala Phe
1650                1655                1660

Leu Glu Leu Ala Tyr Pro Pro Gly Gln Val His Arg Gly Gln Leu
1665                1670                1675                1680

Gln Leu Val Glu Gly Asn Phe Arg His Leu Glu Thr His Asn Pro Val
            1685                1690                1695

Ser Arg Glu Glu Leu Met Met Val Leu Ala Gly Leu Glu Gln Leu Gln
                1700                1705                1710

Ile Arg Ala Leu Phe Ser Gln Thr Ser Ser Ser Val Ser Leu Arg Arg
        1715                1720                1725

Val Val Leu Glu Val Ala Ser Glu Ala Gly Arg Gly Pro Pro Ala Ser
    1730                1735                1740

Asn Val Glu Leu Cys Met Cys Pro Ala Asn Tyr Arg Gly Asp Ser Cys
1745                1750                1755                1760

Gln Glu Cys Ala Pro Gly Tyr Tyr Arg Asp Thr Lys Gly Leu Phe Leu
            1765                1770                1775

Gly Arg Cys Val Pro Cys Gln Cys His Gly His Ser Asp Arg Cys Leu
        1780                1785                1790

Pro Gly Ser Gly Ile Cys Val Gly Cys Gln His Asn Thr Glu Gly Asp
    1795                1800                1805

Gln Cys Glu Arg Cys Arg Pro Gly Phe Val Ser Ser Asp Pro Ser Asn
1810                1815                1820

Pro Ala Ser Pro Cys Val Ser Cys Pro Cys Pro Leu Ala Val Pro Ser
1825                1830                1835                1840

Asn Asn Phe Ala Asp Gly Cys Val Leu Arg Asn Gly Arg Thr Gln Cys
            1845                1850                1855

Leu Cys Arg Pro Gly Tyr Ala Gly Ala Ser Cys Glu Arg Cys Ala Pro
        1860                1865                1870

Gly Phe Phe Gly Asn Pro Leu Val Leu Gly Ser Ser Cys Gln Pro Cys
    1875                1880                1885

Asp Cys Ser Gly Asn Gly Asp Pro Asn Met Ile Phe Ser Asp Cys Asp
1890                1895                1900

Pro Leu Thr Gly Ala Cys Arg Gly Cys Leu Arg His Thr Thr Gly Pro
1905                1910                1915                1920

His Cys Glu Arg Cys Ala Pro Gly Phe Tyr Gly Asn Ala Leu Leu Pro
            1925                1930                1935

Gly Asn Cys Thr Arg Cys Asp Cys Ser Pro Cys Gly Thr Glu Thr Cys
        1940                1945                1950

Asp Pro Gln Ser Gly Arg Cys Leu Cys Lys Ala Gly Val Thr Gly Gln
    1955                1960                1965

Arg Cys Asp Arg Cys Leu Glu Gly Tyr Phe Gly Phe Glu Gln Cys Gln
1970                1975                1980

Gly Cys Arg Pro Cys Ala Cys Gly Pro Ala Ala Lys Gly Ser Glu Cys
1985                1990                1995                2000

His Pro Gln Ser Gly Gln Cys His Cys Gln Pro Gly Thr Thr Gly Pro
            2005                2010                2015
```

-continued

```
Gln Cys Leu Glu Cys Ala Pro Gly Tyr Trp Gly Leu Pro Glu Lys Gly
        2020                2025                2030

Cys Arg Arg Cys Gln Cys Pro Arg Gly His Cys Asp Pro His Thr Gly
            2035                2040                2045

His Cys Thr Cys Pro Pro Gly Leu Ser Gly Arg Cys Asp Thr Cys
    2050                2055                2060

Ser Gln Gln His Gln Val Pro Val Pro Gly Lys Pro Gly His Gly
2065                2070                2075                2080

Ile His Cys Glu Val Cys Asp His Cys Val Val Leu Leu Asp Asp
                2085                2090                2095

Leu Glu Arg Ala Gly Ala Leu Leu Pro Ala Ile Arg Glu Gln Leu Gln
            2100                2105                2110

Gly Ile Asn Ala Ser Ser Ala Ala Trp Ala Arg Leu His Arg Leu Asn
            2115                2120                2125

Ala Ser Ile Ala Asp Leu Gln Ser Lys Leu Arg Arg Pro Pro Gly Pro
        2130                2135                2140

Arg Tyr Gln Ala Ala Gln Gln Leu Gln Thr Leu Glu Gln Gln Ser Ile
2145                2150                2155                2160

Ser Leu Gln Gln Asp Thr Glu Arg Leu Gly Ser Gln Ala Thr Gly Val
            2165                2170                2175

Gln Gly Gln Ala Gly Gln Leu Leu Asp Thr Thr Glu Ser Thr Leu Gly
            2180                2185                2190

Arg Ala Gln Lys Leu Leu Glu Ser Val Arg Ala Val Gly Arg Ala Leu
        2195                2200                2205

Asn Glu Leu Ala Ser Arg Met Gly Gln Gly Ser Pro Gly Asp Ala Leu
    2210                2215                2220

Val Pro Ser Gly Glu Gln Leu Arg Trp Ala Leu Ala Glu Val Glu Arg
2225                2230                2235                2240

Leu Leu Trp Asp Met Arg Thr Arg Asp Leu Gly Ala Gln Gly Ala Val
            2245                2250                2255

Ala Glu Ala Glu Leu Ala Glu Ala Gln Arg Leu Met Ala Arg Val Gln
        2260                2265                2270

Glu Gln Leu Thr Ser Phe Trp Glu Glu Asn Gln Ser Leu Ala Thr His
    2275                2280                2285

Ile Arg Asp Gln Leu Ala Gln Tyr Glu Ser Gly Leu Met Asp Leu Arg
    2290                2295                2300

Glu Ala Leu Asn Gln Ala Val Asn Thr Thr Arg Glu Ala Glu Glu Leu
2305                2310                2315                2320

Asn Ser Arg Asn Gln Glu Arg Val Lys Glu Ala Leu Gln Trp Lys Gln
            2325                2330                2335

Glu Leu Ser Gln Asp Asn Ala Thr Leu Lys Ala Thr Leu Gln Ala Ala
        2340                2345                2350

Ser Leu Ile Leu Gly His Val Ser Glu Leu Leu Gln Gly Ile Asp Gln
        2355                2360                2365

Ala Lys Glu Asp Leu Glu His Leu Ala Ala Ser Leu Asp Gly Ala Trp
    2370                2375                2380

Thr Pro Leu Leu Lys Arg Met Gln Ala Phe Ser Pro Ala Ser Ser Lys
2385                2390                2395                2400

Val Asp Leu Val Glu Ala Ala Glu Ala His Ala Gln Lys Leu Asn Gln
            2405                2410                2415

Leu Ala Ile Asn Leu Ser Gly Ile Ile Leu Gly Ile Asn Gln Asp Arg
        2420                2425                2430

Phe Ile Gln Arg Ala Val Glu Ala Ser Asn Ala Tyr Ser Ser Ile Leu
```

-continued

```
                2435                2440                2445
Gln Ala Val Gln Ala Ala Glu Asp Ala Ala Gly Gln Ala Leu Arg Gln
    2450                2455                2460

Ala Ser Arg Thr Trp Glu Met Val Val Gln Arg Gly Leu Ala Ala Gly
2465                2470                2475                2480

Ala Arg Gln Leu Leu Ala Asn Ser Ser Ala Leu Glu Glu Thr Ile Leu
                2485                2490                2495

Gly His Gln Gly Arg Leu Gly Leu Ala Gln Gly Arg Leu Gln Ala Ala
        2500                2505                2510

Gly Ile Gln Leu His Asn Val Trp Ala Arg Lys Asn Gln Leu Ala Ala
    2515                2520                2525

Gln Ile Gln Glu Ala Gln Ala Met Leu Ala Met Asp Thr Ser Glu Thr
    2530                2535                2540

Ser Glu Lys Ile Ala His Ala Lys Ala Val Ala Ala Glu Ala Leu Ser
2545                2550                2555                2560

Thr Ala Thr His Val Gln Ser Gln Leu Gln Gly Met Gln Lys Asn Val
                2565                2570                2575

Glu Arg Trp Gln Ser Gln Leu Gly Gly Leu Gln Gly Gln Asp Leu Ser
        2580                2585                2590

Gln Val Glu Arg Asp Ala Ser Ser Val Ser Thr Leu Glu Lys Thr
    2595                2600                2605

Leu Pro Gln Leu Leu Ala Lys Leu Ser Arg Leu Glu Asn Arg Gly Val
    2610                2615                2620

His Asn Ala Ser Leu Ala Leu Ser Ala Asn Ile Gly Arg Val Arg Lys
2625                2630                2635                2640

Leu Ile Ala Gln Ala Arg Ser Ala Ala Ser Lys Val Lys Val Ser Met
                2645                2650                2655

Lys Phe Asn Gly Arg Ser Gly Val Arg Leu Arg Pro Pro Arg Asp Leu
        2660                2665                2670

Ala Asp Leu Ala Ala Tyr Thr Ala Leu Lys Phe His Ile Gln Ser Pro
    2675                2680                2685

Val Pro Ala Pro Glu Pro Gly Lys Asn Thr Gly Asp His Phe Val Leu
    2690                2695                2700

Tyr Met Gly Ser Arg Gln Ala Thr Gly Asp Tyr Met Gly Val Ser Leu
2705                2710                2715                2720

Arg Asn Gln Lys Val His Trp Val Tyr Arg Leu Gly Lys Ala Gly Pro
                2725                2730                2735

Thr Thr Leu Ser Ile Asp Glu Asn Ile Gly Glu Gln Phe Ala Ala Val
        2740                2745                2750

Ser Ile Asp Arg Thr Leu Gln Phe Gly His Met Ser Val Thr Val Glu
    2755                2760                2765

Lys Gln Met Val His Glu Ile Lys Gly Asp Thr Val Ala Pro Gly Ser
    2770                2775                2780

Glu Gly Leu Leu Asn Leu His Pro Asp Asp Phe Val Phe Tyr Val Gly
2785                2790                2795                2800

Gly Tyr Pro Ser Asn Phe Thr Pro Pro Glu Pro Leu Arg Phe Pro Gly
                2805                2810                2815

Tyr Leu Gly Cys Ile Glu Met Glu Thr Leu Asn Glu Glu Val Val Ser
        2820                2825                2830

Leu Tyr Asn Phe Glu Gln Thr Phe Met Leu Asp Thr Ala Val Asp Lys
    2835                2840                2845

Pro Cys Ala Arg Ser Lys Ala Thr Gly Asp Pro Trp Leu Thr Asp Gly
    2850                2855                2860
```

```
Ser Tyr Leu Asp Gly Ser Gly Phe Ala Arg Ile Ser Phe Glu Lys Gln
2865                2870                2875                2880

Phe Ser Asn Thr Lys Arg Phe Asp Gln Glu Leu Arg Leu Val Ser Tyr
        2885                2890                2895

Asn Gly Ile Ile Phe Phe Leu Lys Gln Glu Ser Gln Phe Leu Cys Leu
            2900                2905                2910

Ala Val Gln Glu Gly Thr Leu Val Leu Phe Tyr Asp Phe Gly Ser Gly
        2915                2920                2925

Leu Lys Lys Ala Asp Pro Leu Gln Pro Pro Gln Ala Leu Thr Ala Ala
    2930                2935                2940

Ser Lys Ala Ile Gln Val Phe Leu Leu Ala Gly Asn Arg Lys Arg Val
2945                2950                2955                2960

Leu Val Arg Val Glu Arg Ala Thr Val Phe Ser Val Asp Gln Asp Asn
                2965                2970                2975

Met Leu Glu Met Ala Asp Ala Tyr Tyr Leu Gly Gly Val Pro Pro Glu
            2980                2985                2990

Gln Leu Pro Leu Ser Leu Arg Gln Leu Phe Pro Ser Gly Gly Ser Val
        2995                3000                3005

Arg Gly Cys Ile Lys Gly Ile Lys Ala Leu Gly Lys Tyr Val Asp Leu
    3010                3015                3020

Lys Arg Leu Asn Thr Thr Gly Ile Ser Phe Gly Cys Thr Ala Asp Leu
3025                3030                3035                3040

Leu Val Gly Arg Thr Met Thr Phe His Gly His Gly Phe Leu Pro Leu
            3045                3050                3055

Ala Leu Pro Asp Val Ala Pro Ile Thr Glu Val Val Tyr Ser Gly Phe
        3060                3065                3070

Gly Phe Arg Gly Thr Gln Asp Asn Asn Leu Leu Tyr Tyr Arg Thr Ser
    3075                3080                3085

Pro Asp Gly Pro Tyr Gln Val Ser Leu Arg Glu Gly His Val Thr Leu
3090                3095                3100

Arg Phe Met Asn Gln Glu Val Glu Thr Gln Arg Val Phe Ala Asp Gly
3105                3110                3115                3120

Ala Pro His Tyr Val Ala Phe Tyr Ser Asn Val Thr Gly Val Trp Leu
            3125                3130                3135

Tyr Val Asp Asp Gln Leu Gln Leu Val Lys Ser His Glu Arg Thr Thr
        3140                3145                3150

Pro Met Leu Gln Leu Gln Pro Glu Glu Pro Ser Arg Leu Leu Leu Gly
    3155                3160                3165

Gly Leu Pro Val Ser Gly Thr Phe His Asn Phe Ser Gly Cys Ile Ser
    3170                3175                3180

Asn Val Phe Val Gln Arg Leu Arg Gly Pro Gln Arg Val Phe Asp Leu
3185                3190                3195                3200

His Gln Asn Met Gly Ser Val Asn Val Ser Val Gly Cys Thr Pro Ala
            3205                3210                3215

Gln Leu Ile Glu Thr Ser Arg Ala Thr Ala Gln Lys Val Ser Arg Arg
        3220                3225                3230

Ser Arg Gln Pro Ser Gln Asp Leu Ala Cys Thr Thr Pro Trp Leu Pro
    3235                3240                3245

Gly Thr Ile Gln Asp Ala Tyr Gln Phe Gly Gly Pro Leu Pro Ser Tyr
    3250                3255                3260

Leu Gln Phe Val Gly Ile Ser Pro Ser His Arg Asn Arg Leu His Leu
3265                3270                3275                3280
```

```
Ser Met Leu Val Arg Pro His Ala Ala Ser Gln Gly Leu Leu Leu Ser
            3285                3290                3295

Thr Ala Pro Met Ser Gly Arg Ser Pro Ser Leu Val Leu Phe Leu Asn
        3300                3305                3310

His Gly His Phe Val Ala Gln Thr Glu Gly Pro Gly Pro Arg Leu Gln
    3315                3320                3325

Val Gln Ser Arg Gln His Ser Arg Ala Gly Gln Trp His Arg Val Ser
3330                3335                3340

Val Arg Trp Gly Met Gln Gln Ile Gln Leu Val Val Asp Gly Ser Gln
3345                3350                3355                3360

Thr Trp Ser Gln Lys Ala Leu His His Arg Val Pro Arg Ala Glu Arg
            3365                3370                3375

Pro Gln Pro Tyr Thr Leu Ser Val Gly Gly Leu Pro Ala Ser Ser Tyr
        3380                3385                3390

Ser Ser Lys Leu Pro Val Ser Val Gly Phe Ser Gly Cys Leu Lys Lys
    3395                3400                3405

Leu Gln Leu Asp Lys Gln Pro Leu Arg Thr Pro Thr Gln Met Val Gly
    3410                3415                3420

Val Thr Pro Cys Val Ser Gly Pro Leu Glu Asp Gly Leu Phe Phe Pro
3425                3430                3435                3440

Gly Ser Glu Gly Val Val Thr Leu Glu Leu Pro Lys Ala Lys Met Pro
            3445                3450                3455

Tyr Val Ser Leu Glu Leu Glu Met Arg Pro Leu Ala Ala Ala Gly Leu
        3460                3465                3470

Ile Phe His Leu Gly Gln Ala Leu Ala Thr Pro Tyr Met Gln Leu Lys
    3475                3480                3485

Val Leu Thr Glu Gln Val Leu Leu Gln Ala Asn Asp Gly Ala Gly Glu
    3490                3495                3500

Phe Ser Thr Trp Val Thr Tyr Pro Lys Leu Cys Asp Gly Arg Trp His
3505                3510                3515                3520

Arg Val Ala Val Ile Met Gly Arg Asp Thr Leu Arg Leu Glu Val Asp
            3525                3530                3535

Thr Gln Ser Asn His Thr Thr Gly Arg Leu Pro Glu Ser Leu Ala Gly
        3540                3545                3550

Ser Pro Ala Leu Leu His Leu Gly Ser Leu Pro Lys Ser Ser Thr Ala
    3555                3560                3565

Arg Pro Glu Leu Pro Ala Tyr Arg Gly Cys Leu Arg Lys Leu Leu Ile
    3570                3575                3580

Asn Gly Ala Pro Val Asn Val Thr Ala Ser Val Gln Ile Gln Gly Ala
3585                3590                3595                3600

Val Gly Met Arg Gly Cys Pro Ser Gly Thr Leu Ala Leu Ser Lys Gln
            3605                3610                3615

Gly Lys Ala Leu Thr Gln Arg His Ala Lys Pro Ser Val Ser Pro Leu
        3620                3625                3630

Leu Trp His
    3635

<210> SEQ ID NO 5
<211> LENGTH: 5613
<212> TYPE: DNA
<213> ORGANISM: Homo sapiens
<220> FEATURE:
<221> NAME/KEY: CDS
<222> LOCATION: (118)..(5475)
<221> NAME/KEY: sig_peptide
<222> LOCATION: (118)..(180)
```

<400> SEQUENCE: 5

```
cccggagcag ggcgagagct cgcgtcgccg gaaaggaaga cgggaagaaa gggcaggcgg      60
ctcggcgggc gtcttctcca ctcctctgcc gcgtccccgt ggctgcaggg agccggc        117
```

| | | | | | | | | | | | | | | | | |
|---|---|---|---|---|---|---|---|---|---|---|---|---|---|---|---|---|
| atg | ggg | ctt | ctc | cag | ttg | cta | gct | ttc | agt | ttc | tta | gcc | ctg | tgc | aga | 165 |
| Met | Gly | Leu | Leu | Gln | Leu | Leu | Ala | Phe | Ser | Phe | Leu | Ala | Leu | Cys | Arg | |
| 1 | | | | 5 | | | | | 10 | | | | | 15 | | |

| gcc | cga | gtg | cgc | gct | cag | gaa | ccc | gag | ttc | agc | tac | ggc | tgc | gca | gaa | 213 |
|---|---|---|---|---|---|---|---|---|---|---|---|---|---|---|---|---|
| Ala | Arg | Val | Arg | Ala | Gln | Glu | Pro | Glu | Phe | Ser | Tyr | Gly | Cys | Ala | Glu | |
| | | | 20 | | | | | 25 | | | | | 30 | | | |

| ggc | agc | tgc | tat | ccc | gcc | acg | ggc | gac | ctt | ctc | atc | ggc | cga | gca | cag | 261 |
|---|---|---|---|---|---|---|---|---|---|---|---|---|---|---|---|---|
| Gly | Ser | Cys | Tyr | Pro | Ala | Thr | Gly | Asp | Leu | Leu | Ile | Gly | Arg | Ala | Gln | |
| | | 35 | | | | | 40 | | | | | 45 | | | | |

| aag | ctt | tcg | gtg | acc | tcg | acg | tgc | ggg | ctg | cac | aag | ccc | gaa | ccc | tac | 309 |
|---|---|---|---|---|---|---|---|---|---|---|---|---|---|---|---|---|
| Lys | Leu | Ser | Val | Thr | Ser | Thr | Cys | Gly | Leu | His | Lys | Pro | Glu | Pro | Tyr | |
| 50 | | | | | 55 | | | | | 60 | | | | | | |

| tgt | atc | gtc | agc | cac | ttg | cag | gag | gac | aaa | aaa | tgc | ttc | ata | tgc | aat | 357 |
|---|---|---|---|---|---|---|---|---|---|---|---|---|---|---|---|---|
| Cys | Ile | Val | Ser | His | Leu | Gln | Glu | Asp | Lys | Lys | Cys | Phe | Ile | Cys | Asn | |
| 65 | | | | 70 | | | | | 75 | | | | | 80 | | |

| tcc | caa | gat | cct | tat | cat | gag | acc | ctg | aat | cct | gac | agc | cat | ctc | att | 405 |
|---|---|---|---|---|---|---|---|---|---|---|---|---|---|---|---|---|
| Ser | Gln | Asp | Pro | Tyr | His | Glu | Thr | Leu | Asn | Pro | Asp | Ser | His | Leu | Ile | |
| | | | | 85 | | | | | 90 | | | | | 95 | | |

| gaa | aat | gtg | gtc | act | aca | ttt | gct | cca | aac | cgc | ctt | aag | att | tgg | tgg | 453 |
|---|---|---|---|---|---|---|---|---|---|---|---|---|---|---|---|---|
| Glu | Asn | Val | Val | Thr | Thr | Phe | Ala | Pro | Asn | Arg | Leu | Lys | Ile | Trp | Trp | |
| | | | 100 | | | | | 105 | | | | | 110 | | | |

| caa | tct | gaa | aat | ggt | gtg | gaa | aat | gta | act | atc | caa | ctg | gat | ttg | gaa | 501 |
|---|---|---|---|---|---|---|---|---|---|---|---|---|---|---|---|---|
| Gln | Ser | Glu | Asn | Gly | Val | Glu | Asn | Val | Thr | Ile | Gln | Leu | Asp | Leu | Glu | |
| | | | 115 | | | | | 120 | | | | | 125 | | | |

| gca | gaa | ttc | cat | ttt | act | cat | ctc | ata | atg | act | ttc | aag | aca | ttc | cgt | 549 |
|---|---|---|---|---|---|---|---|---|---|---|---|---|---|---|---|---|
| Ala | Glu | Phe | His | Phe | Thr | His | Leu | Ile | Met | Thr | Phe | Lys | Thr | Phe | Arg | |
| | 130 | | | | | 135 | | | | | 140 | | | | | |

| cca | gct | gct | atg | ctg | ata | gaa | cga | tcg | tcc | gac | ttt | ggg | aaa | acc | tgg | 597 |
|---|---|---|---|---|---|---|---|---|---|---|---|---|---|---|---|---|
| Pro | Ala | Ala | Met | Leu | Ile | Glu | Arg | Ser | Ser | Asp | Phe | Gly | Lys | Thr | Trp | |
| 145 | | | | | 150 | | | | | 155 | | | | | 160 | |

| ggt | gtg | tat | aga | tac | ttc | gcc | tat | gac | tgt | gag | gcc | tcg | ttt | cca | ggc | 645 |
|---|---|---|---|---|---|---|---|---|---|---|---|---|---|---|---|---|
| Gly | Val | Tyr | Arg | Tyr | Phe | Ala | Tyr | Asp | Cys | Glu | Ala | Ser | Phe | Pro | Gly | |
| | | | 165 | | | | | 170 | | | | | 175 | | | |

| att | tca | act | ggc | ccc | atg | aaa | aaa | gtc | gat | gac | ata | att | tgt | gat | tct | 693 |
|---|---|---|---|---|---|---|---|---|---|---|---|---|---|---|---|---|
| Ile | Ser | Thr | Gly | Pro | Met | Lys | Lys | Val | Asp | Asp | Ile | Ile | Cys | Asp | Ser | |
| | | | 180 | | | | | 185 | | | | | 190 | | | |

| cga | tat | tct | gac | att | gaa | ccc | tca | act | gaa | gga | gag | gtg | ata | ttt | cgt | 741 |
|---|---|---|---|---|---|---|---|---|---|---|---|---|---|---|---|---|
| Arg | Tyr | Ser | Asp | Ile | Glu | Pro | Ser | Thr | Glu | Gly | Glu | Val | Ile | Phe | Arg | |
| | 195 | | | | | 200 | | | | | 205 | | | | | |

| gct | tta | gat | cct | gct | ttc | aaa | ata | gaa | gat | cct | tat | agc | cca | agg | ata | 789 |
|---|---|---|---|---|---|---|---|---|---|---|---|---|---|---|---|---|
| Ala | Leu | Asp | Pro | Ala | Phe | Lys | Ile | Glu | Asp | Pro | Tyr | Ser | Pro | Arg | Ile | |
| | 210 | | | | | 215 | | | | | 220 | | | | | |

| cag | aat | tta | tta | aaa | att | acc | aac | ttg | aga | atc | aag | ttt | gtg | aaa | ctg | 837 |
|---|---|---|---|---|---|---|---|---|---|---|---|---|---|---|---|---|
| Gln | Asn | Leu | Leu | Lys | Ile | Thr | Asn | Leu | Arg | Ile | Lys | Phe | Val | Lys | Leu | |
| 225 | | | | | 230 | | | | | 235 | | | | | 240 | |

| cat | act | ttg | gga | gat | aac | ctt | ctg | gat | tcc | agg | atg | gaa | atc | aga | gaa | 885 |
|---|---|---|---|---|---|---|---|---|---|---|---|---|---|---|---|---|
| His | Thr | Leu | Gly | Asp | Asn | Leu | Leu | Asp | Ser | Arg | Met | Glu | Ile | Arg | Glu | |
| | | | | 245 | | | | | 250 | | | | | 255 | | |

| aag | tat | tat | tat | gca | gtt | tat | gat | atg | gtg | gtt | cga | gga | aat | tgc | ttc | 933 |
|---|---|---|---|---|---|---|---|---|---|---|---|---|---|---|---|---|
| Lys | Tyr | Tyr | Tyr | Ala | Val | Tyr | Asp | Met | Val | Val | Arg | Gly | Asn | Cys | Phe | |
| | | | 260 | | | | | 265 | | | | | 270 | | | |

| tgc | tat | ggt | cat | gcc | agc | gaa | tgt | gcc | cct | gtg | gat | gga | ttc | aat | gaa | 981 |
|---|---|---|---|---|---|---|---|---|---|---|---|---|---|---|---|---|
| Cys | Tyr | Gly | His | Ala | Ser | Glu | Cys | Ala | Pro | Val | Asp | Gly | Phe | Asn | Glu | |
| | | 275 | | | | | 280 | | | | | 285 | | | | |

```
gaa gtg gaa gga atg gtt cac gga cac tgc atg tgc agg cat aac acc      1029
Glu Val Glu Gly Met Val His Gly His Cys Met Cys Arg His Asn Thr
    290             295                 300 aag ggc tta aac tgt gaa ctc tgc atg gat ttc tac cat gat tta cct      1077
Lys Gly Leu Asn Cys Glu Leu Cys Met Asp Phe Tyr His Asp Leu Pro
305                 310                 315                 320 tgg aga cct gct gaa ggc cga aac agc aac gcc tgt aaa aaa tgt aac      1125
Trp Arg Pro Ala Glu Gly Arg Asn Ser Asn Ala Cys Lys Lys Cys Asn
                325                 330                 335 tgc aat gaa cat tcc atc tct tgt cac ttt gac atg gct gtt tac ctg      1173
Cys Asn Glu His Ser Ile Ser Cys His Phe Asp Met Ala Val Tyr Leu
            340                 345                 350 gcc acg ggg aac gtc agc gga ggc gtg tgt gat gac tgt cag cac aac      1221
Ala Thr Gly Asn Val Ser Gly Gly Val Cys Asp Asp Cys Gln His Asn
        355                 360                 365 acc atg ggg cgc aac tgt gag cag tgc aag ccg ttt tac tac cag cac      1269
Thr Met Gly Arg Asn Cys Glu Gln Cys Lys Pro Phe Tyr Tyr Gln His
    370                 375                 380 cca gag agg gac atc cga gat cct aat ttc tgt gaa cga tgt acg tgt      1317
Pro Glu Arg Asp Ile Arg Asp Pro Asn Phe Cys Glu Arg Cys Thr Cys
385                 390                 395                 400 gac cca gct ggc tct caa aat gag gga att tgt gac agc tat act gat      1365
Asp Pro Ala Gly Ser Gln Asn Glu Gly Ile Cys Asp Ser Tyr Thr Asp
                405                 410                 415 ttt tct act ggt ctc att gct ggc cag tgt cgg tgt aaa tta aat gtg      1413
Phe Ser Thr Gly Leu Ile Ala Gly Gln Cys Arg Cys Lys Leu Asn Val
            420                 425                 430 gaa gga gaa cat tgt gat gtt tgc aaa gaa ggc ttc tat gat tta agc      1461
Glu Gly Glu His Cys Asp Val Cys Lys Glu Gly Phe Tyr Asp Leu Ser
        435                 440                 445 agt gaa gat cca ttt ggt tgt aaa tct tgt gct tgc aat cct ctg gga      1509
Ser Glu Asp Pro Phe Gly Cys Lys Ser Cys Ala Cys Asn Pro Leu Gly
    450                 455                 460 aca att cct gga ggg aat cct tgt gat tcc gag aca ggt cac tgc tac      1557
Thr Ile Pro Gly Gly Asn Pro Cys Asp Ser Glu Thr Gly His Cys Tyr
465                 470                 475                 480 tgc aag cgt ctg gtg aca gga cag cat tgt gac cag tgc ctg cca gag      1605
Cys Lys Arg Leu Val Thr Gly Gln His Cys Asp Gln Cys Leu Pro Glu
                485                 490                 495 cac tgg ggc tta agc aat gat ttg gat gga tgt cga cca tgt gac tgt      1653
His Trp Gly Leu Ser Asn Asp Leu Asp Gly Cys Arg Pro Cys Asp Cys
            500                 505                 510 gac ctt ggg gga gcc tta aac aac agt tgc ttt gcg gag tca ggc cag      1701
Asp Leu Gly Gly Ala Leu Asn Asn Ser Cys Phe Ala Glu Ser Gly Gln
        515                 520                 525 tgc tca tgc cgg cct cac atg att gga cgt cag tgc aac gaa gtg gaa      1749
Cys Ser Cys Arg Pro His Met Ile Gly Arg Gln Cys Asn Glu Val Glu
    530                 535                 540 cct ggt tac tac ttt gcc acc ctg gat cac tac ctc tat gaa gcg gag      1797
Pro Gly Tyr Tyr Phe Ala Thr Leu Asp His Tyr Leu Tyr Glu Ala Glu
545                 550                 555                 560 gaa gcc aac ttg ggg cct ggg gtt agc ata gtg gag cgg caa tat atc      1845
Glu Ala Asn Leu Gly Pro Gly Val Ser Ile Val Glu Arg Gln Tyr Ile
                565                 570                 575 cag gac cgg att ccc tcc tgg act gga gcc ggc ttc gtc cga gtg cct      1893
Gln Asp Arg Ile Pro Ser Trp Thr Gly Ala Gly Phe Val Arg Val Pro
            580                 585                 590 gaa ggg gct tat ttg gag ttt ttc att gac aac ata cca tat tcc atg      1941
Glu Gly Ala Tyr Leu Glu Phe Phe Ile Asp Asn Ile Pro Tyr Ser Met
        595                 600                 605
```

```
gag tac gac atc cta att cgc tac gag cca cag cta ccc gac cac tgg    1989
Glu Tyr Asp Ile Leu Ile Arg Tyr Glu Pro Gln Leu Pro Asp His Trp
    610                 615                 620 gaa aaa gct gtc atc aca gtg cag cga cct gga agg att cca acc agc    2037
Glu Lys Ala Val Ile Thr Val Gln Arg Pro Gly Arg Ile Pro Thr Ser
625                 630                 635                 640 agc cga tgt ggt aat acc atc ccc gat gat gac aac cag gtg gtg tca    2085
Ser Arg Cys Gly Asn Thr Ile Pro Asp Asp Asp Asn Gln Val Val Ser
                645                 650                 655 tta tca cca ggc tca aga tat gtc gtc ctt cct cgg ccg gtg tgc ttt    2133
Leu Ser Pro Gly Ser Arg Tyr Val Val Leu Pro Arg Pro Val Cys Phe
            660                 665                 670 gag aag gga aca aac tac acg gtg agg ttg gag ctg cct cag tac acc    2181
Glu Lys Gly Thr Asn Tyr Thr Val Arg Leu Glu Leu Pro Gln Tyr Thr
        675                 680                 685 tcc tct gat agc gac gtg gag agc ccc tac acg ctg atc gat tct ctt    2229
Ser Ser Asp Ser Asp Val Glu Ser Pro Tyr Thr Leu Ile Asp Ser Leu
    690                 695                 700 gtt ctc atg cca tac tgt aaa tca ctg gac atc ttc acc gtg gga ggt    2277
Val Leu Met Pro Tyr Cys Lys Ser Leu Asp Ile Phe Thr Val Gly Gly
705                 710                 715                 720 tca gga gat ggg gtg gtc acc aac agt gcc tgg gaa acc ttt cag aga    2325
Ser Gly Asp Gly Val Val Thr Asn Ser Ala Trp Glu Thr Phe Gln Arg
                725                 730                 735 tac cga tgt cta gag aac agc aga agc gtt gtg aaa aca ccg atg aca    2373
Tyr Arg Cys Leu Glu Asn Ser Arg Ser Val Val Lys Thr Pro Met Thr
            740                 745                 750 gat gtt tgc aga aac atc atc ttt agc att tct gcc ctg tta cac cag    2421
Asp Val Cys Arg Asn Ile Ile Phe Ser Ile Ser Ala Leu Leu His Gln
        755                 760                 765 aca ggc ctg gct tgt gaa tgc gac cct cag ggt tcg tta agt tcc gtg    2469
Thr Gly Leu Ala Cys Glu Cys Asp Pro Gln Gly Ser Leu Ser Ser Val
    770                 775                 780 tgt gat ccc aac gga ggc cag tgc cag tgc cgg ccc aac gtg gtt gga    2517
Cys Asp Pro Asn Gly Gly Gln Cys Gln Cys Arg Pro Asn Val Val Gly
785                 790                 795                 800 aga acc tgc aac aga tgt gca cct gga act ttt ggc ttt ggc ccc agt    2565
Arg Thr Cys Asn Arg Cys Ala Pro Gly Thr Phe Gly Phe Gly Pro Ser
                805                 810                 815 gga tgc aaa cct tgt gag tgc cat ctg caa gga tct gtc aat gcc ttc    2613
Gly Cys Lys Pro Cys Glu Cys His Leu Gln Gly Ser Val Asn Ala Phe
            820                 825                 830 tgc aat ccc gtc act ggc cag tgc cac tgt ttc cag gga gtg tat gct    2661
Cys Asn Pro Val Thr Gly Gln Cys His Cys Phe Gln Gly Val Tyr Ala
        835                 840                 845 cgg cag tgt gat cgg tgc tta cct ggg cac tgg ggc ttt cca agt tgc    2709
Arg Gln Cys Asp Arg Cys Leu Pro Gly His Trp Gly Phe Pro Ser Cys
    850                 855                 860 cag ccc tgc cag tgc aat ggc cac gcc gat gac tgc gac cca gtg act    2757
Gln Pro Cys Gln Cys Asn Gly His Ala Asp Asp Cys Asp Pro Val Thr
865                 870                 875                 880 ggg gag tgc ttg aac tgc cag gac tac acc atg ggt cat aac tgt gaa    2805
Gly Glu Cys Leu Asn Cys Gln Asp Tyr Thr Met Gly His Asn Cys Glu
                885                 890                 895 agg tgc ttg gct ggt tac tat ggc gac ccc atc att ggg tca ggt gat    2853
Arg Cys Leu Ala Gly Tyr Tyr Gly Asp Pro Ile Ile Gly Ser Gly Asp
            900                 905                 910 cac tgc cgc cct tgc cct tgc cca gat ggt ccc gac agt gga cgc cag    2901
His Cys Arg Pro Cys Pro Cys Pro Asp Gly Pro Asp Ser Gly Arg Gln
```

-continued

| | |
|---|---|
| 915 920 925 | |
| ttt gcc agg agc tgc tac caa gat cct gtt act tta cag ctt gcc tgt<br>Phe Ala Arg Ser Cys Tyr Gln Asp Pro Val Thr Leu Gln Leu Ala Cys<br>930 935 940 | 2949 |
| gtt tgt gat cct gga tac att ggt tcc aga tgt gac gac tgt gcc tca<br>Val Cys Asp Pro Gly Tyr Ile Gly Ser Arg Cys Asp Asp Cys Ala Ser<br>945 950 955 960 | 2997 |
| gga tac ttt ggc aat cca tca gaa gtt ggg ggg tcg tgt cag cct tgc<br>Gly Tyr Phe Gly Asn Pro Ser Glu Val Gly Gly Ser Cys Gln Pro Cys<br>965 970 975 | 3045 |
| cag tgt cac aac aac att gac acg aca gac cca gaa gcc tgt gac aag<br>Gln Cys His Asn Asn Ile Asp Thr Thr Asp Pro Glu Ala Cys Asp Lys<br>980 985 990 | 3093 |
| gag act ggg agg tgt ctc aag tgc ctg tac cac acg gaa ggg gaa cac<br>Glu Thr Gly Arg Cys Leu Lys Cys Leu Tyr His Thr Glu Gly Glu His<br>995 1000 1005 | 3141 |
| tgt cag ttc tgc cgg ttt gga tac tat ggt gat gcc ctc cgg cag gac<br>Cys Gln Phe Cys Arg Phe Gly Tyr Tyr Gly Asp Ala Leu Arg Gln Asp<br>1010 1015 1020 | 3189 |
| tgt cga aag tgt gtc tgt aat tac ctg ggc acc gtg caa gag cac tgt<br>Cys Arg Lys Cys Val Cys Asn Tyr Leu Gly Thr Val Gln Glu His Cys<br>1025 1030 1035 1040 | 3237 |
| aac ggc tct gac tgc cag tgc gac aaa gcc act ggt cag tgc ttg tgt<br>Asn Gly Ser Asp Cys Gln Cys Asp Lys Ala Thr Gly Gln Cys Leu Cys<br>1045 1050 1055 | 3285 |
| ctt cct aat gtg atc ggg cag aac tgt gac cgc tgt gcg ccc aat acc<br>Leu Pro Asn Val Ile Gly Gln Asn Cys Asp Arg Cys Ala Pro Asn Thr<br>1060 1065 1070 | 3333 |
| tgg cag ctg gcc agt ggc act ggc tgt gac cca tgc aac tgc aat gct<br>Trp Gln Leu Ala Ser Gly Thr Gly Cys Asp Pro Cys Asn Cys Asn Ala<br>1075 1080 1085 | 3381 |
| gct cat tcc ttc ggg cca tct tgc aat gag ttc acg ggg cag tgc cag<br>Ala His Ser Phe Gly Pro Ser Cys Asn Glu Phe Thr Gly Gln Cys Gln<br>1090 1095 1100 | 3429 |
| tgc atg cct ggg ttt gga ggc cgc acc tgc agc gag tgc cag gaa ctc<br>Cys Met Pro Gly Phe Gly Gly Arg Thr Cys Ser Glu Cys Gln Glu Leu<br>1105 1110 1115 1120 | 3477 |
| ttc tgg gga gac ccc gac gtg gag tgc cga gcc tgt gac tgt gac ccc<br>Phe Trp Gly Asp Pro Asp Val Glu Cys Arg Ala Cys Asp Cys Asp Pro<br>1125 1130 1135 | 3525 |
| agg ggc att gag acg cca cag tgt gac cag tcc acg ggc cag tgt gtc<br>Arg Gly Ile Glu Thr Pro Gln Cys Asp Gln Ser Thr Gly Gln Cys Val<br>1140 1145 1150 | 3573 |
| tgc gtt gag ggt gtt gag ggt cca cgc tgt gac aag tgc acg cga ggg<br>Cys Val Glu Gly Val Glu Gly Pro Arg Cys Asp Lys Cys Thr Arg Gly<br>1155 1160 1165 | 3621 |
| tac tcg ggg gtc ttc cct gac tgc aca ccc tgc cac cag tgc ttt gct<br>Tyr Ser Gly Val Phe Pro Asp Cys Thr Pro Cys His Gln Cys Phe Ala<br>1170 1175 1180 | 3669 |
| ctc tgg gat gtg atc att gcc gag ctg acc aac agg aca cac aga ttc<br>Leu Trp Asp Val Ile Ile Ala Glu Leu Thr Asn Arg Thr His Arg Phe<br>1185 1190 1195 1200 | 3717 |
| ctg gag aaa gcc aag gcc ttg aag atc agt ggt gtg atc ggg cct tac<br>Leu Glu Lys Ala Lys Ala Leu Lys Ile Ser Gly Val Ile Gly Pro Tyr<br>1205 1210 1215 | 3765 |
| cgt gag act gtg gac tcg gtg gag agg aaa gtc agc gag ata aaa gac<br>Arg Glu Thr Val Asp Ser Val Glu Arg Lys Val Ser Glu Ile Lys Asp<br>1220 1225 1230 | 3813 |
| atc ctg gcg cag agc ccc gca gca gag cca ctg aaa aac att ggg aat<br> Ile Leu Ala Gln Ser Pro Ala Ala Glu Pro Leu Lys Asn Ile Gly Asn | 3861 |

-continued

| | | |
|---|---|---|
| Ile Leu Ala Gln Ser Pro Ala Ala Glu Pro Leu Lys Asn Ile Gly Asn<br>    1235                      1240                      1245 | | |
| ctc ttt gag gaa gca gag aaa ctg att aaa gat gtt aca gaa atg atg<br>Leu Phe Glu Glu Ala Glu Lys Leu Ile Lys Asp Val Thr Glu Met Met<br>    1250                      1255                      1260 | 3909 | |
| gct caa gta gaa gtg aaa tta tct gac aca act tcc caa agc aac agc<br>Ala Gln Val Glu Val Lys Leu Ser Asp Thr Thr Ser Gln Ser Asn Ser<br>1265                      1270                      1275                      1280 | 3957 | |
| aca gcc aaa gaa ctg gat tct cta cag aca gaa gcc gaa agc cta gac<br>Thr Ala Lys Glu Leu Asp Ser Leu Gln Thr Glu Ala Glu Ser Leu Asp<br>                1285                      1290                      1295 | 4005 | |
| aac act gtg aaa gaa ctt gct gaa caa ctg gaa ttt atc aaa aac tca<br>Asn Thr Val Lys Glu Leu Ala Glu Gln Leu Glu Phe Ile Lys Asn Ser<br>            1300                      1305                      1310 | 4053 | |
| gat att cgg ggt gcc ttg gat agc att acc aag tat ttc cag atg tct<br>Asp Ile Arg Gly Ala Leu Asp Ser Ile Thr Lys Tyr Phe Gln Met Ser<br>        1315                      1320                      1325 | 4101 | |
| ctt gag gca gag gag agg gtg aat gcc tcc acc aca gaa ccc aac agc<br>Leu Glu Ala Glu Glu Arg Val Asn Ala Ser Thr Thr Glu Pro Asn Ser<br>    1330                      1335                      1340 | 4149 | |
| act gtg gag cag tca gcc ctc atg aga gac aga gta gaa gac gtg atg<br>Thr Val Glu Gln Ser Ala Leu Met Arg Asp Arg Val Glu Asp Val Met<br>1345                      1350                      1355                      1360 | 4197 | |
| atg gag cga gaa tcc cag ttc aag gaa aaa caa gag gag cag gct cgc<br>Met Glu Arg Glu Ser Gln Phe Lys Glu Lys Gln Glu Glu Gln Ala Arg<br>                1365                      1370                      1375 | 4245 | |
| ctc ctt gat gaa ctg gca ggc aag cta caa agc cta gac ctt tca gcc<br>Leu Leu Asp Glu Leu Ala Gly Lys Leu Gln Ser Leu Asp Leu Ser Ala<br>            1380                      1385                      1390 | 4293 | |
| gct gcc gaa atg acc tgt gga aca ccc cca ggg gcc tcc tgt tcc gag<br>Ala Ala Glu Met Thr Cys Gly Thr Pro Pro Gly Ala Ser Cys Ser Glu<br>        1395                      1400                      1405 | 4341 | |
| act gaa tgt ggc ggg cca aac tgc aga act gac gaa gga gag agg aag<br>Thr Glu Cys Gly Gly Pro Asn Cys Arg Thr Asp Glu Gly Glu Arg Lys<br>    1410                      1415                      1420 | 4389 | |
| tgt ggg ggg cct ggc tgt ggt ggt ctg gtt act gtt gca cac aac gcc<br>Cys Gly Gly Pro Gly Cys Gly Gly Leu Val Thr Val Ala His Asn Ala<br>1425                      1430                      1435                      1440 | 4437 | |
| tgg cag aaa gcc atg gac ttg gac caa gat gtc ctg agt gcc ctg gct<br>Trp Gln Lys Ala Met Asp Leu Asp Gln Asp Val Leu Ser Ala Leu Ala<br>                1445                      1450                      1455 | 4485 | |
| gaa gtg gaa cag ctc tcc aag atg gtc tct gaa gca aaa ctg agg gca<br>Glu Val Glu Gln Leu Ser Lys Met Val Ser Glu Ala Lys Leu Arg Ala<br>            1460                      1465                      1470 | 4533 | |
| gat gag gca aaa caa agt gct gaa gac att ctg ttg aag aca aat gct<br>Asp Glu Ala Lys Gln Ser Ala Glu Asp Ile Leu Leu Lys Thr Asn Ala<br>        1475                      1480                      1485 | 4581 | |
| acc aaa gaa aaa atg gac aag agc aat gag gag ctg aga aat cta atc<br>Thr Lys Glu Lys Met Asp Lys Ser Asn Glu Glu Leu Arg Asn Leu Ile<br>    1490                      1495                      1500 | 4629 | |
| aag caa atc aga aac ttt ttg acc cag gat agt gct gat ttg gac agc<br>Lys Gln Ile Arg Asn Phe Leu Thr Gln Asp Ser Ala Asp Leu Asp Ser<br>1505                      1510                      1515                      1520 | 4677 | |
| att gaa gca gtt gct aat gaa gta ttg aaa atg gag atg cct agc acc<br>Ile Glu Ala Val Ala Asn Glu Val Leu Lys Met Glu Met Pro Ser Thr<br>                1525                      1530                      1535 | 4725 | |
| cca cag cag tta cag aac ttg aca gaa gat ata cgt gaa cga gtt gaa<br>Pro Gln Gln Leu Gln Asn Leu Thr Glu Asp Ile Arg Glu Arg Val Glu<br>            1540                      1545                      1550 | 4773 | |

```
agc ctt tct caa gta gag gtt att ctt cag cat agt gct gct gac att      4821
Ser Leu Ser Gln Val Glu Val Ile Leu Gln His Ser Ala Ala Asp Ile
        1555                1560                1565 gcc aga gct gag atg ttg tta gaa gaa gct aaa aga gca agc aaa agt      4869
Ala Arg Ala Glu Met Leu Leu Glu Glu Ala Lys Arg Ala Ser Lys Ser
    1570                1575                1580 gca aca gat gtt aaa gtc act gca gat atg gta aag gaa gct ctg gaa      4917
Ala Thr Asp Val Lys Val Thr Ala Asp Met Val Lys Glu Ala Leu Glu
1585                1590                1595                1600 gaa gca gaa aag gcc cag gtc gca gca gag aag gca att aaa caa gca      4965
Glu Ala Glu Lys Ala Gln Val Ala Ala Glu Lys Ala Ile Lys Gln Ala
            1605                1610                1615 gat gaa gac att caa gga acc cag aac ctg tta act tcg att gag tct      5013
Asp Glu Asp Ile Gln Gly Thr Gln Asn Leu Leu Thr Ser Ile Glu Ser
        1620                1625                1630 gaa aca gca gct tct gag gaa acc ttg ttc aac gcg tcc cag cgc atc      5061
Glu Thr Ala Ala Ser Glu Glu Thr Leu Phe Asn Ala Ser Gln Arg Ile
    1635                1640                1645 agc gag tta gag agg aat gtg gaa gaa ctt aag cgg aaa gct gcc caa      5109
Ser Glu Leu Glu Arg Asn Val Glu Glu Leu Lys Arg Lys Ala Ala Gln
1650                1655                1660 aac tcc ggg gag gca gaa tat att gaa aaa gta gta tat act gtg aag      5157
Asn Ser Gly Glu Ala Glu Tyr Ile Glu Lys Val Val Tyr Thr Val Lys
1665                1670                1675                1680 caa agt gca gaa gat gtt aag aag act tta gat ggt gaa ctt gat gaa      5205
Gln Ser Ala Glu Asp Val Lys Lys Thr Leu Asp Gly Glu Leu Asp Glu
            1685                1690                1695 aag tat aaa aaa gta gaa aat tta att gcc aaa aaa act gaa gag tca      5253
Lys Tyr Lys Lys Val Glu Asn Leu Ile Ala Lys Lys Thr Glu Glu Ser
        1700                1705                1710 gct gat gcc aga agg aaa gcc gaa atg cta caa aat gaa gca aaa act      5301
Ala Asp Ala Arg Arg Lys Ala Glu Met Leu Gln Asn Glu Ala Lys Thr
    1715                1720                1725 ctt tta gct caa gca aat agc aag ctg caa ctg ctc aaa gat tta gaa      5349
Leu Leu Ala Gln Ala Asn Ser Lys Leu Gln Leu Leu Lys Asp Leu Glu
1730                1735                1740 aga aaa tat gaa gac aat caa aga tac tta gaa gat aaa gct caa gaa      5397
Arg Lys Tyr Glu Asp Asn Gln Arg Tyr Leu Glu Asp Lys Ala Gln Glu
1745                1750                1755                1760 tta gca aga ctg gaa gga gaa gtc cgt tca ctc cta aag gat ata agc      5445
Leu Ala Arg Leu Glu Gly Glu Val Arg Ser Leu Leu Lys Asp Ile Ser
            1765                1770                1775 cag aaa gtt gct gtg tat agc aca tgc ttg taacagagga gaataaaaaa        5495
Gln Lys Val Ala Val Tyr Ser Thr Cys Leu
        1780                1785 tggctgaggt gaacaaggta aaacaactac attttaaaaa ctgacttaat gctcttcaaa    5555
ataaaacatc acctatttaa tgttttttaat cacattttgt atgagttaaa taaagccc     5613

<210> SEQ ID NO 6
<211> LENGTH: 1786
<212> TYPE: PRT
<213> ORGANISM: Homo sapiens

<400> SEQUENCE: 6

Met Gly Leu Leu Gln Leu Leu Ala Phe Ser Phe Leu Ala Leu Cys Arg
 1               5                  10                  15

Ala Arg Val Arg Ala Gln Glu Pro Glu Phe Ser Tyr Gly Cys Ala Glu
             20                  25                  30

Gly Ser Cys Tyr Pro Ala Thr Gly Asp Leu Leu Ile Gly Arg Ala Gln
```

-continued

```
                35                  40                  45
Lys Leu Ser Val Thr Ser Thr Cys Gly Leu His Lys Pro Glu Pro Tyr
         50                  55                  60

Cys Ile Val Ser His Leu Gln Glu Asp Lys Lys Cys Phe Ile Cys Asn
 65                  70                  75                  80

Ser Gln Asp Pro Tyr His Glu Thr Leu Asn Pro Asp Ser His Leu Ile
                 85                  90                  95

Glu Asn Val Val Thr Thr Phe Ala Pro Asn Arg Leu Lys Ile Trp Trp
                100                 105                 110

Gln Ser Glu Asn Gly Val Glu Asn Val Thr Ile Gln Leu Asp Leu Glu
            115                 120                 125

Ala Glu Phe His Phe Thr His Leu Ile Met Thr Phe Lys Thr Phe Arg
        130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
                180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
                260                 265                 270

Cys Tyr Gly His Ala Ser Glu Cys Ala Pro Val Asp Gly Phe Asn Glu
            275                 280                 285

Glu Val Glu Gly Met Val His Gly His Cys Met Cys Arg His Asn Thr
        290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
                340                 345                 350

Ala Thr Gly Asn Val Ser Gly Gly Val Cys Asp Asp Cys Gln His Asn
            355                 360                 365

Thr Met Gly Arg Asn Cys Glu Gln Cys Lys Pro Phe Tyr Tyr Gln His
        370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
                420                 425                 430

Glu Gly Glu His Cys Asp Val Cys Lys Glu Gly Phe Tyr Asp Leu Ser
            435                 440                 445

Ser Glu Asp Pro Phe Gly Cys Lys Ser Cys Ala Cys Asn Pro Leu Gly
450                 455                 460
```

-continued

```
Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                    485                 490                 495

His Trp Gly Leu Ser Asn Asp Leu Asp Gly Cys Arg Pro Cys Asp Cys
            500                 505                 510

Asp Leu Gly Gly Ala Leu Asn Asn Ser Cys Phe Ala Glu Ser Gly Gln
        515                 520                 525

Cys Ser Cys Arg Pro His Met Ile Gly Arg Gln Cys Asn Glu Val Glu
    530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                    565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
        595                 600                 605

Glu Tyr Asp Ile Leu Ile Arg Tyr Glu Pro Gln Leu Pro Asp His Trp
    610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                    645                 650                 655

Leu Ser Pro Gly Ser Arg Tyr Val Val Leu Pro Arg Pro Val Cys Phe
            660                 665                 670

Glu Lys Gly Thr Asn Tyr Thr Val Arg Leu Glu Leu Pro Gln Tyr Thr
        675                 680                 685

Ser Ser Asp Ser Asp Val Glu Ser Pro Tyr Thr Leu Ile Asp Ser Leu
    690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                    725                 730                 735

Tyr Arg Cys Leu Glu Asn Ser Arg Ser Val Val Lys Thr Pro Met Thr
            740                 745                 750

Asp Val Cys Arg Asn Ile Ile Phe Ser Ile Ser Ala Leu Leu His Gln
        755                 760                 765

Thr Gly Leu Ala Cys Glu Cys Asp Pro Gln Gly Ser Leu Ser Ser Val
    770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                    805                 810                 815

Gly Cys Lys Pro Cys Glu Cys His Leu Gln Gly Ser Val Asn Ala Phe
            820                 825                 830

Cys Asn Pro Val Thr Gly Gln Cys His Cys Phe Gln Gly Val Tyr Ala
        835                 840                 845

Arg Gln Cys Asp Arg Cys Leu Pro Gly His Trp Gly Phe Pro Ser Cys
    850                 855                 860

Gln Pro Cys Gln Cys Asn Gly His Ala Asp Asp Cys Asp Pro Val Thr
865                 870                 875                 880
```

-continued

```
Gly Glu Cys Leu Asn Cys Gln Asp Tyr Thr Met Gly His Asn Cys Glu
            885                 890                 895
Arg Cys Leu Ala Gly Tyr Tyr Gly Asp Pro Ile Ile Gly Ser Gly Asp
            900                 905                 910
His Cys Arg Pro Cys Pro Cys Pro Asp Gly Pro Asp Ser Gly Arg Gln
            915                 920                 925
Phe Ala Arg Ser Cys Tyr Gln Asp Pro Val Thr Leu Gln Leu Ala Cys
            930                 935                 940
Val Cys Asp Pro Gly Tyr Ile Gly Ser Arg Cys Asp Cys Ala Ser
945                 950                 955                 960
Gly Tyr Phe Gly Asn Pro Ser Glu Val Gly Ser Cys Gln Pro Cys
            965                 970                 975
Gln Cys His Asn Asn Ile Asp Thr Thr Asp Pro Glu Ala Cys Asp Lys
            980                 985                 990
Glu Thr Gly Arg Cys Leu Lys Cys Leu Tyr His Thr Glu Gly Glu His
            995                 1000                1005
Cys Gln Phe Cys Arg Phe Gly Tyr Tyr Gly Asp Ala Leu Arg Gln Asp
            1010                1015                1020
Cys Arg Lys Cys Val Cys Asn Tyr Leu Gly Thr Val Gln Glu His Cys
1025                1030                1035                1040
Asn Gly Ser Asp Cys Gln Cys Asp Lys Ala Thr Gly Gln Cys Leu Cys
            1045                1050                1055
Leu Pro Asn Val Ile Gly Gln Asn Cys Asp Arg Cys Ala Pro Asn Thr
            1060                1065                1070
Trp Gln Leu Ala Ser Gly Thr Gly Cys Asp Pro Cys Asn Cys Asn Ala
            1075                1080                1085
Ala His Ser Phe Gly Pro Ser Cys Asn Glu Phe Thr Gly Gln Cys Gln
            1090                1095                1100
Cys Met Pro Gly Phe Gly Gly Arg Thr Cys Ser Glu Cys Gln Glu Leu
1105                1110                1115                1120
Phe Trp Gly Asp Pro Asp Val Glu Cys Arg Ala Cys Asp Cys Asp Pro
            1125                1130                1135
Arg Gly Ile Glu Thr Pro Gln Cys Asp Gln Ser Thr Gly Gln Cys Val
            1140                1145                1150
Cys Val Glu Gly Val Glu Gly Pro Arg Cys Asp Lys Cys Thr Arg Gly
            1155                1160                1165
Tyr Ser Gly Val Phe Pro Asp Cys Thr Pro Cys His Gln Cys Phe Ala
            1170                1175                1180
Leu Trp Asp Val Ile Ile Ala Glu Leu Thr Asn Arg Thr His Arg Phe
1185                1190                1195                1200
Leu Glu Lys Ala Lys Ala Leu Lys Ile Ser Gly Val Ile Gly Pro Tyr
            1205                1210                1215
Arg Glu Thr Val Asp Ser Val Glu Arg Lys Val Ser Glu Ile Lys Asp
            1220                1225                1230
Ile Leu Ala Gln Ser Pro Ala Ala Glu Pro Leu Lys Asn Ile Gly Asn
            1235                1240                1245
Leu Phe Glu Glu Ala Glu Lys Leu Ile Lys Asp Val Thr Glu Met Met
            1250                1255                1260
Ala Gln Val Glu Val Lys Leu Ser Asp Thr Thr Ser Gln Ser Asn Ser
1265                1270                1275                1280
Thr Ala Lys Glu Leu Asp Ser Leu Gln Thr Glu Ala Glu Ser Leu Asp
            1285                1290                1295
Asn Thr Val Lys Glu Leu Ala Glu Gln Leu Glu Phe Ile Lys Asn Ser
```

-continued

```
                1300                1305                1310
Asp Ile Arg Gly Ala Leu Asp Ser Ile Thr Lys Tyr Phe Gln Met Ser
            1315                1320                1325
Leu Glu Ala Glu Glu Arg Val Asn Ala Ser Thr Thr Glu Pro Asn Ser
        1330                1335                1340
Thr Val Glu Gln Ser Ala Leu Met Arg Asp Arg Val Glu Asp Val Met
    1345                1350                1355                1360
Met Glu Arg Glu Ser Gln Phe Lys Glu Lys Gln Glu Gln Ala Arg
                1365                1370                1375
Leu Leu Asp Glu Leu Ala Gly Lys Leu Gln Ser Leu Asp Leu Ser Ala
            1380                1385                1390
Ala Ala Glu Met Thr Cys Gly Thr Pro Pro Gly Ala Ser Cys Ser Glu
        1395                1400                1405
Thr Glu Cys Gly Gly Pro Asn Cys Arg Thr Asp Glu Gly Glu Arg Lys
    1410                1415                1420
Cys Gly Gly Pro Gly Cys Gly Gly Leu Val Thr Val Ala His Asn Ala
1425                1430                1435                1440
Trp Gln Lys Ala Met Asp Leu Asp Gln Asp Val Leu Ser Ala Leu Ala
            1445                1450                1455
Glu Val Glu Gln Leu Ser Lys Met Val Ser Glu Ala Lys Leu Arg Ala
        1460                1465                1470
Asp Glu Ala Lys Gln Ser Ala Glu Asp Ile Leu Leu Lys Thr Asn Ala
    1475                1480                1485
Thr Lys Glu Lys Met Asp Lys Ser Asn Glu Glu Leu Arg Asn Leu Ile
    1490                1495                1500
Lys Gln Ile Arg Asn Phe Leu Thr Gln Asp Ser Ala Asp Leu Asp Ser
1505                1510                1515                1520
Ile Glu Ala Val Ala Asn Glu Val Leu Lys Met Glu Met Pro Ser Thr
            1525                1530                1535
Pro Gln Gln Leu Gln Asn Leu Thr Glu Asp Ile Arg Glu Arg Val Glu
        1540                1545                1550
Ser Leu Ser Gln Val Glu Val Ile Leu Gln His Ser Ala Ala Asp Ile
    1555                1560                1565
Ala Arg Ala Glu Met Leu Leu Glu Glu Ala Lys Arg Ala Ser Lys Ser
    1570                1575                1580
Ala Thr Asp Val Lys Val Thr Ala Asp Met Val Lys Glu Ala Leu Glu
1585                1590                1595                1600
Glu Ala Glu Lys Ala Gln Val Ala Ala Glu Lys Ala Ile Lys Gln Ala
            1605                1610                1615
Asp Glu Asp Ile Gln Gly Thr Gln Asn Leu Leu Thr Ser Ile Glu Ser
        1620                1625                1630
Glu Thr Ala Ala Ser Glu Glu Thr Leu Phe Asn Ala Ser Gln Arg Ile
    1635                1640                1645
Ser Glu Leu Glu Arg Asn Val Glu Leu Lys Arg Lys Ala Ala Gln
    1650                1655                1660
Asn Ser Gly Glu Ala Glu Tyr Ile Glu Lys Val Val Tyr Thr Val Lys
1665                1670                1675                1680
Gln Ser Ala Glu Asp Val Lys Lys Thr Leu Asp Gly Glu Leu Asp Glu
            1685                1690                1695
Lys Tyr Lys Lys Val Glu Asn Leu Ile Ala Lys Lys Thr Glu Glu Ser
        1700                1705                1710
Ala Asp Ala Arg Arg Lys Ala Glu Met Leu Gln Asn Glu Ala Lys Thr
    1715                1720                1725
```

```
Leu Leu Ala Gln Ala Asn Ser Lys Leu Gln Leu Leu Lys Asp Leu Glu
    1730                1735                1740

Arg Lys Tyr Glu Asp Asn Gln Arg Tyr Leu Glu Asp Lys Ala Gln Glu
1745                1750                1755                1760

Leu Ala Arg Leu Glu Gly Glu Val Arg Ser Leu Leu Lys Asp Ile Ser
            1765                1770                1775

Gln Lys Val Ala Val Tyr Ser Thr Cys Leu
        1780                1785

<210> SEQ ID NO 7
<211> LENGTH: 5433
<212> TYPE: DNA
<213> ORGANISM: Homo sapiens
<220> FEATURE:
<221> NAME/KEY: CDS
<222> LOCATION: (1)..(5295)

<400> SEQUENCE: 7 cag gaa ccc gag ttc agc tac ggc tgc gca gaa ggc agc tgc tat ccc      48
Gln Glu Pro Glu Phe Ser Tyr Gly Cys Ala Glu Gly Ser Cys Tyr Pro
  1               5                  10                  15 gcc acg ggc gac ctt ctc atc ggc cga gca cag aag ctt tcg gtg acc      96
Ala Thr Gly Asp Leu Leu Ile Gly Arg Ala Gln Lys Leu Ser Val Thr
                 20                  25                  30 tcg acg tgc ggg ctg cac aag ccc gaa ccc tac tgt atc gtc agc cac     144
Ser Thr Cys Gly Leu His Lys Pro Glu Pro Tyr Cys Ile Val Ser His
         35                  40                  45 ttg cag gag gac aaa aaa tgc ttc ata tgc aat tcc caa gat cct tat     192
Leu Gln Glu Asp Lys Lys Cys Phe Ile Cys Asn Ser Gln Asp Pro Tyr
     50                  55                  60 cat gag acc ctg aat cct gac agc cat ctc att gaa aat gtg gtc act     240
His Glu Thr Leu Asn Pro Asp Ser His Leu Ile Glu Asn Val Val Thr
 65                  70                  75                  80 aca ttt gct cca aac cgc ctt aag att tgg tgg caa tct gaa aat ggt     288
Thr Phe Ala Pro Asn Arg Leu Lys Ile Trp Trp Gln Ser Glu Asn Gly
                 85                  90                  95 gtg gaa aat gta act atc caa ctg gat ttg gaa gca gaa ttc cat ttt     336
Val Glu Asn Val Thr Ile Gln Leu Asp Leu Glu Ala Glu Phe His Phe
                100                 105                 110 act cat ctc ata atg act ttc aag aca ttc cgt cca gct gct atg ctg     384
Thr His Leu Ile Met Thr Phe Lys Thr Phe Arg Pro Ala Ala Met Leu
        115                 120                 125 ata gaa cga tcg tcc gac ttt ggg aaa acc tgg ggt gtg tat aga tac     432
Ile Glu Arg Ser Ser Asp Phe Gly Lys Thr Trp Gly Val Tyr Arg Tyr
    130                 135                 140 ttc gcc tat gac tgt gag gcc tcg ttt cca ggc att tca act ggc ccc     480
Phe Ala Tyr Asp Cys Glu Ala Ser Phe Pro Gly Ile Ser Thr Gly Pro
145                 150                 155                 160 atg aaa aaa gtc gat gac ata att tgt gat tct cga tat tct gac att     528
Met Lys Lys Val Asp Asp Ile Ile Cys Asp Ser Arg Tyr Ser Asp Ile
                165                 170                 175 gaa ccc tca act gaa gga gag gtg ata ttt cgt gct tta gat cct gct     576
Glu Pro Ser Thr Glu Gly Glu Val Ile Phe Arg Ala Leu Asp Pro Ala
                180                 185                 190 ttc aaa ata gaa gat cct tat agc cca agg ata cag aat tta tta aaa     624
Phe Lys Ile Glu Asp Pro Tyr Ser Pro Arg Ile Gln Asn Leu Leu Lys
        195                 200                 205 att acc aac ttg aga atc aag ttt gtg aaa ctg cat act ttg gga gat     672
Ile Thr Asn Leu Arg Ile Lys Phe Val Lys Leu His Thr Leu Gly Asp
    210                 215                 220
```

```
aac ctt ctg gat tcc agg atg gaa atc aga gaa aag tat tat tat gca      720
Asn Leu Leu Asp Ser Arg Met Glu Ile Arg Glu Lys Tyr Tyr Tyr Ala
225                 230                 235                 240 gtt tat gat atg gtg gtt cga gga aat tgc ttc tgc tat ggt cat gcc      768
Val Tyr Asp Met Val Val Arg Gly Asn Cys Phe Cys Tyr Gly His Ala
                245                 250                 255 agc gaa tgt gcc cct gtg gat gga ttc aat gaa gaa gtg gaa gga atg      816
Ser Glu Cys Ala Pro Val Asp Gly Phe Asn Glu Glu Val Glu Gly Met
            260                 265                 270 gtt cac gga cac tgc atg tgc agg cat aac acc aag ggc tta aac tgt      864
Val His Gly His Cys Met Cys Arg His Asn Thr Lys Gly Leu Asn Cys
        275                 280                 285 gaa ctc tgc atg gat ttc tac cat gat tta cct tgg aga cct gct gaa      912
Glu Leu Cys Met Asp Phe Tyr His Asp Leu Pro Trp Arg Pro Ala Glu
    290                 295                 300 ggc cga aac agc aac gcc tgt aaa aaa tgt aac tgc aat gaa cat tcc      960
Gly Arg Asn Ser Asn Ala Cys Lys Lys Cys Asn Cys Asn Glu His Ser
305                 310                 315                 320 atc tct tgt cac ttt gac atg gct gtt tac ctg gcc acg ggg aac gtc     1008
Ile Ser Cys His Phe Asp Met Ala Val Tyr Leu Ala Thr Gly Asn Val
                325                 330                 335 agc gga ggc gtg tgt gat gac tgt cag cac aac acc atg ggg cgc aac     1056
Ser Gly Gly Val Cys Asp Asp Cys Gln His Asn Thr Met Gly Arg Asn
            340                 345                 350 tgt gag cag tgc aag ccg ttt tac tac cag cac cca gag agg gac atc     1104
Cys Glu Gln Cys Lys Pro Phe Tyr Tyr Gln His Pro Glu Arg Asp Ile
        355                 360                 365 cga gat cct aat ttc tgt gaa cga tgt acg tgt gac cca gct ggc tct     1152
Arg Asp Pro Asn Phe Cys Glu Arg Cys Thr Cys Asp Pro Ala Gly Ser
    370                 375                 380 caa aat gag gga att tgt gac agc tat act gat ttt tct act ggt ctc     1200
Gln Asn Glu Gly Ile Cys Asp Ser Tyr Thr Asp Phe Ser Thr Gly Leu
385                 390                 395                 400 att gct ggc cag tgt cgg tgt aaa tta aat gtg gaa gga gaa cat tgt     1248
Ile Ala Gly Gln Cys Arg Cys Lys Leu Asn Val Glu Gly Glu His Cys
                405                 410                 415 gat gtt tgc aaa gaa ggc ttc tat gat tta agc agt gaa gat cca ttt     1296
Asp Val Cys Lys Glu Gly Phe Tyr Asp Leu Ser Ser Glu Asp Pro Phe
            420                 425                 430 ggt tgt aaa tct tgt gct tgc aat cct ctg gga aca att cct gga ggg     1344
Gly Cys Lys Ser Cys Ala Cys Asn Pro Leu Gly Thr Ile Pro Gly Gly
        435                 440                 445 aat cct tgt gat tcc gag aca ggt cac tgc tac tgc aag cgt ctg gtg     1392
Asn Pro Cys Asp Ser Glu Thr Gly His Cys Tyr Cys Lys Arg Leu Val
    450                 455                 460 aca gga cag cat tgt gac cag tgc ctg cca gag cac tgg ggc tta agc     1440
Thr Gly Gln His Cys Asp Gln Cys Leu Pro Glu His Trp Gly Leu Ser
465                 470                 475                 480 aat gat ttg gat gga tgt cga cca tgt gac tgt gac ctt ggg gga gcc     1488
Asn Asp Leu Asp Gly Cys Arg Pro Cys Asp Cys Asp Leu Gly Gly Ala
                485                 490                 495 tta aac aac agt tgc ttt gcg gag tca ggc cag tgc tca tgc cgg cct     1536
Leu Asn Asn Ser Cys Phe Ala Glu Ser Gly Gln Cys Ser Cys Arg Pro
            500                 505                 510 cac atg att gga cgt cag tgc aac gaa gtg gaa cct ggt tac tac ttt     1584
His Met Ile Gly Arg Gln Cys Asn Glu Val Glu Pro Gly Tyr Tyr Phe
        515                 520                 525 gcc acc ctg gat cac tac ctc tat gaa gcg gag gaa gcc aac ttg ggg     1632
Ala Thr Leu Asp His Tyr Leu Tyr Glu Ala Glu Glu Ala Asn Leu Gly
```

```
                      530                 535                 540
cct ggg gtt agc ata gtg gag cgg caa tat atc cag gac cgg att ccc      1680
Pro Gly Val Ser Ile Val Glu Arg Gln Tyr Ile Gln Asp Arg Ile Pro
545                 550                 555                 560 tcc tgg act gga gcc ggc ttc gtc cga gtg cct gaa ggg gct tat ttg      1728
Ser Trp Thr Gly Ala Gly Phe Val Arg Val Pro Glu Gly Ala Tyr Leu
                565                 570                 575 gag ttt ttc att gac aac ata cca tat tcc atg gag tac gac atc cta      1776
Glu Phe Phe Ile Asp Asn Ile Pro Tyr Ser Met Glu Tyr Asp Ile Leu
            580                 585                 590 att cgc tac gag cca cag cta ccc gac cac tgg gaa aaa gct gtc atc      1824
Ile Arg Tyr Glu Pro Gln Leu Pro Asp His Trp Glu Lys Ala Val Ile
        595                 600                 605 aca gtg cag cga cct gga agg att cca acc agc agc cga tgt ggt aat      1872
Thr Val Gln Arg Pro Gly Arg Ile Pro Thr Ser Ser Arg Cys Gly Asn
    610                 615                 620 acc atc ccc gat gat gac aac cag gtg gtg tca tta tca cca ggc tca      1920
Thr Ile Pro Asp Asp Asp Asn Gln Val Val Ser Leu Ser Pro Gly Ser
625                 630                 635                 640 aga tat gtc gtc ctt cct cgg ccg gtg tgc ttt gag aag gga aca aac      1968
Arg Tyr Val Val Leu Pro Arg Pro Val Cys Phe Glu Lys Gly Thr Asn
                645                 650                 655 tac acg gtg agg ttg gag ctg cct cag tac acc tcc tct gat agc gac      2016
Tyr Thr Val Arg Leu Glu Leu Pro Gln Tyr Thr Ser Ser Asp Ser Asp
            660                 665                 670 gtg gag agc ccc tac acg ctg atc gat tct ctt gtt ctc atg cca tac      2064
Val Glu Ser Pro Tyr Thr Leu Ile Asp Ser Leu Val Leu Met Pro Tyr
        675                 680                 685 tgt aaa tca ctg gac atc ttc acc gtg gga ggt tca gga gat ggg gtg      2112
Cys Lys Ser Leu Asp Ile Phe Thr Val Gly Gly Ser Gly Asp Gly Val
    690                 695                 700 gtc acc aac agt gcc tgg gaa acc ttt cag aga tac cga tgt cta gag      2160
Val Thr Asn Ser Ala Trp Glu Thr Phe Gln Arg Tyr Arg Cys Leu Glu
705                 710                 715                 720 aac agc aga agc gtt gtg aaa aca ccg atg aca gat gtt tgc aga aac      2208
Asn Ser Arg Ser Val Val Lys Thr Pro Met Thr Asp Val Cys Arg Asn
                725                 730                 735 atc atc ttt agc att tct gcc ctg tta cac cag aca ggc ctg gct tgt      2256
Ile Ile Phe Ser Ile Ser Ala Leu Leu His Gln Thr Gly Leu Ala Cys
            740                 745                 750 gaa tgc gac cct cag ggt tcg tta agt tcc gtg tgt gat ccc aac gga      2304
Glu Cys Asp Pro Gln Gly Ser Leu Ser Ser Val Cys Asp Pro Asn Gly
        755                 760                 765 ggc cag tgc cag tgc cgg ccc aac gtg gtt gga aga acc tgc aac aga      2352
Gly Gln Cys Gln Cys Arg Pro Asn Val Val Gly Arg Thr Cys Asn Arg
    770                 775                 780 tgt gca cct gga act ttt ggc ttt ggc ccc agt gga tgc aaa cct tgt      2400
Cys Ala Pro Gly Thr Phe Gly Phe Gly Pro Ser Gly Cys Lys Pro Cys
785                 790                 795                 800 gag tgc cat ctg caa gga tct gtc aat gcc ttc tgt aat ccc gtc act      2448
Glu Cys His Leu Gln Gly Ser Val Asn Ala Phe Cys Asn Pro Val Thr
                805                 810                 815 ggc cag tgc cac tgt ttc cag gga gtg tat gct cgg cag tgt gat cgg      2496
Gly Gln Cys His Cys Phe Gln Gly Val Tyr Ala Arg Gln Cys Asp Arg
            820                 825                 830 tgc tta cct ggg cac tgg ggc ttt cca agt tgc cag ccc tgc cag tgc      2544
Cys Leu Pro Gly His Trp Gly Phe Pro Ser Cys Gln Pro Cys Gln Cys
        835                 840                 845 aat ggc cac gcc gat gac tgc gac cca gtg act ggg gag tgc ttg aac      2592
```

```
                Asn Gly His Ala Asp Asp Cys Asp Pro Val Thr Gly Glu Cys Leu Asn
                    850                 855                 860 tgc cag gac tac acc atg ggt cat aac tgt gaa agg tgc ttg gct ggt        2640
Cys Gln Asp Tyr Thr Met Gly His Asn Cys Glu Arg Cys Leu Ala Gly
865                 870                 875                 880 tac tat ggc gac ccc atc att ggg tca ggt gat cac tgc cgc cct tgc        2688
Tyr Tyr Gly Asp Pro Ile Ile Gly Ser Gly Asp His Cys Arg Pro Cys
                885                 890                 895 cct tgc cca gat ggt ccc gac agt gga cgc cag ttt gcc agg agc tgc        2736
Pro Cys Pro Asp Gly Pro Asp Ser Gly Arg Gln Phe Ala Arg Ser Cys
            900                 905                 910 tac caa gat cct gtt act tta cag ctt gcc tgt gtt tgt gat cct gga        2784
Tyr Gln Asp Pro Val Thr Leu Gln Leu Ala Cys Val Cys Asp Pro Gly
        915                 920                 925 tac att ggt tcc aga tgt gac gac tgt gcc tca gga tac ttt ggc aat        2832
Tyr Ile Gly Ser Arg Cys Asp Asp Cys Ala Ser Gly Tyr Phe Gly Asn
930                 935                 940 cca tca gaa gtt ggg ggg tcg tgt cag cct tgc cag tgt cac aac aac        2880
Pro Ser Glu Val Gly Gly Ser Cys Gln Pro Cys Gln Cys His Asn Asn
945                 950                 955                 960 att gac acg aca gac cca gaa gcc tgt gac aag gag act ggg agg tgt        2928
Ile Asp Thr Thr Asp Pro Glu Ala Cys Asp Lys Glu Thr Gly Arg Cys
                965                 970                 975 ctc aag tgc ctg tac cac acg gaa ggg gaa cac tgt cag ttc tgc cgg        2976
Leu Lys Cys Leu Tyr His Thr Glu Gly Glu His Cys Gln Phe Cys Arg
            980                 985                 990 ttt gga tac tat ggt gat gcc ctc cgg cag gac tgt cga aag tgt gtc        3024
Phe Gly Tyr Tyr Gly Asp Ala Leu Arg Gln Asp Cys Arg Lys Cys Val
        995                 1000                1005 tgt aat tac ctg ggc acc gtg caa gag cac tgt aac ggc tct gac tgc        3072
Cys Asn Tyr Leu Gly Thr Val Gln Glu His Cys Asn Gly Ser Asp Cys
    1010                1015                1020 cag tgc gac aaa gcc act ggt cag tgc ttg tgt ctt cct aat gtg atc        3120
Gln Cys Asp Lys Ala Thr Gly Gln Cys Leu Cys Leu Pro Asn Val Ile
1025                1030                1035                1040 ggg cag aac tgt gac cgc tgt gcg ccc aat acc tgg cag ctg gcc agt        3168
Gly Gln Asn Cys Asp Arg Cys Ala Pro Asn Thr Trp Gln Leu Ala Ser
                1045                1050                1055 ggc act ggc tgt gac cca tgc aac tgc aat gct gct cat tcc ttc ggg        3216
Gly Thr Gly Cys Asp Pro Cys Asn Cys Asn Ala Ala His Ser Phe Gly
            1060                1065                1070 cca tct tgc aat gag ttc acg ggg cag tgc cag tgc atg cct ggg ttt        3264
Pro Ser Cys Asn Glu Phe Thr Gly Gln Cys Gln Cys Met Pro Gly Phe
        1075                1080                1085 gga ggc cgc acc tgc agc gag tgc cag gaa ctc ttc tgg gga gac ccc        3312
Gly Gly Arg Thr Cys Ser Glu Cys Gln Glu Leu Phe Trp Gly Asp Pro
    1090                1095                1100 gac gtg gag tgc cga gcc tgt gac tgt gac ccc agg ggc att gag acg        3360
Asp Val Glu Cys Arg Ala Cys Asp Cys Asp Pro Arg Gly Ile Glu Thr
1105                1110                1115                1120 cca cag tgt gac cag tcc acg ggc cag tgt gtc tgc gtt gag ggt gtt        3408
Pro Gln Cys Asp Gln Ser Thr Gly Gln Cys Val Cys Val Glu Gly Val
                1125                1130                1135 gag ggt cca cgc tgt gac aag tgc acg cga ggg tac tcg ggg gtc ttc        3456
Glu Gly Pro Arg Cys Asp Lys Cys Thr Arg Gly Tyr Ser Gly Val Phe
            1140                1145                1150 cct gac tgc aca ccc tgc cac cag tgc ttt gct ctc tgg gat gtg atc        3504
Pro Asp Cys Thr Pro Cys His Gln Cys Phe Ala Leu Trp Asp Val Ile
        1155                1160                1165
```

```
att gcc gag ctg acc aac agg aca cac aga ttc ctg gag aaa gcc aag        3552
Ile Ala Glu Leu Thr Asn Arg Thr His Arg Phe Leu Glu Lys Ala Lys
    1170                1175                1180 gcc ttg aag atc agt ggt gtg atc ggg cct tac cgt gag act gtg gac        3600
Ala Leu Lys Ile Ser Gly Val Ile Gly Pro Tyr Arg Glu Thr Val Asp
1185                1190                1195                1200 tcg gtg gag agg aaa gtc agc gag ata aaa gac atc ctg gcg cag agc        3648
Ser Val Glu Arg Lys Val Ser Glu Ile Lys Asp Ile Leu Ala Gln Ser
        1205                1210                1215 ccc gca gca gag cca ctg aaa aac att ggg aat ctc ttt gag gaa gca        3696
Pro Ala Ala Glu Pro Leu Lys Asn Ile Gly Asn Leu Phe Glu Glu Ala
            1220                1225                1230 gag aaa ctg att aaa gat gtt aca gaa atg atg gct caa gta gaa gtg        3744
Glu Lys Leu Ile Lys Asp Val Thr Glu Met Met Ala Gln Val Glu Val
                1235                1240                1245 aaa tta tct gac aca act tcc caa agc aac agc aca gcc aaa gaa ctg        3792
Lys Leu Ser Asp Thr Thr Ser Gln Ser Asn Ser Thr Ala Lys Glu Leu
    1250                1255                1260 gat tct cta cag aca gaa gcc gaa agc cta gac aac act gtg aaa gaa        3840
Asp Ser Leu Gln Thr Glu Ala Glu Ser Leu Asp Asn Thr Val Lys Glu
1265                1270                1275                1280 ctt gct gaa caa ctg gaa ttt atc aaa aac tca gat att cgg ggt gcc        3888
Leu Ala Glu Gln Leu Glu Phe Ile Lys Asn Ser Asp Ile Arg Gly Ala
        1285                1290                1295 ttg gat agc att acc aag tat ttc cag atg tct ctt gag gca gag gag        3936
Leu Asp Ser Ile Thr Lys Tyr Phe Gln Met Ser Leu Glu Ala Glu Glu
            1300                1305                1310 agg gtg aat gcc tcc acc aca gaa ccc aac agc act gtg gag cag tca        3984
Arg Val Asn Ala Ser Thr Thr Glu Pro Asn Ser Thr Val Glu Gln Ser
                1315                1320                1325 gcc ctc atg aga gac aga gta gaa gac gtg atg atg gag cga gaa tcc        4032
Ala Leu Met Arg Asp Arg Val Glu Asp Val Met Met Glu Arg Glu Ser
    1330                1335                1340 cag ttc aag gaa aaa caa gag gag cag gct cgc ctc ctt gat gaa ctg        4080
Gln Phe Lys Glu Lys Gln Glu Glu Gln Ala Arg Leu Leu Asp Glu Leu
1345                1350                1355                1360 gca ggc aag cta caa agc cta gac ctt tca gcc gct gcc gaa atg acc        4128
Ala Gly Lys Leu Gln Ser Leu Asp Leu Ser Ala Ala Ala Glu Met Thr
        1365                1370                1375 tgt gga aca ccc cca ggg gcc tcc tgt tcc gag act gaa tgt ggc ggg        4176
Cys Gly Thr Pro Pro Gly Ala Ser Cys Ser Glu Thr Glu Cys Gly Gly
            1380                1385                1390 cca aac tgc aga act gac gaa gga gag agg aag tgt ggg ggg cct ggc        4224
Pro Asn Cys Arg Thr Asp Glu Gly Glu Arg Lys Cys Gly Gly Pro Gly
                1395                1400                1405 tgt ggt ggt ctg gtt act gtt gca cac aac gcc tgg cag aaa gcc atg        4272
Cys Gly Gly Leu Val Thr Val Ala His Asn Ala Trp Gln Lys Ala Met
    1410                1415                1420 gac ttg gac caa gat gtc ctg agt gcc ctg gct gaa gtg gaa cag ctc        4320
Asp Leu Asp Gln Asp Val Leu Ser Ala Leu Ala Glu Val Glu Gln Leu
1425                1430                1435                1440 tcc aag atg gtc tct gaa gca aaa ctg agg gca gat gag gca aaa caa        4368
Ser Lys Met Val Ser Glu Ala Lys Leu Arg Ala Asp Glu Ala Lys Gln
        1445                1450                1455 agt gct gaa gac att ctg ttg aag aca aat gct acc aaa gaa aaa atg        4416
Ser Ala Glu Asp Ile Leu Leu Lys Thr Asn Ala Thr Lys Glu Lys Met
            1460                1465                1470 gac aag agc aat gag gag ctg aga aat cta atc aag caa atc aga aac        4464
Asp Lys Ser Asn Glu Glu Leu Arg Asn Leu Ile Lys Gln Ile Arg Asn
                1475                1480                1485
```

-continued

| | |
|---|---|
| ttt ttg acc cag gat agt gct gat ttg gac agc att gaa gca gtt gct<br>Phe Leu Thr Gln Asp Ser Ala Asp Leu Asp Ser Ile Glu Ala Val Ala<br>  1490                  1495                 1500 | 4512 |
| aat gaa gta ttg aaa atg gag atg cct agc acc cca cag cag tta cag<br>Asn Glu Val Leu Lys Met Glu Met Pro Ser Thr Pro Gln Gln Leu Gln<br>1505               1510               1515              1520 | 4560 |
| aac ttg aca gaa gat ata cgt gaa cga gtt gaa agc ctt tct caa gta<br>Asn Leu Thr Glu Asp Ile Arg Glu Arg Val Glu Ser Leu Ser Gln Val<br>              1525              1530               1535 | 4608 |
| gag gtt att ctt cag cat agt gct gct gac att gcc aga gct gag atg<br>Glu Val Ile Leu Gln His Ser Ala Ala Asp Ile Ala Arg Ala Glu Met<br>        1540              1545               1550 | 4656 |
| ttg tta gaa gaa gct aaa aga gca agc aaa agt gca aca gat gtt aaa<br>Leu Leu Glu Glu Ala Lys Arg Ala Ser Lys Ser Ala Thr Asp Val Lys<br>    1555              1560               1565 | 4704 |
| gtc act gca gat atg gta aag gaa gct ctg gaa gaa gca gaa aag gcc<br>Val Thr Ala Asp Met Val Lys Glu Ala Leu Glu Glu Ala Glu Lys Ala<br>1570               1575               1580 | 4752 |
| cag gtc gca gca gag aag gca att aaa caa gca gat gaa gac att caa<br>Gln Val Ala Ala Glu Lys Ala Ile Lys Gln Ala Asp Glu Asp Ile Gln<br>1585               1590              1595              1600 | 4800 |
| gga acc cag aac ctg tta act tcg att gag tct gaa aca gca gct tct<br>Gly Thr Gln Asn Leu Leu Thr Ser Ile Glu Ser Glu Thr Ala Ala Ser<br>              1605              1610               1615 | 4848 |
| gag gaa acc ttg ttc aac gcg tcc cag cgc atc agc gag tta gag agg<br>Glu Glu Thr Leu Phe Asn Ala Ser Gln Arg Ile Ser Glu Leu Glu Arg<br>        1620              1625               1630 | 4896 |
| aat gtg gaa gaa ctt aag cgg aaa gct gcc caa aac tcc ggg gag gca<br>Asn Val Glu Glu Leu Lys Arg Lys Ala Ala Gln Asn Ser Gly Glu Ala<br>    1635              1640               1645 | 4944 |
| gaa tat att gaa aaa gta gta tat act gtg aag caa agt gca gaa gat<br>Glu Tyr Ile Glu Lys Val Val Tyr Thr Val Lys Gln Ser Ala Glu Asp<br>1650               1655               1660 | 4992 |
| gtt aag aag act tta gat ggt gaa ctt gat gaa aag tat aaa aaa gta<br>Val Lys Lys Thr Leu Asp Gly Glu Leu Asp Glu Lys Tyr Lys Lys Val<br>1665               1670               1675              1680 | 5040 |
| gaa aat tta att gcc aaa aaa act gaa gag tca gct gat gcc aga agg<br>Glu Asn Leu Ile Ala Lys Lys Thr Glu Glu Ser Ala Asp Ala Arg Arg<br>        1685              1690               1695 | 5088 |
| aaa gcc gaa atg cta caa aat gaa gca aaa act ctt tta gct caa gca<br>Lys Ala Glu Met Leu Gln Asn Glu Ala Lys Thr Leu Leu Ala Gln Ala<br>              1700              1705               1710 | 5136 |
| aat agc aag ctg caa ctg ctc aaa gat tta gaa aga aaa tat gaa gac<br>Asn Ser Lys Leu Gln Leu Leu Lys Asp Leu Glu Arg Lys Tyr Glu Asp<br>    1715              1720               1725 | 5184 |
| aat caa aga tac tta gaa gat aaa gct caa gaa tta gca aga ctg gaa<br>Asn Gln Arg Tyr Leu Glu Asp Lys Ala Gln Glu Leu Ala Arg Leu Glu<br>1730               1735               1740 | 5232 |
| gga gaa gtc cgt tca ctc cta aag gat ata agc cag aaa gtt gct gtg<br>Gly Glu Val Arg Ser Leu Leu Lys Asp Ile Ser Gln Lys Val Ala Val<br>1745               1750               1755              1760 | 5280 |
| tat agc aca tgc ttg taacagagga gaataaaaaa tggctgaggt gaacaaggta<br>Tyr Ser Thr Cys Leu<br>              1765 | 5335 |
| aaacaactac attttaaaaa ctgacttaat gctcttcaaa ataaacatc acctatttaa | 5395 |
| tgtttttaat cacattttgt atgagttaaa taaagccc | 5433 |

<210> SEQ ID NO 8

<211> LENGTH: 1765
<212> TYPE: PRT
<213> ORGANISM: Homo sapiens

<400> SEQUENCE: 8

```
Gln Glu Pro Glu Phe Ser Tyr Gly Cys Ala Glu Gly Ser Cys Tyr Pro
  1               5                  10                  15

Ala Thr Gly Asp Leu Leu Ile Gly Arg Ala Gln Lys Leu Ser Val Thr
             20                  25                  30

Ser Thr Cys Gly Leu His Lys Pro Glu Pro Tyr Cys Ile Val Ser His
         35                  40                  45

Leu Gln Glu Asp Lys Lys Cys Phe Ile Cys Asn Ser Gln Asp Pro Tyr
     50                  55                  60

His Glu Thr Leu Asn Pro Asp Ser His Leu Ile Glu Asn Val Val Thr
 65                  70                  75                  80

Thr Phe Ala Pro Asn Arg Leu Lys Ile Trp Trp Gln Ser Glu Asn Gly
                 85                  90                  95

Val Glu Asn Val Thr Ile Gln Leu Asp Leu Glu Ala Glu Phe His Phe
            100                 105                 110

Thr His Leu Ile Met Thr Phe Lys Thr Phe Arg Pro Ala Ala Met Leu
        115                 120                 125

Ile Glu Arg Ser Ser Asp Phe Gly Lys Thr Trp Gly Val Tyr Arg Tyr
    130                 135                 140

Phe Ala Tyr Asp Cys Glu Ala Ser Phe Pro Gly Ile Ser Thr Gly Pro
145                 150                 155                 160

Met Lys Lys Val Asp Asp Ile Ile Cys Asp Ser Arg Tyr Ser Asp Ile
                165                 170                 175

Glu Pro Ser Thr Glu Gly Glu Val Ile Phe Arg Ala Leu Asp Pro Ala
            180                 185                 190

Phe Lys Ile Glu Asp Pro Tyr Ser Pro Arg Ile Gln Asn Leu Leu Lys
        195                 200                 205

Ile Thr Asn Leu Arg Ile Lys Phe Val Lys Leu His Thr Leu Gly Asp
    210                 215                 220

Asn Leu Leu Asp Ser Arg Met Glu Ile Arg Glu Lys Tyr Tyr Tyr Ala
225                 230                 235                 240

Val Tyr Asp Met Val Val Arg Gly Asn Cys Phe Cys Tyr Gly His Ala
                245                 250                 255

Ser Glu Cys Ala Pro Val Asp Gly Phe Asn Glu Glu Val Glu Gly Met
            260                 265                 270

Val His Gly His Cys Met Cys Arg His Asn Thr Lys Gly Leu Asn Cys
        275                 280                 285

Glu Leu Cys Met Asp Phe Tyr His Asp Leu Pro Trp Arg Pro Ala Glu
    290                 295                 300

Gly Arg Asn Ser Asn Ala Cys Lys Lys Cys Asn Cys Asn Glu His Ser
305                 310                 315                 320

Ile Ser Cys His Phe Asp Met Ala Val Tyr Leu Ala Thr Gly Asn Val
                325                 330                 335

Ser Gly Gly Val Cys Asp Asp Cys Gln His Asn Thr Met Gly Arg Asn
            340                 345                 350

Cys Glu Gln Cys Lys Pro Phe Tyr Tyr Gln His Pro Glu Arg Asp Ile
        355                 360                 365

Arg Asp Pro Asn Phe Cys Glu Arg Cys Thr Cys Asp Pro Ala Gly Ser
    370                 375                 380

Gln Asn Glu Gly Ile Cys Asp Ser Tyr Thr Asp Phe Ser Thr Gly Leu
```

-continued

```
              385                 390                 395                 400
Ile Ala Gly Gln Cys Arg Cys Lys Leu Asn Val Glu Gly Glu His Cys
                405                 410                 415
Asp Val Cys Lys Glu Gly Phe Tyr Asp Leu Ser Ser Glu Asp Pro Phe
                420                 425                 430
Gly Cys Lys Ser Cys Ala Cys Asn Pro Leu Gly Thr Ile Pro Gly Gly
                435                 440                 445
Asn Pro Cys Asp Ser Glu Thr Gly His Cys Tyr Cys Lys Arg Leu Val
                450                 455                 460
Thr Gly Gln His Cys Asp Gln Cys Leu Pro Glu His Trp Gly Leu Ser
465                 470                 475                 480
Asn Asp Leu Asp Gly Cys Arg Pro Cys Asp Cys Asp Leu Gly Gly Ala
                485                 490                 495
Leu Asn Asn Ser Cys Phe Ala Glu Ser Gly Gln Cys Ser Cys Arg Pro
                500                 505                 510
His Met Ile Gly Arg Gln Cys Asn Glu Val Glu Pro Gly Tyr Tyr Phe
                515                 520                 525
Ala Thr Leu Asp His Tyr Leu Tyr Glu Ala Glu Ala Asn Leu Gly
                530                 535                 540
Pro Gly Val Ser Ile Val Glu Arg Gln Tyr Ile Gln Asp Arg Ile Pro
545                 550                 555                 560
Ser Trp Thr Gly Ala Gly Phe Val Arg Val Pro Glu Gly Ala Tyr Leu
                565                 570                 575
Glu Phe Phe Ile Asp Asn Ile Pro Tyr Ser Met Glu Tyr Asp Ile Leu
                580                 585                 590
Ile Arg Tyr Glu Pro Gln Leu Pro Asp His Trp Glu Lys Ala Val Ile
                595                 600                 605
Thr Val Gln Arg Pro Gly Arg Ile Pro Thr Ser Ser Arg Cys Gly Asn
                610                 615                 620
Thr Ile Pro Asp Asp Asp Asn Gln Val Val Ser Leu Ser Pro Gly Ser
625                 630                 635                 640
Arg Tyr Val Val Leu Pro Arg Pro Val Cys Phe Glu Lys Gly Thr Asn
                645                 650                 655
Tyr Thr Val Arg Leu Glu Leu Pro Gln Tyr Thr Ser Ser Asp Ser Asp
                660                 665                 670
Val Glu Ser Pro Tyr Thr Leu Ile Asp Ser Leu Val Leu Met Pro Tyr
                675                 680                 685
Cys Lys Ser Leu Asp Ile Phe Thr Val Gly Gly Ser Gly Asp Gly Val
                690                 695                 700
Val Thr Asn Ser Ala Trp Glu Thr Phe Gln Arg Tyr Arg Cys Leu Glu
705                 710                 715                 720
Asn Ser Arg Ser Val Val Lys Thr Pro Met Thr Asp Val Cys Arg Asn
                725                 730                 735
Ile Ile Phe Ser Ile Ser Ala Leu Leu His Gln Thr Gly Leu Ala Cys
                740                 745                 750
Glu Cys Asp Pro Gln Gly Ser Leu Ser Ser Val Cys Asp Pro Asn Gly
                755                 760                 765
Gly Gln Cys Gln Cys Arg Pro Asn Val Val Gly Arg Thr Cys Asn Arg
                770                 775                 780
Cys Ala Pro Gly Thr Phe Gly Phe Gly Pro Ser Gly Cys Lys Pro Cys
785                 790                 795                 800
Glu Cys His Leu Gln Gly Ser Val Asn Ala Phe Cys Asn Pro Val Thr
                805                 810                 815
```

-continued

```
Gly Gln Cys His Cys Phe Gln Gly Val Tyr Ala Arg Gln Cys Asp Arg
            820                 825                 830

Cys Leu Pro Gly His Trp Gly Phe Pro Ser Cys Gln Pro Cys Gln Cys
        835                 840                 845

Asn Gly His Ala Asp Cys Asp Pro Val Thr Gly Glu Cys Leu Asn
    850                 855                 860

Cys Gln Asp Tyr Thr Met Gly His Asn Cys Glu Arg Cys Leu Ala Gly
865                 870                 875                 880

Tyr Tyr Gly Asp Pro Ile Ile Gly Ser Gly Asp His Cys Arg Pro Cys
                885                 890                 895

Pro Cys Pro Asp Gly Pro Asp Ser Gly Arg Gln Phe Ala Arg Ser Cys
            900                 905                 910

Tyr Gln Asp Pro Val Thr Leu Gln Leu Ala Cys Val Cys Asp Pro Gly
            915                 920                 925

Tyr Ile Gly Ser Arg Cys Asp Asp Cys Ala Ser Gly Tyr Phe Gly Asn
        930                 935                 940

Pro Ser Glu Val Gly Gly Ser Cys Gln Pro Cys Gln Cys His Asn Asn
945                 950                 955                 960

Ile Asp Thr Thr Asp Pro Glu Ala Cys Asp Lys Glu Thr Gly Arg Cys
                965                 970                 975

Leu Lys Cys Leu Tyr His Thr Glu Gly Glu His Cys Gln Phe Cys Arg
            980                 985                 990

Phe Gly Tyr Tyr Gly Asp Ala Leu Arg Gln Asp Cys Arg Lys Cys Val
        995                 1000                1005

Cys Asn Tyr Leu Gly Thr Val Gln Glu His Cys Asn Gly Ser Asp Cys
   1010                 1015                1020

Gln Cys Asp Lys Ala Thr Gly Gln Cys Leu Cys Leu Pro Asn Val Ile
1025                1030                1035                1040

Gly Gln Asn Cys Asp Arg Cys Ala Pro Asn Thr Trp Gln Leu Ala Ser
            1045                1050                1055

Gly Thr Gly Cys Asp Pro Cys Asn Cys Asn Ala Ala His Ser Phe Gly
        1060                1065                1070

Pro Ser Cys Asn Glu Phe Thr Gly Gln Cys Gln Cys Met Pro Gly Phe
        1075                1080                1085

Gly Gly Arg Thr Cys Ser Glu Cys Gln Glu Leu Phe Trp Gly Asp Pro
   1090                1095                1100

Asp Val Glu Cys Arg Ala Cys Asp Cys Asp Pro Arg Gly Ile Glu Thr
1105                1110                1115                1120

Pro Gln Cys Asp Gln Ser Thr Gly Gln Cys Val Cys Val Glu Gly Val
            1125                1130                1135

Glu Gly Pro Arg Cys Asp Lys Cys Thr Arg Gly Tyr Ser Gly Val Phe
            1140                1145                1150

Pro Asp Cys Thr Pro Cys His Gln Cys Phe Ala Leu Trp Asp Val Ile
        1155                1160                1165

Ile Ala Glu Leu Thr Asn Arg Thr His Arg Phe Leu Glu Lys Ala Lys
   1170                1175                1180

Ala Leu Lys Ile Ser Gly Val Ile Gly Pro Tyr Arg Glu Thr Val Asp
1185                1190                1195                1200

Ser Val Glu Arg Lys Val Ser Glu Ile Lys Asp Ile Leu Ala Gln Ser
            1205                1210                1215

Pro Ala Ala Glu Pro Leu Lys Asn Ile Gly Asn Leu Phe Glu Glu Ala
            1220                1225                1230
```

```
Glu Lys Leu Ile Lys Asp Val Thr Glu Met Met Ala Gln Val Glu Val
            1235                1240                1245
Lys Leu Ser Asp Thr Thr Ser Gln Ser Asn Ser Thr Ala Lys Glu Leu
1250                1255                1260
Asp Ser Leu Gln Thr Glu Ala Glu Ser Leu Asp Asn Thr Val Lys Glu
1265                1270                1275                1280
Leu Ala Glu Gln Leu Glu Phe Ile Lys Asn Ser Asp Ile Arg Gly Ala
            1285                1290                1295
Leu Asp Ser Ile Thr Lys Tyr Phe Gln Met Ser Leu Glu Ala Glu Glu
            1300                1305                1310
Arg Val Asn Ala Ser Thr Thr Glu Pro Asn Ser Thr Val Glu Gln Ser
            1315                1320                1325
Ala Leu Met Arg Asp Arg Val Glu Asp Val Met Met Glu Arg Glu Ser
            1330                1335                1340
Gln Phe Lys Glu Lys Gln Glu Glu Gln Ala Arg Leu Leu Asp Glu Leu
1345                1350                1355                1360
Ala Gly Lys Leu Gln Ser Leu Asp Leu Ser Ala Ala Ala Glu Met Thr
            1365                1370                1375
Cys Gly Thr Pro Pro Gly Ala Ser Cys Ser Thr Glu Cys Gly Gly
            1380                1385                1390
Pro Asn Cys Arg Thr Asp Glu Gly Glu Arg Lys Cys Gly Gly Pro Gly
            1395                1400                1405
Cys Gly Gly Leu Val Thr Val Ala His Asn Ala Trp Gln Lys Ala Met
            1410                1415                1420
Asp Leu Asp Gln Asp Val Leu Ser Ala Leu Ala Glu Val Glu Gln Leu
1425                1430                1435                1440
Ser Lys Met Val Ser Glu Ala Lys Leu Arg Ala Asp Glu Ala Lys Gln
            1445                1450                1455
Ser Ala Glu Asp Ile Leu Leu Lys Thr Asn Ala Thr Lys Glu Lys Met
            1460                1465                1470
Asp Lys Ser Asn Glu Glu Leu Arg Asn Leu Ile Lys Gln Ile Arg Asn
            1475                1480                1485
Phe Leu Thr Gln Asp Ser Ala Asp Leu Asp Ser Ile Glu Ala Val Ala
            1490                1495                1500
Asn Glu Val Leu Lys Met Glu Met Pro Ser Thr Pro Gln Gln Leu Gln
1505                1510                1515                1520
Asn Leu Thr Glu Asp Ile Arg Glu Arg Val Glu Ser Leu Ser Gln Val
            1525                1530                1535
Glu Val Ile Leu Gln His Ser Ala Ala Asp Ile Ala Arg Ala Glu Met
            1540                1545                1550
Leu Leu Glu Glu Ala Lys Arg Ala Ser Lys Ser Ala Thr Asp Val Lys
            1555                1560                1565
Val Thr Ala Asp Met Val Lys Glu Ala Leu Glu Glu Ala Glu Lys Ala
            1570                1575                1580
Gln Val Ala Ala Glu Lys Ala Ile Lys Gln Ala Asp Glu Asp Ile Gln
            1585                1590                1595                1600
Gly Thr Gln Asn Leu Leu Thr Ser Ile Glu Ser Glu Thr Ala Ala Ser
            1605                1610                1615
Glu Glu Thr Leu Phe Asn Ala Ser Gln Arg Ile Ser Glu Leu Glu Arg
            1620                1625                1630
Asn Val Glu Glu Leu Lys Arg Lys Ala Ala Gln Asn Ser Gly Glu Ala
            1635                1640                1645
Glu Tyr Ile Glu Lys Val Val Tyr Thr Val Lys Gln Ser Ala Glu Asp
```

```
                  1650               1655               1660
Val Lys Lys Thr Leu Asp Gly Glu Leu Asp Lys Tyr Lys Val
1665                 1670              1675              1680

Glu Asn Leu Ile Ala Lys Lys Thr Glu Glu Ser Ala Asp Ala Arg Arg
                 1685               1690              1695

Lys Ala Glu Met Leu Gln Asn Glu Ala Lys Thr Leu Leu Ala Gln Ala
              1700              1705              1710

Asn Ser Lys Leu Gln Leu Leu Lys Asp Leu Glu Arg Lys Tyr Glu Asp
            1715              1720              1725

Asn Gln Arg Tyr Leu Glu Asp Lys Ala Gln Glu Leu Ala Arg Leu Glu
        1730              1735              1740

Gly Glu Val Arg Ser Leu Leu Lys Asp Ile Ser Gln Lys Val Ala Val
1745               1750              1755              1760

Tyr Ser Thr Cys Leu
            1765

<210> SEQ ID NO 9
<211> LENGTH: 5689
<212> TYPE: DNA
<213> ORGANISM: Mus musculus
<220> FEATURE:
<221> NAME/KEY: CDS
<222> LOCATION: (178)..(5535)
<221> NAME/KEY: sig_peptide
<222> LOCATION: (178)..(240)

<400> SEQUENCE: 9
gcccagcccc cgcttccgtg ggagcggcag gaaatggaag ggccctctc ctctctccca      60 acatttgcct tttctccccg ctacctctcc agaaaggaag acccgaagaa aagcacaggca   120 gcttgcctgc tgcgtcctcc ttcccgtgcc gcgtcccctc gtctgcgagg actggac        177 atg ggg ctg ctc cag gtg ttc gcc ttt ggt gtc cta gcc cta tgg ggc      225
Met Gly Leu Leu Gln Val Phe Ala Phe Gly Val Leu Ala Leu Trp Gly
  1               5                  10                  15 acc cga gtg tgc gct cag gaa ccg gag ttc agc tat ggc tgc gca gaa      273
Thr Arg Val Cys Ala Gln Glu Pro Glu Phe Ser Tyr Gly Cys Ala Glu
                 20                  25                  30 ggc agc tgc tac cct gcc act ggc gac ctt ctc atc ggc cga gcg caa      321
Gly Ser Cys Tyr Pro Ala Thr Gly Asp Leu Leu Ile Gly Arg Ala Gln
             35                  40                  45 aag ctc tcc gtg act tcg aca tgt gga ctg cac aaa cca gag ccc tac      369
Lys Leu Ser Val Thr Ser Thr Cys Gly Leu His Lys Pro Glu Pro Tyr
         50                  55                  60 tgt att gtt agc cac ctg cag gag gac aag aaa tgc ttc ata tgt gac      417
Cys Ile Val Ser His Leu Gln Glu Asp Lys Lys Cys Phe Ile Cys Asp
 65                  70                  75                  80 tcc cga gac cct tat cac gag acc ctc aac ccc gac agc cat ctc att      465
Ser Arg Asp Pro Tyr His Glu Thr Leu Asn Pro Asp Ser His Leu Ile
                 85                  90                  95 gag aac gtg gtc acc aca ttt gct cca aac cgc ctt aag atc tgg tgg      513
Glu Asn Val Val Thr Thr Phe Ala Pro Asn Arg Leu Lys Ile Trp Trp
            100                 105                 110 caa tcg gaa aat ggt gtg gag aac gtg acc atc caa ctg gac ctg gaa      561
Gln Ser Glu Asn Gly Val Glu Asn Val Thr Ile Gln Leu Asp Leu Glu
        115                 120                 125 gca gaa ttc cat ttc act cat ctc atc atg acc ttc aag aca ttc cgc      609
Ala Glu Phe His Phe Thr His Leu Ile Met Thr Phe Lys Thr Phe Arg
    130                 135                 140 cca gcc gcc atg ctg atc gag cgg tct tct gac ttt ggg aag act tgg      657
```

```
Pro Ala Ala Met Leu Ile Glu Arg Ser Ser Asp Phe Gly Lys Thr Trp
145                 150                 155                 160 ggc gtg tac aga tac ttc gcc tac gac tgt gag agc tcg ttc cca ggc      705
Gly Val Tyr Arg Tyr Phe Ala Tyr Asp Cys Glu Ser Ser Phe Pro Gly
                165                 170                 175 att tca act gga ccc atg aag aaa gtg gat gac atc atc tgt gac tct      753
Ile Ser Thr Gly Pro Met Lys Lys Val Asp Asp Ile Ile Cys Asp Ser
            180                 185                 190 cga tat tct gac att gag ccc tcg aca gaa gga gag gta ata ttt cgt      801
Arg Tyr Ser Asp Ile Glu Pro Ser Thr Glu Gly Glu Val Ile Phe Arg
        195                 200                 205 gct tta gat cct gct ttc aaa att gaa gac cct tat agt cca agg ata      849
Ala Leu Asp Pro Ala Phe Lys Ile Glu Asp Pro Tyr Ser Pro Arg Ile
    210                 215                 220 cag aat cta tta aaa atc acc aac ttg aga atc aag ttt gtg aaa ctg      897
Gln Asn Leu Leu Lys Ile Thr Asn Leu Arg Ile Lys Phe Val Lys Leu
225                 230                 235                 240 cac acc ttg ggg gat aac ctt ttg gac tcc aga atg gaa atc cga gag      945
His Thr Leu Gly Asp Asn Leu Leu Asp Ser Arg Met Glu Ile Arg Glu
                245                 250                 255 aag tac tat tac gct gtt tat gat atg gtg gtt cga ggg aac tgc ttc      993
Lys Tyr Tyr Tyr Ala Val Tyr Asp Met Val Val Arg Gly Asn Cys Phe
            260                 265                 270 tgc tat ggc cac gcc agt gaa tgc gcc cct gtg gat gga gtc aat gaa     1041
Cys Tyr Gly His Ala Ser Glu Cys Ala Pro Val Asp Gly Val Asn Glu
        275                 280                 285 gaa gtg gaa gga atg gtt cac ggg cac tgc atg tgc aga cac aac acc     1089
Glu Val Glu Gly Met Val His Gly His Cys Met Cys Arg His Asn Thr
    290                 295                 300 aaa ggc ctg aac tgt gag ctg tgc atg gat ttc tac cac gat ttg ccg     1137
Lys Gly Leu Asn Cys Glu Leu Cys Met Asp Phe Tyr His Asp Leu Pro
305                 310                 315                 320 tgg aga cct gct gaa ggc cgg aac agc aac gcc tgc aaa aaa tgt aac     1185
Trp Arg Pro Ala Glu Gly Arg Asn Ser Asn Ala Cys Lys Lys Cys Asn
                325                 330                 335 tgc aat gaa cat tcc agc tcg tgt cac ttt gac atg gca gtc ttc ctg     1233
Cys Asn Glu His Ser Ser Ser Cys His Phe Asp Met Ala Val Phe Leu
            340                 345                 350 gct act ggc aac gtc agc ggg gga gtg tgt gat aac tgt cag cac aac     1281
Ala Thr Gly Asn Val Ser Gly Gly Val Cys Asp Asn Cys Gln His Asn
        355                 360                 365 acc atg ggg cgc aac tgt gaa cag tgc aaa ccg ttc tac ttc cag cac     1329
Thr Met Gly Arg Asn Cys Glu Gln Cys Lys Pro Phe Tyr Phe Gln His
    370                 375                 380 cct gag agg gac atc cgg gac ccc aat ctc tgt gaa cca tgt acc tgt     1377
Pro Glu Arg Asp Ile Arg Asp Pro Asn Leu Cys Glu Pro Cys Thr Cys
385                 390                 395                 400 gac cca gct ggt tct gag aat ggc ggg atc tgt gat ggg tac act gat     1425
Asp Pro Ala Gly Ser Glu Asn Gly Gly Ile Cys Asp Gly Tyr Thr Asp
                405                 410                 415 ttt tct gtg ggt ctc att gct ggt cag tgt cgg tgc aaa ttg cac gtg     1473
Phe Ser Val Gly Leu Ile Ala Gly Gln Cys Arg Cys Lys Leu His Val
            420                 425                 430 gag gga gag cgc tgt gat gtt tgt aaa gaa ggc ttc tac gac tta agt     1521
Glu Gly Glu Arg Cys Asp Val Cys Lys Glu Gly Phe Tyr Asp Leu Ser
        435                 440                 445 gct gaa gac ccg tat ggt tgt aaa tca tgt gct tgc aat cct ctg gga     1569
Ala Glu Asp Pro Tyr Gly Cys Lys Ser Cys Ala Cys Asn Pro Leu Gly
    450                 455                 460
```

```
aca att cct ggt ggg aat cct tgt gat tct gag act ggc tac tgc tac    1617
Thr Ile Pro Gly Gly Asn Pro Cys Asp Ser Glu Thr Gly Tyr Cys Tyr
465             470                 475                 480 tgt aag cgc ctg gtg aca gga cag cgc tgt gac cag tgc ctg ccg cag    1665
Cys Lys Arg Leu Val Thr Gly Gln Arg Cys Asp Gln Cys Leu Pro Gln
                485                 490                 495 cac tgg ggt tta agc aat gat ttg gat ggg tgt cga cct tgt gac tgt    1713
His Trp Gly Leu Ser Asn Asp Leu Asp Gly Cys Arg Pro Cys Asp Cys
            500                 505                 510 gac ctt gga ggg gcg ctg aac aat agc tgc tcc gag gac tcc ggc cag    1761
Asp Leu Gly Gly Ala Leu Asn Asn Ser Cys Ser Glu Asp Ser Gly Gln
        515                 520                 525 tgc tcc tgc ctg ccc cac atg att ggg cgg cag tgt aac gag gtg gag    1809
Cys Ser Cys Leu Pro His Met Ile Gly Arg Gln Cys Asn Glu Val Glu
    530                 535                 540 tcc ggt tac tac ttc acc acc ctg gac cac tac atc tac gaa gcc gag    1857
Ser Gly Tyr Tyr Phe Thr Thr Leu Asp His Tyr Ile Tyr Glu Ala Glu
545                 550                 555                 560 gaa gcc aat ctg ggg cct gga gtc gtt gtg gtg gaa agg cag tac att    1905
Glu Ala Asn Leu Gly Pro Gly Val Val Val Val Glu Arg Gln Tyr Ile
                565                 570                 575 cag gac cgc att cct tcc tgg aca gga cct ggc ttc gtc cgg gtg cct    1953
Gln Asp Arg Ile Pro Ser Trp Thr Gly Pro Gly Phe Val Arg Val Pro
            580                 585                 590 gaa ggg gct tat ttg gag ttt ttc att gac aac ata cca tat tcc atg    2001
Glu Gly Ala Tyr Leu Glu Phe Phe Ile Asp Asn Ile Pro Tyr Ser Met
        595                 600                 605 gag tat gaa atc ctg att cgc tat gag cca cag ctg ccg gac cac tgg    2049
Glu Tyr Glu Ile Leu Ile Arg Tyr Glu Pro Gln Leu Pro Asp His Trp
    610                 615                 620 gag aaa gct gtc atc act gta cag cgg ccg ggg aag att cca gcc agc    2097
Glu Lys Ala Val Ile Thr Val Gln Arg Pro Gly Lys Ile Pro Ala Ser
625                 630                 635                 640 agc cga tgt ggt aac acc gtt ccc gat gat gac aac cag gtg gtg tcc    2145
Ser Arg Cys Gly Asn Thr Val Pro Asp Asp Asp Asn Gln Val Val Ser
                645                 650                 655 ttg tca ccg ggc tca aga tac gtt gtc ctc cct cgc ccc gtg tgc ttt    2193
Leu Ser Pro Gly Ser Arg Tyr Val Val Leu Pro Arg Pro Val Cys Phe
            660                 665                 670 gag aag gga atg aac tac acg gtg agg ttg gag ctg ccc cag tat acg    2241
Glu Lys Gly Met Asn Tyr Thr Val Arg Leu Glu Leu Pro Gln Tyr Thr
        675                 680                 685 gca tcg ggc agt gac gtg gag agc cct tac acg ttc atc gac tcg ctt    2289
Ala Ser Gly Ser Asp Val Glu Ser Pro Tyr Thr Phe Ile Asp Ser Leu
    690                 695                 700 gtt ctc atg ccc tac tgt aaa tcg ctg gac atc ttc act gtt ggc ggc    2337
Val Leu Met Pro Tyr Cys Lys Ser Leu Asp Ile Phe Thr Val Gly Gly
705                 710                 715                 720 tca ggc gat ggg gag gtc acc aat agt gcc tgg gaa acc ttc cag cgc    2385
Ser Gly Asp Gly Glu Val Thr Asn Ser Ala Trp Glu Thr Phe Gln Arg
                725                 730                 735 tac agg tgt ctg gag aac agc agg agt gtg gta aaa aca ccc atg aca    2433
Tyr Arg Cys Leu Glu Asn Ser Arg Ser Val Val Lys Thr Pro Met Thr
            740                 745                 750 gat gtc tgc aga aac att atc ttc agc att tct gcc ttg att cac cag    2481
Asp Val Cys Arg Asn Ile Ile Phe Ser Ile Ser Ala Leu Ile His Gln
        755                 760                 765 acg ggc ctt gct tgt gaa tgt gac ccc cag gga tct ctg agt tct gtg    2529
Thr Gly Leu Ala Cys Glu Cys Asp Pro Gln Gly Ser Leu Ser Ser Val
    770                 775                 780
```

-continued

| | |
|---|---|
| tgt gac ccc aat ggt ggc cag tgc cag tgc cgt cct aat gtg gtt gga<br>Cys Asp Pro Asn Gly Gly Gln Cys Gln Cys Arg Pro Asn Val Val Gly<br>785                790                795                800 | 2577 |
| aga acc tgc aac agg tgt gcc ccg ggc acc ttt ggc ttt ggc ccc aac<br>Arg Thr Cys Asn Arg Cys Ala Pro Gly Thr Phe Gly Phe Gly Pro Asn<br>                805                810                815 | 2625 |
| gga tgc aaa cct tgt gac tgc cat ctg caa ggg tct gcc agt gcc ttc<br>Gly Cys Lys Pro Cys Asp Cys His Leu Gln Gly Ser Ala Ser Ala Phe<br>        820                825                830 | 2673 |
| tgc gat gcg atc act ggc cag tgc cac tgt ttc cag ggc atc tat gct<br>Cys Asp Ala Ile Thr Gly Gln Cys His Cys Phe Gln Gly Ile Tyr Ala<br>835                840                845 | 2721 |
| cgg cag tgt gac cga tgt ctc cct ggg tat tgg ggc ttt ccc agc tgc<br>Arg Gln Cys Asp Arg Cys Leu Pro Gly Tyr Trp Gly Phe Pro Ser Cys<br>850                855                860 | 2769 |
| cag ccc tgc cag tgt aat ggt cat gct cta gac tgt gac aca gtg aca<br>Gln Pro Cys Gln Cys Asn Gly His Ala Leu Asp Cys Asp Thr Val Thr<br>865                870                875                880 | 2817 |
| ggg gag tgt ctg agc tgt cag gac tac acc acg ggc cac aac tgc gaa<br>Gly Glu Cys Leu Ser Cys Gln Asp Tyr Thr Thr Gly His Asn Cys Glu<br>                885                890                895 | 2865 |
| agg tgc ctg gct ggc tac tac ggt gat ccc atc att ggg tca gga gac<br>Arg Cys Leu Ala Gly Tyr Tyr Gly Asp Pro Ile Ile Gly Ser Gly Asp<br>        900                905                910 | 2913 |
| cac tgt cgc cct tgc cct tgt cct gat ggt cct gac agt gga cga cag<br>His Cys Arg Pro Cys Pro Cys Pro Asp Gly Pro Asp Ser Gly Arg Gln<br>915                920                925 | 2961 |
| ttt gcc agg agc tgt tat caa gac ccc gtc act ctc cag ctt gcg tgt<br>Phe Ala Arg Ser Cys Tyr Gln Asp Pro Val Thr Leu Gln Leu Ala Cys<br>        930                935                940 | 3009 |
| gtt tgt gat cct ggg tac att ggc tcc aga tgt gat gac tgt gcc tct<br>Val Cys Asp Pro Gly Tyr Ile Gly Ser Arg Cys Asp Asp Cys Ala Ser<br>945                950                955                960 | 3057 |
| gga ttt ttt ggc aat ccc tca gac ttt ggg ggt tca tgt caa ccg tgt<br>Gly Phe Phe Gly Asn Pro Ser Asp Phe Gly Gly Ser Cys Gln Pro Cys<br>                965                970                975 | 3105 |
| cag tgc cac cac aac att gac act acc gat cca gaa gcc tgt gac aag<br>Gln Cys His His Asn Ile Asp Thr Thr Asp Pro Glu Ala Cys Asp Lys<br>        980                985                990 | 3153 |
| gac acg gga cga tgc ctc aag tgc ctg tac cac acg gaa ggg gac cat<br>Asp Thr Gly Arg Cys Leu Lys Cys Leu Tyr His Thr Glu Gly Asp His<br>995                1000              1005 | 3201 |
| tgc cag ctc tgc cag tat ggg tac tac ggc gat gct ctt cgg caa gac<br>Cys Gln Leu Cys Gln Tyr Gly Tyr Tyr Gly Asp Ala Leu Arg Gln Asp<br>    1010                1015              1020 | 3249 |
| tgt aga aag tgt gtc tgc aat tac ctg ggc acg gtg aag gaa cat tgt<br>Cys Arg Lys Cys Val Cys Asn Tyr Leu Gly Thr Val Lys Glu His Cys<br>1025              1030              1035              1040 | 3297 |
| aat ggc tct gac tgc cac tgt gac aaa gcc act ggt cag tgc tcg tgc<br>Asn Gly Ser Asp Cys His Cys Asp Lys Ala Thr Gly Gln Cys Ser Cys<br>            1045              1050              1055 | 3345 |
| ctt ccc aat gtg atc ggg cag aac tgt gac cgg tgt gcg ccc aac acc<br>Leu Pro Asn Val Ile Gly Gln Asn Cys Asp Arg Cys Ala Pro Asn Thr<br>            1060              1065              1070 | 3393 |
| tgg cag ctg gct agc ggg act ggc tgc ggg ccc tgc aat tgc aat gct<br>Trp Gln Leu Ala Ser Gly Thr Gly Cys Gly Pro Cys Asn Cys Asn Ala<br>1075              1080 | 3441 |
| gcg cat tcc ttt ggg cca tcc tgc aac gag ttc aca ggg cag tgc cag<br>Ala His Ser Phe Gly Pro Ser Cys Asn Glu Phe Thr Gly Gln Cys Gln | 3489 |

```
                                                                     -continued
     1090               1095              1100
tgc atg ccg ggc ttt gga ggc cga acc tgc agc gag tgc cag gag ctc     3537
Cys Met Pro Gly Phe Gly Gly Arg Thr Cys Ser Glu Cys Gln Glu Leu
1105              1110              1115              1120 ttc tgg gga gac cct gat gtg gaa tgc cga gcc tgt gac tgt gat ccc     3585
Phe Trp Gly Asp Pro Asp Val Glu Cys Arg Ala Cys Asp Cys Asp Pro
              1125              1130              1135 agg ggc att gag aca cct cag tgt gac cag tcc acg ggc cag tgt gtc     3633
Arg Gly Ile Glu Thr Pro Gln Cys Asp Gln Ser Thr Gly Gln Cys Val
         1140              1145              1150 tgt gtg gag ggt gta gag ggt cct cgc tgc gac aag tgc acc aga ggt     3681
Cys Val Glu Gly Val Glu Gly Pro Arg Cys Asp Lys Cys Thr Arg Gly
     1155              1160              1165 tac tcg ggg gtc ttt cct gac tgc aca ccc tgc cac cag tgc ttt gct     3729
Tyr Ser Gly Val Phe Pro Asp Cys Thr Pro Cys His Gln Cys Phe Ala
 1170              1175              1180 ctc tgg gat gct atc att ggt gag ctg acc aac agg acc cac aaa ttc     3777
Leu Trp Asp Ala Ile Ile Gly Glu Leu Thr Asn Arg Thr His Lys Phe
1185              1190              1195              1200 ctg gag aaa gcc aag gct ctg aaa atc agt ggt gtg att ggt ccc tac     3825
Leu Glu Lys Ala Lys Ala Leu Lys Ile Ser Gly Val Ile Gly Pro Tyr
              1205              1210              1215 cga gag acc gtg gac tct gta gag aag aaa gtc aat gag ata aaa gac     3873
Arg Glu Thr Val Asp Ser Val Glu Lys Lys Val Asn Glu Ile Lys Asp
         1220              1225              1230 atc ctg gcc cag agc cca gca gcg gaa cca ctg aaa aac att ggc att     3921
Ile Leu Ala Gln Ser Pro Ala Ala Glu Pro Leu Lys Asn Ile Gly Ile
     1235              1240              1245 ctc ttc gag gag gca gag aaa cta acc aaa gat gtc aca gaa aag atg     3969
Leu Phe Glu Glu Ala Glu Lys Leu Thr Lys Asp Val Thr Glu Lys Met
 1250              1255              1260 gcg cag gta gaa gtg aaa tta act gat aca gct tca cag agt aac agc     4017
Ala Gln Val Glu Val Lys Leu Thr Asp Thr Ala Ser Gln Ser Asn Ser
1265              1270              1275              1280 aca gct gga gag ctc ggc gca ctg cag gca gaa gca gag agc ctt gac     4065
Thr Ala Gly Glu Leu Gly Ala Leu Gln Ala Glu Ala Glu Ser Leu Asp
              1285              1290              1295 aag acc gtg aag gag ctg gca gaa cag ctg gag ttt atc aaa aac tcc     4113
Lys Thr Val Lys Glu Leu Ala Glu Gln Leu Glu Phe Ile Lys Asn Ser
         1300              1305              1310 gat att cag ggc gcc ttg gat agc atc acc aag tat ttc cag atg tct     4161
Asp Ile Gln Gly Ala Leu Asp Ser Ile Thr Lys Tyr Phe Gln Met Ser
     1315              1320              1325 ctt gag gca gag aag cgg gtg aat gcc tcc acc aca gac ccc aac agc     4209
Leu Glu Ala Glu Lys Arg Val Asn Ala Ser Thr Thr Asp Pro Asn Ser
 1330              1335              1340 act gtg gag cag tct gcc ctc acg cga gac aga gta gaa gat ctg atg     4257
Thr Val Glu Gln Ser Ala Leu Thr Arg Asp Arg Val Glu Asp Leu Met
1345              1350              1355              1360 ttg gag cga gag tct ccg ttc aag gag cag cag gag gaa cag gca cgc     4305
Leu Glu Arg Glu Ser Pro Phe Lys Glu Gln Gln Glu Glu Gln Ala Arg
              1365              1370              1375 ctc ctg gac gaa ctg gcc ggc aaa ctg caa agt ctc gac ctg tcg gct     4353
Leu Leu Asp Glu Leu Ala Gly Lys Leu Gln Ser Leu Asp Leu Ser Ala
         1380              1385              1390 gct gca cag atg acc tgt gga aca cct cca ggg gct gac tgt tct gaa     4401
Ala Ala Gln Met Thr Cys Gly Thr Pro Pro Gly Ala Asp Cys Ser Glu
     1395              1400              1405 agt gaa tgt ggt ggc ccc aac tgc aga act gac gaa gga gag aag aag     4449
```

-continued

```
Ser Glu Cys Gly Gly Pro Asn Cys Arg Thr Asp Glu Gly Glu Lys Lys
    1410                1415                1420 tgt ggg ggg cct ggc tgt ggt ggt ctg gtc act gtg gcc cac agt gct      4497
Cys Gly Gly Pro Gly Cys Gly Gly Leu Val Thr Val Ala His Ser Ala
1425                1430                1435                1440 tgg cag aaa gcc atg gat ttt gac cgt gat gtc ctg agt gcc ctg gct      4545
Trp Gln Lys Ala Met Asp Phe Asp Arg Asp Val Leu Ser Ala Leu Ala
                1445                1450                1455 gaa gtc gaa cag ctc tcc aag atg gtc tct gaa gca aaa gtg aga gca      4593
Glu Val Glu Gln Leu Ser Lys Met Val Ser Glu Ala Lys Val Arg Ala
            1460                1465                1470 gat gag gcg aag cag aat gcg cag gat gtc ctg tta aaa aca aat gct      4641
Asp Glu Ala Lys Gln Asn Ala Gln Asp Val Leu Leu Lys Thr Asn Ala
        1475                1480                1485 acc aaa gaa aaa gtg gac aag agc aac gag gac ctg cgg aac ctc atc      4689
Thr Lys Glu Lys Val Asp Lys Ser Asn Glu Asp Leu Arg Asn Leu Ile
    1490                1495                1500 aag cag atc aga aac ttc ctg act gag gat agt gct gat cta gac agt      4737
Lys Gln Ile Arg Asn Phe Leu Thr Glu Asp Ser Ala Asp Leu Asp Ser
1505                1510                1515                1520 att gaa gca gtt gct aat gaa gta ctg aaa agt gga aat gct agc acg      4785
Ile Glu Ala Val Ala Asn Glu Val Leu Lys Ser Gly Asn Ala Ser Thr
                1525                1530                1535 cca cag cag tta cag aac cta aca gaa gac att cgg gag cga gtt gaa      4833
Pro Gln Gln Leu Gln Asn Leu Thr Glu Asp Ile Arg Glu Arg Val Glu
            1540                1545                1550 acc ctc tct caa gta gag gtt att ttg cag cag agt gca gct gac att      4881
Thr Leu Ser Gln Val Glu Val Ile Leu Gln Gln Ser Ala Ala Asp Ile
        1555                1560                1565 gcc aga gct gag ctg ttg ctt gag gaa gct aag aga gca agc aaa agt      4929
Ala Arg Ala Glu Leu Leu Leu Glu Glu Ala Lys Arg Ala Ser Lys Ser
    1570                1575                1580 gca aca gat gtt aaa gtc act gca gac atg gtg aag gaa gca tta gaa      4977
Ala Thr Asp Val Lys Val Thr Ala Asp Met Val Lys Glu Ala Leu Glu
1585                1590                1595                1600 gaa gca gaa aag gcc cag gtt gca gca gag aag gcg att aaa caa gct      5025
Glu Ala Glu Lys Ala Gln Val Ala Ala Glu Lys Ala Ile Lys Gln Ala
                1605                1610                1615 gat gag gat atc caa gga acc caa aac ctg cta aca tcg att gaa tct      5073
Asp Glu Asp Ile Gln Gly Thr Gln Asn Leu Leu Thr Ser Ile Glu Ser
            1620                1625                1630 gaa acg gca gct tct gag gaa acc ctg acc aac gcc tcc cag cgc atc      5121
Glu Thr Ala Ala Ser Glu Glu Thr Leu Thr Asn Ala Ser Gln Arg Ile
        1635                1640                1645 agc aag ctt gag agg aac gtg gaa gag ctt aag cgt aaa gct gcc cag      5169
Ser Lys Leu Glu Arg Asn Val Glu Glu Leu Lys Arg Lys Ala Ala Gln
    1650                1655                1660 aac tct ggg gag gca gaa tat atc gaa aaa gta gta tat tct gta aaa      5217
Asn Ser Gly Glu Ala Glu Tyr Ile Glu Lys Val Val Tyr Ser Val Lys
1665                1670                1675                1680 cag aat gca gac gat gtt aaa aag act cta gat ggc gaa ctt gat gaa      5265
Gln Asn Ala Asp Asp Val Lys Lys Thr Leu Asp Gly Glu Leu Asp Glu
                1685                1690                1695 aag tat aag aag gta gaa agt tta att gcc caa aaa act gaa gag tca      5313
Lys Tyr Lys Lys Val Glu Ser Leu Ile Ala Gln Lys Thr Glu Glu Ser
            1700                1705                1710 gca gat gcc agg agg aaa gct gag ctg cta caa aat gaa gca aaa aca      5361
Ala Asp Ala Arg Arg Lys Ala Glu Leu Leu Gln Asn Glu Ala Lys Thr
        1715                1720                1725
```

-continued

```
ctc ttg gct caa gct aac agc aag ctc cag ctg ttg gaa gac tta gaa    5409
Leu Leu Ala Gln Ala Asn Ser Lys Leu Gln Leu Leu Glu Asp Leu Glu
    1730                1735                1740 aga aaa tat gag gac aat caa aaa tac tta gaa gat aaa gct caa gaa    5457
Arg Lys Tyr Glu Asp Asn Gln Lys Tyr Leu Glu Asp Lys Ala Gln Glu
1745                1750                1755                1760 ttg gtg cga ctg gaa gga gag gtt cgc tcc ctc ctt aag gac ata agt    5505
Leu Val Arg Leu Glu Gly Glu Val Arg Ser Leu Leu Lys Asp Ile Ser
            1765                1770                1775 gag aaa gtt gcg gtt tac agc acc tgc tta taacaggaag gggctgtaga      5555
Glu Lys Val Ala Val Tyr Ser Thr Cys Leu
        1780                1785 gggctcggt gaccaaggta aaccacacgc gcaaaccgag gcagtcatct acaaataacc   5615
catcatctat ttaatgtttt taaccaccta cttttgtatg gagttaaata aaagacattg  5675
gttttgtata aaca                                                    5689
```

<210> SEQ ID NO 10
<211> LENGTH: 1786
<212> TYPE: PRT
<213> ORGANISM: Mus musculus

<400> SEQUENCE: 10

```
Met Gly Leu Leu Gln Val Phe Ala Phe Gly Val Leu Ala Leu Trp Gly
 1                5                  10                 15

Thr Arg Val Cys Ala Gln Glu Pro Glu Phe Ser Tyr Gly Cys Ala Glu
                20                 25                  30

Gly Ser Cys Tyr Pro Ala Thr Gly Asp Leu Leu Ile Gly Arg Ala Gln
            35                  40                  45

Lys Leu Ser Val Thr Ser Thr Cys Gly Leu His Lys Pro Glu Pro Tyr
        50                  55                  60

Cys Ile Val Ser His Leu Gln Glu Asp Lys Lys Cys Phe Ile Cys Asp
    65                  70                  75                  80

Ser Arg Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
               100                 105                 110

Gln Ser Glu Asn Gly Val Glu Asn Val Thr Ile Gln Leu Asp Leu Glu
           115                 120                 125

Ala Glu Phe His Phe Thr His Leu Ile Met Thr Phe Lys Thr Phe Arg
       130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ser Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
```

-continued

```
                260                 265                 270
Cys Tyr Gly His Ala Ser Glu Cys Ala Pro Val Asp Gly Val Asn Glu
            275                 280                 285
Glu Val Glu Gly Met Val His Gly His Cys Met Cys Arg His Asn Thr
290                 295                 300
Lys Gly Leu Asn Cys Glu Leu Cys Met Asp Phe Tyr His Asp Leu Pro
305                 310                 315                 320
Trp Arg Pro Ala Glu Gly Arg Asn Ser Asn Ala Cys Lys Lys Cys Asn
                325                 330                 335
Cys Asn Glu His Ser Ser Cys His Phe Asp Met Ala Val Phe Leu
            340                 345                 350
Ala Thr Gly Asn Val Ser Gly Gly Val Cys Asp Asn Cys Gln His Asn
            355                 360                 365
Thr Met Gly Arg Asn Cys Glu Gln Cys Lys Pro Phe Tyr Phe Gln His
            370                 375                 380
Pro Glu Arg Asp Ile Arg Asp Pro Asn Leu Cys Glu Pro Cys Thr Cys
385                 390                 395                 400
Asp Pro Ala Gly Ser Glu Asn Gly Gly Ile Cys Asp Gly Tyr Thr Asp
                405                 410                 415
Phe Ser Val Gly Leu Ile Ala Gly Gln Cys Arg Cys Lys Leu His Val
            420                 425                 430
Glu Gly Glu Arg Cys Asp Val Cys Lys Glu Gly Phe Tyr Asp Leu Ser
            435                 440                 445
Ala Glu Asp Pro Tyr Gly Cys Lys Ser Cys Ala Cys Asn Pro Leu Gly
            450                 455                 460
Thr Ile Pro Gly Gly Asn Pro Cys Asp Ser Glu Thr Gly Tyr Cys Tyr
465                 470                 475                 480
Cys Lys Arg Leu Val Thr Gly Gln Arg Cys Asp Gln Cys Leu Pro Gln
                485                 490                 495
His Trp Gly Leu Ser Asn Asp Leu Asp Gly Cys Arg Pro Cys Asp Cys
            500                 505                 510
Asp Leu Gly Gly Ala Leu Asn Asn Ser Cys Ser Glu Asp Ser Gly Gln
            515                 520                 525
Cys Ser Cys Leu Pro His Met Ile Gly Arg Gln Cys Asn Glu Val Glu
            530                 535                 540
Ser Gly Tyr Tyr Phe Thr Thr Leu Asp His Tyr Ile Tyr Glu Ala Glu
545                 550                 555                 560
Glu Ala Asn Leu Gly Pro Gly Val Val Val Glu Arg Gln Tyr Ile
                565                 570                 575
Gln Asp Arg Ile Pro Ser Trp Thr Gly Pro Gly Phe Val Arg Val Pro
            580                 585                 590
Glu Gly Ala Tyr Leu Glu Phe Phe Ile Asp Asn Ile Pro Tyr Ser Met
            595                 600                 605
Glu Tyr Glu Ile Leu Ile Arg Tyr Glu Pro Gln Leu Pro Asp His Trp
            610                 615                 620
Glu Lys Ala Val Ile Thr Val Gln Arg Pro Gly Lys Ile Pro Ala Ser
625                 630                 635                 640
Ser Arg Cys Gly Asn Thr Val Pro Asp Asp Asn Gln Val Ser
                645                 650                 655
Leu Ser Pro Gly Ser Arg Tyr Val Val Leu Pro Arg Pro Val Cys Phe
            660                 665                 670
Glu Lys Gly Met Asn Tyr Thr Val Arg Leu Glu Leu Pro Gln Tyr Thr
            675                 680                 685
```

-continued

```
Ala Ser Gly Ser Asp Val Glu Ser Pro Tyr Thr Phe Ile Asp Ser Leu
    690                 695                 700
Val Leu Met Pro Tyr Cys Lys Ser Leu Asp Ile Phe Thr Val Gly Gly
705                 710                 715                 720
Ser Gly Asp Gly Glu Val Thr Asn Ser Ala Trp Glu Thr Phe Gln Arg
                725                 730                 735
Tyr Arg Cys Leu Glu Asn Ser Arg Ser Val Val Lys Thr Pro Met Thr
            740                 745                 750
Asp Val Cys Arg Asn Ile Ile Phe Ser Ile Ser Ala Leu Ile His Gln
        755                 760                 765
Thr Gly Leu Ala Cys Glu Cys Asp Pro Gln Gly Ser Leu Ser Ser Val
    770                 775                 780
Cys Asp Pro Asn Gly Gln Cys Gln Cys Arg Pro Asn Val Val Gly
785                 790                 795                 800
Arg Thr Cys Asn Arg Cys Ala Pro Gly Thr Phe Gly Phe Gly Pro Asn
                805                 810                 815
Gly Cys Lys Pro Cys Asp Cys His Leu Gln Gly Ser Ala Ser Ala Phe
            820                 825                 830
Cys Asp Ala Ile Thr Gly Gln Cys His Cys Phe Gln Gly Ile Tyr Ala
        835                 840                 845
Arg Gln Cys Asp Arg Cys Leu Pro Gly Tyr Trp Gly Phe Pro Ser Cys
    850                 855                 860
Gln Pro Cys Gln Cys Asn Gly His Ala Leu Asp Cys Asp Thr Val Thr
865                 870                 875                 880
Gly Glu Cys Leu Ser Cys Gln Asp Tyr Thr Thr Gly His Asn Cys Glu
                885                 890                 895
Arg Cys Leu Ala Gly Tyr Tyr Gly Asp Pro Ile Ile Gly Ser Gly Asp
            900                 905                 910
His Cys Arg Pro Cys Pro Cys Pro Asp Gly Pro Asp Ser Gly Arg Gln
        915                 920                 925
Phe Ala Arg Ser Cys Tyr Gln Asp Pro Val Thr Leu Gln Leu Ala Cys
    930                 935                 940
Val Cys Asp Pro Gly Tyr Ile Gly Ser Arg Cys Asp Asp Cys Ala Ser
945                 950                 955                 960
Gly Phe Phe Gly Asn Pro Ser Asp Phe Gly Gly Ser Cys Gln Pro Cys
                965                 970                 975
Gln Cys His His Asn Ile Asp Thr Thr Asp Pro Glu Ala Cys Asp Lys
            980                 985                 990
Asp Thr Gly Arg Cys Leu Lys Cys Leu Tyr His Thr Glu Gly Asp His
        995                1000                1005
Cys Gln Leu Cys Gln Tyr Gly Tyr Tyr Gly Asp Ala Leu Arg Gln Asp
   1010                1015                1020
Cys Arg Lys Cys Val Cys Asn Tyr Leu Gly Thr Val Lys Glu His Cys
1025                1030                1035                1040
Asn Gly Ser Asp Cys His Cys Asp Lys Ala Thr Gly Gln Cys Ser Cys
                1045                1050                1055
Leu Pro Asn Val Ile Gly Gln Asn Cys Asp Arg Cys Ala Pro Asn Thr
            1060                1065                1070
Trp Gln Leu Ala Ser Gly Thr Gly Cys Gly Pro Cys Asn Cys Asn Ala
        1075                1080                1085
Ala His Ser Phe Gly Pro Ser Cys Asn Glu Phe Thr Gly Gln Cys Gln
    1090                1095                1100
```

-continued

```
Cys Met Pro Gly Phe Gly Gly Arg Thr Cys Ser Glu Cys Gln Glu Leu
1105                1110                1115                1120

Phe Trp Gly Asp Pro Asp Val Glu Cys Arg Ala Cys Asp Cys Asp Pro
            1125                1130                1135

Arg Gly Ile Glu Thr Pro Gln Cys Asp Gln Ser Thr Gly Gln Cys Val
        1140                1145                1150

Cys Val Glu Gly Val Glu Gly Pro Arg Cys Asp Lys Cys Thr Arg Gly
1155                1160                1165

Tyr Ser Gly Val Phe Pro Asp Cys Thr Pro Cys His Gln Cys Phe Ala
    1170                1175                1180

Leu Trp Asp Ala Ile Ile Gly Glu Leu Thr Asn Arg Thr His Lys Phe
1185                1190                1195                1200

Leu Glu Lys Ala Lys Ala Leu Lys Ile Ser Gly Val Ile Gly Pro Tyr
                1205                1210                1215

Arg Glu Thr Val Asp Ser Val Glu Lys Lys Val Asn Glu Ile Lys Asp
            1220                1225                1230

Ile Leu Ala Gln Ser Pro Ala Ala Glu Pro Leu Lys Asn Ile Gly Ile
        1235                1240                1245

Leu Phe Glu Glu Ala Glu Lys Leu Thr Lys Asp Val Thr Glu Lys Met
    1250                1255                1260

Ala Gln Val Glu Val Lys Leu Thr Asp Thr Ala Ser Gln Ser Asn Ser
1265                1270                1275                1280

Thr Ala Gly Glu Leu Gly Ala Leu Gln Ala Glu Ala Glu Ser Leu Asp
                1285                1290                1295

Lys Thr Val Lys Glu Leu Ala Glu Gln Leu Glu Phe Ile Lys Asn Ser
            1300                1305                1310

Asp Ile Gln Gly Ala Leu Asp Ser Ile Thr Lys Tyr Phe Gln Met Ser
        1315                1320                1325

Leu Glu Ala Glu Lys Arg Val Asn Ala Ser Thr Thr Asp Pro Asn Ser
    1330                1335                1340

Thr Val Glu Gln Ser Ala Leu Thr Arg Asp Arg Val Glu Asp Leu Met
1345                1350                1355                1360

Leu Glu Arg Glu Ser Pro Phe Lys Glu Gln Gln Glu Glu Gln Ala Arg
                1365                1370                1375

Leu Leu Asp Glu Leu Ala Gly Lys Leu Gln Ser Leu Asp Leu Ser Ala
            1380                1385                1390

Ala Ala Gln Met Thr Cys Gly Thr Pro Pro Gly Ala Asp Cys Ser Glu
        1395                1400                1405

Ser Glu Cys Gly Gly Pro Asn Cys Arg Thr Asp Glu Gly Glu Lys Lys
    1410                1415                1420

Cys Gly Gly Pro Gly Cys Gly Gly Leu Val Thr Val Ala His Ser Ala
1425                1430                1435                1440

Trp Gln Lys Ala Met Asp Phe Asp Arg Asp Val Leu Ser Ala Leu Ala
                1445                1450                1455

Glu Val Glu Gln Leu Ser Lys Met Val Ser Glu Ala Lys Val Arg Ala
            1460                1465                1470

Asp Glu Ala Lys Gln Asn Ala Gln Asp Val Leu Leu Lys Thr Asn Ala
        1475                1480                1485

Thr Lys Glu Lys Val Asp Lys Ser Asn Glu Asp Leu Arg Asn Leu Ile
    1490                1495                1500

Lys Gln Ile Arg Asn Phe Leu Thr Glu Asp Ser Ala Asp Leu Asp Ser
1505                1510                1515                1520

Ile Glu Ala Val Ala Asn Glu Val Leu Lys Ser Gly Asn Ala Ser Thr
```

```
                       1525                1530                 1535
Pro Gln Gln Leu Gln Asn Leu Thr Glu Asp Ile Arg Glu Arg Val Glu
        1540                1545                1550

Thr Leu Ser Gln Val Glu Val Ile Leu Gln Gln Ser Ala Ala Asp Ile
    1555                1560                1565

Ala Arg Ala Glu Leu Leu Glu Glu Ala Lys Arg Ala Ser Lys Ser
    1570                1575                1580

Ala Thr Asp Val Lys Val Thr Ala Asp Met Val Lys Glu Ala Leu Glu
1585                1590                1595                1600

Glu Ala Glu Lys Ala Gln Val Ala Ala Glu Lys Ala Ile Lys Gln Ala
        1605                1610                1615

Asp Glu Asp Ile Gln Gly Thr Gln Asn Leu Leu Thr Ser Ile Glu Ser
        1620                1625                1630

Glu Thr Ala Ala Ser Glu Glu Thr Leu Thr Asn Ala Ser Gln Arg Ile
        1635                1640                1645

Ser Lys Leu Glu Arg Asn Val Glu Glu Leu Lys Arg Lys Ala Ala Gln
        1650                1655                1660

Asn Ser Gly Glu Ala Glu Tyr Ile Glu Lys Val Val Tyr Ser Val Lys
1665                1670                1675                1680

Gln Asn Ala Asp Asp Val Lys Lys Thr Leu Asp Gly Glu Leu Asp Glu
        1685                1690                1695

Lys Tyr Lys Lys Val Glu Ser Leu Ile Ala Gln Lys Thr Glu Glu Ser
        1700                1705                1710

Ala Asp Ala Arg Arg Lys Ala Glu Leu Leu Gln Asn Glu Ala Lys Thr
        1715                1720                1725

Leu Leu Ala Gln Ala Asn Ser Lys Leu Gln Leu Leu Glu Asp Leu Glu
        1730                1735                1740

Arg Lys Tyr Glu Asp Asn Gln Lys Tyr Leu Glu Asp Lys Ala Gln Glu
1745                1750                1755                1760

Leu Val Arg Leu Glu Gly Glu Val Arg Ser Leu Leu Lys Asp Ile Ser
        1765                1770                1775

Glu Lys Val Ala Val Tyr Ser Thr Cys Leu
        1780                1785

<210> SEQ ID NO 11
<211> LENGTH: 5329
<212> TYPE: DNA
<213> ORGANISM: Mus musculus
<220> FEATURE:
<221> NAME/KEY: CDS
<222> LOCATION: (1)..(5175)

<400> SEQUENCE: 11 gag ccc tac tgt att gtt agc cac ctg cag gag gac aag aaa tgc ttc      48
Glu Pro Tyr Cys Ile Val Ser His Leu Gln Glu Asp Lys Lys Cys Phe
  1               5                  10                  15 ata tgt gac tcc cga gac cct tat cac gag acc ctc aac ccc gac agc      96
Ile Cys Asp Ser Arg Asp Pro Tyr His Glu Thr Leu Asn Pro Asp Ser
             20                  25                  30 cat ctc att gag aac gtg gtc acc aca ttt gct cca aac cgc ctt aag     144
His Leu Ile Glu Asn Val Val Thr Thr Phe Ala Pro Asn Arg Leu Lys
         35                  40                  45 atc tgg tgg caa tcg gaa aat ggt gtg gag aac gtg acc atc caa ctg     192
Ile Trp Trp Gln Ser Glu Asn Gly Val Glu Asn Val Thr Ile Gln Leu
     50                  55                  60 gac ctg gaa gca gaa ttc cat ttc act cat ctc atc atg acc ttc aag     240
Asp Leu Glu Ala Glu Phe His Phe Thr His Leu Ile Met Thr Phe Lys
 65                  70                  75                  80
```

```
                      65                   70                   75                   80
aca ttc cgc cca gcc gcc atg ctg atc gag cgg tct tct gac ttt ggg       288
Thr Phe Arg Pro Ala Ala Met Leu Ile Glu Arg Ser Ser Asp Phe Gly
                85                   90                   95 aag act tgg ggc gtg tac aga tac ttc gcc tac gac tgt gag agc tcg       336
Lys Thr Trp Gly Val Tyr Arg Tyr Phe Ala Tyr Asp Cys Glu Ser Ser
            100                  105                  110 ttc cca ggc att tca act gga ccc atg aag aaa gtg gat gac atc atc       384
Phe Pro Gly Ile Ser Thr Gly Pro Met Lys Lys Val Asp Asp Ile Ile
        115                  120                  125 tgt gac tct cga tat tct gac att gag ccc tcg aca gaa gga gag gta       432
Cys Asp Ser Arg Tyr Ser Asp Ile Glu Pro Ser Thr Glu Gly Glu Val
    130                  135                  140 ata ttt cgt gct tta gat cct gct ttc aaa att gaa gac cct tat agt       480
Ile Phe Arg Ala Leu Asp Pro Ala Phe Lys Ile Glu Asp Pro Tyr Ser
145                  150                  155                  160 cca agg ata cag aat cta tta aaa atc acc aac ttg aga atc aag ttt       528
Pro Arg Ile Gln Asn Leu Leu Lys Ile Thr Asn Leu Arg Ile Lys Phe
                165                  170                  175 gtg aaa ctg cac acc ttg ggg gat aac ctt ttg gac tcc aga atg gaa       576
Val Lys Leu His Thr Leu Gly Asp Asn Leu Leu Asp Ser Arg Met Glu
            180                  185                  190 atc cga gag aag tac tat tac gct gtt tat gat atg gtg gtt cga ggg       624
Ile Arg Glu Lys Tyr Tyr Tyr Ala Val Tyr Asp Met Val Val Arg Gly
        195                  200                  205 aac tgc ttc tgc tat ggc cac gcc agt gaa tgc gcc cct gtg gat gga       672
Asn Cys Phe Cys Tyr Gly His Ala Ser Glu Cys Ala Pro Val Asp Gly
    210                  215                  220 gtc aat gaa gaa gtg gaa gga atg gtt cac ggg cac tgc atg tgc aga       720
Val Asn Glu Glu Val Glu Gly Met Val His Gly His Cys Met Cys Arg
225                  230                  235                  240 cac aac acc aaa ggc ctg aac tgt gag ctg tgc atg gat ttc tac cac       768
His Asn Thr Lys Gly Leu Asn Cys Glu Leu Cys Met Asp Phe Tyr His
                245                  250                  255 gat ttg ccg tgg aga cct gct gaa ggc cgg aac agc aac gcc tgc aaa       816
Asp Leu Pro Trp Arg Pro Ala Glu Gly Arg Asn Ser Asn Ala Cys Lys
            260                  265                  270 aaa tgt aac tgc aat gaa cat tcc agc tcg tgt cac ttt gac atg gca       864
Lys Cys Asn Cys Asn Glu His Ser Ser Ser Cys His Phe Asp Met Ala
        275                  280                  285 gtc ttc ctg gct act ggc aac gtc agc ggg gga gtg tgt gat aac tgt       912
Val Phe Leu Ala Thr Gly Asn Val Ser Gly Gly Val Cys Asp Asn Cys
    290                  295                  300 cag cac aac acc atg ggg cgc aac tgt gaa cag tgc aaa ccg ttc tac       960
Gln His Asn Thr Met Gly Arg Asn Cys Glu Gln Cys Lys Pro Phe Tyr
305                  310                  315                  320 ttc cag cac cct gag agg gac atc cgg gac ccc aat ctc tgt gaa cca      1008
Phe Gln His Pro Glu Arg Asp Ile Arg Asp Pro Asn Leu Cys Glu Pro
                325                  330                  335 tgt acc tgt gac cca gct ggt tct gag aat ggc ggg atc tgt gat ggg      1056
Cys Thr Cys Asp Pro Ala Gly Ser Glu Asn Gly Gly Ile Cys Asp Gly
            340                  345                  350 tac act gat ttt tct gtg ggt ctc att gct ggt cag tgt cgg tgc aaa      1104
Tyr Thr Asp Phe Ser Val Gly Leu Ile Ala Gly Gln Cys Arg Cys Lys
        355                  360                  365 ttg cac gtg gag gga gag cgc tgt gat gtt tgt aaa gaa ggc ttc tac      1152
Leu His Val Glu Gly Glu Arg Cys Asp Val Cys Lys Glu Gly Phe Tyr
    370                  375                  380 gac tta agt gct gaa gac ccg tat ggt tgt aaa tca tgt gct tgc aat      1200
```

```
                                                  -continued

Asp Leu Ser Ala Glu Asp Pro Tyr Gly Cys Lys Ser Cys Ala Cys Asn
385                 390                 395                 400 cct ctg gga aca att cct ggt ggg aat cct tgt gat tct gag act ggc    1248
Pro Leu Gly Thr Ile Pro Gly Gly Asn Pro Cys Asp Ser Glu Thr Gly
                405                 410                 415 tac tgc tac tgt aag cgc ctg gtg aca gga cag cgc tgt gac cag tgc    1296
Tyr Cys Tyr Cys Lys Arg Leu Val Thr Gly Gln Arg Cys Asp Gln Cys
            420                 425                 430 ctg ccg cag cac tgg ggt tta agc aat gat ttg gat ggg tgt cga cct    1344
Leu Pro Gln His Trp Gly Leu Ser Asn Asp Leu Asp Gly Cys Arg Pro
        435                 440                 445 tgt gac tgt gac ctt gga ggg gcg ctg aac aat agc tgc tcc gag gac    1392
Cys Asp Cys Asp Leu Gly Gly Ala Leu Asn Asn Ser Cys Ser Glu Asp
    450                 455                 460 tcc ggc cag tgc tcc tgc ctg ccc cac atg att ggg cgg cag tgt aac    1440
Ser Gly Gln Cys Ser Cys Leu Pro His Met Ile Gly Arg Gln Cys Asn
465                 470                 475                 480 gag gtg gag tcc ggt tac tac ttc acc acc ctg gac cac tac atc tac    1488
Glu Val Glu Ser Gly Tyr Tyr Phe Thr Thr Leu Asp His Tyr Ile Tyr
                485                 490                 495 gaa gcc gag gaa gcc aat ctg ggg cct gga gtc gtt gtg gtg gaa agg    1536
Glu Ala Glu Glu Ala Asn Leu Gly Pro Gly Val Val Val Val Glu Arg
            500                 505                 510 cag tac att cag gac cgc att cct tcc tgg aca gga cct ggc ttc gtc    1584
Gln Tyr Ile Gln Asp Arg Ile Pro Ser Trp Thr Gly Pro Gly Phe Val
        515                 520                 525 cgg gtg cct gaa ggg gct tat ttg gag ttt ttc att gac aac ata cca    1632
Arg Val Pro Glu Gly Ala Tyr Leu Glu Phe Phe Ile Asp Asn Ile Pro
    530                 535                 540 tat tcc atg gag tat gaa atc ctg att cgc tat gag cca cag ctg ccg    1680
Tyr Ser Met Glu Tyr Glu Ile Leu Ile Arg Tyr Glu Pro Gln Leu Pro
545                 550                 555                 560 gac cac tgg gag aaa gct gtc atc act gta cag cgg ccg ggg aag att    1728
Asp His Trp Glu Lys Ala Val Ile Thr Val Gln Arg Pro Gly Lys Ile
                565                 570                 575 cca gcc agc agc cga tgt ggt aac acc gtt ccc gat gat gac aac cag    1776
Pro Ala Ser Ser Arg Cys Gly Asn Thr Val Pro Asp Asp Asp Asn Gln
            580                 585                 590 gtg gtg tcc ttg tca ccg ggc tca aga tac gtt gtc ctc cct cgc ccc    1824
Val Val Ser Leu Ser Pro Gly Ser Arg Tyr Val Val Leu Pro Arg Pro
        595                 600                 605 gtg tgc ttt gag aag gga atg aac tac acg gtg agg ttg gag ctg ccc    1872
Val Cys Phe Glu Lys Gly Met Asn Tyr Thr Val Arg Leu Glu Leu Pro
    610                 615                 620 cag tat acg gca tcg ggc agt gac gtg gag agc cct tac acg ttc atc    1920
Gln Tyr Thr Ala Ser Gly Ser Asp Val Glu Ser Pro Tyr Thr Phe Ile
625                 630                 635                 640 gac tcg ctt gtt ctc atg ccc tac tgt aaa tcg ctg gac atc ttc act    1968
Asp Ser Leu Val Leu Met Pro Tyr Cys Lys Ser Leu Asp Ile Phe Thr
                645                 650                 655 gtt ggc ggc tca ggc gat ggg gag gtc acc aat agt gcc tgg gaa acc    2016
Val Gly Gly Ser Gly Asp Gly Glu Val Thr Asn Ser Ala Trp Glu Thr
            660                 665                 670 ttc cag cgc tac agg tgt ctg gag aac agc agg agt gtg gta aaa aca    2064
Phe Gln Arg Tyr Arg Cys Leu Glu Asn Ser Arg Ser Val Val Lys Thr
        675                 680                 685 ccc atg aca gat gtc tgc aga aac att atc ttc agc att tct gcc ttg    2112
Pro Met Thr Asp Val Cys Arg Asn Ile Ile Phe Ser Ile Ser Ala Leu
    690                 695                 700
```

```
att cac cag acg ggc ctt gct tgt gaa tgt gac ccc cag gga tct ctg      2160
Ile His Gln Thr Gly Leu Ala Cys Glu Cys Asp Pro Gln Gly Ser Leu
705                 710                 715                 720 agt tct gtg tgt gac ccc aat ggt ggc cag tgc cag tgc cgt cct aat      2208
Ser Ser Val Cys Asp Pro Asn Gly Gly Gln Cys Gln Cys Arg Pro Asn
                725                 730                 735 gtg gtt gga aga acc tgc aac agg tgt gcc ccg ggc acc ttt ggc ttt      2256
Val Val Gly Arg Thr Cys Asn Arg Cys Ala Pro Gly Thr Phe Gly Phe
            740                 745                 750 ggc ccc aac gga tgc aaa cct tgt gac tgc cat ctg caa ggg tct gcc      2304
Gly Pro Asn Gly Cys Lys Pro Cys Asp Cys His Leu Gln Gly Ser Ala
        755                 760                 765 agt gcc ttc tgc gat gcg atc act ggc cag tgc cac tgt ttc cag ggc      2352
Ser Ala Phe Cys Asp Ala Ile Thr Gly Gln Cys His Cys Phe Gln Gly
    770                 775                 780 atc tat gct cgg cag tgt gac cga tgt ctc cct ggg tat tgg ggc ttt      2400
Ile Tyr Ala Arg Gln Cys Asp Arg Cys Leu Pro Gly Tyr Trp Gly Phe
785                 790                 795                 800 ccc agc tgc cag ccc tgc cag tgt aat ggt cat gct cta gac tgt gac      2448
Pro Ser Cys Gln Pro Cys Gln Cys Asn Gly His Ala Leu Asp Cys Asp
                805                 810                 815 aca gtg aca ggg gag tgt ctg agc tgt cag gac tac acc acg ggc cac      2496
Thr Val Thr Gly Glu Cys Leu Ser Cys Gln Asp Tyr Thr Thr Gly His
            820                 825                 830 aac tgc gaa agg tgc ctg gct ggc tac tac ggt gat ccc atc att ggg      2544
Asn Cys Glu Arg Cys Leu Ala Gly Tyr Tyr Gly Asp Pro Ile Ile Gly
        835                 840                 845 tca gga gac cac tgt cgc cct tgc cct tgt cct gat ggt cct gac agt      2592
Ser Gly Asp His Cys Arg Pro Cys Pro Cys Pro Asp Gly Pro Asp Ser
    850                 855                 860 gga cga cag ttt gcc agg agc tgt tat caa gac ccc gtc act ctc cag      2640
Gly Arg Gln Phe Ala Arg Ser Cys Tyr Gln Asp Pro Val Thr Leu Gln
865                 870                 875                 880 ctt gcg tgt gtt tgt gat cct ggg tac att ggc tcc aga tgt gat gac      2688
Leu Ala Cys Val Cys Asp Pro Gly Tyr Ile Gly Ser Arg Cys Asp Asp
                885                 890                 895 tgt gcc tct gga ttt ttt ggc aat ccc tca gac ttt ggg ggt tca tgt      2736
Cys Ala Ser Gly Phe Phe Gly Asn Pro Ser Asp Phe Gly Gly Ser Cys
            900                 905                 910 caa ccg tgt cag tgc cac cac aac att gac act acc gat cca gaa gcc      2784
Gln Pro Cys Gln Cys His His Asn Ile Asp Thr Thr Asp Pro Glu Ala
        915                 920                 925 tgt gac aag gac acg gga cga tgc ctc aag tgc ctg tac cac acg gaa      2832
Cys Asp Lys Asp Thr Gly Arg Cys Leu Lys Cys Leu Tyr His Thr Glu
    930                 935                 940 ggg gac cat tgc cag ctc tgc cag tat ggg tac tac ggc gat gct ctt      2880
Gly Asp His Cys Gln Leu Cys Gln Tyr Gly Tyr Tyr Gly Asp Ala Leu
945                 950                 955                 960 cgg caa gac tgt aga aag tgt gtc tgc aat tac ctg ggc acg gtg aag      2928
Arg Gln Asp Cys Arg Lys Cys Val Cys Asn Tyr Leu Gly Thr Val Lys
                965                 970                 975 gaa cat tgt aat ggc tct gac tgc cac tgt gac aaa gcc act ggt cag      2976
Glu His Cys Asn Gly Ser Asp Cys His Cys Asp Lys Ala Thr Gly Gln
            980                 985                 990 tgc tcg tgc ctt ccc aat gtg atc ggg cag aac tgt gac cgg tgt gcg      3024
Cys Ser Cys Leu Pro Asn Val Ile Gly Gln Asn Cys Asp Arg Cys Ala
        995                 1000                1005 ccc aac acc tgg cag ctg gct agc ggg act ggc tgc ggg ccc tgc aat      3072
Pro Asn Thr Trp Gln Leu Ala Ser Gly Thr Gly Cys Gly Pro Cys Asn
    1010                1015                1020
```

```
                                                          -continued tgc aat gct gcg cat tcc ttt ggg cca tcc tgc aac gag ttc aca ggg    3120
Cys Asn Ala Ala His Ser Phe Gly Pro Ser Cys Asn Glu Phe Thr Gly
1025                1030                1035                1040 cag tgc cag tgc atg ccg ggc ttt gga ggc cga acc tgc agc gag tgc    3168
Gln Cys Gln Cys Met Pro Gly Phe Gly Gly Arg Thr Cys Ser Glu Cys
                1045                1050                1055 cag gag ctc ttc tgg gga gac cct gat gtg gaa tgc cga gcc tgt gac    3216
Gln Glu Leu Phe Trp Gly Asp Pro Asp Val Glu Cys Arg Ala Cys Asp
            1060                1065                1070 tgt gat ccc agg ggc att gag aca cct cag tgt gac cag tcc acg ggc    3264
Cys Asp Pro Arg Gly Ile Glu Thr Pro Gln Cys Asp Gln Ser Thr Gly
        1075                1080                1085 cag tgt gtc tgt gtg gag ggt gta gag ggt cct cgc tgc gac aag tgc    3312
Gln Cys Val Cys Val Glu Gly Val Glu Gly Pro Arg Cys Asp Lys Cys
    1090                1095                1100 acc aga ggt tac tcg ggg gtc ttt cct gac tgc aca ccc tgc cac cag    3360
Thr Arg Gly Tyr Ser Gly Val Phe Pro Asp Cys Thr Pro Cys His Gln
1105                1110                1115                1120 tgc ttt gct ctc tgg gat gct atc att ggt gag ctg acc aac agg acc    3408
Cys Phe Ala Leu Trp Asp Ala Ile Ile Gly Glu Leu Thr Asn Arg Thr
                1125                1130                1135 cac aaa ttc ctg gag aaa gcc aag gct ctg aaa atc agt ggt gtg att    3456
His Lys Phe Leu Glu Lys Ala Lys Ala Leu Lys Ile Ser Gly Val Ile
            1140                1145                1150 ggt ccc tac cga gag acc gtg gac tct gta gag aag aaa gtc aat gag    3504
Gly Pro Tyr Arg Glu Thr Val Asp Ser Val Glu Lys Lys Val Asn Glu
        1155                1160                1165 ata aaa gac atc ctg gcc cag agc cca gca gcg gaa cca ctg aaa aac    3552
Ile Lys Asp Ile Leu Ala Gln Ser Pro Ala Ala Glu Pro Leu Lys Asn
    1170                1175                1180 att ggc att ctc ttc gag gag gca gag aaa cta acc aaa gat gtc aca    3600
Ile Gly Ile Leu Phe Glu Glu Ala Glu Lys Leu Thr Lys Asp Val Thr
1185                1190                1195                1200 gaa aag atg gcg cag gta gaa gtg aaa tta act gat aca gct tca cag    3648
Glu Lys Met Ala Gln Val Glu Val Lys Leu Thr Asp Thr Ala Ser Gln
                1205                1210                1215 agt aac agc aca gct gga gag ctc ggc gca ctg cag gca gaa gca gag    3696
Ser Asn Ser Thr Ala Gly Glu Leu Gly Ala Leu Gln Ala Glu Ala Glu
            1220                1225                1230 agc ctt gac aag acc gtg aag gag ctg gca gaa cag ctg gag ttt atc    3744
Ser Leu Asp Lys Thr Val Lys Glu Leu Ala Glu Gln Leu Glu Phe Ile
        1235                1240                1245 aaa aac tcc gat att cag ggc gcc ttg gat agc atc acc aag tat ttc    3792
Lys Asn Ser Asp Ile Gln Gly Ala Leu Asp Ser Ile Thr Lys Tyr Phe
    1250                1255                1260 cag atg tct ctt gag gca gag aag cgg gtg aat gcc tcc acc aca gac    3840
Gln Met Ser Leu Glu Ala Glu Lys Arg Val Asn Ala Ser Thr Thr Asp
1265                1270                1275                1280 ccc aac agc act gtg gag cag tct gcc ctc acg cga gac aga gta gaa    3888
Pro Asn Ser Thr Val Glu Gln Ser Ala Leu Thr Arg Asp Arg Val Glu
                1285                1290                1295 gat ctg atg ttg gag cga gag tct ccg ttc aag gag cag cag gag gaa    3936
Asp Leu Met Leu Glu Arg Glu Ser Pro Phe Lys Glu Gln Gln Glu Glu
            1300                1305                1310 cag gca cgc ctc ctg gac gaa ctg gcc ggc aaa ctg caa agt ctc gac    3984
Gln Ala Arg Leu Leu Asp Glu Leu Ala Gly Lys Leu Gln Ser Leu Asp
        1315                1320                1325 ctg tcg gct gct gca cag atg acc tgt gga aca cct cca ggg gct gac    4032
Leu Ser Ala Ala Ala Gln Met Thr Cys Gly Thr Pro Pro Gly Ala Asp
```

-continued

| | | |
|---|---|---|
| tgt tct gaa agt gaa tgt ggt ggc ccc aac tgc aga act gac gaa gga<br>Cys Ser Glu Ser Glu Cys Gly Gly Pro Asn Cys Arg Thr Asp Glu Gly<br>1345                    1350                  1355                    1360 | 4080 |
| gag aag aag tgt ggg ggg cct ggc tgt ggt ggt ctg gtc act gtg gcc<br>Glu Lys Lys Cys Gly Gly Pro Gly Cys Gly Gly Leu Val Thr Val Ala<br>             1365                    1370                    1375 | 4128 |
| cac agt gct tgg cag aaa gcc atg gat ttt gac cgt gat gtc ctg agt<br>His Ser Ala Trp Gln Lys Ala Met Asp Phe Asp Arg Asp Val Leu Ser<br>                  1380                    1385                    1390 | 4176 |
| gcc ctg gct gaa gtc gaa cag ctc tcc aag atg gtc tct gaa gca aaa<br>Ala Leu Ala Glu Val Glu Gln Leu Ser Lys Met Val Ser Glu Ala Lys<br>1395                    1400                  1405 | 4224 |
| gtg aga gca gat gag gcg aag cag aat gcg cag gat gtc ctg tta aaa<br>Val Arg Ala Asp Glu Ala Lys Gln Asn Ala Gln Asp Val Leu Leu Lys<br>             1410                    1415                    1420 | 4272 |
| aca aat gct acc aaa gaa aaa gtg gac aag agc aac gag gac ctg cgg<br>Thr Asn Ala Thr Lys Glu Lys Val Asp Lys Ser Asn Glu Asp Leu Arg<br>1425                    1430                  1435                    1440 | 4320 |
| aac ctc atc aag cag atc aga aac ttc ctg act gag gat agt gct gat<br>Asn Leu Ile Lys Gln Ile Arg Asn Phe Leu Thr Glu Asp Ser Ala Asp<br>                  1445                    1450                    1455 | 4368 |
| cta gac agt att gaa gca gtt gct aat gaa gta ctg aaa agt gga aat<br>Leu Asp Ser Ile Glu Ala Val Ala Asn Glu Val Leu Lys Ser Gly Asn<br>             1460                    1465                    1470 | 4416 |
| gct agc acg cca cag cag tta cag aac cta aca gaa gac att cgg gag<br>Ala Ser Thr Pro Gln Gln Leu Gln Asn Leu Thr Glu Asp Ile Arg Glu<br>                  1475                    1480                    1485 | 4464 |
| cga gtt gaa acc ctc tct caa gta gag gtt att ttg cag cag agt gca<br>Arg Val Glu Thr Leu Ser Gln Val Glu Val Ile Leu Gln Gln Ser Ala<br>             1490                    1495                    1500 | 4512 |
| gct gac att gcc aga gct gag ctg ttg ctt gag gaa gct aag aga gca<br>Ala Asp Ile Ala Arg Ala Glu Leu Leu Leu Glu Glu Ala Lys Arg Ala<br>1505                    1510                  1515                    1520 | 4560 |
| agc aaa agt gca aca gat gtt aaa gtc act gca gac atg gtg aag gaa<br>Ser Lys Ser Ala Thr Asp Val Lys Val Thr Ala Asp Met Val Lys Glu<br>                  1525                    1530                    1535 | 4608 |
| gca tta gaa gaa gca gaa aag gcc cag gtt gca gca gag aag gcg att<br>Ala Leu Glu Glu Ala Glu Lys Ala Gln Val Ala Ala Glu Lys Ala Ile<br>             1540                    1545                    1550 | 4656 |
| aaa caa gct gat gag gat atc caa gga acc caa aac ctg cta aca tcg<br>Lys Gln Ala Asp Glu Asp Ile Gln Gly Thr Gln Asn Leu Leu Thr Ser<br>1555                    1560                  1565 | 4704 |
| att gaa tct gaa acg gca gct tct gag gaa acc ctg acc aac gcc tcc<br>Ile Glu Ser Glu Thr Ala Ala Ser Glu Glu Thr Leu Thr Asn Ala Ser<br>1570                    1575                  1580 | 4752 |
| cag cgc atc agc aag ctt gag agg aac gtg gaa gag ctt aag cgt aaa<br>Gln Arg Ile Ser Lys Leu Glu Arg Asn Val Glu Glu Leu Lys Arg Lys<br>1585                    1590                  1595                    1600 | 4800 |
| gct gcc cag aac tct ggg gag gca gaa tat atc gaa aaa gta gta tat<br>Ala Ala Gln Asn Ser Gly Glu Ala Glu Tyr Ile Glu Lys Val Val Tyr<br>                  1605                    1610                    1615 | 4848 |
| tct gta aaa cag aat gca gac gat gtt aaa aag act cta gat ggc gaa<br>Ser Val Lys Gln Asn Ala Asp Asp Val Lys Lys Thr Leu Asp Gly Glu<br>             1620                    1625                    1630 | 4896 |
| ctt gat gaa aag tat aag aag gta gaa agt tta att gcc caa aaa act<br>Leu Asp Glu Lys Tyr Lys Lys Val Glu Ser Leu Ile Ala Gln Lys Thr<br>1635                    1640                  1645 | 4944 |
| gaa gag tca gca gat gcc agg agg aaa gct gag ctg cta caa aat gaa | 4992 |

-continued

```
Glu Glu Ser Ala Asp Ala Arg Arg Lys Ala Glu Leu Leu Gln Asn Glu
    1650                1655                1660 gca aaa aca ctc ttg gct caa gct aac agc aag ctc cag ctg ttg gaa      5040
Ala Lys Thr Leu Leu Ala Gln Ala Asn Ser Lys Leu Gln Leu Leu Glu
1665                1670                1675                1680 gac tta gaa aga aaa tat gag gac aat caa aaa tac tta gaa gat aaa      5088
Asp Leu Glu Arg Lys Tyr Glu Asp Asn Gln Lys Tyr Leu Glu Asp Lys
                1685                1690                1695 gct caa gaa ttg gtg cga ctg gaa gga gag gtt cgc tcc ctc ctt aag      5136
Ala Gln Glu Leu Val Arg Leu Glu Gly Glu Val Arg Ser Leu Leu Lys
            1700                1705                1710 gac ata agt gag aaa gtt gcg gtt tac agc acc tgc tta taacaggaag       5185
Asp Ile Ser Glu Lys Val Ala Val Tyr Ser Thr Cys Leu
        1715                1720                1725 gggctgtaga ggggctcggt gaccaaggta aaccacacgc gcaaaccgag gcagtcatct    5245
acaaataacc catcatctat ttaatgtttt taaccaccta cttttgtatg gagttaaata    5305
aaagacattg gttttgtata aaca                                            5329
```

<210> SEQ ID NO 12
<211> LENGTH: 1725
<212> TYPE: PRT
<213> ORGANISM: Mus musculus

<400> SEQUENCE: 12

```
Glu Pro Tyr Cys Ile Val Ser His Leu Gln Glu Asp Lys Lys Cys Phe
  1               5                  10                  15

Ile Cys Asp Ser Arg Asp Pro Tyr His Glu Thr Leu Asn Pro Asp Ser
             20                  25                  30

His Leu Ile Glu Asn Val Val Thr Thr Phe Ala Pro Asn Arg Leu Lys
         35                  40                  45

Ile Trp Trp Gln Ser Glu Asn Gly Val Glu Asn Val Thr Ile Gln Leu
     50                  55                  60

Asp Leu Glu Ala Glu Phe His Phe Thr His Leu Ile Met Thr Phe Lys
 65                  70                  75                  80

Thr Phe Arg Pro Ala Ala Met Leu Ile Glu Arg Ser Ser Asp Phe Gly
                 85                  90                  95

Lys Thr Trp Gly Val Tyr Arg Tyr Phe Ala Tyr Asp Cys Glu Ser Ser
            100                 105                 110

Phe Pro Gly Ile Ser Thr Gly Pro Met Lys Lys Val Asp Asp Ile Ile
        115                 120                 125

Cys Asp Ser Arg Tyr Ser Asp Ile Glu Pro Ser Thr Glu Gly Glu Val
    130                 135                 140

Ile Phe Arg Ala Leu Asp Pro Ala Phe Lys Ile Glu Asp Pro Tyr Ser
145                 150                 155                 160

Pro Arg Ile Gln Asn Leu Leu Lys Ile Thr Asn Leu Arg Ile Lys Phe
                165                 170                 175

Val Lys Leu His Thr Leu Gly Asp Asn Leu Leu Asp Ser Arg Met Glu
            180                 185                 190

Ile Arg Glu Lys Tyr Tyr Tyr Ala Val Tyr Asp Met Val Val Arg Gly
        195                 200                 205

Asn Cys Phe Cys Tyr Gly His Ala Ser Glu Cys Ala Pro Val Asp Gly
    210                 215                 220

Val Asn Glu Glu Val Glu Gly Met Val His Gly His Cys Met Cys Arg
225                 230                 235                 240

His Asn Thr Lys Gly Leu Asn Cys Glu Leu Cys Met Asp Phe Tyr His
```

```
                    245                 250                 255
Asp Leu Pro Trp Arg Pro Ala Glu Gly Arg Asn Ser Asn Ala Cys Lys
                260                 265                 270
Lys Cys Asn Cys Asn Glu His Ser Ser Cys His Phe Asp Met Ala
            275                 280                 285
Val Phe Leu Ala Thr Gly Asn Val Ser Gly Val Cys Asp Asn Cys
        290                 295                 300
Gln His Asn Thr Met Gly Arg Asn Cys Glu Gln Cys Lys Pro Phe Tyr
305                 310                 315                 320
Phe Gln His Pro Glu Arg Asp Ile Arg Asp Pro Asn Leu Cys Glu Pro
                325                 330                 335
Cys Thr Cys Asp Pro Ala Gly Ser Glu Asn Gly Gly Ile Cys Asp Gly
                340                 345                 350
Tyr Thr Asp Phe Ser Val Gly Leu Ile Ala Gly Gln Cys Arg Cys Lys
            355                 360                 365
Leu His Val Glu Gly Glu Arg Cys Asp Val Cys Lys Glu Gly Phe Tyr
        370                 375                 380
Asp Leu Ser Ala Glu Asp Pro Tyr Gly Cys Lys Ser Cys Ala Cys Asn
385                 390                 395                 400
Pro Leu Gly Thr Ile Pro Gly Gly Asn Pro Cys Asp Ser Glu Thr Gly
                405                 410                 415
Tyr Cys Tyr Cys Lys Arg Leu Val Thr Gly Gln Arg Cys Asp Gln Cys
                420                 425                 430
Leu Pro Gln His Trp Gly Leu Ser Asn Asp Leu Asp Gly Cys Arg Pro
            435                 440                 445
Cys Asp Cys Asp Leu Gly Gly Ala Leu Asn Asn Ser Cys Ser Glu Asp
450                 455                 460
Ser Gly Gln Cys Ser Cys Leu Pro His Met Ile Gly Arg Gln Cys Asn
465                 470                 475                 480
Glu Val Glu Ser Gly Tyr Tyr Phe Thr Thr Leu Asp His Tyr Ile Tyr
                485                 490                 495
Glu Ala Glu Glu Ala Asn Leu Gly Pro Gly Val Val Val Glu Arg
            500                 505                 510
Gln Tyr Ile Gln Asp Arg Ile Pro Ser Trp Thr Gly Pro Gly Phe Val
            515                 520                 525
Arg Val Pro Glu Gly Ala Tyr Leu Glu Phe Ile Asp Asn Ile Pro
        530                 535                 540
Tyr Ser Met Glu Tyr Glu Ile Leu Ile Arg Tyr Glu Pro Gln Leu Pro
545                 550                 555                 560
Asp His Trp Glu Lys Ala Val Ile Thr Val Gln Arg Pro Gly Lys Ile
                565                 570                 575
Pro Ala Ser Ser Arg Cys Gly Asn Thr Val Pro Asp Asp Asn Gln
            580                 585                 590
Val Val Ser Leu Ser Pro Gly Ser Arg Tyr Val Val Leu Pro Arg Pro
            595                 600                 605
Val Cys Phe Glu Lys Gly Met Asn Tyr Thr Val Arg Leu Glu Leu Pro
        610                 615                 620
Gln Tyr Thr Ala Ser Gly Ser Asp Val Glu Ser Pro Tyr Thr Phe Ile
625                 630                 635                 640
Asp Ser Leu Val Leu Met Pro Tyr Cys Lys Ser Leu Asp Ile Phe Thr
            645                 650                 655
Val Gly Gly Ser Gly Asp Gly Glu Val Thr Asn Ser Ala Trp Glu Thr
                660                 665                 670
```

-continued

```
Phe Gln Arg Tyr Arg Cys Leu Glu Asn Ser Arg Ser Val Val Lys Thr
            675                 680                 685
Pro Met Thr Asp Val Cys Arg Asn Ile Ile Phe Ser Ile Ser Ala Leu
        690                 695                 700
Ile His Gln Thr Gly Leu Ala Cys Glu Cys Asp Pro Gln Gly Ser Leu
705                 710                 715                 720
Ser Ser Val Cys Asp Pro Asn Gly Gly Gln Cys Gln Cys Arg Pro Asn
                725                 730                 735
Val Val Gly Arg Thr Cys Asn Arg Cys Ala Pro Gly Thr Phe Gly Phe
            740                 745                 750
Gly Pro Asn Gly Cys Lys Pro Cys Asp Cys His Leu Gln Gly Ser Ala
        755                 760                 765
Ser Ala Phe Cys Asp Ala Ile Thr Gly Gln Cys His Cys Phe Gln Gly
        770                 775                 780
Ile Tyr Ala Arg Gln Cys Asp Arg Cys Leu Pro Gly Tyr Trp Gly Phe
785                 790                 795                 800
Pro Ser Cys Gln Pro Cys Gln Cys Asn Gly His Ala Leu Asp Cys Asp
                805                 810                 815
Thr Val Thr Gly Glu Cys Leu Ser Cys Gln Asp Tyr Thr Thr Gly His
            820                 825                 830
Asn Cys Glu Arg Cys Leu Ala Gly Tyr Tyr Gly Asp Pro Ile Ile Gly
            835                 840                 845
Ser Gly Asp His Cys Arg Pro Cys Pro Cys Pro Asp Gly Pro Asp Ser
        850                 855                 860
Gly Arg Gln Phe Ala Arg Ser Cys Tyr Gln Asp Pro Val Thr Leu Gln
865                 870                 875                 880
Leu Ala Cys Val Cys Asp Pro Gly Tyr Ile Gly Ser Arg Cys Asp Asp
                885                 890                 895
Cys Ala Ser Gly Phe Phe Gly Asn Pro Ser Asp Phe Gly Gly Ser Cys
            900                 905                 910
Gln Pro Cys Gln Cys His His Asn Ile Asp Thr Thr Asp Pro Glu Ala
        915                 920                 925
Cys Asp Lys Asp Thr Gly Arg Cys Leu Lys Cys Leu Tyr His Thr Glu
930                 935                 940
Gly Asp His Cys Gln Leu Cys Gln Tyr Gly Tyr Tyr Gly Asp Ala Leu
945                 950                 955                 960
Arg Gln Asp Cys Arg Lys Cys Val Cys Asn Tyr Leu Gly Thr Val Lys
                965                 970                 975
Glu His Cys Asn Gly Ser Asp Cys His Cys Asp Lys Ala Thr Gly Gln
            980                 985                 990
Cys Ser Cys Leu Pro Asn Val Ile Gly Gln Asn Cys Asp Arg Cys Ala
        995                 1000                1005
Pro Asn Thr Trp Gln Leu Ala Ser Gly Thr Gly Cys Gly Pro Cys Asn
        1010                1015                1020
Cys Asn Ala Ala His Ser Phe Gly Pro Ser Cys Asn Glu Phe Thr Gly
1025                1030                1035                1040
Gln Cys Gln Cys Met Pro Gly Phe Gly Gly Arg Thr Cys Ser Glu Cys
                1045                1050                1055
Gln Glu Leu Phe Trp Gly Asp Pro Asp Val Glu Cys Arg Ala Cys Asp
            1060                1065                1070
Cys Asp Pro Arg Gly Ile Glu Thr Pro Gln Cys Asp Gln Ser Thr Gly
    1075                1080                1085
```

-continued

```
Gln Cys Val Cys Val Glu Gly Val Glu Gly Pro Arg Cys Asp Lys Cys
    1090                1095                1100

Thr Arg Gly Tyr Ser Gly Val Phe Pro Asp Cys Thr Pro Cys His Gln
1105                1110                1115                1120

Cys Phe Ala Leu Trp Asp Ala Ile Ile Gly Glu Leu Thr Asn Arg Thr
                1125                1130                1135

His Lys Phe Leu Glu Lys Ala Lys Ala Leu Lys Ile Ser Gly Val Ile
            1140                1145                1150

Gly Pro Tyr Arg Glu Thr Val Asp Ser Val Glu Lys Lys Val Asn Glu
        1155                1160                1165

Ile Lys Asp Ile Leu Ala Gln Ser Pro Ala Ala Glu Pro Leu Lys Asn
    1170                1175                1180

Ile Gly Ile Leu Phe Glu Glu Ala Glu Lys Leu Thr Lys Asp Val Thr
1185                1190                1195                1200

Glu Lys Met Ala Gln Val Glu Val Lys Leu Thr Asp Thr Ala Ser Gln
                1205                1210                1215

Ser Asn Ser Thr Ala Gly Glu Leu Gly Ala Leu Gln Ala Glu Ala Glu
            1220                1225                1230

Ser Leu Asp Lys Thr Val Lys Glu Leu Ala Glu Gln Leu Glu Phe Ile
        1235                1240                1245

Lys Asn Ser Asp Ile Gln Gly Ala Leu Asp Ser Ile Thr Lys Tyr Phe
    1250                1255                1260

Gln Met Ser Leu Glu Ala Glu Lys Arg Val Asn Ala Ser Thr Thr Asp
1265                1270                1275                1280

Pro Asn Ser Thr Val Glu Gln Ser Ala Leu Thr Arg Asp Arg Val Glu
                1285                1290                1295

Asp Leu Met Leu Glu Arg Glu Ser Pro Phe Lys Glu Gln Gln Glu Glu
            1300                1305                1310

Gln Ala Arg Leu Leu Asp Glu Leu Ala Gly Lys Leu Gln Ser Leu Asp
        1315                1320                1325

Leu Ser Ala Ala Ala Gln Met Thr Cys Gly Thr Pro Pro Gly Ala Asp
    1330                1335                1340

Cys Ser Glu Ser Glu Cys Gly Gly Pro Asn Cys Arg Thr Asp Glu Gly
1345                1350                1355                1360

Glu Lys Lys Cys Gly Gly Pro Gly Cys Gly Gly Leu Val Thr Val Ala
                1365                1370                1375

His Ser Ala Trp Gln Lys Ala Met Asp Phe Asp Arg Asp Val Leu Ser
            1380                1385                1390

Ala Leu Ala Glu Val Glu Gln Leu Ser Lys Met Val Ser Glu Ala Lys
        1395                1400                1405

Val Arg Ala Asp Glu Ala Lys Gln Asn Ala Gln Asp Val Leu Leu Lys
    1410                1415                1420

Thr Asn Ala Thr Lys Glu Lys Val Asp Lys Ser Asn Glu Asp Leu Arg
1425                1430                1435                1440

Asn Leu Ile Lys Gln Ile Arg Asn Phe Leu Thr Glu Asp Ser Ala Asp
                1445                1450                1455

Leu Asp Ser Ile Glu Ala Val Ala Asn Glu Val Leu Lys Ser Gly Asn
            1460                1465                1470

Ala Ser Thr Pro Gln Gln Leu Gln Asn Leu Thr Glu Asp Ile Arg Glu
        1475                1480                1485

Arg Val Glu Thr Leu Ser Gln Val Glu Val Ile Leu Gln Gln Ser Ala
    1490                1495                1500

Ala Asp Ile Ala Arg Ala Glu Leu Leu Leu Glu Glu Ala Lys Arg Ala
```

```
                1505                1510                1515                1520

Ser Lys Ser Ala Thr Asp Val Lys Val Thr Ala Asp Met Val Lys Glu
            1525                1530                1535

Ala Leu Glu Glu Ala Glu Lys Ala Gln Val Ala Ala Glu Lys Ala Ile
        1540                1545                1550

Lys Gln Ala Asp Glu Asp Ile Gln Gly Thr Gln Asn Leu Leu Thr Ser
        1555                1560                1565

Ile Glu Ser Glu Thr Ala Ala Ser Glu Glu Thr Leu Thr Asn Ala Ser
    1570                1575                1580

Gln Arg Ile Ser Lys Leu Glu Arg Asn Val Glu Glu Leu Lys Arg Lys
1585                1590                1595                1600

Ala Ala Gln Asn Ser Gly Glu Ala Glu Tyr Ile Glu Lys Val Val Tyr
            1605                1610                1615

Ser Val Lys Gln Asn Ala Asp Asp Val Lys Lys Thr Leu Asp Gly Glu
        1620                1625                1630

Leu Asp Glu Lys Tyr Lys Lys Val Glu Ser Leu Ile Ala Gln Lys Thr
        1635                1640                1645

Glu Glu Ser Ala Asp Ala Arg Arg Lys Ala Glu Leu Leu Gln Asn Glu
    1650                1655                1660

Ala Lys Thr Leu Leu Ala Gln Ala Asn Ser Lys Leu Gln Leu Leu Glu
1665                1670                1675                1680

Asp Leu Glu Arg Lys Tyr Glu Asp Asn Gln Lys Tyr Leu Glu Asp Lys
            1685                1690                1695

Ala Gln Glu Leu Val Arg Leu Glu Gly Glu Val Arg Ser Leu Leu Lys
            1700                1705                1710

Asp Ile Ser Glu Lys Val Ala Val Tyr Ser Thr Cys Leu
        1715                1720                1725

<210> SEQ ID NO 13
<211> LENGTH: 5306
<212> TYPE: DNA
<213> ORGANISM: Homo sapiens
<220> FEATURE:
<221> NAME/KEY: CDS
<222> LOCATION: (260)..(5086)
<221> NAME/KEY: sig_peptide
<222> LOCATION: (260)..(358)

<400> SEQUENCE: 13
cggggcaggc tgctcccggg gtaggtgagg gaagcgcgga ggcggcgcgc ggggcagtg          60 gtcggcgagc agcgcggtcc tcgctagggg cgcccacccg tcagtctctc cggcgcgagc       120
cgccgccacc gcccgcgccg gagtcaggcc cctgggcccc caggctcaag cagcgaagcg       180
gcctccgggg gacgccgcta ggcgagagga acgcgcggt gcccttgcct tcgccgtgac        240
ccagcgtgcg ggcggcggg atg aga ggg agc cat cgg gcc gcg ccg gcc ctg        292
                     Met Arg Gly Ser His Arg Ala Ala Pro Ala Leu
                      1               5                  10 cgg ccc cgg ggg cgg ctc tgg ccc gtg ctg gcc gtg ctg gcg gcg gcc        340
Arg Pro Arg Gly Arg Leu Trp Pro Val Leu Ala Val Leu Ala Ala Ala
        15                  20                  25 gcc gcg gcg ggc tgt gcc cag gca gcc atg gac gag tgc acg gac gag        388
Ala Ala Ala Gly Cys Ala Gln Ala Ala Met Asp Glu Cys Thr Asp Glu
        30                  35                  40 ggc ggg cgg ccg cag cgc tgc atg ccc gag ttc gtc aac gcc gct ttc        436
Gly Gly Arg Pro Gln Arg Cys Met Pro Glu Phe Val Asn Ala Ala Phe
    45                  50                  55 aac gtg act gtg gtg gcc acc aac acg tgt ggg act ccg ccc gag gaa        484
```

```
Asn Val Thr Val Val Ala Thr Asn Thr Cys Gly Thr Pro Glu Glu
 60              65              70              75 tac tgt gtg cag acc ggg gtg acc ggg gtc acc aag tcc tgt cac ctg      532
Tyr Cys Val Gln Thr Gly Val Thr Gly Val Thr Lys Ser Cys His Leu
             80              85              90 tgc gac gcc ggg cag ccc cac ctg cag cac ggg gca gcc ttc ctg acc      580
Cys Asp Ala Gly Gln Pro His Leu Gln His Gly Ala Ala Phe Leu Thr
             95             100             105 gac tac aac aac cag gcc gac acc acc tgg tgg caa agc cag acc atg      628
Asp Tyr Asn Asn Gln Ala Asp Thr Thr Trp Trp Gln Ser Gln Thr Met
        110             115             120 ctg gcc ggg gtg cag tac ccc agc tcc atc aac ctc acg ctg cac ctg      676
Leu Ala Gly Val Gln Tyr Pro Ser Ser Ile Asn Leu Thr Leu His Leu
    125             130             135 gga aaa gct ttt gac atc acc tat gtg cgt ctc aag ttc cac acc agc      724
Gly Lys Ala Phe Asp Ile Thr Tyr Val Arg Leu Lys Phe His Thr Ser
140             145             150             155 cgc ccg gag agc ttt gcc att tac aag cgc aca cgg gaa gac ggg ccc      772
Arg Pro Glu Ser Phe Ala Ile Tyr Lys Arg Thr Arg Glu Asp Gly Pro
             160             165             170 tgg att cct tac cag tac tac agt ggt tcc tgc gag aac acc tac tcc      820
Trp Ile Pro Tyr Gln Tyr Tyr Ser Gly Ser Cys Glu Asn Thr Tyr Ser
         175             180             185 aag gca aac cgc ggc ttc atc agg aca gga ggg gac gag cag cag gcc      868
Lys Ala Asn Arg Gly Phe Ile Arg Thr Gly Gly Asp Glu Gln Gln Ala
        190             195             200 ttg tgt act gat gaa ttc agt gac att tct ccc ctc act ggg ggc aac      916
Leu Cys Thr Asp Glu Phe Ser Asp Ile Ser Pro Leu Thr Gly Gly Asn
205             210             215 gtg gcc ttt tct acc ctg gaa gga agg ccc agc gcc tat aac ttt gac      964
Val Ala Phe Ser Thr Leu Glu Gly Arg Pro Ser Ala Tyr Asn Phe Asp
220             225             230             235 aat agc cct gtg ctg cag gaa tgg gta act gcc act gac atc aga gta      1012
Asn Ser Pro Val Leu Gln Glu Trp Val Thr Ala Thr Asp Ile Arg Val
             240             245             250 act ctt aat cgc ctg aac act ttt gga gat gaa gtg ttt aac gat ccc      1060
Thr Leu Asn Arg Leu Asn Thr Phe Gly Asp Glu Val Phe Asn Asp Pro
         255             260             265 aaa gtt ctc aag tcc tat tat tat gcc atc tct gat ttt gct gta ggt      1108
Lys Val Leu Lys Ser Tyr Tyr Tyr Ala Ile Ser Asp Phe Ala Val Gly
        270             275             280 ggc aga tgt aaa tgt aat gga cac gca agc gag tgt atg aag aac gaa      1156
Gly Arg Cys Lys Cys Asn Gly His Ala Ser Glu Cys Met Lys Asn Glu
285             290             295 ttt gat aag ctg gtg tgt aat tgc aaa cat aac aca tat gga gta gac      1204
Phe Asp Lys Leu Val Cys Asn Cys Lys His Asn Thr Tyr Gly Val Asp
300             305             310             315 tgt gaa aag tgt ctt cct ttc ttc aat gac cgg ccg tgg agg agg gca      1252
Cys Glu Lys Cys Leu Pro Phe Phe Asn Asp Arg Pro Trp Arg Arg Ala
             320             325             330 act gcg gaa agt gcc agt gaa tgc ctg ccc tgt gat tgc aat ggt cga      1300
Thr Ala Glu Ser Ala Ser Glu Cys Leu Pro Cys Asp Cys Asn Gly Arg
         335             340             345 tcc cag gaa tgc tac ttc gac cct gaa ctc tat cgt tcc act ggc cat      1348
Ser Gln Glu Cys Tyr Phe Asp Pro Glu Leu Tyr Arg Ser Thr Gly His
        350             355             360 ggg ggc cac tgt acc aac tgc cag gat aac aca gat ggc gcc cac tgt      1396
Gly Gly His Cys Thr Asn Cys Gln Asp Asn Thr Asp Gly Ala His Cys
365             370             375
```

-continued

| | | |
|---|---|---|
| gag agg tgc cga gag aac ttc ttc cgc ctt ggc aac aat gaa gcc tgc<br>Glu Arg Cys Arg Glu Asn Phe Phe Arg Leu Gly Asn Asn Glu Ala Cys<br>380                      385                        390                        395 | 1444 | |
| tct tca tgc cac tgt agt cct gtg ggc tct cta agc aca cag tgt gat<br>Ser Ser Cys His Cys Ser Pro Val Gly Ser Leu Ser Thr Gln Cys Asp<br>                    400                        405                        410 | 1492 | |
| agt tac ggc aga tgc agc tgt aag cca gga gtg atg ggg gac aaa tgt<br>Ser Tyr Gly Arg Cys Ser Cys Lys Pro Gly Val Met Gly Asp Lys Cys<br>                415                        420                        425 | 1540 | |
| gac cgt tgc cag cct gga ttc cat tct ctc act gaa gca gga tgc agg<br>Asp Arg Cys Gln Pro Gly Phe His Ser Leu Thr Glu Ala Gly Cys Arg<br>        430                        435                        440 | 1588 | |
| cca tgc tct tgt gat ccc tct ggc agc ata gat gaa tgt aat gtt gaa<br>Pro Cys Ser Cys Asp Pro Ser Gly Ser Ile Asp Glu Cys Asn Val Glu<br>445                      450                        455 | 1636 | |
| aca gga aga tgt gtt tgc aaa gac aat gtc gaa ggc ttc aat tgt gaa<br>Thr Gly Arg Cys Val Cys Lys Asp Asn Val Glu Gly Phe Asn Cys Glu<br>460                      465                        470                        475 | 1684 | |
| aga tgc aaa cct gga ttt ttt aat ctg gaa tca tct aat cct cgg ggt<br>Arg Cys Lys Pro Gly Phe Phe Asn Leu Glu Ser Ser Asn Pro Arg Gly<br>                480                        485                        490 | 1732 | |
| tgc aca ccc tgc ttc tgc ttt ggg cat tct tct gtc tgt aca aac gct<br>Cys Thr Pro Cys Phe Cys Phe Gly His Ser Ser Val Cys Thr Asn Ala<br>                    495                        500                        505 | 1780 | |
| gtt ggc tac agt gtt tat tct atc tcc tct acc ttt cag att gat gag<br>Val Gly Tyr Ser Val Tyr Ser Ile Ser Ser Thr Phe Gln Ile Asp Glu<br>            510                        515                        520 | 1828 | |
| gat ggg tgg cgt gcg gaa cag aga gat ggc tct gaa gca tct ctc gag<br>Asp Gly Trp Arg Ala Glu Gln Arg Asp Gly Ser Glu Ala Ser Leu Glu<br>525                      530                        535 | 1876 | |
| tgg tcc tct gag agg caa gat atc gcc gtg atc tca gac agc tac ttt<br>Trp Ser Ser Glu Arg Gln Asp Ile Ala Val Ile Ser Asp Ser Tyr Phe<br>540                      545                        550                        555 | 1924 | |
| cct cgg tac ttc att gct cct gca aag ttc ttg ggc aag cag gtg ttg<br>Pro Arg Tyr Phe Ile Ala Pro Ala Lys Phe Leu Gly Lys Gln Val Leu<br>                560                        565                        570 | 1972 | |
| agt tat ggt cag aac ctc tcc ttc tcc ttt cga gtg gac agg cga gat<br>Ser Tyr Gly Gln Asn Leu Ser Phe Ser Phe Arg Val Asp Arg Arg Asp<br>            575                        580                        585 | 2020 | |
| act cgc ctc tct gcc gaa gac ctt gtg ctt gag gga gct ggc tta aga<br>Thr Arg Leu Ser Ala Glu Asp Leu Val Leu Glu Gly Ala Gly Leu Arg<br>        590                        595                        600 | 2068 | |
| gta tct gta ccc ttg atc gct cag ggc aat tcc tat cca agt gag acc<br>Val Ser Val Pro Leu Ile Ala Gln Gly Asn Ser Tyr Pro Ser Glu Thr<br>605                      610                        615 | 2116 | |
| act gtg aag tat gtc ttc agg ctc cat gaa gca aca gat tac cct tgg<br>Thr Val Lys Tyr Val Phe Arg Leu His Glu Ala Thr Asp Tyr Pro Trp<br>620                      625                        630                        635 | 2164 | |
| agg cct gct ctt acc cct ttt gaa ttt cag aag ctc cta aac aac ttg<br>Arg Pro Ala Leu Thr Pro Phe Glu Phe Gln Lys Leu Leu Asn Asn Leu<br>                640                        645                        650 | 2212 | |
| acc tct atc aag ata cgt ggg aca tac agt gag aga agt gct gga tat<br>Thr Ser Ile Lys Ile Arg Gly Thr Tyr Ser Glu Arg Ser Ala Gly Tyr<br>                    655                        660                        665 | 2260 | |
| ttg gat gat gtc acc ctg gca agt gct cgt cct ggg cct gga gtc cct<br>Leu Asp Asp Val Thr Leu Ala Ser Ala Arg Pro Gly Pro Gly Val Pro<br>        670                        675                        680 | 2308 | |
| gca act tgg gtg gag tcc tgc acc tgt cct gtg gga tat gga ggg cag<br>Ala Thr Trp Val Glu Ser Cys Thr Cys Pro Val Gly Tyr Gly Gly Gln<br>685                      690                        695 | 2356 | |

```
ttt tgt gag atg tgc ctc tca ggt tac aga aga gaa act cct aat ctt    2404
Phe Cys Glu Met Cys Leu Ser Gly Tyr Arg Arg Glu Thr Pro Asn Leu
700             705                 710                 715 gga cca tac agt cca tgt gtg ctt tgc gcc tgc aat gga cac agc gag    2452
Gly Pro Tyr Ser Pro Cys Val Leu Cys Ala Cys Asn Gly His Ser Glu
            720                 725                 730 acc tgt gat cct gag aca ggt gtt tgt aac tgc aga gac aat acg gct    2500
Thr Cys Asp Pro Glu Thr Gly Val Cys Asn Cys Arg Asp Asn Thr Ala
        735                 740                 745 ggc ccg cac tgt gag aag tgc agt gat ggg tac tat gga gat tca act    2548
Gly Pro His Cys Glu Lys Cys Ser Asp Gly Tyr Tyr Gly Asp Ser Thr
    750                 755                 760 gca ggc acc tcc tcc gat tgc caa ccc tgt ccg tgt cct gga ggt tca    2596
Ala Gly Thr Ser Ser Asp Cys Gln Pro Cys Pro Cys Pro Gly Gly Ser
765                 770                 775 agt tgt gct gtt gtt ccc aag aca aag gag gtg gtg tgc acc aac tgt    2644
Ser Cys Ala Val Val Pro Lys Thr Lys Glu Val Val Cys Thr Asn Cys
780                 785                 790                 795 cct act ggc acc act ggt aag aga tgt gag ctc tgt gat gat ggc tac    2692
Pro Thr Gly Thr Thr Gly Lys Arg Cys Glu Leu Cys Asp Asp Gly Tyr
            800                 805                 810 ttt gga gac ccc ctg ggt aga aac ggc cct gtg aga ctt tgc cgc ctg    2740
Phe Gly Asp Pro Leu Gly Arg Asn Gly Pro Val Arg Leu Cys Arg Leu
        815                 820                 825 tgc cag tgc agt gac aac atc gat ccc aac gca gtt gga aat tgc aat    2788
Cys Gln Cys Ser Asp Asn Ile Asp Pro Asn Ala Val Gly Asn Cys Asn
    830                 835                 840 cgc ttg acg gga gaa tgc ctg aag tgc atc tat aac act gct ggc ttc    2836
Arg Leu Thr Gly Glu Cys Leu Lys Cys Ile Tyr Asn Thr Ala Gly Phe
845                 850                 855 tat tgt gac cgg tgc aaa gac gga ttt ttt gga aat ccc ctg gct ccc    2884
Tyr Cys Asp Arg Cys Lys Asp Gly Phe Phe Gly Asn Pro Leu Ala Pro
860                 865                 870                 875 aat cca gca gac aaa tgc aaa gcc tgc aat tgc aat ccg tat ggg acc    2932
Asn Pro Ala Asp Lys Cys Lys Ala Cys Asn Cys Asn Pro Tyr Gly Thr
            880                 885                 890 atg aag cag cag agc agc tgt aac ccc gtg acg ggg cag tgt gaa tgt    2980
Met Lys Gln Gln Ser Ser Cys Asn Pro Val Thr Gly Gln Cys Glu Cys
        895                 900                 905 ttg cct cac gtg act ggc cag gac tgt ggt gct tgt gac cct gga ttc    3028
Leu Pro His Val Thr Gly Gln Asp Cys Gly Ala Cys Asp Pro Gly Phe
    910                 915                 920 tac aat ctg cag agt ggg caa ggc tgt gag agg tgt gac tgc cat gcc    3076
Tyr Asn Leu Gln Ser Gly Gln Gly Cys Glu Arg Cys Asp Cys His Ala
925                 930                 935 ttg ggc tcc acc aat ggg cag tgt gac atc cgc acc ggc cag tgt gag    3124
Leu Gly Ser Thr Asn Gly Gln Cys Asp Ile Arg Thr Gly Gln Cys Glu
940                 945                 950                 955 tgc cag ccc ggc atc act ggt cag cac tgt gag cgc tgt gag gtc aac    3172
Cys Gln Pro Gly Ile Thr Gly Gln His Cys Glu Arg Cys Glu Val Asn
            960                 965                 970 cac ttt ggg ttt gga cct gaa ggc tgc aaa ccc tgt gac tgt cat cct    3220
His Phe Gly Phe Gly Pro Glu Gly Cys Lys Pro Cys Asp Cys His Pro
        975                 980                 985 gag gga tct ctt tca ctt cag tgc aaa gat gat ggt cgc tgt gaa tgc    3268
Glu Gly Ser Leu Ser Leu Gln Cys Lys Asp Asp Gly Arg Cys Glu Cys
    990                 995                 1000 aga gaa ggc ttt gtg gga aat cgc tgt gac cag tgt gaa gaa aac tat    3316
Arg Glu Gly Phe Val Gly Asn Arg Cys Asp Gln Cys Glu Glu Asn Tyr
```

-continued

```
                 1005                1010                1015
ttc tac aat cgg tct tgg cct ggc tgc cag gaa tgt cca gct tgt tac     3364
Phe Tyr Asn Arg Ser Trp Pro Gly Cys Gln Glu Cys Pro Ala Cys Tyr
1020                1025                1030                1035 cgg ctg gta aag gat aag gtt gct gat cat aga gtg aag ctc cag gaa     3412
Arg Leu Val Lys Asp Lys Val Ala Asp His Arg Val Lys Leu Gln Glu
                1040                1045                1050 tta gag agt ctc ata gca aac ctt gga act ggg gat gag atg gtg aca     3460
Leu Glu Ser Leu Ile Ala Asn Leu Gly Thr Gly Asp Glu Met Val Thr
            1055                1060                1065 gat caa gcc ttc gag gat aga cta aag gaa gca gag agg gaa gtt atg     3508
Asp Gln Ala Phe Glu Asp Arg Leu Lys Glu Ala Glu Arg Glu Val Met
        1070                1075                1080 gac ctc ctt cgt gag gcc cag gat gtc aaa gat gtt gac cag aat ttg     3556
Asp Leu Leu Arg Glu Ala Gln Asp Val Lys Asp Val Asp Gln Asn Leu
    1085                1090                1095 atg gat cgc cta cag aga gtg aat aac act ctg tcc agc caa att agc     3604
Met Asp Arg Leu Gln Arg Val Asn Asn Thr Leu Ser Ser Gln Ile Ser
1100                1105                1110                1115 cgt tta cag aat atc cgg aat acc att gaa gag act gga aac ttg gct     3652
Arg Leu Gln Asn Ile Arg Asn Thr Ile Glu Glu Thr Gly Asn Leu Ala
                1120                1125                1130 gaa caa gcg cgt gcc cat gta gag aac aca gag cgg ttg att gaa atc     3700
Glu Gln Ala Arg Ala His Val Glu Asn Thr Glu Arg Leu Ile Glu Ile
            1135                1140                1145 gca tcc aga gaa ctt gag aaa gca aaa gtc gct gct gcc aat gtg tca     3748
Ala Ser Arg Glu Leu Glu Lys Ala Lys Val Ala Ala Ala Asn Val Ser
        1150                1155                1160 gtc act cag cca gaa tct aca ggg gac cca aac aac atg act ctt ttg     3796
Val Thr Gln Pro Glu Ser Thr Gly Asp Pro Asn Asn Met Thr Leu Leu
    1165                1170                1175 gca gaa gag gct cga aag ctt gct gaa cgt cat aaa cag gaa gct gat     3844
Ala Glu Glu Ala Arg Lys Leu Ala Glu Arg His Lys Gln Glu Ala Asp
1180                1185                1190                1195 gac att gtt cga gtg gca aag aca gcc aat gat acg tca act gag gca     3892
Asp Ile Val Arg Val Ala Lys Thr Ala Asn Asp Thr Ser Thr Glu Ala
                1200                1205                1210 tac aac ctg ctt ctg agg aca ctg gca gga gaa aat caa aca gca ttt     3940
Tyr Asn Leu Leu Leu Arg Thr Leu Ala Gly Glu Asn Gln Thr Ala Phe
            1215                1220                1225 gag att gaa gag ctt aat agg aag tat gaa caa gcg aag aac atc tca     3988
Glu Ile Glu Glu Leu Asn Arg Lys Tyr Glu Gln Ala Lys Asn Ile Ser
        1230                1235                1240 cag gat ctg gaa aaa caa gct gcc cga gta cat gag gag gcc aaa agg     4036
Gln Asp Leu Glu Lys Gln Ala Ala Arg Val His Glu Glu Ala Lys Arg
    1245                1250                1255 gcc ggt gac aaa gct gtg gag atc tat gcc agc gtg gct cag ctg agc     4084
Ala Gly Asp Lys Ala Val Glu Ile Tyr Ala Ser Val Ala Gln Leu Ser
1260                1265                1270                1275 cct ttg gac tct gag aca ctg gag aat gaa gca aat aac ata aag atg     4132
Pro Leu Asp Ser Glu Thr Leu Glu Asn Glu Ala Asn Asn Ile Lys Met
                1280                1285                1290 gaa gct gag aat ctg gaa caa ctg att gac cag aaa tta aaa gat tat     4180
Glu Ala Glu Asn Leu Glu Gln Leu Ile Asp Gln Lys Leu Lys Asp Tyr
            1295                1300                1305 gag gac ctc aga gaa gat atg aga ggg aag gaa ctt gaa gtc aag aac     4228
Glu Asp Leu Arg Glu Asp Met Arg Gly Lys Glu Leu Glu Val Lys Asn
        1310                1315                1320 ctt ctg gag aaa ggc aag act gaa cag cag acc gca gac caa ctc cta     4276
```

```
Leu Leu Glu Lys Gly Lys Thr Glu Gln Gln Thr Ala Asp Gln Leu Leu
    1325                1330                1335 gcc cga gct gat gct gcc aag gcc ctc gct gaa gaa gct gca aag aag      4324
Ala Arg Ala Asp Ala Ala Lys Ala Leu Ala Glu Glu Ala Ala Lys Lys
1340            1345                1350                1355 gga cgg gat acc tta caa gaa gct aat gac att ctc aac aac ctg aaa      4372
Gly Arg Asp Thr Leu Gln Glu Ala Asn Asp Ile Leu Asn Asn Leu Lys
            1360                1365                1370 gat ttt gat agg cgc gtg aac gat aac aag acg gcc gca gag gag gca      4420
Asp Phe Asp Arg Arg Val Asn Asp Asn Lys Thr Ala Ala Glu Glu Ala
        1375                1380                1385 cta agg aag att cct gcc atc aac cag acc atc act gaa gcc aat gaa      4468
Leu Arg Lys Ile Pro Ala Ile Asn Gln Thr Ile Thr Glu Ala Asn Glu
    1390                1395                1400 aag acc aga gaa gcc cag cag gcc ctg ggc agt gct gcg gcg gat gcc      4516
Lys Thr Arg Glu Ala Gln Gln Ala Leu Gly Ser Ala Ala Ala Asp Ala
1405            1410                1415 aca gag gcc aag aac aag gcc cat gag gcg gag agg atc gca agc gct      4564
Thr Glu Ala Lys Asn Lys Ala His Glu Ala Glu Arg Ile Ala Ser Ala
1420            1425                1430                1435 gtc caa aag aat gcc acc agc acc aag gca gaa gct gaa aga act ttt      4612
Val Gln Lys Asn Ala Thr Ser Thr Lys Ala Glu Ala Glu Arg Thr Phe
            1440                1445                1450 gca gaa gtt aca gat ctg gat aat gag gtg aac aat atg ttg aag caa      4660
Ala Glu Val Thr Asp Leu Asp Asn Glu Val Asn Asn Met Leu Lys Gln
        1455                1460                1465 ctg cag gaa gca gaa aaa gag cta aag aga aaa caa gat gac gct gac      4708
Leu Gln Glu Ala Glu Lys Glu Leu Lys Arg Lys Gln Asp Asp Ala Asp
    1470                1475                1480 cag gac atg atg atg gca ggg atg gct tca cag gct gct caa gaa gcc      4756
Gln Asp Met Met Met Ala Gly Met Ala Ser Gln Ala Ala Gln Glu Ala
1485            1490                1495 gag atc aat gcc aga aaa gcc aaa aac tct gtt act agc ctc ctc agc      4804
Glu Ile Asn Ala Arg Lys Ala Lys Asn Ser Val Thr Ser Leu Leu Ser
1500            1505                1510                1515 att att aat gac ctc ttg gag cag ctg ggg cag ctg gat aca gtg gac      4852
Ile Ile Asn Asp Leu Leu Glu Gln Leu Gly Gln Leu Asp Thr Val Asp
            1520                1525                1530 ctg aat aag cta aac gag att gaa ggc acc cta aac aaa gcc aaa gat      4900
Leu Asn Lys Leu Asn Glu Ile Glu Gly Thr Leu Asn Lys Ala Lys Asp
        1535                1540                1545 gaa atg aag gtc agc gat ctt gat agg aaa gtg tct gac ctg gag aat      4948
Glu Met Lys Val Ser Asp Leu Asp Arg Lys Val Ser Asp Leu Glu Asn
    1550                1555                1560 gaa gcc aag aag cag gag gct gcc atc atg gac tat aac cga gat atc      4996
Glu Ala Lys Lys Gln Glu Ala Ala Ile Met Asp Tyr Asn Arg Asp Ile
1565            1570                1575 gag gag atc atg aag gac att cgc aat ctg gag gac atc agg aag acc      5044
Glu Glu Ile Met Lys Asp Ile Arg Asn Leu Glu Asp Ile Arg Lys Thr
1580            1585                1590                1595 tta cca tct ggc tgc ttc aac acc ccg tcc att gaa aag ccc              5086
Leu Pro Ser Gly Cys Phe Asn Thr Pro Ser Ile Glu Lys Pro
            1600                1605 tagtgtcttt agggctggaa ggcagcatcc ctctgacagg ggggcagttg tgaggccaca    5146
gagtgccttg acacaaagat tacattttc agacccccac tcctctgctg ctgtccatca    5206
ctgtcctttt gaaccaggaa aagtcacaga gtttaaagag aagcaaatta aacatcctga   5266
atcgggaaca aagggttta tctaataaag tgtctcttcc                          5306
```

```
<210> SEQ ID NO 14
<211> LENGTH: 1609
<212> TYPE: PRT
<213> ORGANISM: Homo sapiens

<400> SEQUENCE: 14

Met Arg Gly Ser His Arg Ala Ala Pro Ala Leu Arg Pro Arg Gly Arg
  1               5                  10                  15

Leu Trp Pro Val Leu Ala Val Leu Ala Ala Ala Ala Ala Ala Gly Cys
                 20                  25                  30

Ala Gln Ala Ala Met Asp Glu Cys Thr Asp Glu Gly Gly Arg Pro Gln
             35                  40                  45

Arg Cys Met Pro Glu Phe Val Asn Ala Ala Phe Asn Val Thr Val Val
         50                  55                  60

Ala Thr Asn Thr Cys Gly Thr Pro Pro Glu Glu Tyr Cys Val Gln Thr
 65                  70                  75                  80

Gly Val Thr Gly Val Thr Lys Ser Cys His Leu Cys Asp Ala Gly Gln
                 85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
        195                 200                 205

Phe Ser Asp Ile Ser Pro Leu Thr Gly Gly Asn Val Ala Phe Ser Thr
    210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
        275                 280                 285

Asn Gly His Ala Ser Glu Cys Met Lys Asn Glu Phe Asp Lys Leu Val
    290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
        355                 360                 365

Asn Cys Gln Asp Asn Thr Asp Gly Ala His Cys Glu Arg Cys Arg Glu
    370                 375                 380
```

-continued

```
Asn Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
            405                 410                 415

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
        435                 440                 445

Pro Ser Gly Ser Ile Asp Glu Cys Asn Val Glu Thr Gly Arg Cys Val
    450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
            485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
        515                 520                 525

Glu Gln Arg Asp Gly Ser Glu Ala Ser Leu Glu Trp Ser Ser Glu Arg
    530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
            565                 570                 575

Leu Ser Phe Ser Phe Arg Val Asp Arg Arg Asp Thr Arg Leu Ser Ala
            580                 585                 590

Glu Asp Leu Val Leu Glu Gly Ala Gly Leu Arg Val Ser Val Pro Leu
        595                 600                 605

Ile Ala Gln Gly Asn Ser Tyr Pro Ser Glu Thr Thr Val Lys Tyr Val
    610                 615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
            645                 650                 655

Arg Gly Thr Tyr Ser Glu Arg Ser Ala Gly Tyr Leu Asp Asp Val Thr
            660                 665                 670

Leu Ala Ser Ala Arg Pro Gly Pro Gly Val Pro Ala Thr Trp Val Glu
        675                 680                 685

Ser Cys Thr Cys Pro Val Gly Tyr Gly Gly Gln Phe Cys Glu Met Cys
    690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
            725                 730                 735

Thr Gly Val Cys Asn Cys Arg Asp Asn Thr Ala Gly Pro His Cys Glu
            740                 745                 750

Lys Cys Ser Asp Gly Tyr Tyr Gly Asp Ser Thr Ala Gly Thr Ser Ser
        755                 760                 765

Asp Cys Gln Pro Cys Pro Cys Pro Gly Gly Ser Ser Cys Ala Val Val
    770                 775                 780

Pro Lys Thr Lys Glu Val Val Cys Thr Asn Cys Pro Thr Gly Thr Thr
785                 790                 795                 800
```

-continued

```
Gly Lys Arg Cys Glu Leu Cys Asp Asp Gly Tyr Phe Gly Asp Pro Leu
            805                 810                 815

Gly Arg Asn Gly Pro Val Arg Leu Cys Arg Leu Cys Gln Cys Ser Asp
            820                 825                 830

Asn Ile Asp Pro Asn Ala Val Gly Asn Cys Asn Arg Leu Thr Gly Glu
            835                 840                 845

Cys Leu Lys Cys Ile Tyr Asn Thr Ala Gly Phe Tyr Cys Asp Arg Cys
            850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Pro Tyr Gly Thr Met Lys Gln Gln Ser
                    885                 890                 895

Ser Cys Asn Pro Val Thr Gly Gln Cys Glu Cys Leu Pro His Val Thr
                900                 905                 910

Gly Gln Asp Cys Gly Ala Cys Asp Pro Gly Phe Tyr Asn Leu Gln Ser
            915                 920                 925

Gly Gln Gly Cys Glu Arg Cys Asp Cys His Ala Leu Gly Ser Thr Asn
    930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
            995                 1000                1005

Gly Asn Arg Cys Asp Gln Cys Glu Glu Asn Tyr Phe Tyr Asn Arg Ser
    1010                1015                1020

Trp Pro Gly Cys Gln Glu Cys Pro Ala Cys Tyr Arg Leu Val Lys Asp
1025                1030                1035                1040

Lys Val Ala Asp His Arg Val Lys Leu Gln Glu Leu Glu Ser Leu Ile
                1045                1050                1055

Ala Asn Leu Gly Thr Gly Asp Glu Met Val Thr Asp Gln Ala Phe Glu
            1060                1065                1070

Asp Arg Leu Lys Glu Ala Glu Arg Glu Val Met Asp Leu Leu Arg Glu
            1075                1080                1085

Ala Gln Asp Val Lys Asp Val Asp Gln Asn Leu Met Asp Arg Leu Gln
    1090                1095                1100

Arg Val Asn Asn Thr Leu Ser Ser Gln Ile Ser Arg Leu Gln Asn Ile
1105                1110                1115                1120

Arg Asn Thr Ile Glu Glu Thr Gly Asn Leu Ala Glu Gln Ala Arg Ala
                1125                1130                1135

His Val Glu Asn Thr Glu Arg Leu Ile Glu Ile Ala Ser Arg Glu Leu
            1140                1145                1150

Glu Lys Ala Lys Val Ala Ala Ala Asn Val Ser Val Thr Gln Pro Glu
            1155                1160                1165

Ser Thr Gly Asp Pro Asn Asn Met Thr Leu Leu Ala Glu Glu Ala Arg
    1170                1175                1180

Lys Leu Ala Glu Arg His Lys Gln Glu Ala Asp Asp Ile Val Arg Val
1185                1190                1195                1200

Ala Lys Thr Ala Asn Asp Thr Ser Thr Glu Ala Tyr Asn Leu Leu Leu
                1205                1210                1215

Arg Thr Leu Ala Gly Glu Asn Gln Thr Ala Phe Glu Ile Glu Glu Leu
```

-continued

```
                    1220                1225                1230
Asn Arg Lys Tyr Glu Gln Ala Lys Asn Ile Ser Gln Asp Leu Glu Lys
            1235                1240                1245
Gln Ala Ala Arg Val His Glu Glu Ala Lys Arg Ala Gly Asp Lys Ala
        1250                1255                1260
Val Glu Ile Tyr Ala Ser Val Ala Gln Leu Ser Pro Leu Asp Ser Glu
1265                1270                1275                1280
Thr Leu Glu Asn Glu Ala Asn Asn Ile Lys Met Glu Ala Glu Asn Leu
                1285                1290                1295
Glu Gln Leu Ile Asp Gln Lys Leu Lys Asp Tyr Glu Asp Leu Arg Glu
            1300                1305                1310
Asp Met Arg Gly Lys Glu Leu Glu Val Lys Asn Leu Leu Glu Lys Gly
        1315                1320                1325
Lys Thr Glu Gln Gln Thr Ala Asp Gln Leu Leu Ala Arg Ala Asp Ala
    1330                1335                1340
Ala Lys Ala Leu Ala Glu Glu Ala Lys Lys Gly Arg Asp Thr Leu
1345                1350                1355                1360
Gln Glu Ala Asn Asp Ile Leu Asn Asn Leu Lys Asp Phe Asp Arg Arg
                1365                1370                1375
Val Asn Asp Asn Lys Thr Ala Ala Glu Glu Ala Leu Arg Lys Ile Pro
            1380                1385                1390
Ala Ile Asn Gln Thr Ile Thr Glu Ala Asn Glu Lys Thr Arg Glu Ala
        1395                1400                1405
Gln Gln Ala Leu Gly Ser Ala Ala Ala Asp Ala Thr Glu Ala Lys Asn
    1410                1415                1420
Lys Ala His Glu Ala Glu Arg Ile Ala Ser Ala Val Gln Lys Asn Ala
1425                1430                1435                1440
Thr Ser Thr Lys Ala Glu Ala Glu Arg Thr Phe Ala Glu Val Thr Asp
                1445                1450                1455
Leu Asp Asn Glu Val Asn Asn Met Leu Lys Gln Leu Gln Glu Ala Glu
            1460                1465                1470
Lys Glu Leu Lys Arg Lys Gln Asp Asp Ala Asp Gln Asp Met Met Met
        1475                1480                1485
Ala Gly Met Ala Ser Gln Ala Ala Gln Glu Ala Glu Ile Asn Ala Arg
    1490                1495                1500
Lys Ala Lys Asn Ser Val Thr Ser Leu Leu Ser Ile Ile Asn Asp Leu
1505                1510                1515                1520
Leu Glu Gln Leu Gly Gln Leu Asp Thr Val Asp Leu Asn Lys Leu Asn
            1525                1530                1535
Glu Ile Glu Gly Thr Leu Asn Lys Ala Lys Asp Glu Met Lys Val Ser
        1540                1545                1550
Asp Leu Asp Arg Lys Val Ser Asp Leu Glu Asn Glu Ala Lys Lys Gln
    1555                1560                1565
Glu Ala Ala Ile Met Asp Tyr Asn Arg Asp Ile Glu Glu Ile Met Lys
1570                1575                1580
Asp Ile Arg Asn Leu Glu Asp Ile Arg Lys Thr Leu Pro Ser Gly Cys
1585                1590                1595                1600
Phe Asn Thr Pro Ser Ile Glu Lys Pro
                1605
```

<210> SEQ ID NO 15
<211> LENGTH: 4948
<212> TYPE: DNA
<213> ORGANISM: Homo sapiens

<220> FEATURE:
<221> NAME/KEY: CDS
<222> LOCATION: (1)..(4728)

<400> SEQUENCE: 15

| | | | | | | | | | | | | | | | | |
|---|---|---|---|---|---|---|---|---|---|---|---|---|---|---|---|---|
| cag | gca | gcc | atg | gac | gag | tgc | acg | gac | gag | ggc | ggg | cgg | ccg | cag | cgc | 48 |
| Gln | Ala | Ala | Met | Asp | Glu | Cys | Thr | Asp | Glu | Gly | Gly | Arg | Pro | Gln | Arg | |
| 1 | | | | 5 | | | | | 10 | | | | | 15 | | |
| tgc | atg | ccc | gag | ttc | gtc | aac | gcc | gct | ttc | aac | gtg | act | gtg | gtg | gcc | 96 |
| Cys | Met | Pro | Glu | Phe | Val | Asn | Ala | Ala | Phe | Asn | Val | Thr | Val | Val | Ala | |
| | | | 20 | | | | | 25 | | | | | 30 | | | |
| acc | aac | acg | tgt | ggg | act | ccg | ccc | gag | gaa | tac | tgt | gtg | cag | acc | ggg | 144 |
| Thr | Asn | Thr | Cys | Gly | Thr | Pro | Pro | Glu | Glu | Tyr | Cys | Val | Gln | Thr | Gly | |
| | | 35 | | | | | 40 | | | | | 45 | | | | |
| gtg | acc | ggg | gtc | acc | aag | tcc | tgt | cac | ctg | tgc | gac | gcc | ggg | cag | ccc | 192 |
| Val | Thr | Gly | Val | Thr | Lys | Ser | Cys | His | Leu | Cys | Asp | Ala | Gly | Gln | Pro | |
| 50 | | | | | 55 | | | | | 60 | | | | | | |
| cac | ctg | cag | cac | ggg | gca | gcc | ttc | ctg | acc | gac | tac | aac | aac | cag | gcc | 240 |
| His | Leu | Gln | His | Gly | Ala | Ala | Phe | Leu | Thr | Asp | Tyr | Asn | Asn | Gln | Ala | |
| 65 | | | | 70 | | | | | 75 | | | | | 80 | | |
| gac | acc | acc | tgg | tgg | caa | agc | cag | acc | atg | ctg | gcc | ggg | gtg | cag | tac | 288 |
| Asp | Thr | Thr | Trp | Trp | Gln | Ser | Gln | Thr | Met | Leu | Ala | Gly | Val | Gln | Tyr | |
| | | | | 85 | | | | | 90 | | | | | 95 | | |
| ccc | agc | tcc | atc | aac | ctc | acg | ctg | cac | ctg | gga | aaa | gct | ttt | gac | atc | 336 |
| Pro | Ser | Ser | Ile | Asn | Leu | Thr | Leu | His | Leu | Gly | Lys | Ala | Phe | Asp | Ile | |
| | | | 100 | | | | | 105 | | | | | 110 | | | |
| acc | tat | gtg | cgt | ctc | aag | ttc | cac | acc | agc | cgc | ccg | gag | agc | ttt | gcc | 384 |
| Thr | Tyr | Val | Arg | Leu | Lys | Phe | His | Thr | Ser | Arg | Pro | Glu | Ser | Phe | Ala | |
| | | | 115 | | | | | 120 | | | | | 125 | | | |
| att | tac | aag | cgc | aca | cgg | gaa | gac | ggg | ccc | tgg | att | cct | tac | cag | tac | 432 |
| Ile | Tyr | Lys | Arg | Thr | Arg | Glu | Asp | Gly | Pro | Trp | Ile | Pro | Tyr | Gln | Tyr | |
| 130 | | | | | 135 | | | | | 140 | | | | | | |
| tac | agt | ggt | tcc | tgc | gag | aac | acc | tac | tcc | aag | gca | aac | cgc | ggc | ttc | 480 |
| Tyr | Ser | Gly | Ser | Cys | Glu | Asn | Thr | Tyr | Ser | Lys | Ala | Asn | Arg | Gly | Phe | |
| 145 | | | | | 150 | | | | | 155 | | | | | 160 | |
| atc | agg | aca | gga | ggg | gac | gag | cag | cag | gcc | ttg | tgt | act | gat | gaa | ttc | 528 |
| Ile | Arg | Thr | Gly | Gly | Asp | Glu | Gln | Gln | Ala | Leu | Cys | Thr | Asp | Glu | Phe | |
| | | | | 165 | | | | | 170 | | | | | 175 | | |
| agt | gac | att | tct | ccc | ctc | act | ggg | ggc | aac | gtg | gcc | ttt | tct | acc | ctg | 576 |
| Ser | Asp | Ile | Ser | Pro | Leu | Thr | Gly | Gly | Asn | Val | Ala | Phe | Ser | Thr | Leu | |
| | | | 180 | | | | | 185 | | | | | 190 | | | |
| gaa | gga | agg | ccc | agc | gcc | tat | aac | ttt | gac | aat | agc | cct | gtg | ctg | cag | 624 |
| Glu | Gly | Arg | Pro | Ser | Ala | Tyr | Asn | Phe | Asp | Asn | Ser | Pro | Val | Leu | Gln | |
| | | 195 | | | | | 200 | | | | | 205 | | | | |
| gaa | tgg | gta | act | gcc | act | gac | atc | aga | gta | act | ctt | aat | cgc | ctg | aac | 672 |
| Glu | Trp | Val | Thr | Ala | Thr | Asp | Ile | Arg | Val | Thr | Leu | Asn | Arg | Leu | Asn | |
| | 210 | | | | | 215 | | | | | 220 | | | | | |
| act | ttt | gga | gat | gaa | gtg | ttt | aac | gat | ccc | aaa | gtt | ctc | aag | tcc | tat | 720 |
| Thr | Phe | Gly | Asp | Glu | Val | Phe | Asn | Asp | Pro | Lys | Val | Leu | Lys | Ser | Tyr | |
| 225 | | | | | 230 | | | | | 235 | | | | | 240 | |
| tat | tat | gcc | atc | tct | gat | ttt | gct | gta | ggt | ggc | aga | tgt | aaa | tgt | aat | 768 |
| Tyr | Tyr | Ala | Ile | Ser | Asp | Phe | Ala | Val | Gly | Gly | Arg | Cys | Lys | Cys | Asn | |
| | | | | 245 | | | | | 250 | | | | | 255 | | |
| gga | cac | gca | agc | gag | tgt | atg | aag | aac | gaa | ttt | gat | aag | ctg | gtg | tgt | 816 |
| Gly | His | Ala | Ser | Glu | Cys | Met | Lys | Asn | Glu | Phe | Asp | Lys | Leu | Val | Cys | |
| | | | 260 | | | | | 265 | | | | | 270 | | | |
| aat | tgc | aaa | cat | aac | aca | tat | gga | gta | gac | tgt | gaa | aag | tgt | ctt | cct | 864 |
| Asn | Cys | Lys | His | Asn | Thr | Tyr | Gly | Val | Asp | Cys | Glu | Lys | Cys | Leu | Pro | |
| | | 275 | | | | | 280 | | | | | 285 | | | | |
| ttc | ttc | aat | gac | cgg | ccg | tgg | agg | agg | gca | act | gcg | gaa | agt | gcc | agt | 912 |

```
            Phe Phe Asn Asp Arg Pro Trp Arg Arg Ala Thr Ala Glu Ser Ala Ser
                290                 295                 300 gaa tgc ctg ccc tgt gat tgc aat ggt cga tcc cag gaa tgc tac ttc       960
Glu Cys Leu Pro Cys Asp Cys Asn Gly Arg Ser Gln Glu Cys Tyr Phe
305                 310                 315                 320 gac cct gaa ctc tat cgt tcc act ggc cat ggg ggc cac tgt acc aac      1008
Asp Pro Glu Leu Tyr Arg Ser Thr Gly His Gly Gly His Cys Thr Asn
                325                 330                 335 tgc cag gat aac aca gat ggc gcc cac tgt gag agg tgc cga gag aac      1056
Cys Gln Asp Asn Thr Asp Gly Ala His Cys Glu Arg Cys Arg Glu Asn
            340                 345                 350 ttc ttc cgc ctt ggc aac aat gaa gcc tgc tct tca tgc cac tgt agt      1104
Phe Phe Arg Leu Gly Asn Asn Glu Ala Cys Ser Ser Cys His Cys Ser
        355                 360                 365 cct gtg ggc tct cta agc aca cag tgt gat agt tac ggc aga tgc agc      1152
Pro Val Gly Ser Leu Ser Thr Gln Cys Asp Ser Tyr Gly Arg Cys Ser
370                 375                 380 tgt aag cca gga gtg atg ggg gac aaa tgt gac cgt tgc cag cct gga      1200
Cys Lys Pro Gly Val Met Gly Asp Lys Cys Asp Arg Cys Gln Pro Gly
385                 390                 395                 400 ttc cat tct ctc act gaa gca gga tgc agg cca tgc tct tgt gat ccc      1248
Phe His Ser Leu Thr Glu Ala Gly Cys Arg Pro Cys Ser Cys Asp Pro
                405                 410                 415 tct ggc agc ata gat gaa tgt aat gtt gaa aca gga aga tgt gtt tgc      1296
Ser Gly Ser Ile Asp Glu Cys Asn Val Glu Thr Gly Arg Cys Val Cys
                420                 425                 430 aaa gac aat gtc gaa ggc ttc aat tgt gaa aga tgc aaa cct gga ttt      1344
Lys Asp Asn Val Glu Gly Phe Asn Cys Glu Arg Cys Lys Pro Gly Phe
            435                 440                 445 ttt aat ctg gaa tca tct aat cct cgg ggt tgc aca ccc tgc ttc tgc      1392
Phe Asn Leu Glu Ser Ser Asn Pro Arg Gly Cys Thr Pro Cys Phe Cys
        450                 455                 460 ttt ggg cat tct tct gtc tgt aca aac gct gtt ggc tac agt gtt tat      1440
Phe Gly His Ser Ser Val Cys Thr Asn Ala Val Gly Tyr Ser Val Tyr
465                 470                 475                 480 tct atc tcc tct acc ttt cag att gat gag gat ggg tgg cgt gcg gaa      1488
Ser Ile Ser Ser Thr Phe Gln Ile Asp Glu Asp Gly Trp Arg Ala Glu
                485                 490                 495 cag aga gat ggc tct gaa gca tct ctc gag tgg tcc tct gag agg caa      1536
Gln Arg Asp Gly Ser Glu Ala Ser Leu Glu Trp Ser Ser Glu Arg Gln
                500                 505                 510 gat atc gcc gtg atc tca gac agc tac ttt cct cgg tac ttc att gct      1584
Asp Ile Ala Val Ile Ser Asp Ser Tyr Phe Pro Arg Tyr Phe Ile Ala
            515                 520                 525 cct gca aag ttc ttg ggc aag cag gtg ttg agt tat ggt cag aac ctc      1632
Pro Ala Lys Phe Leu Gly Lys Gln Val Leu Ser Tyr Gly Gln Asn Leu
        530                 535                 540 tcc ttc tcc ttt cga gtg gac agg cga gat act cgc ctc tct gcc gaa      1680
Ser Phe Ser Phe Arg Val Asp Arg Arg Asp Thr Arg Leu Ser Ala Glu
545                 550                 555                 560 gac ctt gtg ctt gag gga gct ggc tta aga gta tct gta ccc ttg atc      1728
Asp Leu Val Leu Glu Gly Ala Gly Leu Arg Val Ser Val Pro Leu Ile
                565                 570                 575 gct cag ggc aat tcc tat cca agt gag acc act gtg aag tat gtc ttc      1776
Ala Gln Gly Asn Ser Tyr Pro Ser Glu Thr Thr Val Lys Tyr Val Phe
                580                 585                 590 agg ctc cat gaa gca aca gat tac cct tgg agg cct gct ctt acc cct      1824
Arg Leu His Glu Ala Thr Asp Tyr Pro Trp Arg Pro Ala Leu Thr Pro
            595                 600                 605
```

-continued

| | |
|---|---|
| ttt gaa ttt cag aag ctc cta aac aac ttg acc tct atc aag ata cgt<br>Phe Glu Phe Gln Lys Leu Leu Asn Asn Leu Thr Ser Ile Lys Ile Arg<br>610                                    615                       620 | 1872 |
| ggg aca tac agt gag aga agt gct gga tat ttg gat gat gtc acc ctg<br>Gly Thr Tyr Ser Glu Arg Ser Ala Gly Tyr Leu Asp Asp Val Thr Leu<br>625                   630                       635                  640 | 1920 |
| gca agt gct cgt cct ggg cct gga gtc cct gca act tgg gtg gag tcc<br>Ala Ser Ala Arg Pro Gly Pro Gly Val Pro Ala Thr Trp Val Glu Ser<br>                       645                       650                  655 | 1968 |
| tgc acc tgt cct gtg gga tat gga ggg cag ttt tgt gag atg tgc ctc<br>Cys Thr Cys Pro Val Gly Tyr Gly Gly Gln Phe Cys Glu Met Cys Leu<br>                660                       665                  670 | 2016 |
| tca ggt tac aga aga gaa act cct aat ctt gga cca tac agt cca tgt<br>Ser Gly Tyr Arg Arg Glu Thr Pro Asn Leu Gly Pro Tyr Ser Pro Cys<br>675                                    680                       685 | 2064 |
| gtg ctt tgc gcc tgc aat gga cac agc gag acc tgt gat cct gag aca<br>Val Leu Cys Ala Cys Asn Gly His Ser Glu Thr Cys Asp Pro Glu Thr<br>         690                       695                       700 | 2112 |
| ggt gtt tgt aac tgc aga gac aat acg gct ggc ccg cac tgt gag aag<br>Gly Val Cys Asn Cys Arg Asp Asn Thr Ala Gly Pro His Cys Glu Lys<br>705                                710                       715                  720 | 2160 |
| tgc agt gat ggg tac tat gga gat tca act gca ggc acc tcc tcc gat<br>Cys Ser Asp Gly Tyr Tyr Gly Asp Ser Thr Ala Gly Thr Ser Ser Asp<br>                       725                       730                       735 | 2208 |
| tgc caa ccc tgt ccg tgt cct gga ggt tca agt tgt gct gtt gtt ccc<br>Cys Gln Pro Cys Pro Cys Pro Gly Gly Ser Ser Cys Ala Val Val Pro<br>                740                       745                  750 | 2256 |
| aag aca aag gag gtg gtg tgc acc aac tgt cct act ggc acc act ggt<br>Lys Thr Lys Glu Val Val Cys Thr Asn Cys Pro Thr Gly Thr Thr Gly<br>755                                760                       765 | 2304 |
| aag aga tgt gag ctc tgt gat gat ggc tac ttt gga gac ccc ctg ggt<br>Lys Arg Cys Glu Leu Cys Asp Asp Gly Tyr Phe Gly Asp Pro Leu Gly<br>770                                775                       780 | 2352 |
| aga aac ggc cct gtg aga ctt tgc cgc ctg tgc cag tgc agt gac aac<br>Arg Asn Gly Pro Val Arg Leu Cys Arg Leu Cys Gln Cys Ser Asp Asn<br>785                                790                       795                  800 | 2400 |
| atc gat ccc aac gca gtt gga aat tgc aat cgc ttg acg gga gaa tgc<br>Ile Asp Pro Asn Ala Val Gly Asn Cys Asn Arg Leu Thr Gly Glu Cys<br>                       805                       810                       815 | 2448 |
| ctg aag tgc atc tat aac act gct ggc ttc tat tgt gac cgg tgc aaa<br>Leu Lys Cys Ile Tyr Asn Thr Ala Gly Phe Tyr Cys Asp Arg Cys Lys<br>                820                       825                  830 | 2496 |
| gac gga ttt ttt gga aat ccc ctg gct ccc aat cca gca gac aaa tgc<br>Asp Gly Phe Phe Gly Asn Pro Leu Ala Pro Asn Pro Ala Asp Lys Cys<br>                     835                       840                  845 | 2544 |
| aaa gcc tgc aat tgc aat ccg tat ggg acc atg aag cag cag agc agc<br>Lys Ala Cys Asn Cys Asn Pro Tyr Gly Thr Met Lys Gln Gln Ser Ser<br>850                                855                       860 | 2592 |
| tgt aac ccc gtg acg ggg cag tgt gaa tgt ttg cct cac gtg act ggc<br>Cys Asn Pro Val Thr Gly Gln Cys Glu Cys Leu Pro His Val Thr Gly<br>865                                870                       875                  880 | 2640 |
| cag gac tgt ggt gct tgt gac cct gga ttc tac aat ctg cag agt ggg<br>Gln Asp Cys Gly Ala Cys Asp Pro Gly Phe Tyr Asn Leu Gln Ser Gly<br>                       885                       890                       895 | 2688 |
| caa ggc tgt gag agg tgt gac tgc cat gcc ttg ggc tcc acc aat ggg<br>Gln Gly Cys Glu Arg Cys Asp Cys His Ala Leu Gly Ser Thr Asn Gly<br>                900                       905                  910 | 2736 |
| cag tgt gac atc cgc acc ggc cag tgt gag tgc cag ccc ggc atc act<br>Gln Cys Asp Ile Arg Thr Gly Gln Cys Glu Cys Gln Pro Gly Ile Thr<br>                915                       920                  925 | 2784 |

-continued

| | |
|---|---|
| ggt cag cac tgt gag cgc tgt gag gtc aac cac ttt ggg ttt gga cct<br>Gly Gln His Cys Glu Arg Cys Glu Val Asn His Phe Gly Phe Gly Pro<br>930                    935                  940 | 2832 |
| gaa ggc tgc aaa ccc tgt gac tgt cat cct gag gga tct ctt tca ctt<br>Glu Gly Cys Lys Pro Cys Asp Cys His Pro Glu Gly Ser Leu Ser Leu<br>945                    950                  955                  960 | 2880 |
| cag tgc aaa gat gat ggt cgc tgt gaa tgc aga gaa ggc ttt gtg gga<br>Gln Cys Lys Asp Asp Gly Arg Cys Glu Cys Arg Glu Gly Phe Val Gly<br>                  965                  970                  975 | 2928 |
| aat cgc tgt gac cag tgt gaa gaa aac tat ttc tac aat cgg tct tgg<br>Asn Arg Cys Asp Gln Cys Glu Glu Asn Tyr Phe Tyr Asn Arg Ser Trp<br>980                    985                  990 | 2976 |
| cct ggc tgc cag gaa tgt cca gct tgt tac cgg ctg gta aag gat aag<br>Pro Gly Cys Gln Glu Cys Pro Ala Cys Tyr Arg Leu Val Lys Asp Lys<br>995                    1000                1005 | 3024 |
| gtt gct gat cat aga gtg aag ctc cag gaa tta gag agt ctc ata gca<br>Val Ala Asp His Arg Val Lys Leu Gln Glu Leu Glu Ser Leu Ile Ala<br>    1010                  1015                1020 | 3072 |
| aac ctt gga act ggg gat gag atg gtg aca gat caa gcc ttc gag gat<br>Asn Leu Gly Thr Gly Asp Glu Met Val Thr Asp Gln Ala Phe Glu Asp<br>1025                   1030                1035                1040 | 3120 |
| aga cta aag gaa gca gag agg gaa gtt atg gac ctc ctt cgt gag gcc<br>Arg Leu Lys Glu Ala Glu Arg Glu Val Met Asp Leu Leu Arg Glu Ala<br>                  1045                1050                1055 | 3168 |
| cag gat gtc aaa gat gtt gac cag aat ttg atg gat cgc cta cag aga<br>Gln Asp Val Lys Asp Val Asp Gln Asn Leu Met Asp Arg Leu Gln Arg<br>    1060                  1065                1070 | 3216 |
| gtg aat aac act ctg tcc agc caa att agc cgt tta cag aat atc cgg<br>Val Asn Asn Thr Leu Ser Ser Gln Ile Ser Arg Leu Gln Asn Ile Arg<br>1075                   1080                1085 | 3264 |
| aat acc att gaa gag act gga aac ttg gct gaa caa gcg cgt gcc cat<br>Asn Thr Ile Glu Glu Thr Gly Asn Leu Ala Glu Gln Ala Arg Ala His<br>                  1090                1095                1100 | 3312 |
| gta gag aac aca gag cgg ttg att gaa atc gca tcc aga gaa ctt gag<br>Val Glu Asn Thr Glu Arg Leu Ile Glu Ile Ala Ser Arg Glu Leu Glu<br>1105                   1110                1115                1120 | 3360 |
| aaa gca aaa gtc gct gct gcc aat gtg tca gtc act cag cca gaa tct<br>Lys Ala Lys Val Ala Ala Ala Asn Val Ser Val Thr Gln Pro Glu Ser<br>                  1125                1130                1135 | 3408 |
| aca ggg gac cca aac aac atg act ctt ttg gca gaa gag gct cga aag<br>Thr Gly Asp Pro Asn Asn Met Thr Leu Leu Ala Glu Glu Ala Arg Lys<br>    1140                  1145                1150 | 3456 |
| ctt gct gaa cgt cat aaa cag gaa gct gat gac att gtt cga gtg gca<br>Leu Ala Glu Arg His Lys Gln Glu Ala Asp Asp Ile Val Arg Val Ala<br>1155                   1160                1165 | 3504 |
| aag aca gcc aat gat acg tca act gag gca tac aac ctg ctt ctg agg<br>Lys Thr Ala Asn Asp Thr Ser Thr Glu Ala Tyr Asn Leu Leu Leu Arg<br>                  1170                1175                1180 | 3552 |
| aca ctg gca gga gaa aat caa aca gca ttt gag att gaa gag ctt aat<br>Thr Leu Ala Gly Glu Asn Gln Thr Ala Phe Glu Ile Glu Glu Leu Asn<br>1185                   1190                1195                1200 | 3600 |
| agg aag tat gaa caa gcg aag aac atc tca cag gat ctg gaa aaa caa<br>Arg Lys Tyr Glu Gln Ala Lys Asn Ile Ser Gln Asp Leu Glu Lys Gln<br>                  1205                1210                1215 | 3648 |
| gct gcc cga gta cat gag gag gcc aaa agg gcc ggt gac aaa gct gtg<br>Ala Ala Arg Val His Glu Glu Ala Lys Arg Ala Gly Asp Lys Ala Val<br>    1220                  1225                1230 | 3696 |
| gag atc tat gcc agc gtg gct cag ctg agc cct ttg gac tct gag aca<br>Glu Ile Tyr Ala Ser Val Ala Gln Leu Ser Pro Leu Asp Ser Glu Thr | 3744 |

-continued

```
                1235                1240                1245
ctg gag aat gaa gca aat aac ata aag atg gaa gct gag aat ctg gaa    3792
Leu Glu Asn Glu Ala Asn Asn Ile Lys Met Glu Ala Glu Asn Leu Glu
    1250                1255                1260 caa ctg att gac cag aaa tta aaa gat tat gag gac ctc aga gaa gat    3840
Gln Leu Ile Asp Gln Lys Leu Lys Asp Tyr Glu Asp Leu Arg Glu Asp
1265                1270                1275                1280 atg aga ggg aag gaa ctt gaa gtc aag aac ctt ctg gag aaa ggc aag    3888
Met Arg Gly Lys Glu Leu Glu Val Lys Asn Leu Leu Glu Lys Gly Lys
                1285                1290                1295 act gaa cag cag acc gca gac caa ctc cta gcc cga gct gat gct gcc    3936
Thr Glu Gln Gln Thr Ala Asp Gln Leu Leu Ala Arg Ala Asp Ala Ala
        1300                1305                1310 aag gcc ctc gct gaa gaa gct gca aag aag gga cgg gat acc tta caa    3984
Lys Ala Leu Ala Glu Glu Ala Ala Lys Lys Gly Arg Asp Thr Leu Gln
    1315                1320                1325 gaa gct aat gac att ctc aac aac ctg aaa gat ttt gat agg cgc gtg    4032
Glu Ala Asn Asp Ile Leu Asn Asn Leu Lys Asp Phe Asp Arg Arg Val
1330                1335                1340 aac gat aac aag acg gcc gca gag gag gca cta agg aag att cct gcc    4080
Asn Asp Asn Lys Thr Ala Ala Glu Glu Ala Leu Arg Lys Ile Pro Ala
1345                1350                1355                1360 atc aac cag acc atc act gaa gcc aat gaa aag acc aga gaa gcc cag    4128
Ile Asn Gln Thr Ile Thr Glu Ala Asn Glu Lys Thr Arg Glu Ala Gln
                1365                1370                1375 cag gcc ctg ggc agt gct gcg gcg gat gcc aca gag gcc aag aac aag    4176
Gln Ala Leu Gly Ser Ala Ala Ala Asp Ala Thr Glu Ala Lys Asn Lys
        1380                1385                1390 gcc cat gag gcg gag agg atc gca agc gct gtc caa aag aat gcc acc    4224
Ala His Glu Ala Glu Arg Ile Ala Ser Ala Val Gln Lys Asn Ala Thr
    1395                1400                1405 agc acc aag gca gaa gct gaa aga act ttt gca gaa gtt aca gat ctg    4272
Ser Thr Lys Ala Glu Ala Glu Arg Thr Phe Ala Glu Val Thr Asp Leu
    1410                1415                1420 gat aat gag gtg aac aat atg ttg aag caa ctg cag gaa gca gaa aaa    4320
Asp Asn Glu Val Asn Asn Met Leu Lys Gln Leu Gln Glu Ala Glu Lys
1425                1430                1435                1440 gag cta aag aga aaa caa gat gac gct gac cag gac atg atg atg gca    4368
Glu Leu Lys Arg Lys Gln Asp Asp Ala Asp Gln Asp Met Met Met Ala
                1445                1450                1455 ggg atg gct tca cag gct gct caa gaa gcc gag atc aat gcc aga aaa    4416
Gly Met Ala Ser Gln Ala Ala Gln Glu Ala Glu Ile Asn Ala Arg Lys
        1460                1465                1470 gcc aaa aac tct gtt act agc ctc ctc agc att att aat gac ctc ttg    4464
Ala Lys Asn Ser Val Thr Ser Leu Leu Ser Ile Ile Asn Asp Leu Leu
    1475                1480                1485 gag cag ctg ggg cag ctg gat aca gtg gac ctg aat aag cta aac gag    4512
Glu Gln Leu Gly Gln Leu Asp Thr Val Asp Leu Asn Lys Leu Asn Glu
    1490                1495                1500 att gaa ggc acc cta aac aaa gcc aaa gat gaa atg aag gtc agc gat    4560
Ile Glu Gly Thr Leu Asn Lys Ala Lys Asp Glu Met Lys Val Ser Asp
1505                1510                1515                1520 ctt gat agg aaa gtg tct gac ctg gag aat gaa gcc aag aag cag gag    4608
Leu Asp Arg Lys Val Ser Asp Leu Glu Asn Glu Ala Lys Lys Gln Glu
                1525                1530                1535 gct gcc atc atg gac tat aac cga gat atc gag gag atc atg aag gac    4656
Ala Ala Ile Met Asp Tyr Asn Arg Asp Ile Glu Glu Ile Met Lys Asp
        1540                1545                1550 att cgc aat ctg gag gac atc agg aag acc tta cca tct ggc tgc ttc    4704
```

-continued

```
Ile Arg Asn Leu Glu Asp Ile Arg Lys Thr Leu Pro Ser Gly Cys Phe
    1555                1560                1565 aac acc ccg tcc att gaa aag ccc tagtgtcttt agggctggaa ggcagcatcc    4758
Asn Thr Pro Ser Ile Glu Lys Pro
    1570            1575 ctctgacagg ggggcagttg tgaggccaca gagtgccttg acacaaagat tacattttc    4818 agaccccccac tcctctgctg ctgtccatca ctgtcctttt gaaccaggaa aagtcacaga   4878
gtttaaagag aagcaaatta aacatcctga atcgggaaca aagggttta tctaataaag    4938 tgtctcttcc                                                          4948
```

<210> SEQ ID NO 16
<211> LENGTH: 1576
<212> TYPE: PRT
<213> ORGANISM: Homo sapiens

<400> SEQUENCE: 16

```
Gln Ala Ala Met Asp Glu Cys Thr Asp Glu Gly Gly Arg Pro Gln Arg
1               5                   10                  15

Cys Met Pro Glu Phe Val Asn Ala Ala Phe Asn Val Thr Val Val Ala
            20                  25                  30

Thr Asn Thr Cys Gly Thr Pro Pro Glu Glu Tyr Cys Val Gln Thr Gly
        35                  40                  45

Val Thr Gly Val Thr Lys Ser Cys His Leu Cys Asp Ala Gly Gln Pro
    50                  55                  60

His Leu Gln His Gly Ala Ala Phe Leu Thr Asp Tyr Asn Asn Gln Ala
65                  70                  75                  80

Asp Thr Thr Trp Trp Gln Ser Gln Thr Met Leu Ala Gly Val Gln Tyr
                85                  90                  95

Pro Ser Ser Ile Asn Leu Thr Leu His Leu Gly Lys Ala Phe Asp Ile
            100                 105                 110

Thr Tyr Val Arg Leu Lys Phe His Thr Ser Arg Pro Glu Ser Phe Ala
        115                 120                 125

Ile Tyr Lys Arg Thr Arg Glu Asp Gly Pro Trp Ile Pro Tyr Gln Tyr
    130                 135                 140

Tyr Ser Gly Ser Cys Glu Asn Thr Tyr Ser Lys Ala Asn Arg Gly Phe
145                 150                 155                 160

Ile Arg Thr Gly Gly Asp Glu Gln Gln Ala Leu Cys Thr Asp Glu Phe
                165                 170                 175

Ser Asp Ile Ser Pro Leu Thr Gly Gly Asn Val Ala Phe Ser Thr Leu
            180                 185                 190

Glu Gly Arg Pro Ser Ala Tyr Asn Phe Asp Asn Ser Pro Val Leu Gln
        195                 200                 205

Glu Trp Val Thr Ala Thr Asp Ile Arg Val Thr Leu Asn Arg Leu Asn
    210                 215                 220

Thr Phe Gly Asp Glu Val Phe Asn Asp Pro Lys Val Leu Lys Ser Tyr
225                 230                 235                 240

Tyr Tyr Ala Ile Ser Asp Phe Ala Val Gly Gly Arg Cys Lys Cys Asn
                245                 250                 255

Gly His Ala Ser Glu Cys Met Lys Asn Glu Phe Asp Lys Leu Val Cys
            260                 265                 270

Asn Cys Lys His Asn Thr Tyr Gly Val Asp Cys Glu Lys Cys Leu Pro
        275                 280                 285

Phe Phe Asn Asp Arg Pro Trp Arg Arg Ala Thr Ala Glu Ser Ala Ser
    290                 295                 300
```

-continued

```
Glu Cys Leu Pro Cys Asp Cys Asn Gly Arg Ser Gln Glu Cys Tyr Phe
305                 310                 315                 320

Asp Pro Glu Leu Tyr Arg Ser Thr Gly His Gly His Cys Thr Asn
            325                 330                 335

Cys Gln Asp Asn Thr Asp Gly Ala His Cys Glu Arg Cys Arg Glu Asn
                340                 345                 350

Phe Phe Arg Leu Gly Asn Asn Glu Ala Cys Ser Ser Cys His Cys Ser
        355                 360                 365

Pro Val Gly Ser Leu Ser Thr Gln Cys Asp Ser Tyr Gly Arg Cys Ser
    370                 375                 380

Cys Lys Pro Gly Val Met Gly Asp Lys Cys Asp Arg Cys Gln Pro Gly
385                 390                 395                 400

Phe His Ser Leu Thr Glu Ala Gly Cys Arg Pro Cys Ser Cys Asp Pro
                405                 410                 415

Ser Gly Ser Ile Asp Glu Cys Asn Val Glu Thr Gly Arg Cys Val Cys
            420                 425                 430

Lys Asp Asn Val Glu Gly Phe Asn Cys Glu Arg Cys Lys Pro Gly Phe
        435                 440                 445

Phe Asn Leu Glu Ser Ser Asn Pro Arg Gly Cys Thr Pro Cys Phe Cys
    450                 455                 460

Phe Gly His Ser Ser Val Cys Thr Asn Ala Val Gly Tyr Ser Val Tyr
465                 470                 475                 480

Ser Ile Ser Ser Thr Phe Gln Ile Asp Glu Asp Gly Trp Arg Ala Glu
                485                 490                 495

Gln Arg Asp Gly Ser Glu Ala Ser Leu Glu Trp Ser Ser Glu Arg Gln
            500                 505                 510

Asp Ile Ala Val Ile Ser Asp Ser Tyr Phe Pro Arg Tyr Phe Ile Ala
        515                 520                 525

Pro Ala Lys Phe Leu Gly Lys Gln Val Leu Ser Tyr Gly Gln Asn Leu
    530                 535                 540

Ser Phe Ser Phe Arg Val Asp Arg Arg Asp Thr Arg Leu Ser Ala Glu
545                 550                 555                 560

Asp Leu Val Leu Glu Gly Ala Gly Leu Arg Val Ser Val Pro Leu Ile
                565                 570                 575

Ala Gln Gly Asn Ser Tyr Pro Ser Glu Thr Thr Val Lys Tyr Val Phe
            580                 585                 590

Arg Leu His Glu Ala Thr Asp Tyr Pro Trp Arg Pro Ala Leu Thr Pro
        595                 600                 605

Phe Glu Phe Gln Lys Leu Leu Asn Asn Leu Thr Ser Ile Lys Ile Arg
    610                 615                 620

Gly Thr Tyr Ser Glu Arg Ser Ala Gly Tyr Leu Asp Asp Val Thr Leu
625                 630                 635                 640

Ala Ser Ala Arg Pro Gly Pro Gly Val Pro Ala Thr Trp Val Glu Ser
                645                 650                 655

Cys Thr Cys Pro Val Gly Tyr Gly Gly Gln Phe Cys Glu Met Cys Leu
            660                 665                 670

Ser Gly Tyr Arg Arg Glu Thr Pro Asn Leu Gly Pro Tyr Ser Pro Cys
        675                 680                 685

Val Leu Cys Ala Cys Asn Gly His Ser Glu Thr Cys Asp Pro Glu Thr
    690                 695                 700

Gly Val Cys Asn Cys Arg Asp Asn Thr Ala Gly Pro His Cys Glu Lys
705                 710                 715                 720
```

-continued

```
Cys Ser Asp Gly Tyr Tyr Gly Asp Ser Thr Ala Gly Thr Ser Ser Asp
                725                 730                 735

Cys Gln Pro Cys Pro Cys Pro Gly Gly Ser Ser Cys Ala Val Val Pro
            740                 745                 750

Lys Thr Lys Glu Val Val Cys Thr Asn Cys Pro Thr Gly Thr Thr Gly
        755                 760                 765

Lys Arg Cys Glu Leu Cys Asp Asp Gly Tyr Phe Gly Asp Pro Leu Gly
770                 775                 780

Arg Asn Gly Pro Val Arg Leu Cys Arg Leu Cys Gln Cys Ser Asp Asn
785                 790                 795                 800

Ile Asp Pro Asn Ala Val Gly Asn Cys Asn Arg Leu Thr Gly Glu Cys
                805                 810                 815

Leu Lys Cys Ile Tyr Asn Thr Ala Gly Phe Tyr Cys Asp Arg Cys Lys
            820                 825                 830

Asp Gly Phe Phe Gly Asn Pro Leu Ala Pro Asn Pro Ala Asp Lys Cys
        835                 840                 845

Lys Ala Cys Asn Cys Asn Pro Tyr Gly Thr Met Lys Gln Gln Ser Ser
    850                 855                 860

Cys Asn Pro Val Thr Gly Gln Cys Glu Cys Leu Pro His Val Thr Gly
865                 870                 875                 880

Gln Asp Cys Gly Ala Cys Asp Pro Gly Phe Tyr Asn Leu Gln Ser Gly
                885                 890                 895

Gln Gly Cys Glu Arg Cys Asp Cys His Ala Leu Gly Ser Thr Asn Gly
            900                 905                 910

Gln Cys Asp Ile Arg Thr Gly Gln Cys Glu Cys Gln Pro Gly Ile Thr
        915                 920                 925

Gly Gln His Cys Glu Arg Cys Glu Val Asn His Phe Gly Phe Gly Pro
    930                 935                 940

Glu Gly Cys Lys Pro Cys Asp Cys His Pro Glu Gly Ser Leu Ser Leu
945                 950                 955                 960

Gln Cys Lys Asp Asp Gly Arg Cys Glu Cys Arg Glu Gly Phe Val Gly
                965                 970                 975

Asn Arg Cys Asp Gln Cys Glu Glu Asn Tyr Phe Tyr Asn Arg Ser Trp
            980                 985                 990

Pro Gly Cys Gln Glu Cys Pro Ala Cys Tyr Arg Leu Val Lys Asp Lys
        995                 1000                1005

Val Ala Asp His Arg Val Lys Leu Gln Glu Leu Glu Ser Leu Ile Ala
    1010                1015                1020

Asn Leu Gly Thr Gly Asp Glu Met Val Thr Asp Gln Ala Phe Glu Asp
1025                1030                1035                1040

Arg Leu Lys Glu Ala Glu Arg Glu Val Met Asp Leu Leu Arg Glu Ala
                1045                1050                1055

Gln Asp Val Lys Asp Val Asp Gln Asn Leu Met Asp Arg Leu Gln Arg
            1060                1065                1070

Val Asn Asn Thr Leu Ser Ser Gln Ile Ser Arg Leu Gln Asn Ile Arg
        1075                1080                1085

Asn Thr Ile Glu Glu Thr Gly Asn Leu Ala Glu Gln Ala Arg Ala His
    1090                1095                1100

Val Glu Asn Thr Glu Arg Leu Ile Glu Ile Ala Ser Arg Glu Leu Glu
1105                1110                1115                1120

Lys Ala Lys Val Ala Ala Ala Asn Val Ser Val Thr Gln Pro Glu Ser
                1125                1130                1135

Thr Gly Asp Pro Asn Asn Met Thr Leu Leu Ala Glu Glu Ala Arg Lys
```

-continued

```
            1140                1145                1150
Leu Ala Glu Arg His Lys Gln Glu Ala Asp Asp Ile Val Arg Val Ala
        1155                1160                1165
Lys Thr Ala Asn Asp Thr Ser Thr Glu Ala Tyr Asn Leu Leu Leu Arg
    1170                1175                1180
Thr Leu Ala Gly Glu Asn Gln Thr Ala Phe Glu Ile Glu Glu Leu Asn
1185                1190                1195                1200
Arg Lys Tyr Glu Gln Ala Lys Asn Ile Ser Gln Asp Leu Glu Lys Gln
            1205                1210                1215
Ala Ala Arg Val His Glu Glu Ala Lys Arg Ala Gly Asp Lys Ala Val
        1220                1225                1230
Glu Ile Tyr Ala Ser Val Ala Gln Leu Ser Pro Leu Asp Ser Glu Thr
    1235                1240                1245
Leu Glu Asn Glu Ala Asn Asn Ile Lys Met Glu Ala Glu Asn Leu Glu
        1250                1255                1260
Gln Leu Ile Asp Gln Lys Leu Lys Asp Tyr Glu Asp Leu Arg Glu Asp
1265                1270                1275                1280
Met Arg Gly Lys Glu Leu Glu Val Lys Asn Leu Leu Glu Lys Gly Lys
            1285                1290                1295
Thr Glu Gln Gln Thr Ala Asp Gln Leu Leu Ala Arg Ala Asp Ala Ala
        1300                1305                1310
Lys Ala Leu Ala Glu Glu Ala Ala Lys Lys Gly Arg Asp Thr Leu Gln
    1315                1320                1325
Glu Ala Asn Asp Ile Leu Asn Asn Leu Lys Asp Phe Asp Arg Arg Val
        1330                1335                1340
Asn Asp Asn Lys Thr Ala Ala Glu Gln Ala Leu Arg Lys Ile Pro Ala
1345                1350                1355                1360
Ile Asn Gln Thr Ile Thr Glu Ala Asn Glu Lys Thr Arg Glu Ala Gln
            1365                1370                1375
Gln Ala Leu Gly Ser Ala Ala Ala Asp Ala Thr Glu Ala Lys Asn Lys
        1380                1385                1390
Ala His Glu Ala Glu Arg Ile Ala Ser Ala Val Gln Lys Asn Ala Thr
    1395                1400                1405
Ser Thr Lys Ala Glu Ala Glu Arg Thr Phe Ala Glu Val Thr Asp Leu
        1410                1415                1420
Asp Asn Glu Val Asn Asn Met Leu Lys Gln Leu Gln Glu Ala Glu Lys
1425                1430                1435                1440
Glu Leu Lys Arg Lys Gln Asp Asp Ala Asp Gln Asp Met Met Met Ala
            1445                1450                1455
Gly Met Ala Ser Gln Ala Ala Gln Glu Ala Glu Ile Asn Ala Arg Lys
        1460                1465                1470
Ala Lys Asn Ser Val Thr Ser Leu Leu Ser Ile Ile Asn Asp Leu Leu
    1475                1480                1485
Glu Gln Leu Gly Gln Leu Asp Thr Val Asp Leu Asn Lys Leu Asn Glu
        1490                1495                1500
Ile Glu Gly Thr Leu Asn Lys Ala Lys Asp Glu Met Lys Val Ser Asp
1505                1510                1515                1520
Leu Asp Arg Lys Val Ser Asp Leu Glu Asn Glu Ala Lys Lys Gln Glu
            1525                1530                1535
Ala Ala Ile Met Asp Tyr Asn Arg Asp Ile Glu Glu Ile Met Lys Asp
        1540                1545                1550
Ile Arg Asn Leu Glu Asp Ile Arg Lys Thr Leu Pro Ser Gly Cys Phe
    1555                1560                1565
```

Asn Thr Pro Ser Ile Glu Lys Pro
     1570               1575

<210> SEQ ID NO 17
<211> LENGTH: 7554
<212> TYPE: DNA
<213> ORGANISM: Mus musculus
<220> FEATURE:
<221> NAME/KEY: CDS
<222> LOCATION: (193)..(5007)
<221> NAME/KEY: sig_peptide
<222> LOCATION: (193)..(291)

<400> SEQUENCE: 17

```
cgcaccggga agtagcggag gcagcgcgat cttggctcgg acgcccaccc atcggctctg      60
cgtccggctc tcggcctcca gcccggtcca cagcccggcc tcggcccgca gcggaggatc     120
ggcctcggga tacgccgcta ggcgagtgca gcgcggcacc ccagcctttg ccgaggggcc     180
```

| | | |
|---|---|---|
| cgccgcagcg gg atg acg ggc ggc ggg cgg gcc gcg ctg gcc ctg cag ccc<br>            Met Thr Gly Gly Gly Arg Ala Ala Leu Ala Leu Gln Pro<br>             1             5               10 | | 231 |
| cgg ggg cgg ctg tgg ccg ctg ttg gct gtg ctg gcg gct gtg gcg ggc<br>Arg Gly Arg Leu Trp Pro Leu Leu Ala Val Leu Ala Ala Val Ala Gly<br> 15                  20                  25 | | 279 |
| tgt gtc cgg gcg gcc atg gac gag tgc gcg gat gag ggc ggg cgg ccg<br>Cys Val Arg Ala Ala Met Asp Glu Cys Ala Asp Glu Gly Gly Arg Pro<br>30                  35                  40                  45 | | 327 |
| cag cgc tgc atg ccg gag ttt gtt aat gcc gcc ttc aat gtg acc gtg<br>Gln Arg Cys Met Pro Glu Phe Val Asn Ala Ala Phe Asn Val Thr Val<br>              50                  55                  60 | | 375 |
| gtg gct acc aac acg tgt ggg act ccg ccc gag gag tac tgc gtg cag<br>Val Ala Thr Asn Thr Cys Gly Thr Pro Pro Glu Glu Tyr Cys Val Gln<br>            65                  70                  75 | | 423 |
| act ggg gtg acc gga gtc act aag tcc tgt cac ctg tgc gac gcc ggc<br>Thr Gly Val Thr Gly Val Thr Lys Ser Cys His Leu Cys Asp Ala Gly<br>         80                  85                  90 | | 471 |
| cag cag cac ctg caa cac ggg gca gcc ttc ctg acc gac tac aac aac<br>Gln Gln His Leu Gln His Gly Ala Ala Phe Leu Thr Asp Tyr Asn Asn<br>    95                  100               105 | | 519 |
| cag gcc gac acc acc tgg tgg caa agc cag act atg ctg gcc ggg gtg<br>Gln Ala Asp Thr Thr Trp Trp Gln Ser Gln Thr Met Leu Ala Gly Val<br>110                 115               120               125 | | 567 |
| cag tac ccc aac tcc atc aac ctc acg ctg cac ctg gga aag gct ttt<br>Gln Tyr Pro Asn Ser Ile Asn Leu Thr Leu His Leu Gly Lys Ala Phe<br>              130               135               140 | | 615 |
| gac atc act tac gtg cgc ctc aag ttc cac acc agc cgt cca gag agc<br>Asp Ile Thr Tyr Val Arg Leu Lys Phe His Thr Ser Arg Pro Glu Ser<br>          145               150               155 | | 663 |
| ttc gcc atc tat aag cgc act cgg gaa gac ggg ccc tgg att cct tat<br>Phe Ala Ile Tyr Lys Arg Thr Arg Glu Asp Gly Pro Trp Ile Pro Tyr<br>        160               165               170 | | 711 |
| cag tac tac agt ggg tcc tgt gag aac acg tac tca aag gct aac cgt<br>Gln Tyr Tyr Ser Gly Ser Cys Glu Asn Thr Tyr Ser Lys Ala Asn Arg<br>175                 180               185 | | 759 |
| ggc ttc atc agg acc gga ggg gac gag cag cag gcc ttg tgt act gat<br>Gly Phe Ile Arg Thr Gly Gly Asp Glu Gln Gln Ala Leu Cys Thr Asp<br>190                 195               200               205 | | 807 |
| gaa ttc agt gac att tcc ccc ctc acc ggt ggc aac gtg gcc ttt tca<br>Glu Phe Ser Asp Ile Ser Pro Leu Thr Gly Gly Asn Val Ala Phe Ser<br>              210               215               220 | | 855 |

-continued

| | |
|---|---|
| acc ctg gaa gga cgg ccg agt gcc tac aac ttt gac aac agc cct gtg<br>Thr Leu Glu Gly Arg Pro Ser Ala Tyr Asn Phe Asp Asn Ser Pro Val<br>             225                      230                      235 | 903 |
| ctc cag gaa tgg gta act gcc act gac atc aga gtg acg ctc aat cgc<br>Leu Gln Glu Trp Val Thr Ala Thr Asp Ile Arg Val Thr Leu Asn Arg<br>           240                      245                      250 | 951 |
| ctg aac acc ttt gga gat gaa gtg ttt aac gac ccc aaa gtt ctc aag<br>Leu Asn Thr Phe Gly Asp Glu Val Phe Asn Asp Pro Lys Val Leu Lys<br>255                      260                      265 | 999 |
| tct tac tat tac gca atc tca gac ttt gct gtg ggc ggc agg tgt aaa<br>Ser Tyr Tyr Tyr Ala Ile Ser Asp Phe Ala Val Gly Gly Arg Cys Lys<br>270                      275                      280                      285 | 1047 |
| tgt aac gga cat gcc agc gag tgt gta aag aac gag ttt gac aaa ctc<br>Cys Asn Gly His Ala Ser Glu Cys Val Lys Asn Glu Phe Asp Lys Leu<br>                      290                      295                      300 | 1095 |
| atg tgc aac tgc aaa cat aac aca tac gga gtt gac tgt gaa aag tgc<br>Met Cys Asn Cys Lys His Asn Thr Tyr Gly Val Asp Cys Glu Lys Cys<br>                      305                      310                      315 | 1143 |
| ctg cct ttc ttc aat gac cgg ccg tgg agg agg gcg act gct gag agc<br>Leu Pro Phe Phe Asn Asp Arg Pro Trp Arg Arg Ala Thr Ala Glu Ser<br>           320                      325                      330 | 1191 |
| gcc agc gag tgc ctt cct tgt gac tgc aat ggc cga tcc caa gag tgc<br>Ala Ser Glu Cys Leu Pro Cys Asp Cys Asn Gly Arg Ser Gln Glu Cys<br>335                      340                      345 | 1239 |
| tac ttt gat cct gaa cta tac cgt tcc act gga cat ggt ggc cac tgt<br>Tyr Phe Asp Pro Glu Leu Tyr Arg Ser Thr Gly His Gly Gly His Cys<br>350                      355                      360                      365 | 1287 |
| acc aac tgc cgg gat aac aca gat ggt gcc aag tgc gag agg tgc cgg<br>Thr Asn Cys Arg Asp Asn Thr Asp Gly Ala Lys Cys Glu Arg Cys Arg<br>                      370                      375                      380 | 1335 |
| gag aat ttc ttc cgc ctg ggg aac act gaa gcc tgc tct ccg tgc cac<br>Glu Asn Phe Phe Arg Leu Gly Asn Thr Glu Ala Cys Ser Pro Cys His<br>           385                      390                      395 | 1383 |
| tgc agc cct gtt ggt tct ctc agc aca cag tgt gac agt tac ggc aga<br>Cys Ser Pro Val Gly Ser Leu Ser Thr Gln Cys Asp Ser Tyr Gly Arg<br>400                      405                      410 | 1431 |
| tgc agc tgt aag cca gga gtg atg ggt gac aag tgt gac cgt tgt cag<br>Cys Ser Cys Lys Pro Gly Val Met Gly Asp Lys Cys Asp Arg Cys Gln<br>           415                      420                      425 | 1479 |
| cct ggg ttc cat tcc ctc act gag gca gga tgc agg cca tgc tcc tgc<br>Pro Gly Phe His Ser Leu Thr Glu Ala Gly Cys Arg Pro Cys Ser Cys<br>430                      435                      440                      445 | 1527 |
| gat cct tcg ggc agc aca gac gag tgt aat gtt gaa aca gga aga tgc<br>Asp Pro Ser Gly Ser Thr Asp Glu Cys Asn Val Glu Thr Gly Arg Cys<br>                      450                      455                      460 | 1575 |
| gtt tgc aaa gac aat gtt gaa ggc ttc aac tgt gag aga tgc aaa cct<br>Val Cys Lys Asp Asn Val Glu Gly Phe Asn Cys Glu Arg Cys Lys Pro<br>           465                      470                      475 | 1623 |
| gga ttt ttt aat ctg gag tca tct aat cct aag ggc tgc aca ccc tgc<br>Gly Phe Phe Asn Leu Glu Ser Ser Asn Pro Lys Gly Cys Thr Pro Cys<br>480                      485                      490 | 1671 |
| ttc tgc ttt ggc cat tct tct gtg tgc aca aat gct gtt ggc tac agt<br>Phe Cys Phe Gly His Ser Ser Val Cys Thr Asn Ala Val Gly Tyr Ser<br>495                      500                      505 | 1719 |
| gtt tat gac atc tcc tcc acc ttt cag att gat gag gat ggg tgg cgc<br>Val Tyr Asp Ile Ser Ser Thr Phe Gln Ile Asp Glu Asp Gly Trp Arg<br>510                      515                      520                      525 | 1767 |
| gtg gag cag aga gat ggc tcg gag gcg tct ctg gag tgg tcc tca gac<br>Val Glu Gln Arg Asp Gly Ser Glu Ala Ser Leu Glu Trp Ser Ser Asp<br>                      530                      535                      540 | 1815 |

-continued

| | | |
|---|---|---|
| agg caa tat att gcc gta atc tca gac agt tac ttt cct aga tac ttc<br>Arg Gln Tyr Ile Ala Val Ile Ser Asp Ser Tyr Phe Pro Arg Tyr Phe<br>545                            550                        555 | 1863 |
| atc gcc cct gtg aag ttc ctg ggc aac cag gtc ctg agt tat ggg cag<br>Ile Ala Pro Val Lys Phe Leu Gly Asn Gln Val Leu Ser Tyr Gly Gln<br>    560                       565                     570 | 1911 |
| aat ctt tcc ttc tcc ttc cga gtg gac aga cga gac act cgc ctc tcc<br>Asn Leu Ser Phe Ser Phe Arg Val Asp Arg Arg Asp Thr Arg Leu Ser<br>575                            580                        585 | 1959 |
| gca gag gac ctt gtg ctc gaa gga gct ggc ttg aga gta tcc gtg ccc<br>Ala Glu Asp Leu Val Leu Glu Gly Ala Gly Leu Arg Val Ser Val Pro<br>590                    595                     600                     605 | 2007 |
| ttg atc gct cag ggc aac tcc tac ccc agc gag acc act gtg aag tac<br>Leu Ile Ala Gln Gly Asn Ser Tyr Pro Ser Glu Thr Thr Val Lys Tyr<br>                        610                     615                       620 | 2055 |
| atc ttc agg ctc cat gaa gca acg gat tac cct tgg agg ccc gct ctc<br>Ile Phe Arg Leu His Glu Ala Thr Asp Tyr Pro Trp Arg Pro Ala Leu<br>          625                       630                     635 | 2103 |
| tcc ccg ttt gaa ttt cag aag ctc ctg aac aac ttg acc tct atc aag<br>Ser Pro Phe Glu Phe Gln Lys Leu Leu Asn Asn Leu Thr Ser Ile Lys<br>640                            645                        650 | 2151 |
| atc cgt ggt aca tac agc gag agg agc gct ggg tac ttg gat gat gtc<br>Ile Arg Gly Thr Tyr Ser Glu Arg Ser Ala Gly Tyr Leu Asp Asp Val<br>655                            660                     665 | 2199 |
| acc ttg caa agt gct cgc cct ggg ccc gga gtc cct gca acg tgg gtg<br>Thr Leu Gln Ser Ala Arg Pro Gly Pro Gly Val Pro Ala Thr Trp Val<br>670                            675                     680                     685 | 2247 |
| gag tcc tgc acc tgt cca gtg gga tac ggg gga cag ttc tgt gag acg<br>Glu Ser Cys Thr Cys Pro Val Gly Tyr Gly Gly Gln Phe Cys Glu Thr<br>                       690                     695                       700 | 2295 |
| tgc ctc cca ggg tac aga aga gaa act cca agc ctt gga cct tat agc<br>Cys Leu Pro Gly Tyr Arg Arg Glu Thr Pro Ser Leu Gly Pro Tyr Ser<br>          705                       710                     715 | 2343 |
| ccg tgt gtg ctc tgt acc tgt aat ggg cac agt gag acc tgt gac ccg<br>Pro Cys Val Leu Cys Thr Cys Asn Gly His Ser Glu Thr Cys Asp Pro<br>720                            725                       730 | 2391 |
| gag aca ggt gtc tgt gac tgc aga gac aat aca gcc ggc ccc cac tgt<br>Glu Thr Gly Val Cys Asp Cys Arg Asp Asn Thr Ala Gly Pro His Cys<br>735                            740                     745 | 2439 |
| gag aaa tgt agc gat ggg tac tat ggg gac tca acc ctg ggc acc tcc<br>Glu Lys Cys Ser Asp Gly Tyr Tyr Gly Asp Ser Thr Leu Gly Thr Ser<br>750                            755                     760                     765 | 2487 |
| tct gac tgc cag cct tgt ccc tgc ccc ggt ggc tca agt tgt gcc att<br>Ser Asp Cys Gln Pro Cys Pro Cys Pro Gly Gly Ser Ser Cys Ala Ile<br>                       770                     775                     780 | 2535 |
| gtc cca aag aca aag gaa gtg gtg tgc acg cac tgt ccg act ggc act<br>Val Pro Lys Thr Lys Glu Val Val Cys Thr His Cys Pro Thr Gly Thr<br>785                            790                     795 | 2583 |
| gcc ggc aag aga tgt gaa ctc tgt gat gac ggc tac ttt gga gac cct<br>Ala Gly Lys Arg Cys Glu Leu Cys Asp Asp Gly Tyr Phe Gly Asp Pro<br>800                            805                     810 | 2631 |
| ctg ggc agc aat ggg ccc gtg aga ctg tgc cgc ccg tgc cag tgt aac<br>Leu Gly Ser Asn Gly Pro Val Arg Leu Cys Arg Pro Cys Gln Cys Asn<br>815                            820                     825 | 2679 |
| gac aac ata gac ccc aac gcg gtt ggc aac tgc aac cgc ctg acg ggc<br>Asp Asn Ile Asp Pro Asn Ala Val Gly Asn Cys Asn Arg Leu Thr Gly<br>830                            835                     840                     845 | 2727 |
| gag tgc ctg aag tgc atc tat aac acg gct ggt ttc tac tgc gac cgg<br>Glu Cys Leu Lys Cys Ile Tyr Asn Thr Ala Gly Phe Tyr Cys Asp Arg | 2775 |

-continued

```
              850                 855                 860
tgc aag gaa ggg ttt ttc gga aat ccc ctg gct ccc aat cca gcc gac    2823
Cys Lys Glu Gly Phe Phe Gly Asn Pro Leu Ala Pro Asn Pro Ala Asp
            865                 870                 875 aaa tgc aaa gcc tgc gcc tgc aac tac ggg aca gtg cag caa cag agc    2871
Lys Cys Lys Ala Cys Ala Cys Asn Tyr Gly Thr Val Gln Gln Gln Ser
        880                 885                 890 agc tgt aac ccg gtg acc gga caa tgc cag tgt ctg cct cat gtg tct    2919
Ser Cys Asn Pro Val Thr Gly Gln Cys Gln Cys Leu Pro His Val Ser
    895                 900                 905 ggc cgc gac tgc ggt act tgt gac cct ggc tac tac aac ctg cag agc    2967
Gly Arg Asp Cys Gly Thr Cys Asp Pro Gly Tyr Tyr Asn Leu Gln Ser
910                 915                 920                 925 ggg caa ggc tgc gag agg tgt gac tgc cat gct ttg ggt tcc acc aat    3015
Gly Gln Gly Cys Glu Arg Cys Asp Cys His Ala Leu Gly Ser Thr Asn
                930                 935                 940 ggg cag tgt gac atc cgc acc ggg cag tgt gag tgc cag cct ggc atc    3063
Gly Gln Cys Asp Ile Arg Thr Gly Gln Cys Glu Cys Gln Pro Gly Ile
            945                 950                 955 acc ggt cag cac tgt gag cgc tgt gag acc aac cac ttt ggg ttt gga    3111
Thr Gly Gln His Cys Glu Arg Cys Glu Thr Asn His Phe Gly Phe Gly
        960                 965                 970 cct gaa ggc tgc aaa cct tgt gac tgt cac cat gaa gga tcc ctt tcg    3159
Pro Glu Gly Cys Lys Pro Cys Asp Cys His His Glu Gly Ser Leu Ser
    975                 980                 985 ctc cag tgt aaa gac gac ggc cgt tgt gaa tgc agg gaa ggc ttt gtg    3207
Leu Gln Cys Lys Asp Asp Gly Arg Cys Glu Cys Arg Glu Gly Phe Val
990                 995                 1000                1005 ggc aat cgc tgt gac cag tgt gaa gag aac tat ttc tac aat cgg tcc    3255
Gly Asn Arg Cys Asp Gln Cys Glu Glu Asn Tyr Phe Tyr Asn Arg Ser
                1010                1015                1020 tgg cct ggc tgc cag gag tgt ccg gct tgt tac cga ctt gtg aag gat    3303
Trp Pro Gly Cys Gln Glu Cys Pro Ala Cys Tyr Arg Leu Val Lys Asp
            1025                1030                1035 aag gct gct gag cat cga gtg aaa ctc cag gag tta gag agc ctc atc    3351
Lys Ala Ala Glu His Arg Val Lys Leu Gln Glu Leu Glu Ser Leu Ile
        1040                1045                1050 gcc aac ctt ggc act ggg gat gac atg gtg aca gat caa gcc ttt gag    3399
Ala Asn Leu Gly Thr Gly Asp Asp Met Val Thr Asp Gln Ala Phe Glu
    1055                1060                1065 gac aga ctt aag gaa gca gaa agg gag gtg aca gac ctt ctc cgt gag    3447
Asp Arg Leu Lys Glu Ala Glu Arg Glu Val Thr Asp Leu Leu Arg Glu
1070                1075                1080                1085 gct cag gaa gtc aaa gat gta gat caa aat ctg atg gat cgc ctt cag    3495
Ala Gln Glu Val Lys Asp Val Asp Gln Asn Leu Met Asp Arg Leu Gln
                1090                1095                1100 aga gta aat agc agc ctg cat agc caa att agc cga ctg cag aat atc    3543
Arg Val Asn Ser Ser Leu His Ser Gln Ile Ser Arg Leu Gln Asn Ile
            1105                1110                1115 cgg aat act atc gaa gag acc ggg atc ttg gct gag cga gca cgg tcc    3591
Arg Asn Thr Ile Glu Glu Thr Gly Ile Leu Ala Glu Arg Ala Arg Ser
        1120                1125                1130 cga gtg gag agt aca gag cag ctg att gag atc gcc tcc agg gag ctc    3639
Arg Val Glu Ser Thr Glu Gln Leu Ile Glu Ile Ala Ser Arg Glu Leu
    1135                1140                1145 gag aaa gca aaa atg gcc gcc aat gtg tca atc act cag cca gag tct    3687
Glu Lys Ala Lys Met Ala Ala Asn Val Ser Ile Thr Gln Pro Glu Ser
1150                1155                1160                1165 aca ggg gag cca aac aac atg acc ctc ttg gca gaa gaa gcc cga agg    3735
```

-continued

```
Thr Gly Glu Pro Asn Asn Met Thr Leu Leu Ala Glu Ala Arg Arg
        1170                1175                1180 ctt gca gag cgt cat aaa cag gaa gcc gat gac att gta cga gtg gca    3783
Leu Ala Glu Arg His Lys Gln Glu Ala Asp Asp Ile Val Arg Val Ala
        1185                1190                1195 aag aca gcc aac gag act tca gct gag gca tat aat ctg ctt ttg agg    3831
Lys Thr Ala Asn Glu Thr Ser Ala Glu Ala Tyr Asn Leu Leu Leu Arg
    1200                1205                1210 acc ctg gca gga gaa aat caa act gcg ctg gag att gaa gaa ctt aac    3879
Thr Leu Ala Gly Glu Asn Gln Thr Ala Leu Glu Ile Glu Glu Leu Asn
    1215                1220                1225 cgg aag tac gaa caa gca aag aac atc tct cag gac ctg gag aag cag    3927
Arg Lys Tyr Glu Gln Ala Lys Asn Ile Ser Gln Asp Leu Glu Lys Gln
1230                1235                1240                1245 gct gcc cga gtc cat gag gaa gcc aag cgt gca ggt gac aaa gcc gta    3975
Ala Ala Arg Val His Glu Glu Ala Lys Arg Ala Gly Asp Lys Ala Val
            1250                1255                1260 gag atc tat gcc agt gtg gcc cag ctg acc cct gtg gac tct gag gcc    4023
Glu Ile Tyr Ala Ser Val Ala Gln Leu Thr Pro Val Asp Ser Glu Ala
            1265                1270                1275 ctg gag aat gaa gca aat aaa atc aag aaa gaa gct gca gac ctg gac    4071
Leu Glu Asn Glu Ala Asn Lys Ile Lys Lys Glu Ala Ala Asp Leu Asp
            1280                1285                1290 cgt ctg att gac cag aag cta aag gat tac gag gac ctc agg gaa gac    4119
Arg Leu Ile Asp Gln Lys Leu Lys Asp Tyr Glu Asp Leu Arg Glu Asp
    1295                1300                1305 atg aga gga aag gaa cat gaa gtg aag aac ctt cta gag aag ggg aaa    4167
Met Arg Gly Lys Glu His Glu Val Lys Asn Leu Leu Glu Lys Gly Lys
1310                1315                1320                1325 gct gaa cag cag acc gcc gac caa ctc cta gct cga gcc gat gct gcc    4215
Ala Glu Gln Gln Thr Ala Asp Gln Leu Leu Ala Arg Ala Asp Ala Ala
                1330                1335                1340 aag gcc ctt gct gaa gaa gct gct aag aag gga cgc agt acc tta caa    4263
Lys Ala Leu Ala Glu Glu Ala Ala Lys Lys Gly Arg Ser Thr Leu Gln
            1345                1350                1355 gaa gcc aat gac att ctc aac aac ctg aaa gat ttt gat aga cgt gtg    4311
Glu Ala Asn Asp Ile Leu Asn Asn Leu Lys Asp Phe Asp Arg Arg Val
        1360                1365                1370 aac gat aac aag aca gcc gcg gaa gaa gct cta agg aga att ccc gcc    4359
Asn Asp Asn Lys Thr Ala Ala Glu Glu Ala Leu Arg Arg Ile Pro Ala
    1375                1380                1385 atc aac cgg acc ata gct gaa gcc aat gag aag aca agg gag gcc cag    4407
Ile Asn Arg Thr Ile Ala Glu Ala Asn Glu Lys Thr Arg Glu Ala Gln
1390                1395                1400                1405 cta gcg ctg ggc aat gct gcc gct gac gcc acg gag gcc aag aac aag    4455
Leu Ala Leu Gly Asn Ala Ala Ala Asp Ala Thr Glu Ala Lys Asn Lys
                1410                1415                1420 gcc cat gag gca gag agg atc gcc agc gcc gcg cag aag aat gcc acc    4503
Ala His Glu Ala Glu Arg Ile Ala Ser Ala Ala Gln Lys Asn Ala Thr
            1425                1430                1435 agt acc aag gcg gac gca gaa aga acc ttc ggg gaa gtt aca gat ctg    4551
Ser Thr Lys Ala Asp Ala Glu Arg Thr Phe Gly Glu Val Thr Asp Leu
        1440                1445                1450 gat aat gag gtg aac ggt atg ctg agg cag cta gag gag gca gag aat    4599
Asp Asn Glu Val Asn Gly Met Leu Arg Gln Leu Glu Glu Ala Glu Asn
    1455                1460                1465 gag ctg aag agg aag caa gat gac gcc gac cag gac atg atg atg gcg    4647
Glu Leu Lys Arg Lys Gln Asp Asp Ala Asp Gln Asp Met Met Met Ala
1470                1475                1480                1485
```

-continued

| | |
|---|---|
| ggg atg gct tcg caa gcc gct cag gag gct gag ctc aat gcc aga aag<br>Gly Met Ala Ser Gln Ala Ala Gln Glu Ala Glu Leu Asn Ala Arg Lys<br>                  1490                          1495                        1500 | 4695 |
| gcc aaa aac tct gtc agc agc ctc ctc agc cag ctg aac aac ctc ttg<br>Ala Lys Asn Ser Val Ser Ser Leu Leu Ser Gln Leu Asn Asn Leu Leu<br>1505                      1510                        1515 | 4743 |
| gat cag cta gga cag ctg gac aca gtg gac ctg aac aag ctc aat gag<br>Asp Gln Leu Gly Gln Leu Asp Thr Val Asp Leu Asn Lys Leu Asn Glu<br>                  1520                        1525                      1530 | 4791 |
| atc gaa ggc tcc ctg aac aaa gcc aaa gac gaa atg aag gcc agc gac<br>Ile Glu Gly Ser Leu Asn Lys Ala Lys Asp Glu Met Lys Ala Ser Asp<br>    1535                      1540                        1545 | 4839 |
| ctg gac agg aag gtg tct gac ctg gag agc gag gct cgg aag cag gaa<br>Leu Asp Arg Lys Val Ser Asp Leu Glu Ser Glu Ala Arg Lys Gln Glu<br>1550                      1555                        1560                      1565 | 4887 |
| gca gcc atc atg gac tat aac cgg gac ata gca gag atc att aag gat<br>Ala Ala Ile Met Asp Tyr Asn Arg Asp Ile Ala Glu Ile Ile Lys Asp<br>                  1570                        1575                      1580 | 4935 |
| att cac aac ctg gag gac atc aag aag acc cta cca acc ggc tgc ttc<br>Ile His Asn Leu Glu Asp Ile Lys Lys Thr Leu Pro Thr Gly Cys Phe<br>    1585                      1590                        1595 | 4983 |
| aac acc ccg tct atc gag aag ccc tagtggcgag agggctgtaa ggcagtgtcc<br>Asn Thr Pro Ser Ile Glu Lys Pro<br>1600                    1605 | 5037 |
| ctgacagggg accctgtgag gcctcggtgc cttgacacaa agattacact tttcagaccc | 5097 |
| ccacttctct gctgctctcc atcactgtcc ttttgaccca agaaaagtca gagtttaaag | 5157 |
| agaagcaagt taaacatctt taaccaggaa caaagggttt tgcctaataa agtctctcct | 5217 |
| ccacttctgt cagcacccta ccggaacttt cccttgtttg cctgaagtca cggcatcttc | 5277 |
| caggggccta cccacatcat gtgaaccttt taatgccagg gcagacccag cccctcccc | 5337 |
| tctctcaaca ccagcaggac ctatctcagt actcatgttt ctatgaagga atctttggc | 5397 |
| tcctcatcgt agcattgaga tggccagtat gtccgctctg catcttctgc ctcctctttg | 5457 |
| aaaggaaata aacatcctcg tgccaaaggt attggtcatt tagaatagtg gtggccatcc | 5517 |
| atcagacatg ctggctggct gagcatagga cacagagccg tcgtgggtga gcgtagttac | 5577 |
| atgtgggtcc ccaggagaac atggctcaaa gatgcttagg gttcctcctg ttttcattga | 5637 |
| ctaggaagat gaatgtttcc caaatcctca ggcagctgat aaaaagtctg gatgggcagc | 5697 |
| tcgcacgcac cactacgtga ggtagctttt gatatttta taagcaggac ttaatgcaga | 5757 |
| agaaacagat gtgataacca ctcaagtttt ttttccccaag tagtactaat tcttaaagct | 5817 |
| ttgttagtgt tagtcttgga actgttggta agatagctgt caaaacagtt gtcctctaag | 5877 |
| gtcatgacca atgaaagaag agcaaatctc ctttctccca tattttctgg gaagtggctg | 5937 |
| taatcgggat gtaaccgctc tcattaggat tccatgagtg catttctttt tctctttttc | 5997 |
| ttggagagag atgtgacgtt tggcccttag ctccattctc ttctgatgtt tccgttcttt | 6057 |
| ctagaactct tcagagcaca tcgttgtttg ccaggtcctg gtggcaaaca cccgctcaca | 6117 |
| gtgtttctca aggctgccaa ccccatctag ttcctgcact ttgtcggtcc gcccactcca | 6177 |
| agcctttcct ctgtgtggag agggaagatc catacgtggc atttcctagt gggcttctca | 6237 |
| acctctgatc ctcagctcgg tggtctcctt aagaccacac tgtgacagtt ccctgccaca | 6297 |
| catccccttc ctcctaccta cctgcctctg agattcatat ttagccttta acactatgca | 6357 |
| attttgtact ttgcgtacgg ggggaaagaa actattatct gacacactgg tgctattatt | 6417 |
| tgaaatttat attttttgtg tgaatggatt ttgtttatca tgattataga gtaaggaatt | 6477 |

-continued

```
tatgtaaata tccccggtcc tcctagaacg gcactgtctg ctcacgtctc tgctcagttg    6537
tccctctcac tggcacagga acctgtacca tgcctggtca cgtcgtgcct ggtccccagt    6597
gttttgctcc acctctgcct tgtgtttgca gcaccttcac tgtctgaccg gaagcctgct    6657
cacctccaca acttgactga agagggccct cttccccgtg gctctgacca tctgagctgc    6717
agctcctcaa ggttctcatg cctgcccgga gcagtagcca agctgacagg gtaaagggat    6777
taggaacgtt tgtttgtgga accttcccac acgggtcagt tttctaaggg agcatgtgat    6837
gactgaacac ttgagggcat cagcaccgtg ctactgatga cagaggggag gctctgttca    6897
gcctgtctcc atctcggaga ttgccacaaa atctcagctt ggcatcctcc gaggcctttt    6957
gtgccacggc aagaaggcgt ggcctcacca agttcagtgc tgattggcta gttcctctat    7017
tccgagctca ccaccttaac attttggtca cagttgcaag aaaatggctg aaacagacca    7077
ccaccagcat cctttgggtc aactccactc cagcaggccc gaggcgctgg tgggtggggt    7137
gttttggttt gttttctcca gcttttgtgg tatattttta aacagaattt tatttttaa    7197 aatgaaagtt atttacaaga tgataccta ttacgctcct tcgacacagc cattgcttta    7257
ttgtatagtt ccaataatct gtattttatg taatgaaatg gacagaatgg ctgctgtaga    7317
atgcggggtg ccgcacagaa cagattgttt tatccctccc ccgccccgc ccatggaatt    7377 ttcctttgat tccaactgtg gccctttca atgtgccttc actttagctg tttgccttaa    7437
tctctacagc cttccccct cagggagggc aataaagcgc aacacttggc attttttat    7497 gtttaaaaag aaaacagtat tttatttata ataaaatctg aatatttgta acccttt     7554
```

<210> SEQ ID NO 18
<211> LENGTH: 1605
<212> TYPE: PRT
<213> ORGANISM: Mus musculus

<400> SEQUENCE: 18

```
Met Thr Gly Gly Gly Arg Ala Ala Leu Ala Leu Gln Pro Arg Gly Arg
 1               5                  10                  15

Leu Trp Pro Leu Leu Ala Val Leu Ala Ala Val Ala Gly Cys Val Arg
             20                  25                  30

Ala Ala Met Asp Glu Cys Ala Asp Glu Gly Gly Arg Pro Gln Arg Cys
         35                  40                  45

Met Pro Glu Phe Val Asn Ala Ala Phe Asn Val Thr Val Ala Thr
     50                  55                  60

Asn Thr Cys Gly Thr Pro Pro Glu Glu Tyr Cys Val Gln Thr Gly Val
 65                  70                  75                  80

Thr Gly Val Thr Lys Ser Cys His Leu Cys Asp Ala Gly Gln Gln His
                 85                  90                  95

Leu Gln His Gly Ala Ala Phe Leu Thr Asp Tyr Asn Asn Gln Ala Asp
            100                 105                 110

Thr Thr Trp Trp Gln Ser Gln Thr Met Leu Ala Gly Val Gln Tyr Pro
        115                 120                 125

Asn Ser Ile Asn Leu Thr Leu His Leu Gly Lys Ala Phe Asp Ile Thr
    130                 135                 140

Tyr Val Arg Leu Lys Phe His Thr Ser Arg Pro Glu Ser Phe Ala Ile
145                 150                 155                 160

Tyr Lys Arg Thr Arg Glu Asp Gly Pro Trp Ile Pro Tyr Gln Tyr Tyr
                165                 170                 175

Ser Gly Ser Cys Glu Asn Thr Tyr Ser Lys Ala Asn Arg Gly Phe Ile
```

-continued

```
                180             185             190
Arg Thr Gly Gly Asp Glu Gln Gln Ala Leu Cys Thr Asp Glu Phe Ser
            195                 200                 205
Asp Ile Ser Pro Leu Thr Gly Gly Asn Val Ala Phe Ser Thr Leu Glu
            210                 215                 220
Gly Arg Pro Ser Ala Tyr Asn Phe Asp Asn Ser Pro Val Leu Gln Glu
225                 230                 235                 240
Trp Val Thr Ala Thr Asp Ile Arg Val Thr Leu Asn Arg Leu Asn Thr
                245                 250                 255
Phe Gly Asp Glu Val Phe Asn Asp Pro Lys Val Leu Lys Ser Tyr Tyr
            260                 265                 270
Tyr Ala Ile Ser Asp Phe Ala Val Gly Gly Arg Cys Lys Cys Asn Gly
            275                 280                 285
His Ala Ser Glu Cys Val Lys Asn Glu Phe Asp Lys Leu Met Cys Asn
            290                 295                 300
Cys Lys His Asn Thr Tyr Gly Val Asp Cys Glu Lys Cys Leu Pro Phe
305                 310                 315                 320
Phe Asn Asp Arg Pro Trp Arg Arg Ala Thr Ala Glu Ser Ala Ser Glu
                325                 330                 335
Cys Leu Pro Cys Asp Cys Asn Gly Arg Ser Gln Glu Cys Tyr Phe Asp
            340                 345                 350
Pro Glu Leu Tyr Arg Ser Thr Gly His Gly Gly His Cys Thr Asn Cys
            355                 360                 365
Arg Asp Asn Thr Asp Gly Ala Lys Cys Glu Arg Cys Arg Glu Asn Phe
            370                 375                 380
Phe Arg Leu Gly Asn Thr Glu Ala Cys Ser Pro Cys His Cys Ser Pro
385                 390                 395                 400
Val Gly Ser Leu Ser Thr Gln Cys Asp Ser Tyr Gly Arg Cys Ser Cys
                405                 410                 415
Lys Pro Gly Val Met Gly Asp Lys Cys Asp Arg Cys Gln Pro Gly Phe
            420                 425                 430
His Ser Leu Thr Glu Ala Gly Cys Arg Pro Cys Ser Cys Asp Pro Ser
            435                 440                 445
Gly Ser Thr Asp Glu Cys Asn Val Glu Thr Gly Arg Cys Val Cys Lys
            450                 455                 460
Asp Asn Val Glu Gly Phe Asn Cys Glu Arg Cys Lys Pro Gly Phe Phe
465                 470                 475                 480
Asn Leu Glu Ser Ser Asn Pro Lys Gly Cys Thr Pro Cys Phe Cys Phe
                485                 490                 495
Gly His Ser Ser Val Cys Thr Asn Ala Val Gly Tyr Ser Val Tyr Asp
            500                 505                 510
Ile Ser Ser Thr Phe Gln Ile Asp Glu Asp Gly Trp Arg Val Glu Gln
            515                 520                 525
Arg Asp Gly Ser Glu Ala Ser Leu Glu Trp Ser Ser Asp Arg Gln Tyr
            530                 535                 540
Ile Ala Val Ile Ser Asp Ser Tyr Phe Pro Arg Tyr Phe Ile Ala Pro
545                 550                 555                 560
Val Lys Phe Leu Gly Asn Gln Val Leu Ser Tyr Gly Gln Asn Leu Ser
                565                 570                 575
Phe Ser Phe Arg Val Asp Arg Arg Asp Thr Arg Leu Ser Ala Glu Asp
            580                 585                 590
Leu Val Leu Glu Gly Ala Gly Leu Arg Val Ser Val Pro Leu Ile Ala
            595                 600                 605
```

-continued

```
Gln Gly Asn Ser Tyr Pro Ser Glu Thr Thr Val Lys Tyr Ile Phe Arg
    610                 615                 620

Leu His Glu Ala Thr Asp Tyr Pro Trp Arg Pro Ala Leu Ser Pro Phe
625                 630                 635                 640

Glu Phe Gln Lys Leu Leu Asn Asn Leu Thr Ser Ile Lys Ile Arg Gly
            645                 650                 655

Thr Tyr Ser Glu Arg Ser Ala Gly Tyr Leu Asp Asp Val Thr Leu Gln
                660                 665                 670

Ser Ala Arg Pro Gly Pro Gly Val Pro Ala Thr Trp Val Glu Ser Cys
            675                 680                 685

Thr Cys Pro Val Gly Tyr Gly Gly Gln Phe Cys Glu Thr Cys Leu Pro
        690                 695                 700

Gly Tyr Arg Arg Glu Thr Pro Ser Leu Gly Pro Tyr Ser Pro Cys Val
705                 710                 715                 720

Leu Cys Thr Cys Asn Gly His Ser Glu Thr Cys Asp Pro Glu Thr Gly
                725                 730                 735

Val Cys Asp Cys Arg Asp Asn Thr Ala Gly Pro His Cys Glu Lys Cys
            740                 745                 750

Ser Asp Gly Tyr Tyr Gly Asp Ser Thr Leu Gly Thr Ser Ser Asp Cys
        755                 760                 765

Gln Pro Cys Pro Cys Pro Gly Gly Ser Ser Cys Ala Ile Val Pro Lys
770                 775                 780

Thr Lys Glu Val Val Cys Thr His Cys Pro Thr Gly Thr Ala Gly Lys
785                 790                 795                 800

Arg Cys Glu Leu Cys Asp Asp Gly Tyr Phe Gly Asp Pro Leu Gly Ser
                805                 810                 815

Asn Gly Pro Val Arg Leu Cys Arg Pro Cys Gln Cys Asn Asp Asn Ile
            820                 825                 830

Asp Pro Asn Ala Val Gly Asn Cys Asn Arg Leu Thr Gly Glu Cys Leu
        835                 840                 845

Lys Cys Ile Tyr Asn Thr Ala Gly Phe Tyr Cys Asp Arg Cys Lys Glu
850                 855                 860

Gly Phe Phe Gly Asn Pro Leu Ala Pro Asn Pro Ala Asp Lys Cys Lys
865                 870                 875                 880

Ala Cys Ala Cys Asn Tyr Gly Thr Val Gln Gln Gln Ser Ser Cys Asn
                885                 890                 895

Pro Val Thr Gly Gln Cys Gln Cys Leu Pro His Val Ser Gly Arg Asp
            900                 905                 910

Cys Gly Thr Cys Asp Pro Gly Tyr Tyr Asn Leu Gln Ser Gly Gln Gly
        915                 920                 925

Cys Glu Arg Cys Asp Cys His Ala Leu Gly Ser Thr Asn Gly Gln Cys
        930                 935                 940

Asp Ile Arg Thr Gly Gln Cys Glu Cys Gln Pro Gly Ile Thr Gly Gln
945                 950                 955                 960

His Cys Glu Arg Cys Glu Thr Asn His Phe Gly Phe Gly Pro Glu Gly
                965                 970                 975

Cys Lys Pro Cys Asp Cys His His Glu Gly Ser Leu Ser Leu Gln Cys
            980                 985                 990

Lys Asp Asp Gly Arg Cys Glu Cys Arg Glu Gly Phe Val Gly Asn Arg
        995                 1000                1005

Cys Asp Gln Cys Glu Glu Asn Tyr Phe Tyr Asn Arg Ser Trp Pro Gly
    1010                1015                1020
```

-continued

```
Cys Gln Glu Cys Pro Ala Cys Tyr Arg Leu Val Lys Asp Lys Ala Ala
1025                1030                1035                1040

Glu His Arg Val Lys Leu Gln Glu Leu Glu Ser Leu Ile Ala Asn Leu
            1045                1050                1055

Gly Thr Gly Asp Asp Met Val Thr Asp Gln Ala Phe Glu Asp Arg Leu
        1060                1065                1070

Lys Glu Ala Glu Arg Glu Val Thr Asp Leu Leu Arg Glu Ala Gln Glu
    1075                1080                1085

Val Lys Asp Val Asp Gln Asn Leu Met Asp Arg Leu Gln Arg Val Asn
1090                1095                1100

Ser Ser Leu His Ser Gln Ile Ser Arg Leu Gln Asn Ile Arg Asn Thr
1105                1110                1115                1120

Ile Glu Glu Thr Gly Ile Leu Ala Glu Arg Ala Arg Ser Arg Val Glu
            1125                1130                1135

Ser Thr Glu Gln Leu Ile Glu Ile Ala Ser Arg Glu Leu Glu Lys Ala
        1140                1145                1150

Lys Met Ala Ala Asn Val Ser Ile Thr Gln Pro Glu Ser Thr Gly Glu
    1155                1160                1165

Pro Asn Asn Met Thr Leu Leu Ala Glu Glu Ala Arg Arg Leu Ala Glu
1170                1175                1180

Arg His Lys Gln Glu Ala Asp Asp Ile Val Arg Val Ala Lys Thr Ala
1185                1190                1195                1200

Asn Glu Thr Ser Ala Glu Ala Tyr Asn Leu Leu Leu Arg Thr Leu Ala
            1205                1210                1215

Gly Glu Asn Gln Thr Ala Leu Glu Ile Glu Glu Leu Asn Arg Lys Tyr
        1220                1225                1230

Glu Gln Ala Lys Asn Ile Ser Gln Asp Leu Glu Lys Gln Ala Ala Arg
    1235                1240                1245

Val His Glu Glu Ala Lys Arg Ala Gly Asp Lys Ala Val Glu Ile Tyr
    1250                1255                1260

Ala Ser Val Ala Gln Leu Thr Pro Val Asp Ser Glu Ala Leu Glu Asn
1265                1270                1275                1280

Glu Ala Asn Lys Ile Lys Lys Glu Ala Ala Asp Leu Asp Arg Leu Ile
            1285                1290                1295

Asp Gln Lys Leu Lys Asp Tyr Glu Asp Leu Arg Glu Asp Met Arg Gly
        1300                1305                1310

Lys Glu His Glu Val Lys Asn Leu Leu Glu Lys Gly Lys Ala Glu Gln
    1315                1320                1325

Gln Thr Ala Asp Gln Leu Leu Ala Arg Ala Asp Ala Ala Lys Ala Leu
    1330                1335                1340

Ala Glu Glu Ala Ala Lys Lys Gly Arg Ser Thr Leu Gln Glu Ala Asn
1345                1350                1355                1360

Asp Ile Leu Asn Asn Leu Lys Asp Phe Asp Arg Arg Val Asn Asp Asn
            1365                1370                1375

Lys Thr Ala Ala Glu Glu Ala Leu Arg Arg Ile Pro Ala Ile Asn Arg
        1380                1385                1390

Thr Ile Ala Glu Ala Asn Glu Lys Thr Arg Glu Ala Gln Leu Ala Leu
    1395                1400                1405

Gly Asn Ala Ala Ala Asp Ala Thr Glu Ala Lys Asn Lys Ala His Glu
    1410                1415                1420

Ala Glu Arg Ile Ala Ser Ala Ala Gln Lys Asn Ala Thr Ser Thr Lys
1425                1430                1435                1440

Ala Asp Ala Glu Arg Thr Phe Gly Glu Val Thr Asp Leu Asp Asn Glu
```

```
                    1445              1450              1455
        Val Asn Gly Met Leu Arg Gln Leu Glu Glu Ala Glu Asn Glu Leu Lys
                1460              1465              1470

Arg Lys Gln Asp Asp Ala Asp Gln Asp Met Met Met Ala Gly Met Ala
                1475              1480              1485

Ser Gln Ala Ala Gln Glu Ala Glu Leu Asn Ala Arg Lys Ala Lys Asn
                1490              1495              1500

Ser Val Ser Ser Leu Leu Ser Gln Leu Asn Asn Leu Leu Asp Gln Leu
        1505              1510              1515              1520

Gly Gln Leu Asp Thr Val Asp Leu Asn Lys Leu Asn Glu Ile Glu Gly
                1525              1530              1535

Ser Leu Asn Lys Ala Lys Asp Glu Met Lys Ala Ser Asp Leu Asp Arg
                1540              1545              1550

Lys Val Ser Asp Leu Glu Ser Glu Ala Arg Lys Gln Glu Ala Ala Ile
                1555              1560              1565

Met Asp Tyr Asn Arg Asp Ile Ala Glu Ile Ile Lys Asp Ile His Asn
                1570              1575              1580

Leu Glu Asp Ile Lys Lys Thr Leu Pro Thr Gly Cys Phe Asn Thr Pro
        1585              1590              1595              1600

Ser Ile Glu Lys Pro
                1605

<210> SEQ ID NO 19
<211> LENGTH: 7263
<212> TYPE: DNA
<213> ORGANISM: Mus musculus
<220> FEATURE:
<221> NAME/KEY: CDS
<222> LOCATION: (1)..(4716)

<400> SEQUENCE: 19 gcc atg gac gag tgc gcg gat gag ggc ggg cgg ccg cag cgc tgc atg      48
Ala Met Asp Glu Cys Ala Asp Glu Gly Gly Arg Pro Gln Arg Cys Met
 1               5                  10                  15 ccg gag ttt gtt aat gcc gcc ttc aat gtg acc gtg gtg gct acc aac      96
Pro Glu Phe Val Asn Ala Ala Phe Asn Val Thr Val Val Ala Thr Asn
             20                  25                  30 acg tgt ggg act ccg ccc gag gag tac tgc gtg cag act ggg gtg acc     144
Thr Cys Gly Thr Pro Pro Glu Glu Tyr Cys Val Gln Thr Gly Val Thr
         35                  40                  45 gga gtc act aag tcc tgt cac ctg tgc gac gcc ggc cag cag cac ctg     192
Gly Val Thr Lys Ser Cys His Leu Cys Asp Ala Gly Gln Gln His Leu
     50                  55                  60 caa cac ggg gca gcc ttc ctg acc gac tac aac aac cag gcc gac acc     240
Gln His Gly Ala Ala Phe Leu Thr Asp Tyr Asn Asn Gln Ala Asp Thr
 65                  70                  75                  80 acc tgg tgg caa agc cag act atg ctg gcc ggg gtg cag tac ccc aac     288
Thr Trp Trp Gln Ser Gln Thr Met Leu Ala Gly Val Gln Tyr Pro Asn
                 85                  90                  95 tcc atc aac ctc acg ctg cac ctg gga aag gct ttt gac atc act tac     336
Ser Ile Asn Leu Thr Leu His Leu Gly Lys Ala Phe Asp Ile Thr Tyr
            100                 105                 110 gtg cgc ctc aag ttc cac acc agc cgt cca gag agc ttc gcc atc tat     384
Val Arg Leu Lys Phe His Thr Ser Arg Pro Glu Ser Phe Ala Ile Tyr
        115                 120                 125 aag cgc act cgg gaa gac ggg ccc tgg att cct tat cag tac tac agt     432
Lys Arg Thr Arg Glu Asp Gly Pro Trp Ile Pro Tyr Gln Tyr Tyr Ser
    130                 135                 140
```

-continued

| | | |
|---|---|---|
| ggg tcc tgt gag aac acg tac tca aag gct aac cgt ggc ttc atc agg<br>Gly Ser Cys Glu Asn Thr Tyr Ser Lys Ala Asn Arg Gly Phe Ile Arg<br>145               150                   155               160 | 480 |
| acc gga ggg gac gag cag cag gcc ttg tgt act gat gaa ttc agt gac<br>Thr Gly Gly Asp Glu Gln Gln Ala Leu Cys Thr Asp Glu Phe Ser Asp<br>               165                   170                   175 | 528 |
| att tcc ccc ctc acc ggt ggc aac gtg gcc ttt tca acc ctg gaa gga<br>Ile Ser Pro Leu Thr Gly Gly Asn Val Ala Phe Ser Thr Leu Glu Gly<br>               180                   185                   190 | 576 |
| cgg ccg agt gcc tac aac ttt gac aac agc cct gtg ctc cag gaa tgg<br>Arg Pro Ser Ala Tyr Asn Phe Asp Asn Ser Pro Val Leu Gln Glu Trp<br>           195                   200                   205 | 624 |
| gta act gcc act gac atc aga gtg acg ctc aat cgc ctg aac acc ttt<br>Val Thr Ala Thr Asp Ile Arg Val Thr Leu Asn Arg Leu Asn Thr Phe<br>210                   215                   220 | 672 |
| gga gat gaa gtg ttt aac gac ccc aaa gtt ctc aag tct tac tat tac<br>Gly Asp Glu Val Phe Asn Asp Pro Lys Val Leu Lys Ser Tyr Tyr Tyr<br>225                   230                   235               240 | 720 |
| gca atc tca gac ttt gct gtg ggc ggc agg tgt aaa tgt aac gga cat<br>Ala Ile Ser Asp Phe Ala Val Gly Gly Arg Cys Lys Cys Asn Gly His<br>               245                   250                   255 | 768 |
| gcc agc gag tgt gta aag aac gag ttt gac aaa ctc atg tgc aac tgc<br>Ala Ser Glu Cys Val Lys Asn Glu Phe Asp Lys Leu Met Cys Asn Cys<br>           260                   265                   270 | 816 |
| aaa cat aac aca tac gga gtt gac tgt gaa aag tgc ctg cct ttc ttc<br>Lys His Asn Thr Tyr Gly Val Asp Cys Glu Lys Cys Leu Pro Phe Phe<br>           275                   280                   285 | 864 |
| aat gac cgg ccg tgg agg agg gcg act gct gag agc gcc agc gag tgc<br>Asn Asp Arg Pro Trp Arg Arg Ala Thr Ala Glu Ser Ala Ser Glu Cys<br>290                   295                   300 | 912 |
| ctt cct tgt gac tgc aat ggc cga tcc caa gag tgc tac ttt gat cct<br>Leu Pro Cys Asp Cys Asn Gly Arg Ser Gln Glu Cys Tyr Phe Asp Pro<br>305                   310                   315               320 | 960 |
| gaa cta tac cgt tcc act gga cat ggt ggc cac tgt acc aac tgc cgg<br>Glu Leu Tyr Arg Ser Thr Gly His Gly Gly His Cys Thr Asn Cys Arg<br>           325                   330                   335 | 1008 |
| gat aac aca gat ggt gcc aag tgc gag agg tgc cgg gag aat ttc ttc<br>Asp Asn Thr Asp Gly Ala Lys Cys Glu Arg Cys Arg Glu Asn Phe Phe<br>               340                   345                   350 | 1056 |
| cgc ctg ggg aac act gaa gcc tgc tct ccg tgc cac tgc agc cct gtt<br>Arg Leu Gly Asn Thr Glu Ala Cys Ser Pro Cys His Cys Ser Pro Val<br>           355                   360                   365 | 1104 |
| ggt tct ctc agc aca cag tgt gac agt tac ggc aga tgc agc tgt aag<br>Gly Ser Leu Ser Thr Gln Cys Asp Ser Tyr Gly Arg Cys Ser Cys Lys<br>370                   375                   380 | 1152 |
| cca gga gtg atg ggt gac aag tgt gac cgt tgt cag cct ggg ttc cat<br>Pro Gly Val Met Gly Asp Lys Cys Asp Arg Cys Gln Pro Gly Phe His<br>385                   390                   395               400 | 1200 |
| tcc ctc act gag gca gga tgc agg cca tgc tcc tgc gat cct tcg ggc<br>Ser Leu Thr Glu Ala Gly Cys Arg Pro Cys Ser Cys Asp Pro Ser Gly<br>               405                   410                   415 | 1248 |
| agc aca gac gag tgt aat gtt gaa aca gga aga tgc gtt tgc aaa gac<br>Ser Thr Asp Glu Cys Asn Val Glu Thr Gly Arg Cys Val Cys Lys Asp<br>           420                   425                   430 | 1296 |
| aat gtt gaa ggc ttc aac tgt gag aga tgc aaa cct gga ttt ttt aat<br>Asn Val Glu Gly Phe Asn Cys Glu Arg Cys Lys Pro Gly Phe Phe Asn<br>           435                   440                   445 | 1344 |
| ctg gag tca tct aat cct aag ggc tgc aca ccc tgc ttc tgc ttt ggc<br>Leu Glu Ser Ser Asn Pro Lys Gly Cys Thr Pro Cys Phe Cys Phe Gly<br>450                   455                   460 | 1392 |

```
cat tct tct gtg tgc aca aat gct gtt ggc tac agt gtt tat gac atc    1440
His Ser Ser Val Cys Thr Asn Ala Val Gly Tyr Ser Val Tyr Asp Ile
465                 470                 475                 480 tcc tcc acc ttt cag att gat gag gat ggg tgg cgc gtg gag cag aga    1488
Ser Ser Thr Phe Gln Ile Asp Glu Asp Gly Trp Arg Val Glu Gln Arg
                485                 490                 495 gat ggc tcg gag gcg tct ctg gag tgg tcc tca gac agg caa tat att    1536
Asp Gly Ser Glu Ala Ser Leu Glu Trp Ser Ser Asp Arg Gln Tyr Ile
        500                 505                 510 gcc gta atc tca gac agt tac ttt cct aga tac ttc atc gcc cct gtg    1584
Ala Val Ile Ser Asp Ser Tyr Phe Pro Arg Tyr Phe Ile Ala Pro Val
    515                 520                 525 aag ttc ctg ggc aac cag gtc ctg agt tat ggg cag aat ctt tcc ttc    1632
Lys Phe Leu Gly Asn Gln Val Leu Ser Tyr Gly Gln Asn Leu Ser Phe
530                 535                 540 tcc ttc cga gtg gac aga cga gac act cgc ctc tcc gca gag gac ctt    1680
Ser Phe Arg Val Asp Arg Arg Asp Thr Arg Leu Ser Ala Glu Asp Leu
545                 550                 555                 560 gtg ctc gaa gga gct ggc ttg aga gta tcc gtg ccc ttg atc gct cag    1728
Val Leu Glu Gly Ala Gly Leu Arg Val Ser Val Pro Leu Ile Ala Gln
                565                 570                 575 ggc aac tcc tac ccc agc gag acc act gtg aag tac atc ttc agg ctc    1776
Gly Asn Ser Tyr Pro Ser Glu Thr Thr Val Lys Tyr Ile Phe Arg Leu
            580                 585                 590 cat gaa gca acg gat tac cct tgg agg ccc gct ctc tcc ccg ttt gaa    1824
His Glu Ala Thr Asp Tyr Pro Trp Arg Pro Ala Leu Ser Pro Phe Glu
        595                 600                 605 ttt cag aag ctc ctg aac aac ttg acc tct atc aag atc cgt ggt aca    1872
Phe Gln Lys Leu Leu Asn Asn Leu Thr Ser Ile Lys Ile Arg Gly Thr
610                 615                 620 tac agc gag agg agc gct ggg tac ttg gat gat gtc acc ttg caa agt    1920
Tyr Ser Glu Arg Ser Ala Gly Tyr Leu Asp Asp Val Thr Leu Gln Ser
625                 630                 635                 640 gct cgc cct ggg ccc gga gtc cct gca acg tgg gtg gag tcc tgc acc    1968
Ala Arg Pro Gly Pro Gly Val Pro Ala Thr Trp Val Glu Ser Cys Thr
                645                 650                 655 tgt cca gtg gga tac ggg gga cag ttc tgt gag acg tgc ctc cca ggg    2016
Cys Pro Val Gly Tyr Gly Gly Gln Phe Cys Glu Thr Cys Leu Pro Gly
            660                 665                 670 tac aga aga gaa act cca agc ctt gga cct tat agc ccg tgt gtg ctc    2064
Tyr Arg Arg Glu Thr Pro Ser Leu Gly Pro Tyr Ser Pro Cys Val Leu
        675                 680                 685 tgt acc tgt aat ggg cac agt gag acc tgt gac ccg gag aca ggt gtc    2112
Cys Thr Cys Asn Gly His Ser Glu Thr Cys Asp Pro Glu Thr Gly Val
690                 695                 700 tgt gac tgc aga gac aat aca gcc ggc ccc cac tgt gag aaa tgt agc    2160
Cys Asp Cys Arg Asp Asn Thr Ala Gly Pro His Cys Glu Lys Cys Ser
705                 710                 715                 720 gat ggg tac tat ggg gac tca acc ctg ggc acc tcc tct gac tgc cag    2208
Asp Gly Tyr Tyr Gly Asp Ser Thr Leu Gly Thr Ser Ser Asp Cys Gln
                725                 730                 735 cct tgt ccc tgc ccc ggt ggc tca agt tgt gcc att gtc cca aag aca    2256
Pro Cys Pro Cys Pro Gly Gly Ser Ser Cys Ala Ile Val Pro Lys Thr
            740                 745                 750 aag gaa gtg gtg tgc acg cac tgt ccg act ggc act gcc ggc aag aga    2304
Lys Glu Val Val Cys Thr His Cys Pro Thr Gly Thr Ala Gly Lys Arg
        755                 760                 765 tgt gaa ctc tgt gat gac ggc tac ttt gga gac cct ctg ggc agc aat    2352
Cys Glu Leu Cys Asp Asp Gly Tyr Phe Gly Asp Pro Leu Gly Ser Asn
```

```
                770                 775                 780
ggg ccc gtg aga ctg tgc cgc ccg tgc cag tgt aac gac aac ata gac      2400
Gly Pro Val Arg Leu Cys Arg Pro Cys Gln Cys Asn Asp Asn Ile Asp
785                 790                 795                 800 ccc aac gcg gtt ggc aac tgc aac cgc ctg acg ggc gag tgc ctg aag      2448
Pro Asn Ala Val Gly Asn Cys Asn Arg Leu Thr Gly Glu Cys Leu Lys
                805                 810                 815 tgc atc tat aac acg gct ggt ttc tac tgc gac cgg tgc aag gaa ggg      2496
Cys Ile Tyr Asn Thr Ala Gly Phe Tyr Cys Asp Arg Cys Lys Glu Gly
            820                 825                 830 ttt ttc gga aat ccc ctg gct ccc aat cca gcc gac aaa tgc aaa gcc      2544
Phe Phe Gly Asn Pro Leu Ala Pro Asn Pro Ala Asp Lys Cys Lys Ala
        835                 840                 845 tgc gcc tgc aac tac ggg aca gtg cag caa cag agc agc tgt aac ccg      2592
Cys Ala Cys Asn Tyr Gly Thr Val Gln Gln Gln Ser Ser Cys Asn Pro
850                 855                 860 gtg acc gga caa tgc cag tgt ctg cct cat gtg tct ggc cgc gac tgc      2640
Val Thr Gly Gln Cys Gln Cys Leu Pro His Val Ser Gly Arg Asp Cys
865                 870                 875                 880 ggt act tgt gac cct ggc tac tac aac ctg cag agc ggg caa ggc tgc      2688
Gly Thr Cys Asp Pro Gly Tyr Tyr Asn Leu Gln Ser Gly Gln Gly Cys
                885                 890                 895 gag agg tgt gac tgc cat gct ttg ggt tcc acc aat ggg cag tgt gac      2736
Glu Arg Cys Asp Cys His Ala Leu Gly Ser Thr Asn Gly Gln Cys Asp
            900                 905                 910 atc cgc acc ggg cag tgt gag tgc cag cct ggc atc acc ggt cag cac      2784
Ile Arg Thr Gly Gln Cys Glu Cys Gln Pro Gly Ile Thr Gly Gln His
        915                 920                 925 tgt gag cgc tgt gag acc aac cac ttt ggg ttt gga cct gaa ggc tgc      2832
Cys Glu Arg Cys Glu Thr Asn His Phe Gly Phe Gly Pro Glu Gly Cys
930                 935                 940 aaa cct tgt gac tgt cac cat gaa gga tcc ctt tcg ctc cag tgt aaa      2880
Lys Pro Cys Asp Cys His His Glu Gly Ser Leu Ser Leu Gln Cys Lys
945                 950                 955                 960 gac gac ggc cgt tgt gaa tgc agg gaa ggc ttt gtg ggc aat cgc tgt      2928
Asp Asp Gly Arg Cys Glu Cys Arg Glu Gly Phe Val Gly Asn Arg Cys
                965                 970                 975 gac cag tgt gaa gag aac tat ttc tac aat cgg tcc tgg cct ggc tgc      2976
Asp Gln Cys Glu Glu Asn Tyr Phe Tyr Asn Arg Ser Trp Pro Gly Cys
            980                 985                 990 cag gag tgt ccg gct tgt tac cga ctt gtg aag gat aag gct gct gag      3024
Gln Glu Cys Pro Ala Cys Tyr Arg Leu Val Lys Asp Lys Ala Ala Glu
        995                 1000                1005 cat cga gtg aaa ctc cag gag tta gag agc ctc atc gcc aac ctt ggc      3072
His Arg Val Lys Leu Gln Glu Leu Glu Ser Leu Ile Ala Asn Leu Gly
    1010                1015                1020 act ggg gat gac atg gtg aca gat caa gcc ttt gag gac aga ctt aag      3120
Thr Gly Asp Asp Met Val Thr Asp Gln Ala Phe Glu Asp Arg Leu Lys
1025                1030                1035                1040 gaa gca gaa agg gag gtg aca gac ctt ctc cgt gag gct cag gaa gtc      3168
Glu Ala Glu Arg Glu Val Thr Asp Leu Leu Arg Glu Ala Gln Glu Val
                1045                1050                1055 aaa gat gta gat caa aat ctg atg gat cgc ctt cag aga gta aat agc      3216
Lys Asp Val Asp Gln Asn Leu Met Asp Arg Leu Gln Arg Val Asn Ser
            1060                1065                1070 agc ctg cat agc caa att agc cga ctg cag aat atc cgg aat act atc      3264
Ser Leu His Ser Gln Ile Ser Arg Leu Gln Asn Ile Arg Asn Thr Ile
        1075                1080                1085 gaa gag acc ggg atc ttg gct gag cga gca cgg tcc cga gtg gag agt      3312
```

-continued

```
                Glu Glu Thr Gly Ile Leu Ala Glu Arg Ala Arg Ser Arg Val Glu Ser
                    1090                1095                1100 aca gag cag ctg att gag atc gcc tcc agg gag ctc gag aaa gca aaa        3360
Thr Glu Gln Leu Ile Glu Ile Ala Ser Arg Glu Leu Glu Lys Ala Lys
1105                1110                1115                1120 atg gcc gcc aat gtg tca atc act cag cca gag tct aca ggg gag cca        3408
Met Ala Ala Asn Val Ser Ile Thr Gln Pro Glu Ser Thr Gly Glu Pro
                1125                1130                1135 aac aac atg acc ctc ttg gca gaa gaa gcc cga agg ctt gca gag cgt        3456
Asn Asn Met Thr Leu Leu Ala Glu Glu Ala Arg Arg Leu Ala Glu Arg
            1140                1145                1150 cat aaa cag gaa gcc gat gac att gta cga gtg gca aag aca gcc aac        3504
His Lys Gln Glu Ala Asp Asp Ile Val Arg Val Ala Lys Thr Ala Asn
        1155                1160                1165 gag act tca gct gag gca tat aat ctg ctt ttg agg acc ctg gca gga        3552
Glu Thr Ser Ala Glu Ala Tyr Asn Leu Leu Leu Arg Thr Leu Ala Gly
    1170                1175                1180 gaa aat caa act gcg ctg gag att gaa gaa ctt aac cgg aag tac gaa        3600
Glu Asn Gln Thr Ala Leu Glu Ile Glu Glu Leu Asn Arg Lys Tyr Glu
1185                1190                1195                1200 caa gca aag aac atc tct cag gac ctg gag aag cag gct gcc cga gtc        3648
Gln Ala Lys Asn Ile Ser Gln Asp Leu Glu Lys Gln Ala Ala Arg Val
                1205                1210                1215 cat gag gaa gcc aag cgt gca ggt gac aaa gcc gta gag atc tat gcc        3696
His Glu Glu Ala Lys Arg Ala Gly Asp Lys Ala Val Glu Ile Tyr Ala
            1220                1225                1230 agt gtg gcc cag ctg acc cct gtg gac tct gag gcc ctg gag aat gaa        3744
Ser Val Ala Gln Leu Thr Pro Val Asp Ser Glu Ala Leu Glu Asn Glu
        1235                1240                1245 gca aat aaa atc aag aaa gaa gct gca gac ctg gac cgt ctg att gac        3792
Ala Asn Lys Ile Lys Lys Glu Ala Ala Asp Leu Asp Arg Leu Ile Asp
    1250                1255                1260 cag aag cta aag gat tac gag gac ctc agg gaa gac atg aga gga aag        3840
Gln Lys Leu Lys Asp Tyr Glu Asp Leu Arg Glu Asp Met Arg Gly Lys
1265                1270                1275                1280 gaa cat gaa gtg aag aac ctt cta gag aag ggg aaa gct gaa cag cag        3888
Glu His Glu Val Lys Asn Leu Leu Glu Lys Gly Lys Ala Glu Gln Gln
                1285                1290                1295 acc gcc gac caa ctc cta gct cga gcc gat gct gcc aag gcc ctt gct        3936
Thr Ala Asp Gln Leu Leu Ala Arg Ala Asp Ala Ala Lys Ala Leu Ala
            1300                1305                1310 gaa gaa gct gct aag aag gga cgc agt acc tta caa gaa gcc aat gac        3984
Glu Glu Ala Ala Lys Lys Gly Arg Ser Thr Leu Gln Glu Ala Asn Asp
        1315                1320                1325 att ctc aac aac ctg aaa gat ttt gat aga cgt gtg aac gat aac aag        4032
Ile Leu Asn Asn Leu Lys Asp Phe Asp Arg Arg Val Asn Asp Asn Lys
    1330                1335                1340 aca gcc gcg gaa gaa gct cta agg aga att ccc gcc atc aac cgg acc        4080
Thr Ala Ala Glu Glu Ala Leu Arg Arg Ile Pro Ala Ile Asn Arg Thr
1345                1350                1355                1360 ata gct gaa gcc aat gag aag aca agg gag gcc cag cta gcg ctg ggc        4128
Ile Ala Glu Ala Asn Glu Lys Thr Arg Glu Ala Gln Leu Ala Leu Gly
                1365                1370                1375 aat gct gcc gct gac gcc acg gag gcc aag aac aag gcc cat gag gca        4176
Asn Ala Ala Ala Asp Ala Thr Glu Ala Lys Asn Lys Ala His Glu Ala
            1380                1385                1390 gag agg atc gcc agc gcc gcg cag aag aat gcc acc agt acc aag gcg        4224
Glu Arg Ile Ala Ser Ala Ala Gln Lys Asn Ala Thr Ser Thr Lys Ala
        1395                1400                1405
```

-continued

| | | |
|---|---|---|
| gac gca gaa aga acc ttc ggg gaa gtt aca gat ctg gat aat gag gtg<br>Asp Ala Glu Arg Thr Phe Gly Glu Val Thr Asp Leu Asp Asn Glu Val<br>   1410                      1415                    1420 | 4272 |
| aac ggt atg ctg agg cag cta gag gag gca gag aat gag ctg aag agg<br>Asn Gly Met Leu Arg Gln Leu Glu Glu Ala Glu Asn Glu Leu Lys Arg<br>1425                  1430                    1435                    1440 | 4320 |
| aag caa gat gac gcc gac cag gac atg atg atg gcg ggg atg gct tcg<br>Lys Gln Asp Asp Ala Asp Gln Asp Met Met Met Ala Gly Met Ala Ser<br>                1445                    1450                    1455 | 4368 |
| caa gcc gct cag gag gct gag ctc aat gcc aga aag gcc aaa aac tct<br>Gln Ala Ala Gln Glu Ala Glu Leu Asn Ala Arg Lys Ala Lys Asn Ser<br>   1460                      1465                    1470 | 4416 |
| gtc agc agc ctc ctc agc cag ctg aac aac ctc ttg gat cag cta gga<br>Val Ser Ser Leu Leu Ser Gln Leu Asn Asn Leu Leu Asp Gln Leu Gly<br>                1475                    1480                    1485 | 4464 |
| cag ctg gac aca gtg gac ctg aac aag ctc aat gag atc gaa ggc tcc<br>Gln Leu Asp Thr Val Asp Leu Asn Lys Leu Asn Glu Ile Glu Gly Ser<br>   1490                      1495                    1500 | 4512 |
| ctg aac aaa gcc aaa gac gaa atg aag gcc agc gac ctg gac agg aag<br>Leu Asn Lys Ala Lys Asp Glu Met Lys Ala Ser Asp Leu Asp Arg Lys<br>1505                  1510                    1515                    1520 | 4560 |
| gtg tct gac ctg gag agc gag gct cgg aag cag gaa gca gcc atc atg<br>Val Ser Asp Leu Glu Ser Glu Ala Arg Lys Gln Glu Ala Ala Ile Met<br>                1525                    1530                    1535 | 4608 |
| gac tat aac cgg gac ata gca gag atc att aag gat att cac aac ctg<br>Asp Tyr Asn Arg Asp Ile Ala Glu Ile Ile Lys Asp Ile His Asn Leu<br>   1540                      1545                    1550 | 4656 |
| gag gac atc aag aag acc cta cca acc ggc tgc ttc aac acc ccg tct<br>Glu Asp Ile Lys Lys Thr Leu Pro Thr Gly Cys Phe Asn Thr Pro Ser<br>                1555                    1560                    1565 | 4704 |
| atc gag aag ccc tagtggcgag agggctgtaa ggcagtgtcc ctgacagggg<br>Ile Glu Lys Pro<br>   1570 | 4756 |
| accctgtgag gcctcggtgc cttgacacaa agattacact tttcagaccc ccacttctct | 4816 |
| gctgctctcc atcactgtcc ttttgaccca agaaaagtca gagtttaaag agaagcaagt | 4876 |
| taaacatctt taaccaggaa caaagggttt tgcctaataa agtctctcct ccacttctgt | 4936 |
| cagcaccta ccggaacttt cccttgtttg cctgaagtca cggcatcttc caggggccta | 4996 |
| cccacatcat gtgaaccttt taatgccagg gcagacccag cccctcccc tctctcaaca | 5056 |
| ccagcaggac ctatctcagt actcatgttt ctatgaagga atctttggc tcctcatcgt | 5116 |
| agcattgaga tggccagtat gtccgctctg catcttctgc ctcctctttg aaaggaaata | 5176 |
| aacatcctcg tgccaaaggt attggtcatt tagaatagtg gtggccatcc atcagacatg | 5236 |
| ctggctggct gagcatagga cacagagccg tcgtgggtga gcgtagttac atgtgggtcc | 5296 |
| ccaggagaac atggctcaaa gatgcttagg gttcctcctg ttttcattga ctaggaagat | 5356 |
| gaatgtttcc caaatcctca ggcagctgat aaaaagtctg gatgggcagc tcgcacgcac | 5416 |
| cactacgtga ggtagctttt gatattttta taagcaggac ttaatgcaga agaaacagat | 5476 |
| gtgataacca ctcaagtttt tttcccccaag tagtactaat tcttaaagct ttgttagtgt | 5536 |
| tagtcttgga actgttggta agatagctgt caaaacagtt gtcctctaag gtcatgacca | 5596 |
| atgaaagaag agcaaatctc ctttttcccca tattttctgg gaagtggctg taatcgggat | 5656 |
| gtaaccgctc tcattaggat tccatgagtg catttctttt tctcttttc ttggagagag | 5716 |
| atgtgacgtt tggcccttag ctccattctc ttctgatgtt tccgttcttt ctagaactct | 5776 |
| tcagagcaca tcgttgtttg ccaggtcctg gtggcaaaca cccgctcaca gtgtttctca | 5836 |

```
aggctgccaa ccccatctag ttcctgcact ttgtcggtcc gcccactcca agcctttcct    5896
ctgtgtggag agggaagatc catacgtggc atttcctagt gggcttctca acctctgatc    5956
ctcagctcgg tggtctcctt aagaccacac tgtgacagtt ccctgccaca catcccttc     6016 ctcctaccta cctgcctctg agattcatat ttagccttta acactatgca attttgtact    6076
ttgcgtacgg ggggaaagaa actattatct gacacactgg tgctattatt tgaaatttat    6136
attttttgtg tgaatggatt ttgtttatca tgattataga gtaaggaatt tatgtaaata    6196
tccccggtcc tcctagaacg gcactgtctg ctcacgtctc tgctcagttg tccctctcac    6256
tggcacagga acctgtacca tgcctggtca cgtcgtgcct ggtccccagt gttttgctcc    6316
acctctgcct tgtgtttgca gcaccttcac tgtctgaccg gaagcctgct cacctccaca    6376
acttgactga agagggccct cttccccgtg gctctgacca tctgagctgc agctcctcaa    6436
ggttctcatg cctgcccgga gcagtagcca agctgacagg gtaaagggat taggaacgtt    6496
tgtttgtgga accttcccac acgggtcagt tttctaaggg agcatgtgat gactgaacac    6556
ttgagggcat cagcaccgtg ctactgatga cagaggggag gctctgttca gcctgtctcc    6616
atctcggaga ttgccacaaa atctcagctt ggcatcctcc gaggcctttt gtgccacggc    6676
aagaaggcgt ggcctcacca agttcagtgc tgattggcta gttcctctat tccgagctca    6736
ccaccttaac attttggtca cagttgcaag aaaatggctg aaacagacca ccaccagcat    6796
cctttgggtc aactccactc cagcaggccc gaggcgctgg tgggtggggt gttttggttt    6856
gttttctcca gcttttgtgg tatattttta aacagaattt tattttttaa aatgaaagtt    6916
atttacaaga tgataccttc ttacgctcct tcgacacagc cattgcttta ttgtatagtt    6976
ccaataatct gtattttatg taatgaaatg gacagaatgc tgctgtagaa atgcggggtg    7036
ccgcacagaa cagattgttt tatccctccc ccgcccccgc ccatggaatt ttcctttgat    7096
tccaactgtg gcccttttca atgtgccttc actttagctg tttgccttaa tctctacagc    7156
cttcccccct cagggagggc aataaagcgc aacacttggc attttttat gtttaaaaag     7216 aaaacagtat tttatttata ataaaatctg aatatttgta acccttt                  7263
```

<210> SEQ ID NO 20
<211> LENGTH: 1572
<212> TYPE: PRT
<213> ORGANISM: Mus musculus

<400> SEQUENCE: 20

```
Ala Met Asp Glu Cys Ala Asp Glu Gly Gly Arg Pro Gln Arg Cys Met
 1               5                  10                  15

Pro Glu Phe Val Asn Ala Ala Phe Asn Val Thr Val Ala Thr Asn
                20                  25                  30

Thr Cys Gly Thr Pro Glu Glu Tyr Cys Val Gln Thr Gly Val Thr
            35                  40                  45

Gly Val Thr Lys Ser Cys His Leu Cys Asp Ala Gly Gln Gln His Leu
     50                  55                  60

Gln His Gly Ala Ala Phe Leu Thr Asp Tyr Asn Gln Ala Asp Thr
 65                  70                  75                  80

Thr Trp Trp Gln Ser Gln Thr Met Leu Ala Gly Val Gln Tyr Pro Asn
                85                  90                  95

Ser Ile Asn Leu Thr Leu His Leu Gly Lys Ala Phe Asp Ile Thr Tyr
                100                 105                 110

Val Arg Leu Lys Phe His Thr Ser Arg Pro Glu Ser Phe Ala Ile Tyr
```

```
            115                 120                 125
Lys Arg Thr Arg Glu Asp Gly Pro Trp Ile Pro Tyr Gln Tyr Tyr Ser
    130                 135                 140

Gly Ser Cys Glu Asn Thr Tyr Ser Lys Ala Asn Arg Gly Phe Ile Arg
145                 150                 155                 160

Thr Gly Gly Asp Glu Gln Gln Ala Leu Cys Thr Asp Glu Phe Ser Asp
                165                 170                 175

Ile Ser Pro Leu Thr Gly Gly Asn Val Ala Phe Ser Thr Leu Glu Gly
            180                 185                 190

Arg Pro Ser Ala Tyr Asn Phe Asp Asn Ser Pro Val Leu Gln Glu Trp
        195                 200                 205

Val Thr Ala Thr Asp Ile Arg Val Thr Leu Asn Arg Leu Asn Thr Phe
    210                 215                 220

Gly Asp Glu Val Phe Asn Asp Pro Lys Val Leu Lys Ser Tyr Tyr Tyr
225                 230                 235                 240

Ala Ile Ser Asp Phe Ala Val Gly Gly Arg Cys Lys Cys Asn Gly His
                245                 250                 255

Ala Ser Glu Cys Val Lys Asn Glu Phe Asp Lys Leu Met Cys Asn Cys
            260                 265                 270

Lys His Asn Thr Tyr Gly Val Asp Cys Glu Lys Cys Leu Pro Phe Phe
        275                 280                 285

Asn Asp Arg Pro Trp Arg Arg Ala Thr Ala Glu Ser Ala Ser Glu Cys
    290                 295                 300

Leu Pro Cys Asp Cys Asn Gly Arg Ser Gln Glu Cys Tyr Phe Asp Pro
305                 310                 315                 320

Glu Leu Tyr Arg Ser Thr Gly His Gly Gly His Cys Thr Asn Cys Arg
                325                 330                 335

Asp Asn Thr Asp Gly Ala Lys Cys Glu Arg Cys Arg Glu Asn Phe Phe
            340                 345                 350

Arg Leu Gly Asn Thr Glu Ala Cys Ser Pro Cys His Cys Ser Pro Val
        355                 360                 365

Gly Ser Leu Ser Thr Gln Cys Asp Ser Tyr Gly Arg Cys Ser Cys Lys
    370                 375                 380

Pro Gly Val Met Gly Asp Lys Cys Asp Arg Cys Gln Pro Gly Phe His
385                 390                 395                 400

Ser Leu Thr Glu Ala Gly Cys Arg Pro Cys Ser Cys Asp Pro Ser Gly
                405                 410                 415

Ser Thr Asp Glu Cys Asn Val Glu Thr Gly Arg Cys Val Cys Lys Asp
            420                 425                 430

Asn Val Glu Gly Phe Asn Cys Glu Arg Cys Lys Pro Gly Phe Phe Asn
        435                 440                 445

Leu Glu Ser Ser Asn Pro Lys Gly Cys Thr Pro Cys Phe Cys Phe Gly
    450                 455                 460

His Ser Ser Val Cys Thr Asn Ala Val Gly Tyr Ser Val Tyr Asp Ile
465                 470                 475                 480

Ser Ser Thr Phe Gln Ile Asp Glu Asp Gly Trp Arg Val Glu Gln Arg
                485                 490                 495

Asp Gly Ser Glu Ala Ser Leu Glu Trp Ser Ser Asp Arg Gln Tyr Ile
            500                 505                 510

Ala Val Ile Ser Asp Ser Tyr Phe Pro Arg Tyr Phe Ile Ala Pro Val
        515                 520                 525

Lys Phe Leu Gly Asn Gln Val Leu Ser Tyr Gly Gln Asn Leu Ser Phe
    530                 535                 540
```

```
Ser Phe Arg Val Asp Arg Arg Asp Thr Arg Leu Ser Ala Glu Asp Leu
545                 550                 555                 560

Val Leu Glu Gly Ala Gly Leu Arg Val Ser Val Pro Leu Ile Ala Gln
            565                 570                 575

Gly Asn Ser Tyr Pro Ser Glu Thr Thr Val Lys Tyr Ile Phe Arg Leu
            580                 585                 590

His Glu Ala Thr Asp Tyr Pro Trp Arg Pro Ala Leu Ser Pro Phe Glu
            595                 600                 605

Phe Gln Lys Leu Leu Asn Asn Leu Thr Ser Ile Lys Ile Arg Gly Thr
610                 615                 620

Tyr Ser Glu Arg Ser Ala Gly Tyr Leu Asp Asp Val Thr Leu Gln Ser
625                 630                 635                 640

Ala Arg Pro Gly Pro Gly Val Pro Ala Thr Trp Val Glu Ser Cys Thr
            645                 650                 655

Cys Pro Val Gly Tyr Gly Gly Gln Phe Cys Glu Thr Cys Leu Pro Gly
            660                 665                 670

Tyr Arg Arg Glu Thr Pro Ser Leu Gly Pro Tyr Ser Pro Cys Val Leu
            675                 680                 685

Cys Thr Cys Asn Gly His Ser Glu Thr Cys Asp Pro Glu Thr Gly Val
            690                 695                 700

Cys Asp Cys Arg Asp Asn Thr Ala Gly Pro His Cys Glu Lys Cys Ser
705                 710                 715                 720

Asp Gly Tyr Tyr Gly Asp Ser Thr Leu Gly Thr Ser Asp Cys Gln
                725                 730                 735

Pro Cys Pro Cys Pro Gly Gly Ser Ser Cys Ala Ile Val Pro Lys Thr
            740                 745                 750

Lys Glu Val Val Cys Thr His Cys Pro Thr Gly Thr Ala Gly Lys Arg
            755                 760                 765

Cys Glu Leu Cys Asp Asp Gly Tyr Phe Gly Asp Pro Leu Gly Ser Asn
770                 775                 780

Gly Pro Val Arg Leu Cys Arg Pro Cys Gln Cys Asn Asp Asn Ile Asp
785                 790                 795                 800

Pro Asn Ala Val Gly Asn Cys Asn Arg Leu Thr Gly Glu Cys Leu Lys
            805                 810                 815

Cys Ile Tyr Asn Thr Ala Gly Phe Tyr Cys Asp Arg Cys Lys Glu Gly
            820                 825                 830

Phe Phe Gly Asn Pro Leu Ala Pro Asn Pro Ala Asp Lys Cys Lys Ala
            835                 840                 845

Cys Ala Cys Asn Tyr Gly Thr Val Gln Gln Ser Ser Cys Asn Pro
850                 855                 860

Val Thr Gly Gln Cys Gln Cys Leu Pro His Val Ser Gly Arg Asp Cys
865                 870                 875                 880

Gly Thr Cys Asp Pro Gly Tyr Tyr Asn Leu Gln Ser Gly Gln Gly Cys
            885                 890                 895

Glu Arg Cys Asp Cys His Ala Leu Gly Ser Thr Asn Gly Gln Cys Asp
            900                 905                 910

Ile Arg Thr Gly Gln Cys Glu Cys Gln Pro Gly Ile Thr Gly Gln His
            915                 920                 925

Cys Glu Arg Cys Glu Thr Asn His Phe Gly Phe Gly Pro Glu Gly Cys
            930                 935                 940

Lys Pro Cys Asp Cys His His Glu Gly Ser Leu Ser Leu Gln Cys Lys
945                 950                 955                 960
```

-continued

Asp Asp Gly Arg Cys Glu Cys Arg Glu Gly Phe Val Gly Asn Arg Cys
                965                 970                 975

Asp Gln Cys Glu Glu Asn Tyr Phe Tyr Asn Arg Ser Trp Pro Gly Cys
            980                 985                 990

Gln Glu Cys Pro Ala Cys Tyr Arg Leu Val Lys Asp Lys Ala Ala Glu
            995                 1000                1005

His Arg Val Lys Leu Gln Glu Leu Glu Ser Leu Ile Ala Asn Leu Gly
        1010                1015                1020

Thr Gly Asp Asp Met Val Thr Asp Gln Ala Phe Glu Asp Arg Leu Lys
1025                1030                1035                1040

Glu Ala Glu Arg Glu Val Thr Asp Leu Leu Arg Glu Ala Gln Glu Val
                1045                1050                1055

Lys Asp Val Asp Gln Asn Leu Met Asp Arg Leu Gln Arg Val Asn Ser
            1060                1065                1070

Ser Leu His Ser Gln Ile Ser Arg Leu Gln Asn Ile Arg Asn Thr Ile
        1075                1080                1085

Glu Glu Thr Gly Ile Leu Ala Glu Arg Ala Arg Ser Arg Val Glu Ser
    1090                1095                1100

Thr Glu Gln Leu Ile Glu Ile Ala Ser Arg Glu Leu Glu Lys Ala Lys
1105                1110                1115                1120

Met Ala Ala Asn Val Ser Ile Thr Gln Pro Glu Ser Thr Gly Glu Pro
                1125                1130                1135

Asn Asn Met Thr Leu Leu Ala Glu Glu Ala Arg Arg Leu Ala Glu Arg
            1140                1145                1150

His Lys Gln Glu Ala Asp Asp Ile Val Arg Val Ala Lys Thr Ala Asn
        1155                1160                1165

Glu Thr Ser Ala Glu Ala Tyr Asn Leu Leu Leu Arg Thr Leu Ala Gly
    1170                1175                1180

Glu Asn Gln Thr Ala Leu Glu Ile Glu Glu Leu Asn Arg Lys Tyr Glu
1185                1190                1195                1200

Gln Ala Lys Asn Ile Ser Gln Asp Leu Glu Lys Gln Ala Ala Arg Val
            1205                1210                1215

His Glu Glu Ala Lys Arg Ala Gly Asp Lys Ala Val Glu Ile Tyr Ala
        1220                1225                1230

Ser Val Ala Gln Leu Thr Pro Val Asp Ser Glu Ala Leu Glu Asn Glu
    1235                1240                1245

Ala Asn Lys Ile Lys Lys Glu Ala Ala Asp Leu Asp Arg Leu Ile Asp
    1250                1255                1260

Gln Lys Leu Lys Asp Tyr Glu Asp Leu Arg Glu Asp Met Arg Gly Lys
1265                1270                1275                1280

Glu His Glu Val Lys Asn Leu Leu Glu Lys Gly Lys Ala Glu Gln Gln
        1285                1290                1295

Thr Ala Asp Gln Leu Leu Ala Arg Ala Asp Ala Ala Lys Ala Leu Ala
    1300                1305                1310

Glu Glu Ala Ala Lys Lys Gly Arg Ser Thr Leu Gln Glu Ala Asn Asp
    1315                1320                1325

Ile Leu Asn Asn Leu Lys Asp Phe Asp Arg Arg Val Asn Asp Asn Lys
    1330                1335                1340

Thr Ala Ala Glu Glu Ala Leu Arg Arg Ile Pro Ala Ile Asn Arg Thr
1345                1350                1355                1360

Ile Ala Glu Ala Asn Glu Lys Thr Arg Glu Ala Gln Leu Ala Leu Gly
        1365                1370                1375

Asn Ala Ala Ala Asp Ala Thr Glu Ala Lys Asn Lys Ala His Glu Ala

-continued

```
                        1380              1385              1390
Glu Arg Ile Ala Ser Ala Ala Gln Lys Asn Ala Thr Ser Thr Lys Ala
        1395              1400              1405
Asp Ala Glu Arg Thr Phe Gly Glu Val Thr Asp Leu Asp Asn Glu Val
    1410              1415              1420
Asn Gly Met Leu Arg Gln Leu Glu Glu Ala Glu Asn Glu Leu Lys Arg
1425              1430              1435              1440
Lys Gln Asp Asp Ala Asp Gln Asp Met Met Met Ala Gly Met Ala Ser
                1445              1450              1455
Gln Ala Ala Gln Glu Ala Glu Leu Asn Ala Arg Lys Ala Lys Asn Ser
            1460              1465              1470
Val Ser Ser Leu Leu Ser Gln Leu Asn Asn Leu Leu Asp Gln Leu Gly
        1475              1480              1485
Gln Leu Asp Thr Val Asp Leu Asn Lys Leu Asn Glu Ile Glu Gly Ser
    1490              1495              1500
Leu Asn Lys Ala Lys Asp Glu Met Lys Ala Ser Asp Leu Asp Arg Lys
1505              1510              1515              1520
Val Ser Asp Leu Glu Ser Glu Ala Arg Lys Gln Glu Ala Ala Ile Met
                1525              1530              1535
Asp Tyr Asn Arg Asp Ile Ala Glu Ile Ile Lys Asp Ile His Asn Leu
            1540              1545              1550
Glu Asp Ile Lys Lys Thr Leu Pro Thr Gly Cys Phe Asn Thr Pro Ser
        1555              1560              1565
Ile Glu Lys Pro
    1570
```

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Primer KZK1

<400> SEQUENCE: 21
gccaccatgg cgaagcggct ctg                                          23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer Ba3r

<400> SEQUENCE: 22
aagggcagga tccactgggg                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer Bam4

<400> SEQUENCE: 23
ctactgcgaa gctggctctt                                              20

<210> SEQ ID NO 24
<211> LENGTH: 19
<212> TYPE: DNA
<213> ORGANISM: Artificial Sequence

```
<220> FEATURE:
<223> OTHER INFORMATION: Description of Artificial Sequence: Primer Bcl1r

<400> SEQUENCE: 24
ccaggtggtc ctgggtatc                                                19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer Bcl2

<400> SEQUENCE: 25
gcgacaactg cctcctctac                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer Not4r

<400> SEQUENCE: 26
agtgggttcc caaagaatcc                                               20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Primer Bpu1F

<400> SEQUENCE: 27
cctctgtgac gagctcacg                                                19

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Primer D29

<400> SEQUENCE: 28
gatgtgtccc ttgtcagtgc cat                                           23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Primer D301

<400> SEQUENCE: 29
tgtcgtgttc agccgcttga ggt                                           23

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer Not3

<400> SEQUENCE: 30
ctctcagtgc cttccaacaa c                                             21
```

-continued

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Primer Sal4r

<400> SEQUENCE: 31
ctgactgtcg aagctgatgc                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer Sal5

<400> SEQUENCE: 32
ggaggtggtc agcctctaca                                                    20

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Primer FLAG1

<400> SEQUENCE: 33
ttacttgtca tcgtcgtcct tgtagtcggc ggctgggcag                              40

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Primer m19R

<400> SEQUENCE: 34
aatggtgcca gactcagg                                                      18

<210> SEQ ID NO 35
<211> LENGTH: 8296
<212> TYPE: DNA
<213> ORGANISM: Homo sapiens
<220> FEATURE:
<221> NAME/KEY: CDS
<222> LOCATION: (68)..(8296)
<221> NAME/KEY: sig_peptide
<222> LOCATION: (68)..(173)

<400> SEQUENCE: 35
agacccgccg ggctcccgcc gcgcgcgctg tccctggagc tcggggacgc ggcccggagc        60 cggggaag atg gcg aag cgg ctc tgc gcg ggg agc gca ctg tgt gtt cgc       109
         Met Ala Lys Arg Leu Cys Ala Gly Ser Ala Leu Cys Val Arg
           1               5                  10 ggc ccc cgg ggc ccc gcg ccg ctg ctg ctg gtc ggg ctg gcg ctg ctg       157
Gly Pro Arg Gly Pro Ala Pro Leu Leu Leu Val Gly Leu Ala Leu Leu
 15                  20                  25                  30 ggc gcg gcg cgg gcg cgg gag gag gcg ggc ggc ggc ttc agc ctg cac       205
Gly Ala Ala Arg Ala Arg Glu Glu Ala Gly Gly Gly Phe Ser Leu His
                 35                  40                  45 ccg ccc tac ttc aac ctg gcc gag ggc gcc cgc atc gcc gcc tcc gcg       253
Pro Pro Tyr Phe Asn Leu Ala Glu Gly Ala Arg Ile Ala Ala Ser Ala
             50                  55                  60

```
acc tgc gga gag gag gcc ccg gcg cgc ggc tcc ccg cgc ccc acc gag        301
Thr Cys Gly Glu Glu Ala Pro Ala Arg Gly Ser Pro Arg Pro Thr Glu
         65                  70                  75 gac ctt tac tgc aag ctg gta ggg ggc ccc gtg gcc ggc ggc gac ccc        349
Asp Leu Tyr Cys Lys Leu Val Gly Gly Pro Val Ala Gly Gly Asp Pro
 80                  85                  90 aac cag acc atc cgg ggc cag tac tgc gac atc tgc acg gct gcc aac        397
Asn Gln Thr Ile Arg Gly Gln Tyr Cys Asp Ile Cys Thr Ala Ala Asn
 95                 100                 105                 110 agc aac aag gca cac ccc gcg agc aat gcc atc gat ggc acg gag cgc        445
Ser Asn Lys Ala His Pro Ala Ser Asn Ala Ile Asp Gly Thr Glu Arg
            115                 120                 125 tgg tgg cag agt cca ccg ctg tcc cgc ggc ctg gag tac aac gag gtc        493
Trp Trp Gln Ser Pro Pro Leu Ser Arg Gly Leu Glu Tyr Asn Glu Val
            130                 135                 140 aac gtc acc ctg gac ctg ggc cag gtc ttc cac gtg gcc tac gtc ctc        541
Asn Val Thr Leu Asp Leu Gly Gln Val Phe His Val Ala Tyr Val Leu
            145                 150                 155 atc aag ttt gcc aac tca ccc cgg ccg gac ctc tgg gtg ctg gag cgg        589
Ile Lys Phe Ala Asn Ser Pro Arg Pro Asp Leu Trp Val Leu Glu Arg
160                 165                 170 tcc atg gac ttc ggc cgc acc tac cag ccc tgg cag ttc ttt gcc tcc        637
Ser Met Asp Phe Gly Arg Thr Tyr Gln Pro Trp Gln Phe Phe Ala Ser
175                 180                 185                 190 tct aag agg gac tgt ctg gag cgg ttc ggg cca cag acg ctg gag cgc        685
Ser Lys Arg Asp Cys Leu Glu Arg Phe Gly Pro Gln Thr Leu Glu Arg
                195                 200                 205 atc aca cgg gac gac gca gcc atc tgc acc acc gag tac tca cgc atc        733
Ile Thr Arg Asp Asp Ala Ala Ile Cys Thr Thr Glu Tyr Ser Arg Ile
            210                 215                 220 gtg ccc ctg gag aac gga gag atc gtg gtg tcc ctg gtg aac gga cgt        781
Val Pro Leu Glu Asn Gly Glu Ile Val Val Ser Leu Val Asn Gly Arg
            225                 230                 235 ccg ggc gcc atg aat ttc tcc tac tcg ccg ctg cta cgt gag ttc acc        829
Pro Gly Ala Met Asn Phe Ser Tyr Ser Pro Leu Leu Arg Glu Phe Thr
240                 245                 250 aag gcc acc aac gtc cgc ctg cgc ttc ctg cgt acc aac acg ctg ctg        877
Lys Ala Thr Asn Val Arg Leu Arg Phe Leu Arg Thr Asn Thr Leu Leu
255                 260                 265                 270 ggc cat ctc atg ggg aag gcg ctg cgg gac ccc acg gtc acc cgc cgg        925
Gly His Leu Met Gly Lys Ala Leu Arg Asp Pro Thr Val Thr Arg Arg
                275                 280                 285 tat tat tac agc atc aag gat atc agc atc gga ggc cgc tgt gtc tgc        973
Tyr Tyr Tyr Ser Ile Lys Asp Ile Ser Ile Gly Gly Arg Cys Val Cys
            290                 295                 300 cac ggc cac gcg gat gcc tgc gat gcc aaa gac ccc acg gac ccg ttc       1021
His Gly His Ala Asp Ala Cys Asp Ala Lys Asp Pro Thr Asp Pro Phe
            305                 310                 315 agg ctg cag tgc acc tgc cag cac aac acc tgc ggg ggc acc tgc gac       1069
Arg Leu Gln Cys Thr Cys Gln His Asn Thr Cys Gly Gly Thr Cys Asp
            320                 325                 330 cgc tgc tgc ccc ggc ttc aat cag cag ccg tgg aag cct gcg act gcc       1117
Arg Cys Cys Pro Gly Phe Asn Gln Gln Pro Trp Lys Pro Ala Thr Ala
335                 340                 345                 350 aac agt gcc aac gag tgc cag tcc tgt aac tgc tac ggc cat gcc acc       1165
Asn Ser Ala Asn Glu Cys Gln Ser Cys Asn Cys Tyr Gly His Ala Thr
                355                 360                 365 gac tgt tac tac gac cct gag gtg gac cgg cgc cgc gcc agc cag agc       1213
Asp Cys Tyr Tyr Asp Pro Glu Val Asp Arg Arg Arg Ala Ser Gln Ser
            370                 375                 380
```

-continued

```
ctg gat ggc acc tat cag ggt ggg ggt gtc tgt atc gac tgc cag cac    1261
Leu Asp Gly Thr Tyr Gln Gly Gly Gly Val Cys Ile Asp Cys Gln His
        385                 390                 395 cac acc gcc ggc gtc aac tgt gag cgc tgc ctg ccc ggc ttc tac cgc    1309
His Thr Ala Gly Val Asn Cys Glu Arg Cys Leu Pro Gly Phe Tyr Arg
400                 405                 410 tct ccc aac cac cct ctc gac tcg ccc cac gtc tgc cgc cgc tgc aac    1357
Ser Pro Asn His Pro Leu Asp Ser Pro His Val Cys Arg Arg Cys Asn
415                 420                 425                 430 tgc gag tcc gac ttc acg gat ggc acc tgc gag gac ctg acg ggt cga    1405
Cys Glu Ser Asp Phe Thr Asp Gly Thr Cys Glu Asp Leu Thr Gly Arg
                435                 440                 445 tgc tac tgc cgg ccc aac ttc tct ggg gag cgg tgt gac gtg tgt gcc    1453
Cys Tyr Cys Arg Pro Asn Phe Ser Gly Glu Arg Cys Asp Val Cys Ala
            450                 455                 460 gag ggc ttc acg ggc ttc cca agc tgc tac ccg acg ccc tcg tcc tcc    1501
Glu Gly Phe Thr Gly Phe Pro Ser Cys Tyr Pro Thr Pro Ser Ser Ser
        465                 470                 475 aat gac acc agg gag cag gtg ctg cca gct ggc cag att gtg aat tgt    1549
Asn Asp Thr Arg Glu Gln Val Leu Pro Ala Gly Gln Ile Val Asn Cys
480                 485                 490 gac tgc agc gcg gca ggg acc cag ggc aac gcc tgc cgg aag gac cca    1597
Asp Cys Ser Ala Ala Gly Thr Gln Gly Asn Ala Cys Arg Lys Asp Pro
495                 500                 505                 510 agg gtg gga cgc tgt ctg tgc aaa ccc aac ttc caa ggc acc cat tgt    1645
Arg Val Gly Arg Cys Leu Cys Lys Pro Asn Phe Gln Gly Thr His Cys
                515                 520                 525 gag ctc tgc gcg cca ggg ttc tac ggc ccc ggc tgc cag ccc tgc cag    1693
Glu Leu Cys Ala Pro Gly Phe Tyr Gly Pro Gly Cys Gln Pro Cys Gln
            530                 535                 540 tgt tcc agc cct gga gtg gcc gat gac cgc tgt gac cct gac aca ggc    1741
Cys Ser Ser Pro Gly Val Ala Asp Asp Arg Cys Asp Pro Asp Thr Gly
        545                 550                 555 cag tgc agg tgc cga gtg ggc ttc gag ggg gcc aca tgt gat cgc tgt    1789
Gln Cys Arg Cys Arg Val Gly Phe Glu Gly Ala Thr Cys Asp Arg Cys
560                 565                 570 gcc ccc ggc tac ttt cac ttc cct ctc tgc cag ttg tgt ggc tgc agc    1837
Ala Pro Gly Tyr Phe His Phe Pro Leu Cys Gln Leu Cys Gly Cys Ser
575                 580                 585                 590 cct gca gga acc ttg ccc gag ggc tgc gat gag gcc ggc cgc tgc cta    1885
Pro Ala Gly Thr Leu Pro Glu Gly Cys Asp Glu Ala Gly Arg Cys Leu
                595                 600                 605 tgc cag cct gag ttt gct gga cct cat tgt gac cgg tgc cgc cct ggc    1933
Cys Gln Pro Glu Phe Ala Gly Pro His Cys Asp Arg Cys Arg Pro Gly
            610                 615                 620 tac cat ggt ttc ccc aac tgc caa gca tgc acc tgc gac cct cgg gga    1981
Tyr His Gly Phe Pro Asn Cys Gln Ala Cys Thr Cys Asp Pro Arg Gly
        625                 630                 635 gcc ctg gac cag ctc tgt ggg gcg gga ggt ttg tgc cgc tgc cgc ccc    2029
Ala Leu Asp Gln Leu Cys Gly Ala Gly Gly Leu Cys Arg Cys Arg Pro
640                 645                 650 ggc tac aca ggc act gcc tgc cag gaa tgc agc ccc ggc ttt cac ggc    2077
Gly Tyr Thr Gly Thr Ala Cys Gln Glu Cys Ser Pro Gly Phe His Gly
655                 660                 665                 670 ttc ccc agc tgt gtc ccc tgc cac tgc tct gct gaa ggc tcc ctg cac    2125
Phe Pro Ser Cys Val Pro Cys His Cys Ser Ala Glu Gly Ser Leu His
                675                 680                 685 gca gcc tgt gac ccc cgg agt ggg cag tgc agc tgc cgg ccc cgt gtg    2173
Ala Ala Cys Asp Pro Arg Ser Gly Gln Cys Ser Cys Arg Pro Arg Val
```

-continued

```
                690                 695                 700
acg ggg ctg cgg tgt gac acg tgt gtg ccc ggt gcc tac aac ttc ccc     2221
Thr Gly Leu Arg Cys Asp Thr Cys Val Pro Gly Ala Tyr Asn Phe Pro
        705                 710                 715 tac tgc gaa gct ggc tct tgc cac cct gcc ggt ctg gcc cca gtg gat     2269
Tyr Cys Glu Ala Gly Ser Cys His Pro Ala Gly Leu Ala Pro Val Asp
    720                 725                 730 cct gcc ctt cct gag gca cag gtt ccc tgt atg tgc cgg gct cac gtg     2317
Pro Ala Leu Pro Glu Ala Gln Val Pro Cys Met Cys Arg Ala His Val
735                 740                 745                 750 gag ggg ccg agc tgt gac cgc tgc aaa cct ggg ttc tgg gga ctg agc     2365
Glu Gly Pro Ser Cys Asp Arg Cys Lys Pro Gly Phe Trp Gly Leu Ser
                755                 760                 765 ccc agc aac ccc gag ggc tgt acc cgc tgc agc tgc gac ctc agg ggc     2413
Pro Ser Asn Pro Glu Gly Cys Thr Arg Cys Ser Cys Asp Leu Arg Gly
            770                 775                 780 aca ctg ggt gga gtt gct gag tgc cag ccg ggc acc ggc cag tgc ttc     2461
Thr Leu Gly Gly Val Ala Glu Cys Gln Pro Gly Thr Gly Gln Cys Phe
        785                 790                 795 tgc aag ccc cac gtg tgc ggc cag gcc tgc gcg tcc tgc aag gat ggc     2509
Cys Lys Pro His Val Cys Gly Gln Ala Cys Ala Ser Cys Lys Asp Gly
    800                 805                 810 ttc ttt gga ctg gat cag gct gac tat ttt ggc tgc cgc agc tgc cgg     2557
Phe Phe Gly Leu Asp Gln Ala Asp Tyr Phe Gly Cys Arg Ser Cys Arg
815                 820                 825                 830 tgt gac att ggc ggt gca ctg ggc cag agc tgt gaa ccg agg acg ggc     2605
Cys Asp Ile Gly Gly Ala Leu Gly Gln Ser Cys Glu Pro Arg Thr Gly
                835                 840                 845 gtc tgc cgg tgc cgc ccc aac acc cag ggc ccc acc tgc agc gag cct     2653
Val Cys Arg Cys Arg Pro Asn Thr Gln Gly Pro Thr Cys Ser Glu Pro
            850                 855                 860 gcg agg gac cac tac ctc ccg gac ctg cac cac ctg cgc ctg gag ctg     2701
Ala Arg Asp His Tyr Leu Pro Asp Leu His His Leu Arg Leu Glu Leu
        865                 870                 875 gag gag gct gcc aca cct gag ggt cac gcc gtg cgc ttt ggc ttc aac     2749
Glu Glu Ala Ala Thr Pro Glu Gly His Ala Val Arg Phe Gly Phe Asn
    880                 885                 890 ccc ctc gag ttc gag aac ttc agc tgg agg ggc tac gcg cag atg gca     2797
Pro Leu Glu Phe Glu Asn Phe Ser Trp Arg Gly Tyr Ala Gln Met Ala
895                 900                 905                 910 cct gtc cag ccc agg atc gtg gcc agg ctg aac ctg acc tcc ccc gac     2845
Pro Val Gln Pro Arg Ile Val Ala Arg Leu Asn Leu Thr Ser Pro Asp
                915                 920                 925 ctt ttc tgg ctc gtc ttc cga tac gtc aac cgg ggg gcc atg agt gtg     2893
Leu Phe Trp Leu Val Phe Arg Tyr Val Asn Arg Gly Ala Met Ser Val
            930                 935                 940 agc ggg cgg gtc tct gtg cga gag gag ggc agg tcg gcc gcc tgt gcc     2941
Ser Gly Arg Val Ser Val Arg Glu Glu Gly Arg Ser Ala Ala Cys Ala
        945                 950                 955 aac tgc aca gca cag agt cag ccc gtg gcc ttc cca ccc agc acg gag     2989
Asn Cys Thr Ala Gln Ser Gln Pro Val Ala Phe Pro Pro Ser Thr Glu
    960                 965                 970 cct gcc ttc atc acc gtg ccc cag agg ggc ttc gga gag ccc ttt gtg     3037
Pro Ala Phe Ile Thr Val Pro Gln Arg Gly Phe Gly Glu Pro Phe Val
975                 980                 985                 990 ctg aac cct ggc acc tgg gcc ctg cgt gtg gag gcc gaa ggg gtg ctc     3085
Leu Asn Pro Gly Thr Trp Ala Leu Arg Val Glu Ala Glu Gly Val Leu
                995                 1000                1005 ctg gac tac gtg gtt ctg ctg cct agc gca tac tac gag gcg gcg ctc     3133
```

```
                    Leu Asp Tyr Val Val Leu Leu Pro Ser Ala Tyr Tyr Glu Ala Ala Leu
                                    1010                1015                1020 ctg cag ctg cgg gtg act gag gcc tgc aca tac cgt ccc tct gcc cag              3181
Leu Gln Leu Arg Val Thr Glu Ala Cys Thr Tyr Arg Pro Ser Ala Gln
            1025                1030                1035 cag tct ggc gac aac tgc ctc ctc tac aca cac ctc ccc ctg gat ggc              3229
Gln Ser Gly Asp Asn Cys Leu Leu Tyr Thr His Leu Pro Leu Asp Gly
    1040                1045                1050 ttc ccc tcg gcc gcc ggg ctg gag gcc ctg tgt cgc cag gac aac agc              3277
Phe Pro Ser Ala Ala Gly Leu Glu Ala Leu Cys Arg Gln Asp Asn Ser
1055                1060                1065                1070 ctg ccc cgg ccc tgc ccc acg gag cag ctc agc ccg tcg cac ccg cca              3325
Leu Pro Arg Pro Cys Pro Thr Glu Gln Leu Ser Pro Ser His Pro Pro
                1075                1080                1085 ctg atc acc tgc acg ggc agt gat gtg gac gtc cag ctt caa gtg gca              3373
Leu Ile Thr Cys Thr Gly Ser Asp Val Asp Val Gln Leu Gln Val Ala
        1090                1095                1100 gtg cca cag cca ggc cgc tat gcc cta gtg gtg gag tac gcc aat gag              3421
Val Pro Gln Pro Gly Arg Tyr Ala Leu Val Val Glu Tyr Ala Asn Glu
    1105                1110                1115 gat gcc cgc cag gag gtg ggc gtg gct gtg cac acc cca cag cgg gcc              3469
Asp Ala Arg Gln Glu Val Gly Val Ala Val His Thr Pro Gln Arg Ala
1120                1125                1130 ccc cag cag ggg ctg ctc tcc ctg cac ccc tgc ctg tac agc acc ctg              3517
Pro Gln Gln Gly Leu Leu Ser Leu His Pro Cys Leu Tyr Ser Thr Leu
1135                1140                1145                1150 tgc cgg ggc act gcc cgg gat acc cag gac cac ctg gct gtc ttc cac              3565
Cys Arg Gly Thr Ala Arg Asp Thr Gln Asp His Leu Ala Val Phe His
                1155                1160                1165 ctg gac tcg gag gcc agc gtg agg ctc aca gcc gag cag gca cgc ttc              3613
Leu Asp Ser Glu Ala Ser Val Arg Leu Thr Ala Glu Gln Ala Arg Phe
        1170                1175                1180 ttc ctg cac ggg gtc act ctg gtg ccc att gag gag ttc agc ccg gag              3661
Phe Leu His Gly Val Thr Leu Val Pro Ile Glu Glu Phe Ser Pro Glu
    1185                1190                1195 ttc gtg gag ccc cgg gtc agc tgc atc agc agc cac ggc gcc ttt ggc              3709
Phe Val Glu Pro Arg Val Ser Cys Ile Ser Ser His Gly Ala Phe Gly
1200                1205                1210 ccc aac agt gcc gcc tgt ctg ccc tcg cgc ttc cca aag ccg ccc cag              3757
Pro Asn Ser Ala Ala Cys Leu Pro Ser Arg Phe Pro Lys Pro Pro Gln
1215                1220                1225                1230 ccc atc atc ctc agg gac tgc cag gtg atc ccg ctg ccg ccc ggc ctc              3805
Pro Ile Ile Leu Arg Asp Cys Gln Val Ile Pro Leu Pro Pro Gly Leu
                1235                1240                1245 ccg ctg acc cac gcg cag gat ctc act cca gcc acg tcc cca gct gga              3853
Pro Leu Thr His Ala Gln Asp Leu Thr Pro Ala Thr Ser Pro Ala Gly
        1250                1255                1260 ccc cga cct cgg ccc ccc acc gct gtg gac cct gat gca gag ccc acc              3901
Pro Arg Pro Arg Pro Pro Thr Ala Val Asp Pro Asp Ala Glu Pro Thr
    1265                1270                1275 ctg ctg cgt gag ccc cag gcc acc gtg gtc ttc acc acc cat gtg ccc              3949
Leu Leu Arg Glu Pro Gln Ala Thr Val Val Phe Thr Thr His Val Pro
1280                1285                1290 acg ctg ggc cgc tat gcc ttc ctg ctg cac ggc tac cag cca gcc cac              3997
Thr Leu Gly Arg Tyr Ala Phe Leu Leu His Gly Tyr Gln Pro Ala His
1295                1300                1305                1310 ccc acc ttc ccc gtg gaa gtc ctc atc aac gcc ggc cgc gtg tgg cag              4045
Pro Thr Phe Pro Val Glu Val Leu Ile Asn Ala Gly Arg Val Trp Gln
                1315                1320                1325
```

-continued

| | |
|---|---|
| ggc cac gcc aac gcc agc ttc tgt cca cat ggc tac ggc tgc cgc acc<br>Gly His Ala Asn Ala Ser Phe Cys Pro His Gly Tyr Gly Cys Arg Thr<br>1330                       1335                    1340 | 4093 |
| ctg gtg gtg tgt gag ggc cag gcc ctg ctg gac gtg acc cac agc gag<br>Leu Val Val Cys Glu Gly Gln Ala Leu Leu Asp Val Thr His Ser Glu<br>    1345                    1350                    1355 | 4141 |
| ctc act gtg acc gtg cgt gtg ccc gag ggc cgg tgg ctc tgg ctg gat<br>Leu Thr Val Thr Val Arg Val Pro Glu Gly Arg Trp Leu Trp Leu Asp<br>1360                       1365                    1370 | 4189 |
| tat gta ctc gtg gtc cct gag aac gtc tac agc ttt ggc tac ctc cgg<br>Tyr Val Leu Val Val Pro Glu Asn Val Tyr Ser Phe Gly Tyr Leu Arg<br>1375                       1380                    1385                    1390 | 4237 |
| gag gag ccc ctg gat aaa tcc tat gac ttc atc agc cac tgc gca gcc<br>Glu Glu Pro Leu Asp Lys Ser Tyr Asp Phe Ile Ser His Cys Ala Ala<br>    1395                    1400                    1405 | 4285 |
| cag ggc tac cac atc agc ccc agc agc tca tcc ctg ttc tgc cga aac<br>Gln Gly Tyr His Ile Ser Pro Ser Ser Ser Leu Phe Cys Arg Asn<br>        1410                    1415                    1420 | 4333 |
| gct gct gct tcc ctc tcc ctc ttc tat aac aac gga gcc cgt cca tgt<br>Ala Ala Ala Ser Leu Ser Leu Phe Tyr Asn Asn Gly Ala Arg Pro Cys<br>1425                       1430                    1435 | 4381 |
| ggc tgc cac gaa gta ggt gct aca ggc ccc acg tgt gag ccc ttc ggg<br>Gly Cys His Glu Val Gly Ala Thr Gly Pro Thr Cys Glu Pro Phe Gly<br>    1440                    1445                    1450 | 4429 |
| ggc cag tgt ccc tgc cat gcc cat gtc att ggc cgt gac tgc tcc cgc<br>Gly Gln Cys Pro Cys His Ala His Val Ile Gly Arg Asp Cys Ser Arg<br>1455                       1460                    1465                    1470 | 4477 |
| tgt gcc acc gga tac tgg ggc ttc ccc aac tgc agg ccc tgt gac tgc<br>Cys Ala Thr Gly Tyr Trp Gly Phe Pro Asn Cys Arg Pro Cys Asp Cys<br>                            1475                    1480                    1485 | 4525 |
| ggt gcc cgc ctc tgt gac gag ctc acg ggc cag tgc atc tgc ccg cca<br>Gly Ala Arg Leu Cys Asp Glu Leu Thr Gly Gln Cys Ile Cys Pro Pro<br>1490                       1495                    1500 | 4573 |
| cgc acc atc ccg ccc gac tgc ctg ctg tgc cag ccc cag acc ttt ggc<br>Arg Thr Ile Pro Pro Asp Cys Leu Leu Cys Gln Pro Gln Thr Phe Gly<br>    1505                    1510                    1515 | 4621 |
| tgc cac ccc ctg gtc ggc tgt gag gag tgt aac tgc tca ggg ccc ggc<br>Cys His Pro Leu Val Gly Cys Glu Glu Cys Asn Cys Ser Gly Pro Gly<br>1520                       1525                    1530 | 4669 |
| atc cag gag ctc aca gac cct acc tgt gac aca gac agc ggc cag tgc<br>Ile Gln Glu Leu Thr Asp Pro Thr Cys Asp Thr Asp Ser Gly Gln Cys<br>1535                       1540                    1545                    1550 | 4717 |
| aag tgc aga ccc aac gtg act ggg cgc cgc tgt gat acc tgc tct ccg<br>Lys Cys Arg Pro Asn Val Thr Gly Arg Arg Cys Asp Thr Cys Ser Pro<br>                            1555                    1560                    1565 | 4765 |
| ggc ttc cat ggc tac ccc cgc tgc cgc ccc tgt gac tgt cac gag gcg<br>Gly Phe His Gly Tyr Pro Arg Cys Arg Pro Cys Asp Cys His Glu Ala<br>1570                       1575                    1580 | 4813 |
| ggc act gcg cct ggc gtg tgt gac ccc ctc aca ggg cag tgc tac tgt<br>Gly Thr Ala Pro Gly Val Cys Asp Pro Leu Thr Gly Gln Cys Tyr Cys<br>    1585                    1590                    1595 | 4861 |
| aag gag aac gtg cag ggc ccc aaa tgt gac cag tgc agc ctt ggg acc<br>Lys Glu Asn Val Gln Gly Pro Lys Cys Asp Gln Cys Ser Leu Gly Thr<br>1600                       1605                    1610 | 4909 |
| ttc tca ctg gat gct gcc aac ccc aaa ggt tgc acc cgc tgc ttc tgc<br>Phe Ser Leu Asp Ala Ala Asn Pro Lys Gly Cys Thr Arg Cys Phe Cys<br>1615                       1620                    1625                    1630 | 4957 |
| ttt ggg gcc acg gag cgc tgc cgg agc tcg tcc tac acc cgc cag gag<br>Phe Gly Ala Thr Glu Arg Cys Arg Ser Ser Ser Tyr Thr Arg Gln Glu<br>                            1635                    1640                    1645 | 5005 |

-continued

```
ttc gtg gat atg gag gga tgg gtg ctg ctg agc act gac cgg cag gtg       5053
Phe Val Asp Met Glu Gly Trp Val Leu Leu Ser Thr Asp Arg Gln Val
        1650                1655                1660 gtg ccc cac gag cgg cag cca ggg acg gag atg ctc cgt gca gac ctg       5101
Val Pro His Glu Arg Gln Pro Gly Thr Glu Met Leu Arg Ala Asp Leu
    1665                1670                1675 cgg cac gtg cct gag gct gtg ccc gag gct ttc ccc gag ctg tac tgg       5149
Arg His Val Pro Glu Ala Val Pro Glu Ala Phe Pro Glu Leu Tyr Trp
    1680                1685                1690 cag gcc cca ccc tcc tac ctg ggg gac cgg gtg tca tcc tac ggt ggg       5197
Gln Ala Pro Pro Ser Tyr Leu Gly Asp Arg Val Ser Ser Tyr Gly Gly
1695                1700                1705                1710 acc ctc cgt tat gaa ctg cac tca gag acc cag cgg gga gat gtc ttt       5245
Thr Leu Arg Tyr Glu Leu His Ser Glu Thr Gln Arg Gly Asp Val Phe
                1715                1720                1725 gtc ccc atg gag agc agg ccg gat gtg gtg ctg cag ggc aac cag atg       5293
Val Pro Met Glu Ser Arg Pro Asp Val Val Leu Gln Gly Asn Gln Met
    1730                1735                1740 agc atc aca ttc ctg gag ccg gca tac ccc acg cct ggc cac gtt cac       5341
Ser Ile Thr Phe Leu Glu Pro Ala Tyr Pro Thr Pro Gly His Val His
        1745                1750                1755 cgt ggg cag ctg cag ctg gtg gag ggg aac ttc cgg cat acg gag act       5389
Arg Gly Gln Leu Gln Leu Val Glu Gly Asn Phe Arg His Thr Glu Thr
    1760                1765                1770 cgc aac act gtg tcc cgc gag gag ctc atg atg gtg ctg gcc agc ctg       5437
Arg Asn Thr Val Ser Arg Glu Glu Leu Met Met Val Leu Ala Ser Leu
1775                1780                1785                1790 gag cag ctg cag atc cgt gcc ctc ttc tca cag atc tcc tcg gct gtc       5485
Glu Gln Leu Gln Ile Arg Ala Leu Phe Ser Gln Ile Ser Ser Ala Val
                1795                1800                1805 tcc ctg cgc agg gtg gca ctg gag gtg gcc agc cca gca ggc cag ggg       5533
Ser Leu Arg Arg Val Ala Leu Glu Val Ala Ser Pro Ala Gly Gln Gly
    1810                1815                1820 gcc ctg gcc agc aat gtg gag ctg tgc ctg tgc ccc gcc agc tac cgg       5581
Ala Leu Ala Ser Asn Val Glu Leu Cys Leu Cys Pro Ala Ser Tyr Arg
        1825                1830                1835 ggg gac tca tgc cag gaa tgt gcc ccc ggc ttc tat cgg gac gtc aaa       5629
Gly Asp Ser Cys Gln Glu Cys Ala Pro Gly Phe Tyr Arg Asp Val Lys
    1840                1845                1850 ggt ctc ttc ctg ggc cga tgt gtc cct tgt cag tgc cat gga cac tca       5677
Gly Leu Phe Leu Gly Arg Cys Val Pro Cys Gln Cys His Gly His Ser
1855                1860                1865                1870 gac cgc tgc ctc cct ggc tct ggc gtc tgt gtg gac tgc cag cac aac       5725
Asp Arg Cys Leu Pro Gly Ser Gly Val Cys Val Asp Cys Gln His Asn
                1875                1880                1885 acc gaa ggg gcc cac tgt gag cgc tgc cag gct ggc ttc atg agc agc       5773
Thr Glu Gly Ala His Cys Glu Arg Cys Gln Ala Gly Phe Met Ser Ser
    1890                1895                1900 agg gac gac ccc agc gcc ccc tgt gtc agc tgc ccc tgc ccc ctc tca       5821
Arg Asp Asp Pro Ser Ala Pro Cys Val Ser Cys Pro Cys Pro Leu Ser
        1905                1910                1915 gtg cct tcc aac aac ttc gcc gag ggc tgt gtc ctg cga ggc ggc cgc       5869
Val Pro Ser Asn Asn Phe Ala Glu Gly Cys Val Leu Arg Gly Gly Arg
    1920                1925                1930 acc cag tgc ctc tgc aaa cct ggt tat gca ggt gcc tcc tgc gag cgg       5917
Thr Gln Cys Leu Cys Lys Pro Gly Tyr Ala Gly Ala Ser Cys Glu Arg
1935                1940                1945                1950 tgt gcg ccc gga ttc ttt ggg aac cca ctg gtg ctg ggc agc tcc tgc       5965
Cys Ala Pro Gly Phe Phe Gly Asn Pro Leu Val Leu Gly Ser Ser Cys
```

-continued

```
                1955                1960                1965
cag cca tgc gac tgc agc ggc aac ggt gac ccc aac ttg ctc ttc agc    6013
Gln Pro Cys Asp Cys Ser Gly Asn Gly Asp Pro Asn Leu Leu Phe Ser
        1970                1975                1980 gac tgc gac ccc ctg acg ggc gcc tgc gtg ggc tgc ctg cgc cac acc    6061
Asp Cys Asp Pro Leu Thr Gly Ala Cys Val Gly Cys Leu Arg His Thr
    1985                1990                1995 act ggg ccc cgc tgc gag atc tgt gcc ccc ggc ttc tac ggc aac gcc    6109
Thr Gly Pro Arg Cys Glu Ile Cys Ala Pro Gly Phe Tyr Gly Asn Ala
    2000                2005                2010 ctg ctg ccc ggc aac tgc acc cgg tgc gac tgt acc cca tgt ggg aca    6157
Leu Leu Pro Gly Asn Cys Thr Arg Cys Asp Cys Thr Pro Cys Gly Thr
2015                2020                2025                2030 gag gcc tgc gac ccc cac agc ggg cac tgc ctg tgc aag gcg ggc gtg    6205
Glu Ala Cys Asp Pro His Ser Gly His Cys Leu Cys Lys Ala Gly Val
            2035                2040                2045 act ggg cgg cgc tgt gac cgc tgc cag gag gga cat ttt ggt ttc aat    6253
Thr Gly Arg Arg Cys Asp Arg Cys Gln Glu Gly His Phe Gly Phe Asn
    2050                2055                2060 ggc tgc ggg ggc tgc cgc ccg tgt gct tgt gga ccg gcc gcc gag ggc    6301
Gly Cys Gly Gly Cys Arg Pro Cys Ala Cys Gly Pro Ala Ala Glu Gly
    2065                2070                2075 tcc gag tgc cac ccc cag agc gga cag tgc cac tgc cga cca ggg acc    6349
Ser Glu Cys His Pro Gln Ser Gly Gln Cys His Cys Arg Pro Gly Thr
    2080                2085                2090 atg gga ccc cag tgc cgc gag tgt gcc cct ggc tac tgg ggg ctc cct    6397
Met Gly Pro Gln Cys Arg Glu Cys Ala Pro Gly Tyr Trp Gly Leu Pro
2095                2100                2105                2110 gag cag ggc tgc agg cgc tgc cag tgc cct ggg ggc cgc tgt gac cct    6445
Glu Gln Gly Cys Arg Arg Cys Gln Cys Pro Gly Gly Arg Cys Asp Pro
            2115                2120                2125 cac acg ggc cgc tgc aac tgc ccc ccg ggg ctc agc ggg gag cgc tgc    6493
His Thr Gly Arg Cys Asn Cys Pro Pro Gly Leu Ser Gly Glu Arg Cys
    2130                2135                2140 gac acc tgc agc cag cag cat cag gtg cct gtt cca ggc ggg cct gtg    6541
Asp Thr Cys Ser Gln Gln His Gln Val Pro Val Pro Gly Gly Pro Val
    2145                2150                2155 ggc cac agc atc cac tgt gaa gtg tgt gac cac tgt gtg gtc ctg ctc    6589
Gly His Ser Ile His Cys Glu Val Cys Asp His Cys Val Val Leu Leu
    2160                2165                2170 ctg gat gac ctg gaa cgg gcc ggc gcc ctc ctc ccc gcc att cac gag    6637
Leu Asp Asp Leu Glu Arg Ala Gly Ala Leu Leu Pro Ala Ile His Glu
2175                2180                2185                2190 caa ctg cgt ggc atc aat gcc agc tcc atg gcc tgg gcc cgt ctg cac    6685
Gln Leu Arg Gly Ile Asn Ala Ser Ser Met Ala Trp Ala Arg Leu His
            2195                2200                2205 agg ctg aac gcc tcc atc gct gac ctg cag agc cag ctc cgg agc ccc    6733
Arg Leu Asn Ala Ser Ile Ala Asp Leu Gln Ser Gln Leu Arg Ser Pro
    2210                2215                2220 ctg ggc ccc cgc cat gag acg gca cag cag ctg gag gtg ctg gag cag    6781
Leu Gly Pro Arg His Glu Thr Ala Gln Gln Leu Glu Val Leu Glu Gln
    2225                2230                2235 cag agc aca agc ctc ggg cag gac gca cgg cgg cta ggc ggc cag gcc    6829
Gln Ser Thr Ser Leu Gly Gln Asp Ala Arg Arg Leu Gly Gly Gln Ala
    2240                2245                2250 gtg ggg acc cga gac cag gcg agc caa ttg ctg gcc ggc acc gag gcc    6877
Val Gly Thr Arg Asp Gln Ala Ser Gln Leu Leu Ala Gly Thr Glu Ala
2255                2260                2265                2270 aca ctg ggc cat gcg aag acg ctg ttg gcg gcc atc cgg gct gtg gac    6925
Thr Leu Gly His Ala Lys Thr Leu Leu Ala Ala Ile Arg Ala Val Asp
```

```
                Thr Leu Gly His Ala Lys Thr Leu Leu Ala Ala Ile Arg Ala Val Asp
                                2275                2280                2285 cgc acc ctg agc gag ctc atg tcc cag acg ggc cac ctg ggg ctg gcc           6973
Arg Thr Leu Ser Glu Leu Met Ser Gln Thr Gly His Leu Gly Leu Ala
                2290                2295                2300 aat gcc tcg gct cca tca ggt gag cag ctg ctc cgg aca ctg gcc gag           7021
Asn Ala Ser Ala Pro Ser Gly Glu Gln Leu Leu Arg Thr Leu Ala Glu
        2305                2310                2315 gtg gag cgg ctg ctc tgg gag atg cgg gcc cgg gac ctg ggg gcc ccg           7069
Val Glu Arg Leu Leu Trp Glu Met Arg Ala Arg Asp Leu Gly Ala Pro
    2320                2325                2330 cag gca gca gct gag gct gag ttg gct gca gca cag aga ttg ctg gcc           7117
Gln Ala Ala Ala Glu Ala Glu Leu Ala Ala Ala Gln Arg Leu Leu Ala
2335                2340                2345                2350 cgg gtg cag gag cag ctg agc agc ctc tgg gag gag aac cag gca ctg           7165
Arg Val Gln Glu Gln Leu Ser Ser Leu Trp Glu Glu Asn Gln Ala Leu
                2355                2360                2365 gcc aca caa acc cgc gac cgg ctg gcc cag cac gag gcc ggc ctc atg           7213
Ala Thr Gln Thr Arg Asp Arg Leu Ala Gln His Glu Ala Gly Leu Met
        2370                2375                2380 gac ctg cga gag gct ttg aac cgg gca gtg gac gcc aca cgg gag gcc           7261
Asp Leu Arg Glu Ala Leu Asn Arg Ala Val Asp Ala Thr Arg Glu Ala
    2385                2390                2395 cag gag ctc aac agc cgc aac cag gag cgc ctg gag gaa gcc ctg caa           7309
Gln Glu Leu Asn Ser Arg Asn Gln Glu Arg Leu Glu Glu Ala Leu Gln
2400                2405                2410 agg aag cag gag ctg tcc cgg gac aat gcc acc ctg cag gcc act ctg           7357
Arg Lys Gln Glu Leu Ser Arg Asp Asn Ala Thr Leu Gln Ala Thr Leu
2415                2420                2425                2430 cat gcg gct agg gac acc ctg gcc agc gtc ttc aga ttg ctg cac agc           7405
His Ala Ala Arg Asp Thr Leu Ala Ser Val Phe Arg Leu Leu His Ser
                2435                2440                2445 ctg gac cag gct aag gag gag ctg gag cgc ctc gcc gcc agc ctg gac           7453
Leu Asp Gln Ala Lys Glu Glu Leu Glu Arg Leu Ala Ala Ser Leu Asp
        2450                2455                2460 ggg gct cgg acc cca ctg ctg cag agg atg cag acc ttc tcc ccg gcg           7501
Gly Ala Arg Thr Pro Leu Leu Gln Arg Met Gln Thr Phe Ser Pro Ala
    2465                2470                2475 ggc agc aag ctg cgt cta gtg gag gcc gcc gag gcc cac gca cag cag           7549
Gly Ser Lys Leu Arg Leu Val Glu Ala Ala Glu Ala His Ala Gln Gln
2480                2485                2490 ctg ggc cag ctg gca ctc aat ctg tcc agc atc atc ctg gac gtc aac           7597
Leu Gly Gln Leu Ala Leu Asn Leu Ser Ser Ile Ile Leu Asp Val Asn
2495                2500                2505                2510 cag gac cgc ctc acc cag agg gcc atc gag gcc tcc aac gcc tac agc           7645
Gln Asp Arg Leu Thr Gln Arg Ala Ile Glu Ala Ser Asn Ala Tyr Ser
                2515                2520                2525 cgc atc ctg cag gcc gtg cag gct gcc gag gat gct gct ggc cag gcc           7693
Arg Ile Leu Gln Ala Val Gln Ala Ala Glu Asp Ala Ala Gly Gln Ala
        2530                2535                2540 ctg cag cag gcg gac cac acg tgg gcg acg gtg gtg cgg cag ggc ctg           7741
Leu Gln Gln Ala Asp His Thr Trp Ala Thr Val Val Arg Gln Gly Leu
    2545                2550                2555 gtg gac cga gcc cag cag ctc ctg gcc aac agc act gca cta gaa gag           7789
Val Asp Arg Ala Gln Gln Leu Leu Ala Asn Ser Thr Ala Leu Glu Glu
2560                2565                2570 gcc atg ctc cag gaa cag cag agg ctg ggc ctt gtg tgg gct gcc ctc           7837
Ala Met Leu Gln Glu Gln Gln Arg Leu Gly Leu Val Trp Ala Ala Leu
2575                2580                2585                2590
```

-continued

| | |
|---|---|
| cag ggt gcc agg acc cag ctc cga gat gtc cgg gcc aag aag gac cag<br>Gln Gly Ala Arg Thr Gln Leu Arg Asp Val Arg Ala Lys Lys Asp Gln<br>                2595                        2600                        2605 | 7885 |
| ctg gag gcg cac atc cag gcg gcg cag gcc atg ctt gcc atg gac aca<br>Leu Glu Ala His Ile Gln Ala Ala Gln Ala Met Leu Ala Met Asp Thr<br>2610                        2615                        2620 | 7933 |
| gac gag aca agc aag aag atc gca cat gcc aag gct gtg gct gct gaa<br>Asp Glu Thr Ser Lys Lys Ile Ala His Ala Lys Ala Val Ala Ala Glu<br>2625                        2630                        2635 | 7981 |
| gcc cag gac acc gcc acc cgt gtg cag tcc cag ctg cag gcc atg cag<br>Ala Gln Asp Thr Ala Thr Arg Val Gln Ser Gln Leu Gln Ala Met Gln<br>2640                        2645                        2650 | 8029 |
| gag aat gtg gag cgg tgg cag ggc cag tac gag ggc ctg cgg ggc cag<br>Glu Asn Val Glu Arg Trp Gln Gly Gln Tyr Glu Gly Leu Arg Gly Gln<br>2655                        2660                        2665                        2670 | 8077 |
| gac ctg ggc cag gca gtg ctt gac gca ggc cac tca gtg tcc acc ctg<br>Asp Leu Gly Gln Ala Val Leu Asp Ala Gly His Ser Val Ser Thr Leu<br>                  2675                        2680                        2685 | 8125 |
| gag aag acg ctg ccc cag ctg ctg gcc aag ctg agc atc ctg gag aac<br>Glu Lys Thr Leu Pro Gln Leu Leu Ala Lys Leu Ser Ile Leu Glu Asn<br>                  2690                        2695                        2700 | 8173 |
| cgt ggg gtg cac aac gcc agc ctg gcc ctg tcc gcc agc att ggc cgc<br>Arg Gly Val His Asn Ala Ser Leu Ala Leu Ser Ala Ser Ile Gly Arg<br>                  2705                        2710                        2715 | 8221 |
| gtg cga gag ctc att gcc cag gcc cgg ggg gct gcc agt aag gtc aag<br>Val Arg Glu Leu Ile Ala Gln Ala Arg Gly Ala Ala Ser Lys Val Lys<br>2720                        2725                        2730 | 8269 |
| gtg ccc atg aag ttc aac ggg cgc tca<br>Val Pro Met Lys Phe Asn Gly Arg Ser<br>2735                        2740 | 8296 |

<210> SEQ ID NO 36
<211> LENGTH: 2743
<212> TYPE: PRT
<213> ORGANISM: Homo sapiens

<400> SEQUENCE: 36

Met Ala Lys Arg Leu Cys Ala Gly Ser Ala Leu Cys Val Arg Gly Pro
1               5                  10                 15

Arg Gly Pro Ala Pro Leu Leu Val Gly Leu Ala Leu Leu Gly Ala
               20                  25                  30

Ala Arg Ala Arg Glu Glu Ala Gly Gly Phe Ser Leu His Pro Pro
        35                  40                  45

Tyr Phe Asn Leu Ala Glu Gly Ala Arg Ile Ala Ala Ser Ala Thr Cys
 50                 55                  60

Gly Glu Glu Ala Pro Ala Arg Gly Ser Pro Arg Pro Thr Glu Asp Leu
65               70                  75                  80

Tyr Cys Lys Leu Val Gly Gly Pro Val Ala Gly Gly Asp Pro Asn Gln
               85                  90                  95

Thr Ile Arg Gly Gln Tyr Cys Asp Ile Cys Thr Ala Ala Asn Ser Asn
            100                105               110

Lys Ala His Pro Ala Ser Asn Ala Ile Asp Gly Thr Glu Arg Trp Trp
       115                120               125

Gln Ser Pro Pro Leu Ser Arg Gly Leu Glu Tyr Asn Glu Val Asn Val
  130                135                140

Thr Leu Asp Leu Gly Gln Val Phe His Val Ala Tyr Val Leu Ile Lys
145              150                 155               160

Phe Ala Asn Ser Pro Arg Pro Asp Leu Trp Val Leu Glu Arg Ser Met

-continued

```
                165                 170                 175
Asp Phe Gly Arg Thr Tyr Gln Pro Trp Gln Phe Phe Ala Ser Ser Lys
            180                 185                 190
Arg Asp Cys Leu Glu Arg Phe Gly Pro Gln Thr Leu Glu Arg Ile Thr
            195                 200                 205
Arg Asp Asp Ala Ala Ile Cys Thr Thr Glu Tyr Ser Arg Ile Val Pro
            210                 215                 220
Leu Glu Asn Gly Glu Ile Val Val Ser Leu Val Asn Gly Arg Pro Gly
225                 230                 235                 240
Ala Met Asn Phe Ser Tyr Ser Pro Leu Leu Arg Glu Phe Thr Lys Ala
            245                 250                 255
Thr Asn Val Arg Leu Arg Phe Leu Arg Thr Asn Thr Leu Leu Gly His
            260                 265                 270
Leu Met Gly Lys Ala Leu Arg Asp Pro Thr Val Thr Arg Arg Tyr Tyr
            275                 280                 285
Tyr Ser Ile Lys Asp Ile Ser Ile Gly Gly Arg Cys Val Cys His Gly
            290                 295                 300
His Ala Asp Ala Cys Asp Ala Lys Asp Pro Thr Asp Pro Phe Arg Leu
305                 310                 315                 320
Gln Cys Thr Cys Gln His Asn Thr Cys Gly Gly Thr Cys Asp Arg Cys
            325                 330                 335
Cys Pro Gly Phe Asn Gln Pro Trp Lys Pro Ala Thr Ala Asn Ser
            340                 345                 350
Ala Asn Glu Cys Gln Ser Cys Asn Cys Tyr Gly His Ala Thr Asp Cys
            355                 360                 365
Tyr Tyr Asp Pro Glu Val Asp Arg Arg Arg Ala Ser Gln Ser Leu Asp
            370                 375                 380
Gly Thr Tyr Gln Gly Gly Val Cys Ile Asp Cys Gln His His Thr
385                 390                 395                 400
Ala Gly Val Asn Cys Glu Arg Cys Leu Pro Gly Phe Tyr Arg Ser Pro
            405                 410                 415
Asn His Pro Leu Asp Ser Pro His Val Cys Arg Arg Cys Asn Cys Glu
            420                 425                 430
Ser Asp Phe Thr Asp Gly Thr Cys Glu Asp Leu Thr Gly Arg Cys Tyr
            435                 440                 445
Cys Arg Pro Asn Phe Ser Gly Glu Arg Cys Asp Val Cys Ala Glu Gly
            450                 455                 460
Phe Thr Gly Phe Pro Ser Cys Tyr Pro Thr Pro Ser Ser Ser Asn Asp
465                 470                 475                 480
Thr Arg Glu Gln Val Leu Pro Ala Gly Gln Ile Val Asn Cys Asp Cys
            485                 490                 495
Ser Ala Ala Gly Thr Gln Gly Asn Ala Cys Arg Lys Asp Pro Arg Val
            500                 505                 510
Gly Arg Cys Leu Cys Lys Pro Asn Phe Gln Gly Thr His Cys Glu Leu
            515                 520                 525
Cys Ala Pro Gly Phe Tyr Gly Pro Gly Cys Gln Pro Cys Gln Cys Ser
            530                 535                 540
Ser Pro Gly Val Ala Asp Asp Arg Cys Asp Pro Asp Thr Gly Gln Cys
545                 550                 555                 560
Arg Cys Arg Val Gly Phe Glu Gly Ala Thr Cys Asp Arg Cys Ala Pro
            565                 570                 575
Gly Tyr Phe His Phe Pro Leu Cys Gln Leu Cys Gly Cys Ser Pro Ala
            580                 585                 590
```

```
Gly Thr Leu Pro Glu Gly Cys Asp Glu Ala Gly Arg Cys Leu Cys Gln
            595                 600                 605

Pro Glu Phe Ala Gly Pro His Cys Asp Arg Cys Arg Pro Gly Tyr His
        610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
        675                 680                 685

Cys Asp Pro Arg Ser Gly Gln Cys Ser Cys Arg Pro Arg Val Thr Gly
        690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
        755                 760                 765

Asn Pro Glu Gly Cys Thr Arg Cys Ser Cys Asp Leu Arg Gly Thr Leu
        770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
            820                 825                 830

Ile Gly Gly Ala Leu Gly Gln Ser Cys Glu Pro Arg Thr Gly Val Cys
        835                 840                 845

Arg Cys Arg Pro Asn Thr Gln Gly Pro Thr Cys Ser Glu Pro Ala Arg
        850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe
        915                 920                 925

Trp Leu Val Phe Arg Tyr Val Asn Arg Gly Ala Met Ser Val Ser Gly
        930                 935                 940

Arg Val Ser Val Arg Glu Glu Gly Arg Ser Ala Ala Cys Ala Asn Cys
945                 950                 955                 960

Thr Ala Gln Ser Gln Pro Val Ala Phe Pro Pro Ser Thr Glu Pro Ala
                965                 970                 975

Phe Ile Thr Val Pro Gln Arg Gly Phe Gly Glu Pro Phe Val Leu Asn
            980                 985                 990

Pro Gly Thr Trp Ala Leu Arg Val Glu Ala Glu Gly Val Leu Leu Asp
        995                 1000                1005
```

-continued

Tyr Val Leu Leu Pro Ser Ala Tyr Tyr Glu Ala Ala Leu Leu Gln
     1010             1015             1020

Leu Arg Val Thr Glu Ala Cys Thr Tyr Arg Pro Ser Ala Gln Gln Ser
1025             1030             1035             1040

Gly Asp Asn Cys Leu Leu Tyr Thr His Leu Pro Leu Asp Gly Phe Pro
         1045             1050             1055

Ser Ala Ala Gly Leu Glu Ala Leu Cys Arg Gln Asp Asn Ser Leu Pro
         1060             1065             1070

Arg Pro Cys Pro Thr Glu Gln Leu Ser Pro Ser His Pro Pro Leu Ile
         1075             1080             1085

Thr Cys Thr Gly Ser Asp Val Asp Val Gln Leu Gln Val Ala Val Pro
         1090             1095             1100

Gln Pro Gly Arg Tyr Ala Leu Val Val Glu Tyr Ala Asn Glu Asp Ala
1105             1110             1115             1120

Arg Gln Glu Val Gly Val Ala Val His Thr Pro Gln Arg Ala Pro Gln
         1125             1130             1135

Gln Gly Leu Leu Ser Leu His Pro Cys Leu Tyr Ser Thr Leu Cys Arg
         1140             1145             1150

Gly Thr Ala Arg Asp Thr Gln Asp His Leu Ala Val Phe His Leu Asp
         1155             1160             1165

Ser Glu Ala Ser Val Arg Leu Thr Ala Glu Gln Ala Arg Phe Phe Leu
         1170             1175             1180

His Gly Val Thr Leu Val Pro Ile Glu Glu Phe Ser Pro Glu Phe Val
1185             1190             1195             1200

Glu Pro Arg Val Ser Cys Ile Ser Ser His Gly Ala Phe Gly Pro Asn
         1205             1210             1215

Ser Ala Ala Cys Leu Pro Ser Arg Phe Pro Lys Pro Pro Gln Pro Ile
         1220             1225             1230

Ile Leu Arg Asp Cys Gln Val Ile Pro Leu Pro Pro Gly Leu Pro Leu
         1235             1240             1245

Thr His Ala Gln Asp Leu Thr Pro Ala Thr Ser Pro Ala Gly Pro Arg
         1250             1255             1260

Pro Arg Pro Pro Thr Ala Val Asp Pro Asp Ala Glu Pro Thr Leu Leu
1265             1270             1275             1280

Arg Glu Pro Gln Ala Thr Val Val Phe Thr Thr His Val Pro Thr Leu
         1285             1290             1295

Gly Arg Tyr Ala Phe Leu Leu His Gly Tyr Gln Pro Ala His Pro Thr
         1300             1305             1310

Phe Pro Val Glu Val Leu Ile Asn Ala Gly Arg Val Trp Gln Gly His
         1315             1320             1325

Ala Asn Ala Ser Phe Cys Pro His Gly Tyr Gly Cys Arg Thr Leu Val
         1330             1335             1340

Val Cys Glu Gly Gln Ala Leu Leu Asp Val Thr His Ser Glu Leu Thr
1345             1350             1355             1360

Val Thr Val Arg Val Pro Glu Gly Arg Trp Leu Trp Leu Asp Tyr Val
         1365             1370             1375

Leu Val Val Pro Glu Asn Val Tyr Ser Phe Gly Tyr Leu Arg Glu Glu
         1380             1385             1390

Pro Leu Asp Lys Ser Tyr Asp Phe Ile Ser His Cys Ala Ala Gln Gly
         1395             1400             1405

Tyr His Ile Ser Pro Ser Ser Ser Leu Phe Cys Arg Asn Ala Ala
         1410             1415             1420

Ala Ser Leu Ser Leu Phe Tyr Asn Asn Gly Ala Arg Pro Cys Gly Cys

```
             1425                1430                1435                1440
His Glu Val Gly Ala Thr Gly Pro Thr Cys Glu Pro Phe Gly Gly Gln
                    1445                1450                1455
Cys Pro Cys His Ala His Val Ile Gly Arg Asp Cys Ser Arg Cys Ala
        1460                1465                1470
Thr Gly Tyr Trp Gly Phe Pro Asn Cys Arg Pro Cys Asp Cys Gly Ala
            1475                1480                1485
Arg Leu Cys Asp Glu Leu Thr Gly Gln Cys Ile Cys Pro Pro Arg Thr
    1490                1495                1500
Ile Pro Pro Asp Cys Leu Leu Cys Gln Pro Gln Thr Phe Gly Cys His
1505                1510                1515                1520
Pro Leu Val Gly Cys Glu Glu Cys Asn Cys Ser Gly Pro Gly Ile Gln
            1525                1530                1535
Glu Leu Thr Asp Pro Thr Cys Asp Thr Asp Ser Gly Gln Cys Lys Cys
        1540                1545                1550
Arg Pro Asn Val Thr Gly Arg Arg Cys Asp Thr Cys Ser Pro Gly Phe
    1555                1560                1565
His Gly Tyr Pro Arg Cys Arg Pro Cys Asp Cys His Glu Ala Gly Thr
    1570                1575                1580
Ala Pro Gly Val Cys Asp Pro Leu Thr Gly Gln Cys Tyr Cys Lys Glu
1585                1590                1595                1600
Asn Val Gln Gly Pro Lys Cys Asp Gln Cys Ser Leu Gly Thr Phe Ser
            1605                1610                1615
Leu Asp Ala Ala Asn Pro Lys Gly Cys Thr Arg Cys Phe Cys Phe Gly
        1620                1625                1630
Ala Thr Glu Arg Cys Arg Ser Ser Tyr Thr Arg Gln Glu Phe Val
        1635                1640                1645
Asp Met Glu Gly Trp Val Leu Leu Ser Thr Asp Arg Gln Val Val Pro
        1650                1655                1660
His Glu Arg Gln Pro Gly Thr Glu Met Leu Arg Ala Asp Leu Arg His
1665                1670                1675                1680
Val Pro Glu Ala Val Pro Glu Ala Phe Pro Glu Leu Tyr Trp Gln Ala
            1685                1690                1695
Pro Pro Ser Tyr Leu Gly Asp Arg Val Ser Ser Tyr Gly Gly Thr Leu
        1700                1705                1710
Arg Tyr Glu Leu His Ser Glu Thr Gln Arg Gly Asp Val Phe Val Pro
    1715                1720                1725
Met Glu Ser Arg Pro Asp Val Val Leu Gln Gly Asn Gln Met Ser Ile
    1730                1735                1740
Thr Phe Leu Glu Pro Ala Tyr Pro Thr Pro Gly His Val His Arg Gly
1745                1750                1755                1760
Gln Leu Gln Leu Val Glu Gly Asn Phe Arg His Thr Glu Thr Arg Asn
            1765                1770                1775
Thr Val Ser Arg Glu Glu Leu Met Met Val Leu Ala Ser Leu Glu Gln
            1780                1785                1790
Leu Gln Ile Arg Ala Leu Phe Ser Gln Ile Ser Ser Ala Val Ser Leu
        1795                1800                1805
Arg Arg Val Ala Leu Glu Val Ala Ser Pro Ala Gly Gln Gly Ala Leu
    1810                1815                1820
Ala Ser Asn Val Glu Leu Cys Leu Cys Pro Ala Ser Tyr Arg Gly Asp
1825                1830                1835                1840
Ser Cys Gln Glu Cys Ala Pro Gly Phe Tyr Arg Asp Val Lys Gly Leu
            1845                1850                1855
```

-continued

Phe Leu Gly Arg Cys Val Pro Cys Gln Cys His Gly His Ser Asp Arg
        1860                1865                1870

Cys Leu Pro Gly Ser Gly Val Cys Val Asp Cys Gln His Asn Thr Glu
        1875                1880                1885

Gly Ala His Cys Glu Arg Cys Gln Ala Gly Phe Met Ser Ser Arg Asp
        1890                1895                1900

Asp Pro Ser Ala Pro Cys Val Ser Cys Pro Cys Pro Leu Ser Val Pro
1905                1910                1915                1920

Ser Asn Asn Phe Ala Glu Gly Cys Val Leu Arg Gly Arg Thr Gln
        1925                1930                1935

Cys Leu Cys Lys Pro Gly Tyr Ala Gly Ala Ser Cys Glu Arg Cys Ala
        1940                1945                1950

Pro Gly Phe Phe Gly Asn Pro Leu Val Leu Gly Ser Ser Cys Gln Pro
        1955                1960                1965

Cys Asp Cys Ser Gly Asn Gly Asp Pro Asn Leu Leu Phe Ser Asp Cys
        1970                1975                1980

Asp Pro Leu Thr Gly Ala Cys Arg Gly Cys Leu Arg His Thr Thr Gly
1985                1990                1995                2000

Pro Arg Cys Glu Ile Cys Ala Pro Gly Phe Tyr Gly Asn Ala Leu Leu
        2005                2010                2015

Pro Gly Asn Cys Thr Arg Cys Asp Cys Thr Pro Cys Gly Thr Glu Ala
        2020                2025                2030

Cys Asp Pro His Ser Gly His Cys Leu Cys Lys Ala Gly Val Thr Gly
        2035                2040                2045

Arg Arg Cys Asp Arg Cys Gln Glu Gly His Phe Gly Phe Asn Gly Cys
        2050                2055                2060

Gly Gly Cys Arg Pro Cys Ala Cys Gly Pro Ala Ala Glu Gly Ser Glu
2065                2070                2075                2080

Cys His Pro Gln Ser Gly Gln Cys His Cys Arg Pro Gly Thr Met Gly
        2085                2090                2095

Pro Gln Cys Arg Glu Cys Ala Pro Gly Tyr Trp Gly Leu Pro Glu Gln
        2100                2105                2110

Gly Cys Arg Arg Cys Gln Cys Pro Gly Gly Arg Cys Asp Pro His Thr
        2115                2120                2125

Gly Arg Cys Asn Cys Pro Pro Gly Leu Ser Gly Glu Arg Cys Asp Thr
        2130                2135                2140

Cys Ser Gln Gln His Gln Val Pro Val Pro Gly Gly Pro Val Gly His
2145                2150                2155                2160

Ser Ile His Cys Glu Val Cys Asp His Cys Val Val Leu Leu Leu Asp
        2165                2170                2175

Asp Leu Glu Arg Ala Gly Ala Leu Leu Pro Ala Ile His Glu Gln Leu
        2180                2185                2190

Arg Gly Ile Asn Ala Ser Ser Met Ala Trp Ala Arg Leu His Arg Leu
        2195                2200                2205

Asn Ala Ser Ile Ala Asp Leu Gln Ser Gln Leu Arg Ser Pro Leu Gly
        2210                2215                2220

Pro Arg His Glu Thr Ala Gln Gln Leu Glu Val Leu Glu Gln Gln Ser
2225                2230                2235                2240

Thr Ser Leu Gly Gln Asp Ala Arg Arg Leu Gly Gly Gln Ala Val Gly
        2245                2250                2255

Thr Arg Asp Gln Ala Ser Gln Leu Leu Ala Gly Thr Glu Ala Thr Leu
        2260                2265                2270

-continued

Gly His Ala Lys Thr Leu Leu Ala Ala Ile Arg Ala Val Asp Arg Thr
            2275                2280                2285

Leu Ser Glu Leu Met Ser Gln Thr Gly His Leu Gly Leu Ala Asn Ala
    2290                2295                2300

Ser Ala Pro Ser Gly Glu Gln Leu Leu Arg Thr Leu Ala Glu Val Glu
2305                2310                2315                2320

Arg Leu Leu Trp Glu Met Arg Ala Arg Asp Leu Gly Ala Pro Gln Ala
            2325                2330                2335

Ala Ala Glu Ala Glu Leu Ala Ala Gln Arg Leu Leu Ala Arg Val
            2340                2345                2350

Gln Glu Gln Leu Ser Ser Leu Trp Glu Glu Asn Gln Ala Leu Ala Thr
            2355                2360                2365

Gln Thr Arg Asp Arg Leu Ala Gln His Glu Ala Gly Leu Met Asp Leu
    2370                2375                2380

Arg Glu Ala Leu Asn Arg Ala Val Asp Ala Thr Arg Glu Ala Gln Glu
2385                2390                2395                2400

Leu Asn Ser Arg Asn Gln Glu Arg Leu Glu Glu Ala Leu Gln Arg Lys
            2405                2410                2415

Gln Glu Leu Ser Arg Asp Asn Ala Thr Leu Gln Ala Thr Leu His Ala
            2420                2425                2430

Ala Arg Asp Thr Leu Ala Ser Val Phe Arg Leu Leu His Ser Leu Asp
            2435                2440                2445

Gln Ala Lys Glu Glu Leu Glu Arg Leu Ala Ala Ser Leu Asp Gly Ala
            2450                2455                2460

Arg Thr Pro Leu Leu Gln Arg Met Gln Thr Phe Ser Pro Ala Gly Ser
2465                2470                2475                2480

Lys Leu Arg Leu Val Glu Ala Ala Glu Ala His Ala Gln Gln Leu Gly
            2485                2490                2495

Gln Leu Ala Leu Asn Leu Ser Ser Ile Ile Leu Asp Val Asn Gln Asp
            2500                2505                2510

Arg Leu Thr Gln Arg Ala Ile Glu Ala Ser Asn Ala Tyr Ser Arg Ile
            2515                2520                2525

Leu Gln Ala Val Gln Ala Ala Glu Asp Ala Ala Gly Gln Ala Leu Gln
            2530                2535                2540

Gln Ala Asp His Thr Trp Ala Thr Val Val Arg Gln Gly Leu Val Asp
2545                2550                2555                2560

Arg Ala Gln Gln Leu Leu Ala Asn Ser Thr Ala Leu Glu Glu Ala Met
            2565                2570                2575

Leu Gln Glu Gln Gln Arg Leu Gly Leu Val Trp Ala Ala Leu Gln Gly
            2580                2585                2590

Ala Arg Thr Gln Leu Arg Asp Val Arg Ala Lys Lys Asp Gln Leu Glu
            2595                2600                2605

Ala His Ile Gln Ala Ala Gln Ala Met Leu Ala Met Asp Thr Asp Glu
            2610                2615                2620

Thr Ser Lys Lys Ile Ala His Ala Lys Ala Val Ala Ala Glu Ala Gln
2625                2630                2635                2640

Asp Thr Ala Thr Arg Val Gln Ser Gln Leu Gln Ala Met Gln Glu Asn
            2645                2650                2655

Val Glu Arg Trp Gln Gly Gln Tyr Glu Gly Leu Arg Gly Gln Asp Leu
            2660                2665                2670

Gly Gln Ala Val Leu Asp Ala Gly His Ser Val Ser Thr Leu Glu Lys
            2675                2680                2685

Thr Leu Pro Gln Leu Leu Ala Lys Leu Ser Ile Leu Glu Asn Arg Gly

```
                      2690              2695              2700
Val His Asn Ala Ser Leu Ala Leu Ser Ala Ser Ile Gly Arg Val Arg
2705                2710              2715                  2720

Glu Leu Ile Ala Gln Ala Arg Gly Ala Ala Ser Lys Val Lys Val Pro
              2725              2730              2735

Met Lys Phe Asn Gly Arg Ser
          2740
```